(12) United States Patent
Engler et al.

(10) Patent No.: US 7,109,229 B2
(45) Date of Patent: Sep. 19, 2006

(54) METHODS AND COMPOUNDS FOR TREATING PROLIFERATIVE DISEASES

(75) Inventors: Thomas Albert Engler, Indianapolis, IN (US); Kelly Wayne Furness, Avon, IN (US); Sushant Malhotra, Indianapolis, IN (US); Stephen Lyle Briggs, Indianapolis, IN (US); Harold Burns Brooks, Carmel, IN (US); David K yes Clawson, Indianapolis, IN (US); Concepcion Sanchez-Martinez, Madrid (ES); Faming Zhang, Carmel, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 448 days.

(21) Appl. No.: 10/344,245

(22) PCT Filed: Sep. 24, 2001

(86) PCT No.: PCT/US01/27728

§ 371 (c)(1),
(2), (4) Date: Feb. 7, 2003

(87) PCT Pub. No.: WO02/28861

PCT Pub. Date: Apr. 11, 2002

(65) Prior Publication Data

US 2004/0048915 A1 Mar. 11, 2004

Related U.S. Application Data

(60) Provisional application No. 60/236,616, filed on Sep. 29, 2000.

(51) Int. Cl.
*A61K 31/40* (2006.01)
*C07D 481/00* (2006.01)
(52) U.S. Cl. .................. 514/410; 548/416; 548/417
(58) Field of Classification Search ............. 548/416, 548/417; 514/410
See application file for complete search history.

(56) References Cited

U.S. PATENT DOCUMENTS 5,883,114 A 3/1999 Kleinschroth et al. ...... 514/410

*Primary Examiner*—Joseph K. McKane
*Assistant Examiner*—Robert Shiao
(74) *Attorney, Agent, or Firm*—Tina M. Tucker

(57) ABSTRACT

The compounds disclosed herein are indolocarbazoles of Formula (I), which are potent CDK4 inhibitors, and are useful in the treatment of cell proliferative disorders, including cancer. Formula (I).

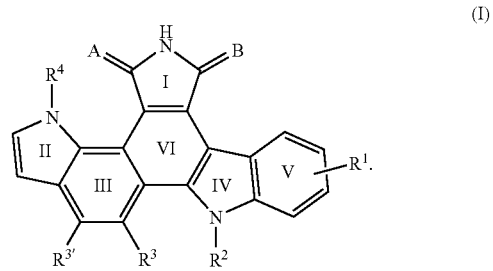

8 Claims, No Drawings

METHODS AND COMPOUNDS FOR TREATING PROLIFERATIVE DISEASES

This application is the U.S. National Stage filing of PCT/US01/27728, filed Sep. 24, 2001, which claims the benefit of U.S. Provisional Application Ser. No. 60/236,616, filed on Sep. 29, 2000.

The present invention relates to a method of treating proliferative diseases using indolo[6,7-a]pyrrolo[3,4-c]carbazole-6,8-diones as therapeutic agents. Cancer is a heterogeneous group of diseases presenting in various forms in various tissues but having in common the characteristic of uncontrolled cell proliferation. For some time, cancer has been recognized as a disease of uncontrolled cell proliferation. Thus, the rapidly proliferating cell has been the target of cancer chemotherapy. The goal is to find agents that are more effective against cancer cells than against normal cells. As the basic science of the cell progressed, it was shown that certain anticancer agents were more effective against malignant cells at certain stages of the cell cycle than against cells at other stages of the cell cycle.

Attempts were made to develop treatment regimens that took advantage of these observations (SHACKNEY, S. E. et al Cell Kinetics. IN: Bruce Chabner (ed.), Pharmacologic Principles of Cancer Treatment; W. B. Saunder Company: Philadelphia, pp. 45–76, (1982)). Cell replication is now recognized to be controlled by the transient, sequential, highly-regulated expression of a series of cyclins which associate with specific cyclin-dependent kinases (CDK's) (TAULES, M., et al, *J. Biol. Chem.* 273, 33279–33286 (1998; FISHER, R. P. *Current Opinion in Genetics & Develop.* 7, 32–38 (1997); ARELLANO, M. et al., *Int. J. Biochem. Cell Biol.* 29, 559–573 (1997); and RAVITZ, M. J., et al. *Adv. Cancer Res.* 1997, 165–207 (1997)). These are serine/threonine protein kinases, which activate various enzymes and thereby initiate a cascade of phosphorylations allowing the cell to progress to the next stage of replication (COLLINS, et al., *Proc. Natl. Acad. Sci. USA* 94, 2776–2778 (1997); JACKS, T. et al., *Science* 280, 1035–1036 (1998)).

It has been found that cancerous cells often have mutated or missing components in the chain of proteins and enzymes, which control cell division. For example, the Rb protein, often called Rb, is a substrate for the cyclin-CDK's and is frequently missing or mutated in human tumors (KONSTANTINIDIS, A. K. et al, *J. Biol. Chem.* 273, 26506–26515 (1998); HARRINGTON, E. A., et al., *Proc. Natl. Acad. Sci. USA* 95, 11945–11950 (1998); YAMAMOTO, et al., *Oncol. Rep.* 5, 447–451 (1997); BARTEK, J., et al., *Exp. Cell Res.* 237, 1–6 (1997); SELLERS, et al., *J. Clin. Oncol.* 15, 3301–3312 (1997); HERWIG, S. et al., *Eur. J. Biochem.* 246, 581–601 (1997)).

In addition to the kinases, which can help to move the cell from one phase of division to the next, there are CDK inhibitors (CKIs) that block the actions of specific cyclin-CDK complexes. The CKIs halt cell cycle progression and cause cells to enter the quiescent $G_0$ phase. The CKIs of the INK4 group, including p15, p16, p18, and p19, block the cyclin-CDK4 and cyclin-CDK6 complexes.

Calmodulin is essential for cyclin-dependent kinase 4 (CDK4) activity and nuclear accumulation of cyclin D1-CDK4 during the $G_1$ phase (TAULES, M., et al, *J. Biol. Chem.* 273, 33279–33286 (1998)). CDKs and cyclins are important in transition(s) (FISHER, R. P. *Current Opinion in Genetics & Develop.* 7, 32–38 (1997)). CDK/cyclin complexes are regulated during the cell cycle (ARELLANO, M. et al., *Int. J. Biochem. Cell Biol.* 29, 559–573 (1997)). Cyclin-dependent kinase during the $G_1$ phase, and the cell cycle generally are regulated by TGF-$\beta$ (RAVITZ, M. J., et al. *Adv. Cancer Res.* 1997, 165–207 (1997)).

The most frequent alteration in human malignant disease thus far recognized is the overexpression, mutation, and/or disregulation of cyclin D (IMOTO, M., et al., *Exp. Cell Res.* 236, 173–180 (1997); JUAN, G., et al., *Cell Prolif.* 29, 259–266 (1996); GONG, J. et al., *Cell Prolif.* 28, 337–346 (1995) et al., 1995). The cyclin D1 gene, CCND1, is amplified in about 20% of breast cancers and the protein, cyclin D1, is overexpressed in about 50% of breast cancers (BARNES, D. M. et al., *Breast Cancer Res. Treat.* 52, 1–15 (1998); KAMALATI, T., et al., *Clin. Exp. Metastasis* 16, 415–426 (1998); STEEG, P. S. et al. *Breast Cancer Res. Treat.* 52, 17–28 (1998); LANDBERG, G. et al., *APMIS* 105, 575–589 (1997); ALLE, et al., *Clin. Cancer Res.* 4, 847–854 (1998)). Overexpression of cyclin D1 has been reported in proliferative breast disease and in ductal carcinoma in situ, indicating that this change is important at the earliest stages of breast oncogenesis (ALLE, et al., *Clin. Cancer Res.* 4, 847–854 (1998); STEEG, et al., *Breast Cancer Res. Treat.* 52, 17–28 (1998)).

One researcher (KAMALATI, T., et al., *Clin. Exp. Metastasis* 16, 415–426 (1998) et al. (1998)) treated normal human epithelial cells so that they overexpressed cyclin D1. These transfected cells had reduced growth factor dependency, a shortened cell cycle time, thus providing the cells with a growth advantage. In 123 colorectal carcinoma specimens, those staining strongly for cyclin D1 corresponded to patients with a 5-year survival rate of 53.3% while those that were negative or weakly staining had 5-year survival rates of 96.2 and 78.8% (MEEDA, K., et al., *Oncology* 55, 145–151 (1998); PALMQVIST, R., et al., *Europ. J. Cancer* 34, 1575–1581 (1998)).

Amplification of CCND1 was found in 25% of dysplastic head-and-neck lesions, and 22% of head-and-neck carcinomas. Overexpression of cyclin D1 was found in 53% of head-and-neck carcinomas. This indicates that in this disease, like breast cancer, alterations in cyclin D1 occur at the very earliest stages of tumorigenesis (KYOMOTO, R., et al., *Int. J. Cancer (Pred. Oncol.)* 74, 576–581 (1997); PIGNATARO, L., et al., *J. Clin. Oncol.* 16, 3069–3077 (1998) et al., 1998). In a study of 218 specimens of esophageal squamous cell carcinoma, patients with cyclin D1-positive tumors had significantly worse survival than patients with cyclin D1-negative tumors (SARBIA, M. et al., *Int. J. Cancer (Pred. Oncol.* 84, 86–91 (1999)).

In eight human esophageal carcinoma cell lines, 7 (87.5%) and 6 (75%) cell lines had homozygous deletions of the p16 and p15 genes (KITAHARA, K. et al., *J. Exp. Therap. Oncol.* 1, 7–12 (1996)). All of the p16-negative cell lines express high levels of cyclin D1 and CDK4.

The Rustgi laboratory (MUELLER, A, et al., *Cancer Res.* 57, 5542–5549 (1997); NAKAGAWA, H, et al., *Oncogene* 14, 1185–1190 (1997)) developed a transgenic mouse in which the Epstein-Barr virus ED-L2 promoter was linked to human cyclin D1 cDNA. The transgene protein localizes to squamous epithelium in the tongue and esophagus, resulting in a dysplastic phenotype associated with increased cell proliferation and indicating that cyclin D1 overexpression may be a tumor-initiating event. In a series of 84 specimens of soft-tissue sarcomas, there was no amplification of the CCND1 gene but there was overexpression of cyclin D1 in 29% of cases. The overexpression of cyclin D1 was significantly associated with worse overall survival (KIM, S. H., et al., *Clin. Cancer Res.* 4, 2377–2382 (1998); YAO, J., et al., *Clin. Cancer Res.* 4, 1065–1070 (1998)).

Another researcher (MARCHETTI, A., et al., *Int. J. Cancer* 75, 187–192 (1998)) found that abnormalities of cyclin D1 and/or Rb at the gene and/or expression level were present in more than 90% of a series of non-small cell lung cancer specimens, indicating that cyclin D1 and/or Rb alterations represent an important step in lung tumorigenesis. In 49 out of 50 pancreatic carcinomas (98%), the Rb/p16 pathway was abrogated exclusively through inactivation of the p16 gene (SCHUTTE, M., et al., *Cancer Res.* 57, 3126–3130 (1997)).

Mantle cell lymphoma is defined as a subentity of malignant lymphomas characterized by the chromosomal translocation t(11;14) (q13;q32) resulting in overexpression of cyclin D1 and, in addition, about 50% of these tumors have deletion of the p16 gene (DREYLING, M. H., et al., *Cancer Res.* 57, 4608–4614 (1997); TANIGUCHI, T., et al., *Jpn. J. Cancer Res.* 89, 159–166 (1998)).

In a series of 17 hepatoblastomas, 76% showed overexpression of cyclin D1 and 88% showed overexpression of CDK4 (KIM, H., et al., *Cancer Lett.* 131, 177–183 (1998)). There was a correlation between high level cyclin D1 expression and tumor recurrence. Alterations in the cyclin D1/CDK4/pRb pathway have also been associated with a high percentage of prostate carcinomas (HAN, E. K. H., et al., *The Prostate* 35, 95–101 (1998)), ovarian carcinomas (MASCIULLO, V., et al., *Int. J. Cancer Pred. Oncol.* 74, 390–395 (1997)) and osteosarcomas (WEI, G., et al., *Int. J. Cancer* 80, 199–204 (1999) et al., 1999).

Several distinct classes of small molecules have been identified as inhibitors of CDKs: the purine-based compound olomoucine and analogs, butyrolactone, flavopiridol, staurosporine and UCN-01, suramin, 9-hydroxyellipticine, indirubin, paullones, diaryl ureas, quinazolines, indenopyrazoles, [2,3-d]pyridopyrimidines, fascaplysin, and 5-arylamino-4,7-dioxobenzothiazoles, for example (CARLSON et al., *Cancer Res.* 56, 2973–2978 (1996); DE AZEVEDO, et al., *Eur. J. Biochem.* 243, 518–526 (1997); BRIDGES, A. J. *Exp. Opin. Ther. Patents* 5, 1245–1257 (1995); ORR, M. S., et al., REINHOLD, W., et al., *J. Biol. Chem.* 278, 3803–3807 (1998) et al., 1998; KAKEYA, H., et al., *Cancer Res.* 58, 704–710 (1998); HARPER, J. W. *Cancer Surveys* 29, 91–107 (1997); HARRINGTON, E. A., et al., *Proc. Natl. Acad. Sci. USA* 95, 11945–11950 (1998); GARRETT, M. D. et al., *Current Opin. Genetics Develop.* 9, 104–111 (1999); MGBONYEBI, O. P., et al., *Cancer Res.* 59, 1903–1910 (1999); HOESSEL et al., *Nature Cell Biology*, 1, 60–67 (1999); ZAHAREVITZ et al., *Cancer Res.* 59, 2566–2569 (1999); HONMA, T., et. al. 221$^{st}$ National Meeting of the American Chemical Society, Apr. 1–5, 2001, San Diego, Calif.: Abstract MEDI 136; SIELECKI, T. M., et. al., *Bioorg. Med. Chem. Lett.* 11, 1157–1160 (2001); NUGIEL, D. A., et. al., *J. Med. Chem.* 44, 1334–1336 (2001); Fry, D. W., et. al., *J. Biol. Chem.*, 276, 16617–16623 (2001); SONI, R., et al., *Biochem. Biophys. Res. Commun.*, 275, 877 (2000); RYU, C-K., et al., *Bioorg. Med. Chem. Lett.*, 10, 461 (2000); JEONG, H-W., et al., *Bioorg. Med. Chem. Lett.*, 10, 1819 (2000)).

Olomoucine is an inhibitor of Cdc2, CDK2, CDK5 and MAP kinase in micromolar concentrations and has much weaker effects toward CDK4 and CDK6 (GARRETT, M. D. *Current Opin. Genetics Develop.* 9, 104–111 (1999)). Olomoucine has been reported to arrest several cell lines in $G_1$ and $G_2$ phases of the cell cycle and block known CDK-dependent cellular activities.

Flavopiridol, a novel synthetic flavone, potently inhibits several cyclin-dependent kinases including CDK1, CDK2, CDK4 and CDK7 (SEDLACEK, H. H., et al., *Int. J. Cancer* 65, 1143–1168 (1996); CZECH, J., et al., *Int. J. Oncol.* 6, 31–36 (1995); BIBLE, K. C. et al., *Cancer Res.* 56, 4856–4861 (1996); SCHRUMP, D. S., et al., *Clin. Cancer Res.* 4, 2885–2890 (1998); BRUSSELBACH, S., et al., *Int. J. Cancer*, 77, 146–152 (1998); JAGER, W., et al., *Life Sciences* 62, 1861–1873 (1998); SENDEROWICZ, A. M., et al., *J. Clin. Oncol.* 16, 2986–2999 (1998)). Exposure to flavopiridol can cause cells to arrest in both the $G_1$ and $G_2$ phases of the cell cycle, at concentrations similar to those required for cell growth inhibition (BIBLE, K. C. et al., *Cancer Res.* 56, 4856–4861 (1996); SCHRUMP, D. S., et al., *Clin. Cancer Res.* 4, 2885–2890 (1998)). Flavopiridol inhibits the CDK's in a manner competitive with ATP and noncompetitive with the substrate. Flavopiridol also inhibits other protein kinases such as protein kinase C, protein kinase A, and EGFR but at concentrations of 10 µM/L or greater. Flavopiridol is an active antitumor agent in several human tumor xenograft models including Colo-205 colon carcinoma, and DU-145 and LNCaP prostate carcinomas (SEDLACEK, H. H., et al., *Int. J. Cancer* 65, 1143–1168 (1996); CZECH, J., et al., *Int. J. Oncol.* 6, 31–36 (1995)). Flavopiridol has shown completed Phase I clinical trial administered as a 72-hour continuous intravenous infusion every 2 weeks (SENDEROWICZ, A. M., et al., *J. Clin. Oncol.* 16, 2986–2999 (1998), and phase II trials are underway.

Much has already been published on the antineoplastic properties of certain compounds such as bisindolylmaleimides, indolocarbazoles, and derivations thereof. Staurosporine and UCN-01 are members of this broad molecular class (COLEMAN, K. G., et al., *Ann. Reps. Med. Chem.* 32, 171–179 (1997)). For example, U.S. Pat. No. 5,856,517 discloses substituted pyrroles, which are useful as antiproliferative agents in the treatment of cancer. U.S. Pat. No. 5,292,747 discloses substituted pyrroles useful in the prevention or control of oncological disorders. U.S. Pat. No. 5,721,245 discloses indolylpyrrolones useful in controlling oncological disorders. U.S. Pat. No. 5,438,050 (Godecke) discloses indolocarbazole derivatives useful in the prevention and treatment of cancer. U.S. Pat. No. 5,705,511 and U.S. Pat. No. 5,591,855 discloses fused pyrrolocarbazoles for the inhibition of growth associated with hyperproliferative states.

In addition to the kinases, which control the cell division cycle, there are over several hundred other kinases found in the human body. These kinases perform such diverse functions as growth factor and cytokine signal transduction, inflammatory mediators, biochemical routes controlling activity of nuclear transcription factors and apoptotic pathways. Kinase inhibitors tend to be broadly active against all kinases. Treating patients with broadly active kinase inhibitors not only inhibits the kinases, which have a role in the disease state being treated, but also inhibits many other kinases as well. Such treatment leads to unintended side effects and is not generally acceptable. In treating proliferative diseases, it is particularly desirable to use a kinase inhibitor with narrow activity. Anti-cancer agents are generally given at high doses in order to kill as many cancer cells as possible. With such high dosing, side effects due to broad kinase inhibition can become a serious problem. Accordingly, to treat proliferative diseases, it is desirable to use kinase inhibitors, which inhibit the kinases controlling cell division while not inhibiting other unrelated kinases.

The compounds disclosed herein are indolocarbazoles, which are potent CDK4 inhibitors, and are useful in the treatment of cell proliferative disorders, including cancer.

The present invention provides compounds of Formula I

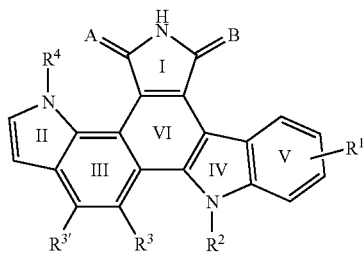

Formula I wherein

A and B are independently O or S;

$R^1$ is hydrogen, $C_1-C_4$ alkyl, $C_1-C_4$ alkoxy, hydroxy, hydroxy($C_1-C_4$)alkyl, halogen, cyano, halo($C_1-C_4$)alkyl, ($C_1-C_4$ alkyl)-$NR^5R^6$, or ($C_1-C_4$ alkyl)-($C_1-C_4$ alkyl ester of an amino acid residue);

$R^2$ is hydrogen, $C_1-C_4$ alkyl, hydroxy($C_1-C_4$)alkyl, ($C_1-C_4$ alkyl)-$NR^5R^6$, ($C_1-C_4$ alkyl)-$C(O)NR^5R^6$, or ($C_1-C_4$ alkyl)-($C_1-C_4$ alkyl ester of an amino acid residue);

$R^3$ and $R^{3'}$ are independently hydrogen, $C_1-C_4$ alkyl, $C_1-C_4$ alkoxy, or halogen;

$R^4$ is hydrogen or $C_1-C_4$ alkyl;

$R^5$ is independently at each occurrence hydrogen, $C_1-C_4$ alkyl, hydroxy($C_1-C_4$)alkyl, ($C_1-C_4$ alkyl)-$NR^7R^8$, $C(O)NR^7R^8$, $C(O)-(C_1-C_4$ alkyl), or optionally substituted $C_3-C_8$ cycloalkyl; and $R^6$ is independently at each occurrence hydrogen or $C_1-C_4$ alkyl; or $R^5$ and $R^6$ are taken together with the nitrogen to which they are attached to form an optionally substituted saturated heterocycle;

$R^7$ and $R^8$ are independently at each occurrence hydrogen or $C_1-C_4$ alkyl;

or a pharmaceutically acceptable salt thereof.

Furthermore, the present invention provides a method for the inhibition of CDK4 in a mammal comprising administering to a mammal in need of such treatment an effective amount of a compound of Formula I. Furthermore, the present invention provides the use of a compound of Formula I for the preparation of a medicament useful for the inhibition of CDK4.

Additionally, the present invention provides a pharmaceutical formulation comprising a compound of Formula I or a pharmaceutically acceptable salt thereof, in association with a pharmaceutically acceptable carrier, diluent or excipient.

Also, the present invention provides compounds of Formula II

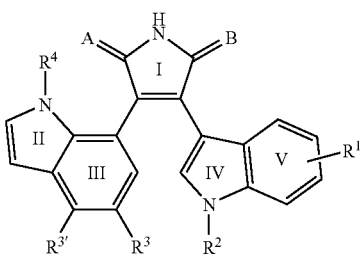

Formula II wherein

A and B are independently O or S;

$R^1$ is hydrogen, $C_1-C_4$ alkyl, $C_1-C_4$ alkoxy, hydroxy, hydroxy($C_1-C_4$)alkyl, halogen, cyano, halo($C_1-C_4$)alkyl, ($C_1-C_4$ alkyl)-$NR^5R^6$, or ($C_1-C_4$ alkyl)-($C_1-C_4$ alkyl ester of an amino acid residue);

$R^2$ is hydrogen, $C_1-C_4$ alkyl, hydroxy($C_1-C_4$)alkyl, ($C_1-C_4$ alkyl)-$NR^5R^6$, ($C_1-C_4$ alkyl)-$C(O)NR^5R^6$, or ($C_1-C_4$ alkyl)-($C_1-C_4$ alkyl ester of an amino acid residue);

$R^3$ and $R^{3'}$ are independently hydrogen, $C_1-C_4$ alkyl, $C_1-C_4$ alkoxy, or halogen;

$R^4$ is hydrogen or $C_1-C_4$ alkyl;

$R^5$ is independently at each occurrence hydrogen, $C_1-C_4$ alkyl, hydroxy($C_1-C_4$)alkyl, ($C_1-C_4$ alkyl)-$NR^7R^8$, $C(O)NR^7R^8$, $C(O)-(C_1-C_4$ alkyl), or optionally substituted $C_3-C_8$ cycloalkyl; and $R^6$ is independently at each occurrence hydrogen or $C_1-C_4$ alkyl; or $R^5$ and $R^6$ are taken together with the nitrogen to which they are attached to form an optionally substituted saturated heterocycle;

$R^7$ and $R^8$ are independently at each occurrence hydrogen or $C_1-C_4$ alkyl;

or a pharmaceutically acceptable salt thereof, useful as intermediates for making compounds of Formula I.

The following definitions are to set forth the meaning and scope of the various terms used herein. The general terms used herein have their usual meanings.

As used herein, the "hyperproliferative state" refers to those cells whose unregulated and/or abnormal growth can lead to the development of an unwanted condition, for example, a cancerous condition or a psoriatic condition.

As used herein, the term "psoriatic condition" refers to disorders involving keratinocyte hyperproliferation, inflammatory cell infiltration, and cytokine alteration.

As used herein, the term "proliferative diseases" refers to diseases in which some tissue in a patient proliferates at a greater than normal rate. Proliferative diseases may be cancerous or non-cancerous. Non-cancerous proliferative diseases include epidermic and dermoid cysts, lipomas, adenomas, capillary and cutaneous hemangiomas, lymphangiomas, nevi lesions, teratomas, nephromas, myofibromatosis, osteoplastic tumors, other dysplastic masses and the like.

The types of proliferative diseases which may be treated are epidermic and dermoid cysts, lipomas, adenomas, capillary and cutaneous hemangiomas, lymphangiomas, nevi lesions, teratomas, nephromas, myofibromatosis, osteoplastic tumors, other dysplastic masses and the like.

The types of cancers which may be treated with compounds and compositions of the present invention include: Breast Carcinoma, Bladder Carcinoma, Brain Cancer, Colorectal Carcinoma, Esophageal Carcinoma, Gastric Carcinoma, Germ Cell Carcinoma e.g. Testicular Cancer, Gynecologic Carcinoma, Hepatocellular Carcinoma, Small Cell Lung Carcinoma, Non-small Cell Lung Carcinoma, Lymphomas, Hodgkin's Lymphoma, Non-Hodgkin's Lymphoma, Malignant Melanoma, Multiple Myeloma, Neurologic Carcinoma, Ovarian Carcinoma, Pancreatic Carcinoma, Prostate Carcinoma, Renal Cell Carcinoma, Ewings Sarcoma, Osteosarcoma, Soft Tissue Sarcoma, Pediatric Malignancies and the like.

The term "effective amount" as used in "an effective amount of a compound of Formula I," for example, refers to an amount of a compound of the present invention that is capable of inhibiting CDK4.

The general chemical terms used herein have their usual. meanings. For example, as used herein, the term "$C_1-C_4$ alkyl," alone or in combination, denotes a straight-chain or branched-chain $C_1$–$C_4$ alkyl group consisting of carbon and hydrogen atoms, examples of which are methyl, ethyl, propyl, isopropyl, butyl, sec-butyl, tert-butyl, and the like.

The term "$C_3$–$C_8$ cycloalkyl" refers to cyclopropyl, cyclobutyl, cyclopentyl, cyclohexyl, cycloheptyl, and cyclooctyl. The term "optionally substituted $C_3$–$C_8$ cycloalkyl" refers to a $C_3$–$C_8$ cycloalkyl as defined herein unsubstituted or substituted once with hydroxy, $C_1$–$C_4$ alkyl, hydroxy($C_1$–$C_4$)alkyl, $NR^7R^8$, $C(=O)OR^7$, or $C(=O)NR^7R^8$.

The term "$C_1$–$C_4$ alkoxy," alone or in combination, denotes an alkyl group as defined earlier which is attached via an oxygen atom, such as, for example, methoxy, ethoxy, propoxy, isopropoxy, butoxy, tert-butoxy, and the like. The term "hydroxy," alone or in combination, represents an —OH moiety. As used herein, the term "hydroxy($C_1$–$C_4$)alkyl" represents a straight or branched alkyl group as defined earlier bonded through a carbon containing a —OH group as a substituent on the carbon chain.

As used herein, the term "halo" or "halogen" represents fluorine, chlorine, bromine, or iodine. A halo($C_1$–$C_4$)alkyl is an alkyl group as defined earlier substituted with one or more halo atoms, preferably one to three halo atoms. However, all the hydrogen atoms in alkyl group may be replaced by halogens. As more halogens are added to an alkyl group, fluorine is preferred over the other halogens. An example of a haloalkyl is trifluoromethyl.

As used herein, the term "saturated heterocycle" is taken to be a 4–9 membered ring containing nitrogen and optionally one other atom selected from oxygen, nitrogen, and sulfur. The term "optionally substituted saturated heterocycle" is taken to be a saturated heterocycle as defined herein unsubstituted or substituted once with hydroxy, $C_1$–$C_4$ alkyl, hydroxy($C_1$–$C_4$)alkyl, $NR^7R^8$, $C(=O)OR^7$, or $C(=O)NR^7R^8$.

As used herein the term "amino acid residue" means the product of an amino acid derivative coupled to a compound of Formula I through the N-terminus of the amino acid. The term includes both naturally occurring and synthetic amino acids and includes both the D and L form of the acids as well as the racemic form. More specifically, amino acids contain up to ten carbon atoms. They may contain an additional carboxyl group, and heteroatoms such as nitrogen and sulfur. Preferably the amino acids are α- and β-amino acids. The term α-amino acid refers to amino acids in which the amino group is attached to the carbon directly attached to the carboxyl group, which is the α-carbon. The term β-amino acid refers to amino acids in which the amino group is attached to a carbon one removed from the carboxyl group, which is the β-carbon. Some common α-amino acid residues are shown in Table I wherein the residues are given the name of the amino acids from which they are derived.

TABLE I

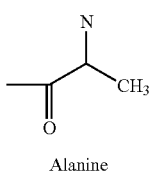

Alanine

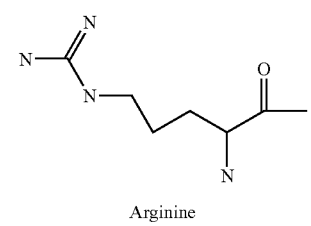

Arginine

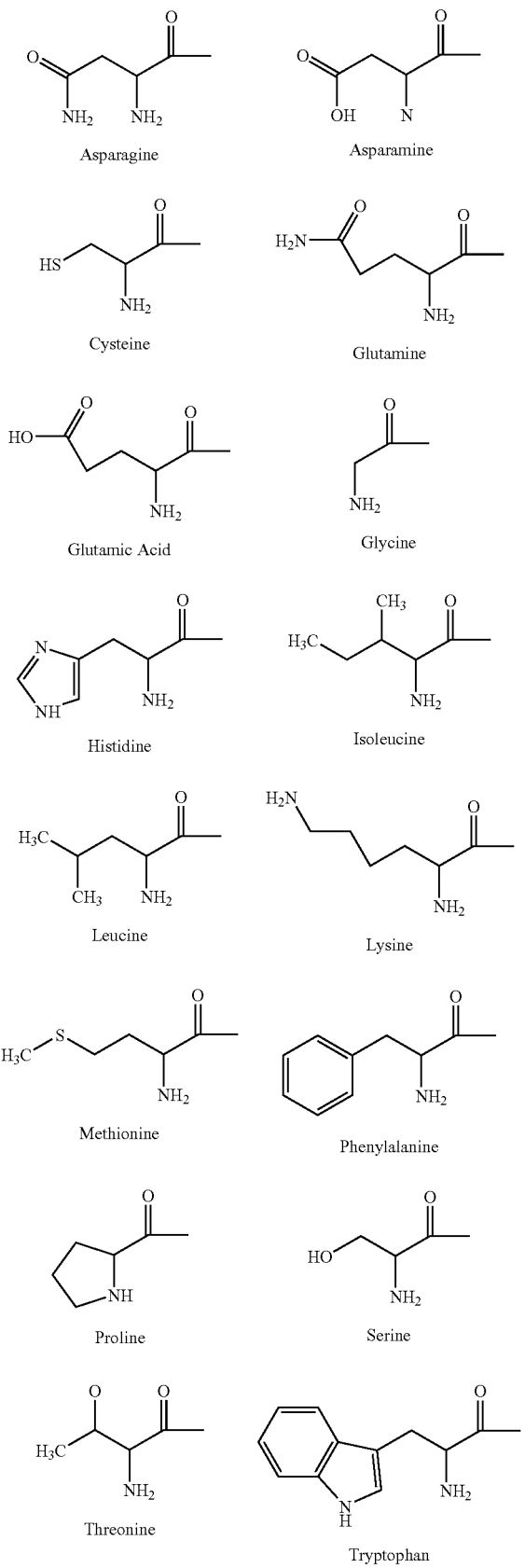

TABLE I-continued

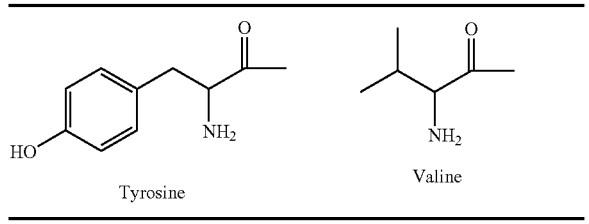

Suitable β-amino acid residues can be the β-amino derivative of any suitable α-amino acid residue wherein the amino group is attached to the residue through the β-carbon rather than the α-carbon relative to the carboxyl group, for example, 3-aminopropionoic acid, 3-amino-3-phenylpropionoic acid, 3-aminobutyric acid and the like:

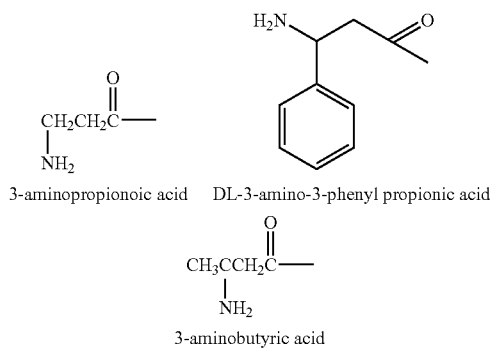

As used herein, the term "pharmaceutically acceptable salt" includes acid and basic addition salts. Such pharmaceutically acceptable salts include inorganic acid addition salts such as hydrochloride, sulfate, and phosphate, and organic acid addition salts such as acetate, maleate, fumarate, tartrate, citrate, and methane sulfonate. Examples of pharmaceutically acceptable basic salts include metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable amine addition salts are salts with morpholine and piperidine. Examples of pharmaceutically acceptable amino acid addition salts are salts with lysine, glycine, and phenylalanine.

Although all of the compounds of Formula I are useful CDK4 inhibitors, certain compounds are preferred. The following paragraphs define preferred classes.

a) $R^1$ is a substituent other than hydrogen at the 6-indole position.
b) $R^1$ is a substituent other than hydrogen at the 7-indole position.
c) $R^1$ is hydrogen.
d) $R^1$ is $C_1$–$C_4$ alkyl.
e) $R^1$ is $C_1$–$C_4$ alkoxy.
f) $R^1$ is methoxy.
g) $R^1$ is hydroxy.
h) $R^1$ is hydroxy($C_1$–$C_4$)alkyl.
i) $R^1$ is 2-hydroxyethyl.
j) $R^1$ is 3-hydroxypropyl.
k) $R^1$ is halogen.
l) $R^1$ is halo($C_1$–$C_4$)alkyl.
m) $R^1$ is trifluoromethyl.
n) $R^1$ is ($C_1$–$C_4$ alkyl)-$NR^5R^6$.
o) $R^1$ is ethylene-$NR^5R^6$.
p) $R^1$ is propylene-$NR^5R^6$.
q) $R^1$ is ($C_1$–$C_4$ alkylene)-($C_1$–$C_4$ alkyl ester of an amino acid).
r) $R^1$ is ethylene-($C_1$–$C_4$ alkyl ester of an amino acid).
s) $R^1$ is propylene-($C_1$–$C_4$ alkyl ester of an amino acid).
t) $R^2$ is hydrogen.
u) $R^2$ is hydroxy($C_1$–$C_4$)alkyl.
v) $R^2$ is 2-hydroxyethyl.
w) $R^2$ is 3-hydroxypropyl.
x) $R^2$ is ($C_1$–$C_4$ alkyl)-$NR^5R^6$.
y) $R^2$ is ethyl-$NR^5R^6$.
z) $R^2$ is propyl-$NR^5R^6$.
aa) $R^2$ is ($C_1$–$C_4$ alkyl)-($C_1$–$C_4$ alkyl ester of an amino acid).
bb) $R^2$ is propyl-($C_1$–$C_4$ alkyl ester of an amino acid).
cc) $R^3$ is hydrogen.
dd) $R^3$ is $C_1$–$C_4$ alkyl.
ee) $R^3$ is methyl.
ff) $R^3$ is $C_1$–$C_4$ alkoxy.
gg) $R^3$ is methoxy.
hh) $R^3$ is halogen.
ii) $R^{3'}$ is hydrogen.
jj) $R^{3'}$ is $C_1$–$C_4$ alkyl.
kk) $R^{3'}$ is methyl.
ll) $R^{3'}$ is $C_1$–$C_4$ alkoxy.
mm) $R^{3'}$ is methoxy.
nn) $R^{3'}$ is halogen.
oo) $R^4$ is hydrogen.
pp) $R^4$ is methyl.
qq) $R^4$ is ethyl.
rr) $R^5$ is hydrogen.
ss) $R^5$ is $C_1$–$C_4$ alkyl.
tt) $R^5$ is methyl.
uu) $R^5$ is ethyl.
vv) $R^5$ is hydroxy($C_1$–$C_4$)alkyl.
ww) $R^5$ is ($C_1$–$C_4$ alkyl)-$NR^7R^8$.
xx) $R^5$ is ethyl-$NR^7R^8$.
yy) $R^5$ is an optionally substituted $C_3$–$C_8$ cycloalkyl.
zz) $R^5$ is an optionally substituted cyclohexyl.
aaa) $R^5$ is a $C_3$–$C_8$ cycloalkyl substituted with hydroxy.
bbb) $R^5$ is a $C_3$–$C_8$ cycloalkyl substituted with $NR^7R^8$.
ccc) $R^6$ is hydrogen.
ddd) $R^6$ is $C_1$–$C_4$ alkyl.
eee) $R^6$ is methyl.
fff) $R^6$ is ethyl.
ggg) $R^5$ and $R^6$ are taken together to form an optionally substituted saturated heterocycle.
hhh) $R^5$ and $R^6$ are taken together to form an optionally substituted pyrrolidine.
iii) $R^5$ and $R^6$ are taken together to form an optionally substituted piperidine.
jjj) $R^5$ and $R^6$ are taken together to form an optionally substituted piperazine.
kkk) $R^5$ and $R^6$ are taken together to form an optionally substituted morpholine.
lll) $R^5$ and $R^6$ are taken together to form a saturated heterocycle substituted with hydroxy.
mmm) $R^5$ and $R^6$ are taken together to form a saturated heterocycle substituted with $C_1$–$C_4$ alkyl.
nnn) $R^5$ and $R^6$ are taken together to form a saturated heterocycle substituted with methyl.
ooo) $R^5$ and $R^6$ are taken together to form a saturated heterocycle substituted with hydroxy($C_1$–$C_4$)alkyl.
ppp) $R^5$ and $R^6$ are taken together to form a saturated heterocycle substituted with hydroxymethyl.
qqq) $R^5$ and $R^6$ are taken together to form a saturated heterocycle substituted with $NR^7R^8$.
rrr) $R^5$ and $R^6$ are taken together to form a saturated heterocycle substituted with $C(=O)OR^7$.

sss) $R^5$ and $R^6$ are taken together to form a saturated heterocycle substituted with $C(=O)NR^7R^8$.
ttt) $R^7$ is hydrogen.
uuu) $R^7$ is $C_1$–$C_4$ alkyl.
vvv) $R^7$ is methyl.
www) $R^7$ is ethyl.
xxx) $R^8$ is hydrogen.
yyy) $R^8$ is $C_1$–$C_4$ alkyl.
zzz) $R^8$ is methyl.
aaaa) $R^8$ is ethyl.

The preceding paragraphs may be combined to define additional preferred classes of compounds.

The compounds of Formula I are useful for the treatment of disorders of mammals, and the preferred mammal is a human.

The skilled artisan will appreciate that the introduction of certain substituents will create asymmetry in the compounds of Formula I. The present invention contemplates all enantiomers and mixtures of enantiomers, including racemates. It is preferred that the compounds of the invention containing chiral centers are single enantiomers. The present invention further contemplates all diastereomers.

The compounds of the present invention can be prepared by a variety of procedures, some of which are illustrated in the Schemes below. It will be recognized by one of skill in the art that the individual steps in the following schemes may be varied to provide the compounds of Formula I. Some of these variations are discussed below. The particular order of steps required to produce the compounds of Formula I is dependent upon the particular compound being synthesized, the starting compound, and the relative lability of the substituted moieties. Some substituents have been eliminated in the following schemes for the sake of clarity, and are not intended to limit the teaching of the schemes in any way.

Scheme I

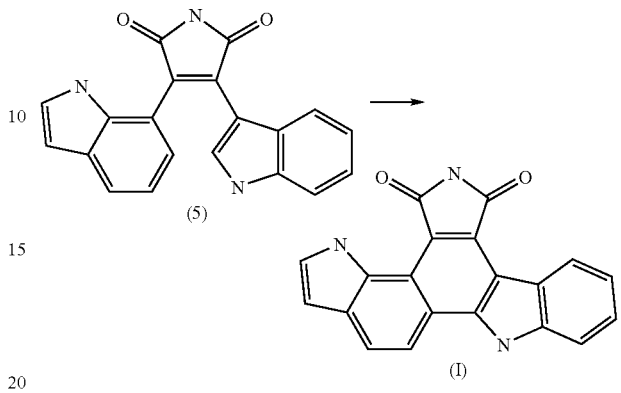

A maleimide of Formula (5) and iodine and DDQ in a suitable solvent, such as dioxane, may be reacted via irradiation by a medium-pressure mercury lamp. The reaction mixture is irradiated for about 10 minutes to about 24 hours. The resulting carbazole Formula (I) may be isolated and purified by standard techniques.

The requisite maleimides of Formula (5) may be prepared from an appropriately substituted oxoacetic acid ester and an appropriately substituted acetamide as illustrated in Scheme II.

Scheme II

Method A

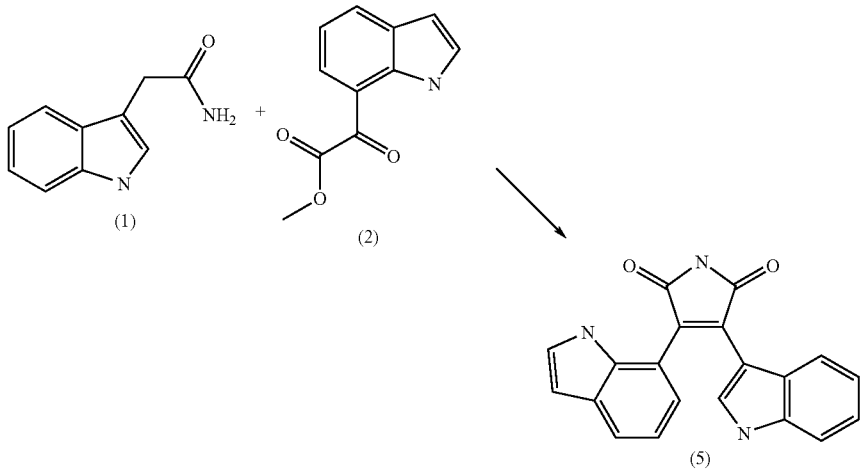

Method B

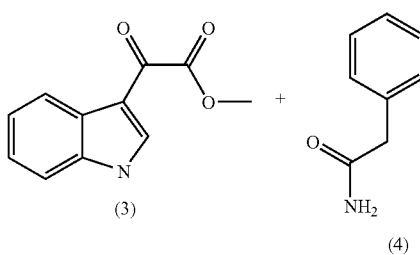

In Scheme II, maleimides of Formula (5) may be prepared from an appropriately substituted oxoacetic acid ester of Formula (2) with an appropriately substituted acetamide of Formula (1) as illustrated in Method A. Alternatively, maleimides of Formula (5) may be prepared from an appropriately substituted oxoacetic acid ester of Formula (3) with an appropriately substituted acetamide of Formula (4) as illustrated in Method B. This reaction involves a base-mediated condensation of the acetamide with the ester as described in FAUL, M. A.; WINNEROSKI, L. L.; KRUMRICH, C. A. *J. Org. Chem.*, 63, 6053–6058 (1998). Potassium t-butoxide is preferred, either as potassium t-butoxide in t-butanol or potassium t-butoxide in THF. Preferred solvents include DMF and THF.

Scheme IIIa

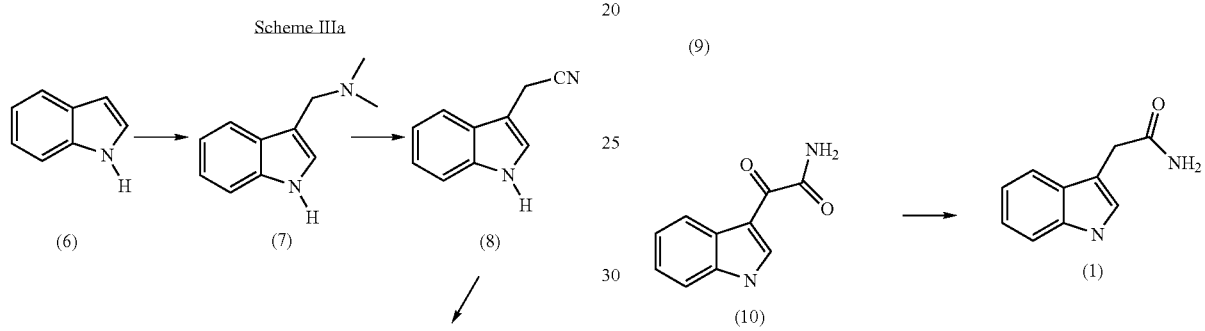

Scheme IIIb

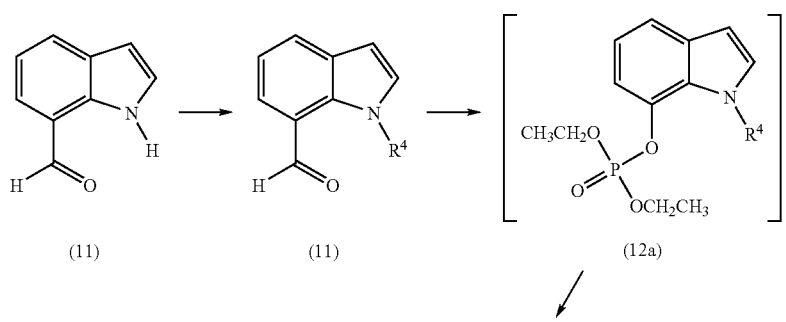

Scheme IIIc

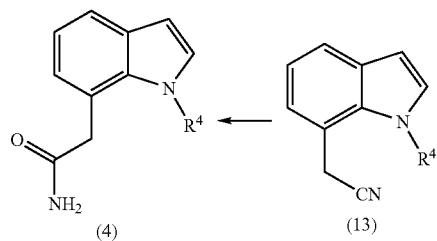

The formation of the indolylacetamides, Formula (1), is depicted in Scheme IIIa and IIIb. In Scheme IIIa, an appropriately substituted indole of Formula (6) is alkylated at the 3-position by N,N-dimethylmethylene ammonium chloride. An exchange of the dimethylamine to cyano is performed in the presence of sodium nitrile at reflux temperatures of dimethylformamide to afford the compounds of Formula (8). Alkylation of the indole of Formula (8) by sodium hydride and an appropriate alkylating reagent is performed to incorporate $R^2$ substitution in Formula (8a). Reaction of the acetonitrile group of Formula (8a) with hydroxide results in the formation of a compound of Formula (1).

Alternatively, as in Scheme IIIb, a compound of Formula (9) is acylated with an oxalyl halide reagent, followed by the addition of ammonium hydroxide to give the indole-3-glyoxamides of Formula (10). A selective reduction of the glyoxamide to the acetamide is accomplished by reacting a compound of Formula (10) with palladium on carbon in the presence of sodium dihydrogenphosphate monohydrate, in an aqueous-dioxane solution at elevated temperatures, to afford a compound of Formula (1).

The formation of the indolylacetamides of Formula (4) is depicted in Scheme IIIc. Alkylation of an indole of Formula (11) by sodium hydride and the appropriate alkylating reagent is performed to incorporate $R^4$ substitution in Formula (12). With the appropriate substituted 7-carboxaldehyde-indoles, indolylacetamides of Formula (4) are produced by reduction of derived phosphorylated cyanohydrins of Formula (12a) to afford compounds of Formula (13). See, for example, YONEDA, R.; HARUSAWA, S.; KURIHARA, T. Tetrahedron Lett. 1989, 30, 3681–3684; YONEDA, R.; HARUSAWA, S.; KURIHARA, T. J. Org. Chem. 1991, 56, 1827–1832. This is followed by hydrolysis of the acetonitrile group to the acetamides of Formula (4). Similar conversions of Formula (13) to give a compounds of Formula (4) are well known and appreciated in the art (See, for example, LAROCK, R. C., Comprehensive Organic Transformations, $2^{nd}$ Ed., John Wiley & Sons, pp 1988–1989 (1999)).

The resulting indolylacetamides of Formula (1) and (4) are isolated by standard techniques and may be purified by crystallization or chromatography as described above.

Scheme IVa

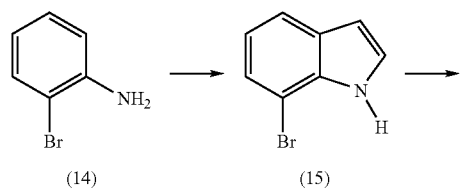

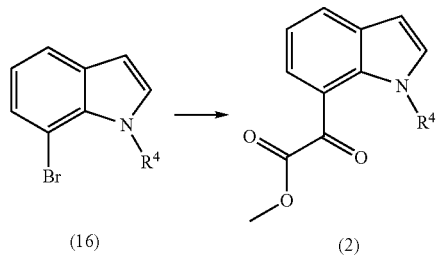

Scheme IVb

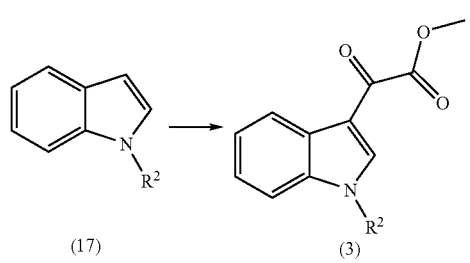

In Scheme IVa, The compounds of Formula (2), are prepared from appropriately substituted 7-bromo-indoles of Formula (15) or appropriately substituted 2-bromo-anilines of Formula (14), which are commercially available. The anilines are subjected to the indole syntheses procedures, as described in ROBINSON, The Fischer Indole Synthesis, Wiley, New York (1983); HAMEL, et al., Journal of Organic Chemistry, 59, 6372 (1994); and RUSSELL, et al., Organic Preparations and Procedures International, 17, 391 (1985), to give the 7-bromo-indoles of Formula (15). Alkylation of the indoles of Formula (15), by sodium hydride and the appropriate alkylating agent in dimethylformamide give the appropriate $R^4$ substitution groups of Formula (16). A compound of Formula (16) is then subjected to a lithium-halogen exchange, following which the lithium anion is quenched by dimethyl or diethyl oxalate at low temperatures, to give compounds of Formula (2).

In Scheme IVb, the formation of Formula (3) follows the procedure described in FAUL, M. A.; WINNEROSKI, L. L.; KRUMRICH, C. A. J. Org. Chem., 63, 6053–6058 (1998). For example, an indole of Formula (17) is reacted with oxalyl chloride followed by sodium methoxide at low temperatures to give the corresponding indole-glyoxylates of Formula (3).

The resulting indole-glyoxylates of Formula (2) or (3) are isolated by standard techniques and may be purified by crystallization or chromatography as described above.

Scheme Va
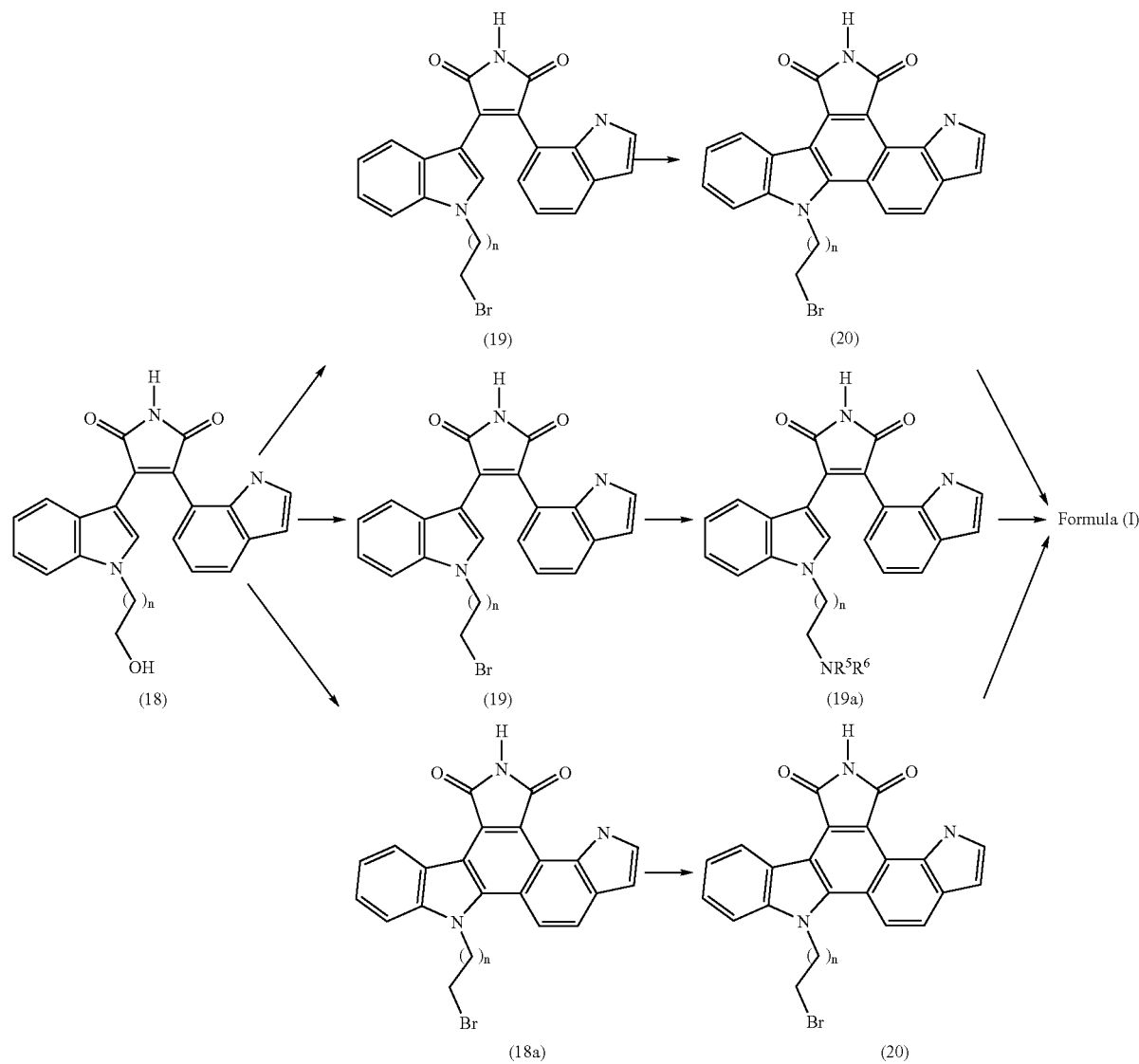
n = 1–3
Scheme Vb
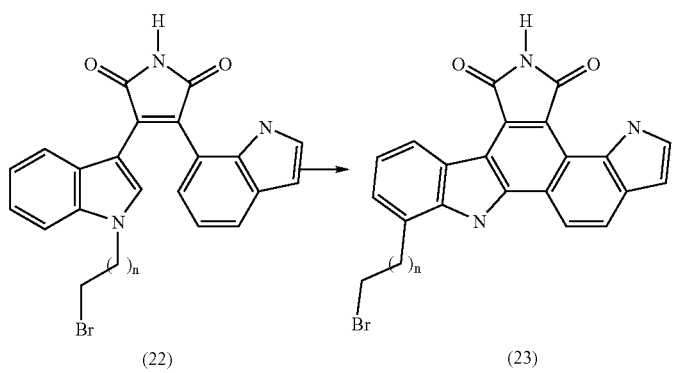

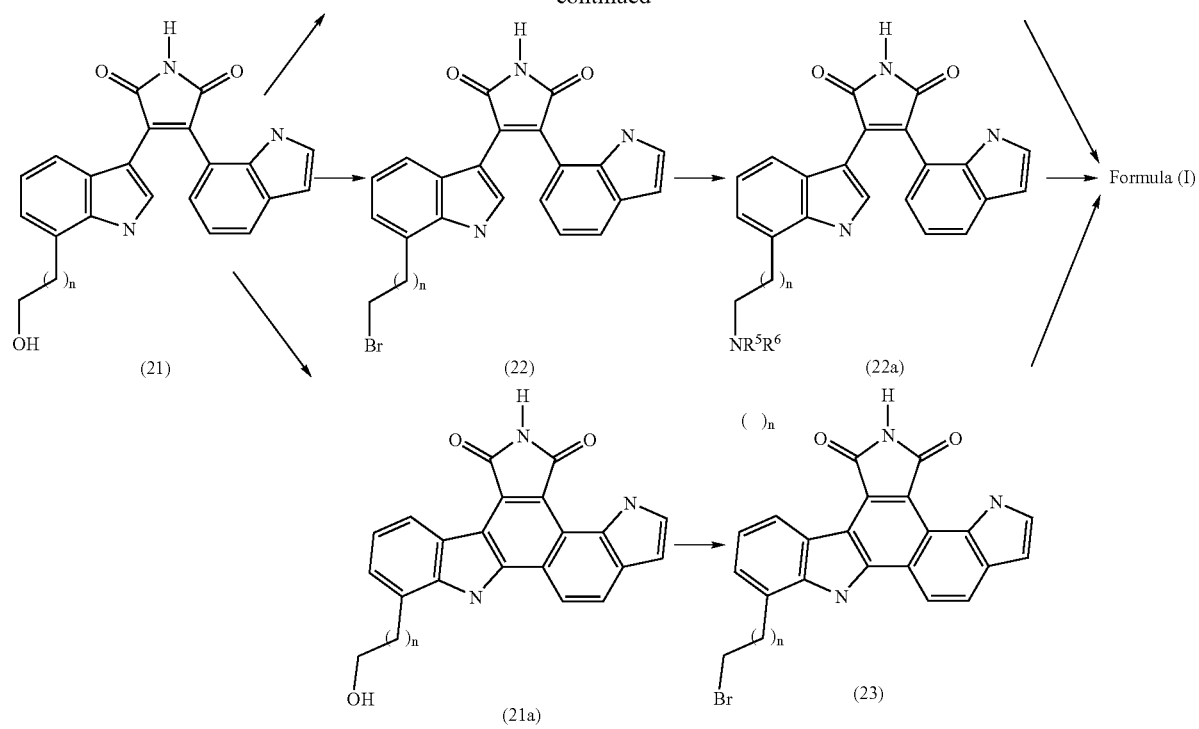

n = 1–3

Schemes Va and Vb depict the formation of the optionally substituted $C_1$–$C_4$ alkyl amines or heterocycles. The hydroxy($C_1$–$C_4$)alkyl-maleimides of Formulae (18) and (21) are converted to the bromoalkyl-indolocarbazoles by a hydroxy to bromide conversion. This type of conversion is well-known and appreciated in the art and is referenced in LAROCK, R. C., *Comprehensive Organic Transformations*, $2^{nd}$ Ed., John Wiley & Sons, pp 689–697 (1999). Compounds of Formulae (19) and (22) are then subjected to conditions of Scheme I, followed by a displacement of the bromide with the appropriate amine or heterocyclic-amine to further give compounds of Formula (I).

The skilled artisan also will appreciate that the individual steps in Schemes Va and Vb may be varied to provide the compounds of Formula I. For example, hydroxy($C_1$–$C_4$) alkyl-maleimides of Formulae (18) and (21) may be converted first by a hydroxy to bromide conversion to the bromoalkyl-indolocarbazoles of Formulae (19) and (22), respectively; then bromide displacement by an amine or heterocyclic-amine to form compound of Formulae (19a) and (22a), respectively; and finally cyclization according to Scheme I to form compounds of Formula (I). Alternatively, hydroxy($C_1$–$C_4$)alkyl-maleimides of Formulae (18) and (21) may be first cyclized according to Scheme I to form compounds of Formulae (18a) and (21a), respectively; then, hydroxy to bromide conversion to the bromoalkyl-indolocarbazoles of Formulae (20) and (23), respectively; and finally bromide displacement by an amine or heterocyclic-amine to form compound of Formula (I). The particular order of steps required to produce the compounds of Formula I is dependent upon the particular compound being synthesized, the starting compound, and the relative lability of the substituted moieties.

The skilled artisan will appreciate that compounds of the invention where variables A and B are independently S may be prepared by treating either the final compound or an appropriate carbonyl starting material with [2,4-bis(4-methoxyphenyl)-1,3-dithia-2,4-diphosphetane-2,4-disulfide] (Lawesson's Reagent) or phosphorus pentasulfide.

Many of the compounds of the present invention are not only inhibitors of CDK4, but are also useful intermediates for the preparation of additional compounds of the present invention. For example, secondary amines may be acylated, alkylated or coupled with simple carboxylic acids or amino acids under standard conditions. Furthermore, ester moieties may be reduced to the corresponding alcohols. These alcohols may then be activated and displaced by a number of nucleophiles to provide other compounds of the invention. The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example "° C.", "N", "mmol", "g", "mL", "M", "HPLC", "IR", "MS(FD)", "MS(IS)", "MS(FIA)", "MS(FAB)", "MS(EI)", "MS(ES)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, electron spray mass spectrometry, ultraviolet spectrometry, and proton nuclear magnetic resonance spectrometry respectively. In addition, the absorption maxima listed for the IR spectra are only those of interest and not all of the maxima observed.

Preparation of
2-(1-Methyl-1H-indol-7-yl)-acetamide

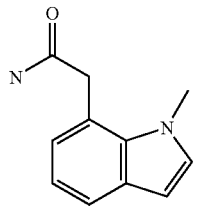

(a) 1-Methyl-1H-indole-7-carboxaldehyde

To a solution of 1H-indole-7-carboxaldehyde (20.0 g, 137 mmol) and dimethylsulfate (19.1 g, 151 mmol) in DMF (400 mL) at 0° C. was added a 60% dispersion of NaH in mineral oil (6.60 g, 165 mmol). The reaction was stirred and allowed to warm to room temperature over 30 minutes. The reaction was quenched with H$_2$O, diluted with EtOAc (1 L) and H$_2$O. The two layers were separated and the aqueous layer was extracted with EtOAc (250 mL). The combined organic layers were washed with H$_2$O (3×500 mL), brine, saturated aq LiCl, and brine. The solution was dried (MgSO$_4$), filtered and concentrated to afford the title compound as an off white solid of sufficient quality to use directly in the next step. Flash chromatography (80% hexane/EtOAc) can be used to afford the title compound pure, as a white solid. $^1$H NMR (400 MHz, DMSO-d$_6$) 10.39 (s, 1H), 7.91 (d, J=7 Hz, 1H), 7.75 (d, J=7 Hz, 1H), 7.42 (d, J=3 Hz, 1H), 7.21 (dd, J=7, 7 Hz, 1H), 6.60 (d, J=3 Hz, 1H), 4.08 (s, 3H). MS (electrospray, m/z) 160 (M$^+$+1).

(b) (1-Methyl-1H-indol-7-yl)-acetonitrile (adapted from the procedure described in YONEDA, R.; HARUSAWA, S.; KURIHARA, T. Tetrahedron Lett. 1989, 30, 3681–3684; YONEDA, R.; HARUSAWA, S.; KURIHARA, T. J. Org. Chem. 1991, 56, 1827–1832). A solution of 1-methyl-1H-indole-7-carboxaldehyde (137 mmol, crude material prepared as described above), LiCN 1.5 THF complex (1.94 g, 13.7 mmol), and diethylcyanophosphonate (27.1 mL, 179 mmol) in THF (400 mL) was stirred at room temperature overnight. Tert-butanol (13.1 mL, 137.7 mmol) was introduced and the mixture was transferred via cannula into a 0.1 M solution of SmI$_2$ in THF (3.6 L, 360 mmol) and the mixture stirred for 30 minutes. The mixture was concentrated to dryness, the residue was taken up in EtOAc (2 L), and the solution was washed with 1N HCl (3×500 mL), saturated aq NaHCO$_3$, and brine. The solution was dried (MgSO$_4$), passed through a pad of silica gel, and concentrated to give the title compound in sufficient purity for use in the next step. Flash chromatography (90% hexane/EtOAc) can be used to afford the title compound pure, as an off-white crystalline solid. $^1$H (400 MHz, DMSO-d$_6$) 7.51 (d, J=7.5 Hz, 1H), 7.28 (d, J=3 Hz, 1H), 7.09 (d, J=7.5 Hz, 1H), 6.99 (dd, J=7.5, 7.5 Hz, 1H), 6.43 (d, J=3 Hz, 1H), 4.58 (s, 2H), 4.07 (s, 3H). $^{13}$C NMR (75.5 MHz, DMSO-d$_6$) 133.56, 131.89, 130.06, 122.38, 120.74, 119.53, 119.16, 114.47, 100.59, 35.86, 20.43. IR (CHCl$_3$, cm$^{-1}$) 2252. MS (electrospray, m/z) 171 (M$^+$+1). Anal. Calcd for C$_{11}$H$_{10}$N$_2$: C, 77.62; H, 5.92; N, 16.46. Found: C, 77.62; H, 5.96; N, 16.38.

(c) 2-(1-Methyl-1H-indol-7-yl)-acetamide

A slurry of (1-methyl-1H-indol-7-yl)-acetonitrile (137 mmol, crude material prepared as described above) in tert-butanol (240 mL) was heated to reflux, KOH (85%, 88.3 g, 1.57 mol) was added and mixture was stirred at reflux for 15 minutes. H$_2$O (1 mL) was introduced and the mixture was heated at reflux for an additional 5 minutes. The solution was allowed to cool, decanted, and diluted with EtOAc (1 L) and H$_2$O. The two layers were separated and the organic solution was washed with H$_2$O and brine. The crude solution was dried (MgSO$_4$), filtered and concentrated to an off-white solid. Trituration with refluxing ether gave the title compound (16.90 g, 65% from 1H-indole-7-carboxaldehyde). $^1$H NMR (400 MHz, DMSO-d$_6$) 3.87 (s, 2H), 4.03 (s, 3H), 6.39 (d, J=3.2 Hz, 1H), 6.83–7.01 (m, 3H), 7.20 (d, J=3.3 Hz, 1H), 7.30–7.46 (m, 2H). MS (electrospray, m/z) 189.0 (M$^+$+1). Anal. Calcd for C$_{11}$H$_{12}$N$_2$O: C, 70.19; H, 6.43; N, 14.88. Found: C, 70.03; H, 6.41; N, 14.63.

Preparation of 6-Bromoindole-3-acetamide

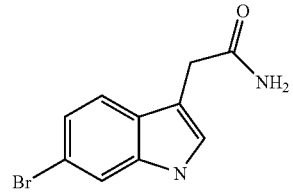

(a)
6-Bromo-N,N-dimethyl-1H-indole-3-methanamine

To a solution of 6-bromoindole (7.18 g, 36.6 mmol) in CH$_2$Cl$_2$ (140 mL) was added N,N-dimethylmethylene ammonium chloride (5.48 g, 58.6 mmol, 1.60 eq.) in one portion and the resultant mixture was stirred at rt for 2 h under N$_2$. Water (150 mL) and 1M NaOH (62 mL, 62 mmol) were added, and the reaction mixture was extracted with EtOAc (300 mL). The organic layer was washed with aqueous saturated NaCl and dried (MgSO$_4$). The solvent was removed in vacuo to give 9.29 g (100%) of the title compound.

(b) 6-Bromo-1H-indole-3-acetonitrile

6-Bromo-N,N-dimethyl-1H-indole-3-methanamine (7.76 g, 30.6 mmol) and NaCN (1.95 g, 39.8 mmol, 1.30 eq.) were combined with DMF (40 mL) and water (40 mL). The mixture was heated to reflux for 6 hours, then cooled to rt. Aqueous 1N HCl (40 mL) was added, and the product was extracted with EtOAc. The organic layer was washed with water and dried (MgSO$_4$). The solvent was removed in vacuo to give 5.70 g (79%) of the title compound, that was 79% pure by HPLC area, containing 14% 6-bromoindole. The material was used without purification in the subsequent step.

(c) 6-Bromo-1H-indole-3-acetamide

Powdered K$_2$CO$_3$ (408 mg, 2.95 mmol, 1.60 eq.) was heated to 50° C. in DMSO (3 mL) for 20 min, then cooled to rt. 6-Bromo-1H-indole-3-acetonitrile (434 mg, 1.85 mmol) was dissolved in DMSO (3 mL) and added to the reaction slurry. Water (0.2 mL) and aqueous 30% H$_2$O$_2$ (0.46 mL, 4.0 mmol, 2.2 eq.) were added, and the reaction mixture was stirred for 2–3 hours at rt. The reaction was quenched with 1N HCl and extracted with EtOAc. The organic layer was washed with 1.5 N sodium thiosulfate and dried (MgSO$_4$). The solvent was removed in vacuo, and the residue crystallized from CH$_2$Cl$_2$ to give 273 mg (55%) of the title compound.

Preparation of 6-Methoxyindole-3-acetamide

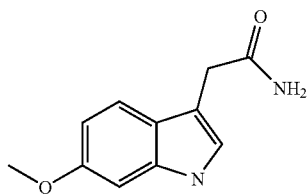

(a) 6-Methoxy indole-3-glyoxamide

A solution of 6-methoxyindole (40 g) in THF (600 ml) was cooled to −5° C. and treated dropwise with oxalyl chloride (26.1 mL, 1.1 equiv) at such a rate that the reaction temperature did not exceed 1° C. (2–4 min). The reaction was stirred at −4° C. for 1.5 h, then added by cannula to 29% NH$_4$OH (200 mL) at such a rate that the reaction remained below 10° C. (10 min). The resultant yellow slurry was stirred at −5° C. for 15 min then filtered (slow). The filter cake was washed with water (3×100 mL) and dried to afford 40.2 g of a yellow powder. The filtrate was concentrated in vacuo to a volume of 400 mL and the brown solid that precipitated was filtered, washed with water (3×100 mL) and dried to afford an additional 20.14 g of solid. The isolated solids were combined in acetone (250 mL) and the mixture heated briefly to reflux, then cooled to 0–5° C. and stirred for 10–15 min. The yellow solid obtained was filtered, washed with the minimal amount of acetone and dried to afford 53.58 g (90%) of the title compound. $^1$H NMR (300 MHz, DMSO-d$_6$) δ 11.87 (s, 1H), 8.60 (s, 1H), 8.09 (d, 1H, J=8.73 Hz), 8.05 (s, 1H), 7.68 (s, 1H), 7.05 (d, 1H, J=2.20 Hz), 6.91 (app.dd, 1H, J=8.60 Hz, 2.38 Hz), 3.81 (s, 3H); $^{13}$C NMR (75 MHz, DMSO-d$_6$) δ 182.74, 165.97, 156.68, 137.40, 137.22, 121.84, 119.93, 112.17, 111.95, 95.69, 55.21. IR (KBr) v 3403, 3210, 2832, 1698, 1624, 1587, 1519, 1448, 1396, 1348, 1295, 1260, 1147, 1093, 1023 cm$^{-1}$ UV (EtOH) λmax 332 nm (ε 7572), 283 (ε 10360). HRMS (ES+) exact mass calcd for C$_{11}$H$_{10}$N$_2$O$_3$ 218.0691. found 218.0694.

(b) 6-Methoxy indole-3-acetamide

6-Methoxy indole-3-glyoxamide (97.35 g) and 10% Pd—C (19.5 g) were taken up in 50:50 water:dioxane (350 mL) and diluted with dioxane (875 mL). The reaction mixture was stirred and treated dropwise over 1.5 h with a solution of NaH$_2$PO$_2$ in water (325 mL). During the addition the reaction mixture was heated to reflux and stirred for 9 h. The reaction mixture was cooled to room temperature, treated with hyflo (50 g), stirred for 15 min, then filtered through a pad of hyflo (130 g prepared from 25% dioxane/H$_2$O). The filter cake was washed with 9:1 dioxane:water (4×200 mL) and the filtrate concentrated in vacuo. The wet residue was diluted with water (800 mL) and concentrated in vacuo until 2350 mL distillate was collected. Water (350 mL) was added to the reaction mixture, which was cooled in an ice water bath for 20 min. The tan solid that precipitated out of solution was filtered, washed with water and dried (78.67 g). The isolated material was treated with EtOAc (200 mL), heated to reflux then cooled and stirred at 0–5° C. for 30 min. The solution was filtered to afford 73.9 g (81%) of the title compound, as a light tan solid 73.9 g (81%). $^1$H NMR (300 MHz, DMSO-d$_6$) δ 10.63 (s, 1H), 7.42 (d, 1H, J=8.78 Hz), 7.24 (s, 1H,), 7.04 (d, 1H, J=2.19 Hz), 6.85 (d,1H, J=2.19 Hz). 6.81 (s, 1H), 6.40 (app.dd, 1H, J=8.59 Hz, 4.76 Hz), 3.74 (s, 3H), 3.43 (s, 2H); $^{13}$C NMR (75 MHz, DMSO-d$_6$) δ 172.89, 155.42, 136.74, 122.24, 121.63, 119.18, 108.90, 108.42, 94.34, 55.07, 32.56. IR (KBr) v 3378, 3189, 1652, 1627, 1580, 1559, 1502, 1456, 1396, 1287, 1266, 1205, 1165, 1128, 1026, 815 cm$^{-1}$. UV (EtOH) λmax 292 nm (ε 5877), 273 (ε 5289), 222 (ε 35467). HRMS (ES+) exact mass calcd for C$_{11}$H$_{12}$N$_2$O$_2$ 204.0899. found 204.0899.

Preparation of N-(3-hydroxypropyl)indole-3-acetamide

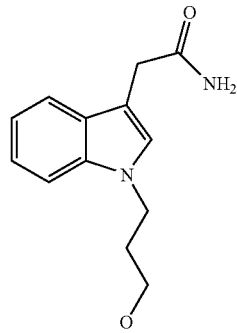

(a) N-(3 hydroxypropyl indole-3-acetamide

To a solution of NaH (3.59 g, 89.6 mmol) in DMF (20 mL) cooled to 0° C. was added a solution of indole-3-acetonitrile (10.0 g, 64.0 mmol) in DMF (80 mL) and the mixture was allowed to come to rt and stir for 30 min, becoming dark brown. It was cooled back to 0° C. and 3-bromopropylacetate (89.6 mmol) was added by syringe, slowly to control foaming. The reaction was stirred vigorously at rt for 4 h and then diluted with EtOAc and quenched with a 0.5 M solution of HCl. The organic layer was washed with a saturated aqueous solution of NaCl, dried (MgSO4) and the solvent removed in vacuo to give a brown oil. This was dissolved in t-butanol (175 mL) and freshly ground KOH (42.2 g, 640 mmol) was added with vigorous stirring. The reaction was heated to reflux for 1.5 h. It was then cooled to 30° C. and poured onto ice (500 mL). 6N HCl was added until the pH of the mixture was 1.0. The reaction was diluted with EtOAc the layers separated. The organic layer was washed with a saturated aqueous solution of NaCl, dried (MgSO4) and the solvent removed in vacuo to give a brown oil which was purified by column chromatography (Start 1:1 hexanes:acetone until product begins eluting, wash off with 95:5 acetone:MeOH) to afford 374076 the title compound (60%) as a creme colored solid.

Preparation of 6-Trifluoromethyl indole-3-acetamide

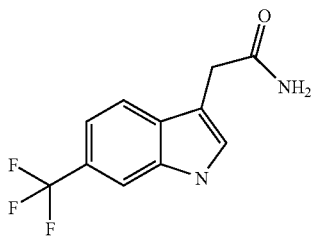

(a) 6-Trifluoromethyl-N,N-dimethyl-1H-indole-3-methanamine.

To a solution of 6-trifluoromethylindole (1.0 g, 5.4 mmol) in CH$_2$Cl$_2$ (10 mL) was added N,N-dimethylmethylene ammonium chloride (0.63 g, 6.75 mmol, 1.25 eq.) in one portion and the resultant mixture was stirred at rt for 2 h under N$_2$. 1M NaOH (6.75 mL,) was added, and the reaction mixture was extracted into methylene chloride. The organic layer was washed with aqueous saturated NaCl and dried (MgSO$_4$). The solvent was removed in vacuo to give 1.3 g (100%) of title compound.

(b) 6-Trifluoromethyl-1H-indole-3-acetonitrile

6-Trifluoromethyl-N,N-dimethyl-1H-indole-3-methanamine (1.2 g, 4.95 mmol) and NaCN (0.72 g, 14.86 mmol, 3.0 eq.) were combined with DMF (10 mL) and EtOAc (2 mL). The mixture was heated to reflux for 6 hours, then cooled to rt. The product was extracted with EtOAc and the organic layer was washed with water and dried (MgSO$_4$). The solvent was removed in vacuo to give 0.66 g (60%) of the title compound after column chromatography (Hex: EtOAc 1:1).

(c) 6-Triflurormethyl-1H-indole-3-acetamide

A 250 mL round bottom flask was charged with 5.0 g of the nitrile and KOH (6.25 g) in 100 mL tert-BuOH. The reaction was heated to reflux until complete. The reaction was extracted with EtOAc and the product purified by column chromatography to afford 1.58 g (28%) the title compound.

EXAMPLE 1

11-Methoxy-5-methyl-5H,13H-indolo[6,7-a]pyrrolo[3,4-c]carbazole-6,8-dione (a) 3-(6-Methoxy-1H-indol-3-yl)-4-(1-methyl-1H-indol-7-yl)-pyrrole-2,5-dione To a cold (0° C.) solution of 2-(1-methyl-1H-indol-7-yl)-acetamide (2.42 g, 12.9 mmol) and 3-(6-methoxy-1H-indol-3-yl)-oxo-acetic acid methyl ester (3.00 g, 12.9 mmol) in DMF (50 mL) under N$_2$ was added a 1.0 M solution of potassium-tert-butoxide in THF (12.9 mL, 12.9 mmol) dropwise over 5 minutes. The reaction was stirred at 0° C. for 20 min and additional KOtBu (25.7 mL, 25.7 mmol) added. The mixture was heated at at 50° C. for 2 h, then cooled to room temperature, quenched with 1N HCl (excess) and poured into EtOAc. The organic layer was separated, washed with saturated aq NaHCO$_3$, and brine, dried (MgSO$_4$), filtered and concentrated to a red solid. Flash chromatography (40% hexane/EtOAc) gave the title compound (3.35 g, 70%) as a red solid. $^1$H NMR (400 MHz, DMSO-d$_6$) 3.641 (s, 3H), 3.647 (s, 3H), 6.06–6.17 (m, 2H), 6.47 (d, J=3 Hz, 1H), 6.80 (d, J=2 Hz, 1H), 6.86 (d, J=7.2 Hz, 1H), 6.97 (dd, J=7.2, 7.2 Hz, 1H), 7.24 (d, J=3 Hz, 1H), 7.59 (d, J=8 Hz, 1H), 7.80 (d, J=2 Hz, 1H), 11.09 (s, 1H), 11.63 (s, 1H). MS (electrospray, m/z) 370 (M$^-$–1). Anal. Calcd for C$_{22}$H$_{17}$N$_3$O$_3$: C, 71.15; H, 4.61; N, 11.31. Found: C, 71.14; H, 4.69; N, 11.24.

(b) 11-Methoxy-5-methyl-7H,13H-indolo[6,7-a]pyrrolo[3,4-c]carbazole-6,8-dione

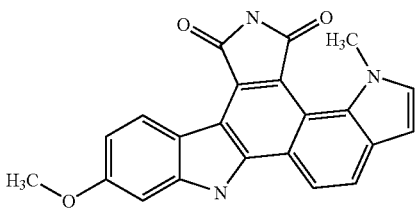

A solution of 3-(6-methoxy-1H-indol-3-yl)-4-(1-methyl-1H-indol-7-yl)-pyrrole-2,5-dione (0.999 g, 2.69 mmol) and DDQ (0.61 g, 2.69 mmol) in EtOAc (1 L) was photolyzed with 450 W Hanovia lamp fitted with pyrex filter for 60 minutes. The mixture was washed with 0.1 N NaOH (2×200 mL) and brine (200 mL), dried (MgSO$_4$), filtered and concentrated to an orange solid. Trituration with hot CH$_2$Cl$_2$ (35–40° C.) gave the title compound which was dried under vacuum at 70° C. overnight affording an orange solid (0.90 g, 91%). $^1$H NMR (400 MHz, DMSO-d$_6$) 3.86 (s, 3H), 3.91 (s, 3H), 6.81 (d, J=3 Hz, 1H), 6.98 (dd, J=2, 8 Hz, 1H), 7.14 (d, J=2 Hz, 1H), 7.55 (d, J=3 Hz, 1H), 8.00 (d, J=8 Hz, 1H), 8.18 (d, J=8 Hz, 1H), 8.78 (d, J=8 Hz, 1H), 11.03 (s, 1H), 12.59 (s, 1H). MS (electrospray, m/z) 370.1 (M$^+$+1).

EXAMPLE 2

5-Methyl-7H,13H-indolo[6,7-a]-pyrrolo[3,4-c]-carbazole-6,8-dione

(a) (1-Methyl-1H-indol-7-yl)-oxo-acetic acid methyl ester

A 60% dispersion of sodium hydride in mineral oil (1.40 g, 97 mmol) was washed with hexanes (3×10 mL, 1×5 mL), suspended in THF (50 mL) and CH$_3$I added (1.64 mL, 26.3 mmol) followed by a solution of 7-bromoindole (4.06 g, 20.7 mmol) in THF (15 mL), with vigorous gas evolution. After 1 h at rt, the mixture was treated with additional CH$_3$I (0.28 mL, 4.5 mmol) and stirred overnight. Saturated aq NaHCO$_3$ was added and the mixture poured into EtOAc, which was separated, washed with saturated aq NaHCO$_3$, dried (MgSO$_4$) and concentrated to afford 1-methyl-7-bromoindole as an off-white semisolid which was used without further purification.

A solution of 1-methyl-7-bromoindole (1.53 g, 7.29 mmol) in THF (50 mL) was cooled to −78° C. and a 1.7 M solution of tBuLi in pentanes (10 mL, 17 mmol) added dropwise over 10 min. After 15 min, the resultant bright yellow suspension was transferred over 15 min via a cannula cooled with dry ice to a solution of dimethyl oxalate (2.13 g., 18.1 mmol) in THF (40 mL) maintained at −78° C. After 15 min, the mixture was allowed to warm to room temperature and stirred 4 h. The cloudy yellow mixture was treated with pH 7.0 buffer, poured into EtOAc and the EtOAc washed with pH 7.0 buffer, saturated aq NaHCO$_3$, brine, dried (MgSO$_4$) and concentrated to a cloudy oil. Flash chromatography (10% EtOAc/hexanes) afforded the title compound (896 mg, 57%) as a bright yellow oil. $^1$H NMR (400 MHz, DMSO-d$_6$) 7.97 (d, J=8 Hz, 1H), 7.58 (d, J=8 Hz, 1H), 7.48 (d, J=3 Hz, 1H), 7.20 (dd, J=8 Hz, 1H), 6.66 (d, J=3 Hz, 1H), 3.95 (s, 3H), 3.79 (s, 3H). $^{13}$C (75.5 MHz, DMSO-d$_6$) 185.80, 164.31, 133.64, 133.02, 131.23, 128.07, 127.04, 118.77, 118.25, 102.15, 53.01, 37.49. IR (CHCl$_3$, cm$^{-1}$) 1739, 1678. Anal. Calcd for C$_{12}$H$_{11}$NO$_3$: C, 66.35; H, 5.10; N, 6.45. Found: C, 66.48; H, 5.23; N, 6.51.

(b) 3-(1H-Indol-3-yl)-4-(1-methyl-1H-indol-7-yl)-pyrrole-2,5-dione

A 1.0 M solution of KOtBu in THF (6 mL, 6 mmol) was added to a solution of 2-(1H-indol-3-yl)-acetamide (296 mg, 1.70 mmol) and (1-methyl-1H-indol-7-yl)-oxo-acetic acid ethyl ester (381 mg, 1.65 mmol) in DMF (20 mL). The deep red-orange solution was stirred 7 h at 60° C., allowed to cool overnight and 1N HCl added. The orange mixture was poured into EtOAc, and the EtOAc layer was separated and washed with 1N HCl, water (3×), saturated aq NaHCO$_3$ (2×) and brine, dried (MgSO$_4$), filtered and concentrated onto SiO$_2$. Flash chromatography (1:1 EtOAc:hexanes) afforded the title compound as a 1:1 solvate with EtOAc (514 mg, 72%) as a bright orange-red solid. Heating under vacuum at 70° C. afforded material which was used without further purification. $^1$H NMR (400 MHz, DMSO-d6) 11.85 (br s, 1H), 11.13 (s, 1H), 7.93 (d, J=3 Hz, 1H), 7.61 (dd, J=8, 1.5 Hz, 1H), 7.33 (d, J=8 Hz, 1H), 7.26 (d, J=3 Hz, 1H), 6.93–7.0 (m, 2H), 6.88 (d, J=7 Hz, 1H), 6.46–6.52 (d, J=7 Hz, 1H), 6.35 (d, J=7 Hz, 1H), 3.68 (s, 3H). MS (electrospray, m/z) 342.1 (M$^+$+1), 340.2 (M$^-$−1). HRMS 342.1249 (M$^+$+1, calcd for C$_{21}$H$_{16}$N$_3$O$_2$ 342.1242).

(c) 5-Methyl-7H,13H-indolo[6,7-a]-pyrrolo[3,4-c]-carbazole-6,8-dione

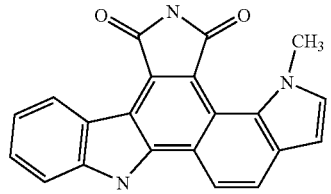

A solution of 3-(1H-indo-3-yl)-4-(1-methyl-1H-indol-7-yl)-pyrrole-2,5-dione (877 mg, 2.57 mmol) and DDQ (584 mg, 2.57 mmol) in dioxane (200 mL) was irradiated with a 450 W Hanovia medium pressure lamp through a pyrex filter for 2 h. During the photolysis, the temperature of the reaction mixture rose to ~65° C. The dark red mixture was concentrated to ~100 mL, poured into EtOAc (400 mL) and washed with saturated aq NaHCO$_3$ (3×), dried (MgSO$_4$) and concentrated to ~50 mL. The red-black solution was filtered through a column of SiO$_2$ and a fast-moving red band was collected and concentrated onto SiO$_2$ (a slower moving moving band was discarded). Flash chromatography (1:1 EtOAc:hexanes) afforded the title compound (431 mg, 49%) as an orange-red solid. Fractions containing a mixture of products (TLC) were combined, concentrated onto SiO$_2$ and chromatographed a second time to afford additional product (48 mg, 8%). $^1$H (400 MHz, DMSO-d$_6$) 12.74 (s, 1H), 11.10 (s, 1H), 8.96 (d, J=8 Hz, 1H), 8.27 (d, J=8 Hz, 1H), 8.05 (d, J=8 Hz, 1H), 7.72 (d, J=8 Hz, 1H), 7.59 (d, J=3 Hz, 1H), 7.55 (ddd, J=8, 8, 1 Hz, 1H), 7.37 (ddd, J=8, 8, 1 Hz, 1H), 6.84 (d, J=3 Hz, 1H), 3.88 (s, 3H). $^{13}$C NMR (75.5 MHz, DMSO-d$_6$) 170.61, 170.52, 141.67, 140.34, 132.68, 131.83, 127.81, 127.27, 126.34, 124.24, 123.24, 121.45, 120.47, 120.41, 117.72, 114.18, 113.63, 111.47, 103.52, 38.47. MS (electrospray, m/z) 340 (M$^+$+1), 338 (M$^-$−1).

EXAMPLE 3

5-Methyl-12-(2-hydroxyethyl)-7H,13H-indolo[6,7-a]-pyrrolo[3,4-c]-carbazole-6,8-dione

(a) tert-Butyl-dimethyl-[2-(2-nitro-phenyl)-ethoxy]-silane

A solution of 2-(2-nitro-phenyl)ethanol (10 g, 59 mmol) in CH$_2$Cl$_2$ (100 mL), was treated with imidazole (11.72 g, 77.7 mmol) followed by tert-butyl-dimethylsilylchloride (5.62 g, 82.6 mmol). A white precipitate formed upon the addition and the reaction was stirred 2.5 hours. The mixture was filtered and diluted with CH$_2$Cl$_2$ (100 mL) and was washed with 0.1 N HCl, H$_2$O, saturated aq NaHCO$_3$, and brine. The organic layer was dried over MgSO$_4$, filtered and concentrated to give a transparent oil which was placed under high vacuum overnight to give the title compound (16.8 g, 100%) as a transparent oil. $^1$H NMR (400 MHz, DMSO-d$_6$) −0.11 (s, 6H), 0.77 (s, 9H), 3.03 (t, J=6 Hz, 2H), 3.79 (t, J=6 Hz), 7.42–7.54 (m, 2H), 7.62 (ddd, J=<1, 6, 7 Hz, 1H), 7.88 (dd, J=<1, 7 Hz, 1H). MS (electrospray, m/z) 282 (M$^+$+1).

(b) 7-[2-(tert-Butyl-dimethyl-silanyloxy)-ethyl]-1H-indole

A solution of tert-butyl-dimethyl-[2-(2-nitro-phenyl)-ethoxy]-silane (5.0 g, 17.76 mmol) in THF (74 mL) was cooled to −65° C. and a 1.0 M solution of vinyl magnesium bromide in THF (53 mL, 53 mmol) was introduced while maintaining a temperature of <−40° C. The reaction was stirred for 15 minutes at −40° C., additional vinyl magnesium bromide (9 mL, 9 mmol) was added and the reaction was stirred at −45 to −40° C. for 25 minutes. The reaction was poured into saturated aq ammonium chloride and diluted with EtOAc (300 mL). The two layers were separated and the organic layer was dried (MgSO$_4$), filtered and concentrated. Flash chromatography (95%hexane/EtOAc) gave the title compound (1.47 g, 30%) as a transparent oil. $^1$H NMR (400 MHz, DMSO-d$_6$) −0.11 (s, 6H), 0.80 (s, 9H), 3.03 (t, J=6.8 Hz, 2H), 3.85 (t, J=6.8 Hz, 2H), 6.39 (dd, J=1.2, 3.2 Hz, 1H), 6.86–6.92 (m, 2H), 7.28 (dd, J=3, 3 Hz, 1H), 7.36 (dd, J=4.8, 4.8 Hz, 1H), 11.02 (br s, 1H). MS (electrospray, m/z) 276 (M$^+$+1).

(c) [7-(2-Hydroxyl-ethyl)-1H-indol-3-yl]-oxo-acetic acid methyl ester

A solution of 7-[2-(tert-butyl-dimethyl-silanyloxy)-ethyl]-1H-indole (6.17 g, 22.4 mmol) in Et$_2$O (50 mL) was cooled to 0° C. (ice bath) and oxalyl chloride (2.0 mL, 24 mmol) added dropwise. The ice bath was removed and the reaction was allowed to warm to room temperature (1.5 h). The reaction was then cooled to −78° C. and solution of NaOMe in MeOH (10.8 mL, 25% wt, 47.3 mmol) was introduced over 5 minutes. The cold bath was removed and the reaction was allowed to warm to room temperature (1 h). The reaction was quenched with H$_2$O and poured into EtOAc. The water layer was separated and extracted with EtOAc (20 mL) and the combined organic layer was washed with saturated aq NH$_4$Cl and brine, dried over MgSO$_4$, filtered and concentrated. Flash chromatography (50% EtOAc/CH$_2$Cl$_2$) gave the title compound (2.79 g, 50%) as a yellow solid. $^1$H NMR (400 MHz, DMSO-d$_6$) 3.04 (t, J=6.8 Hz, 1H), 3.70 (m, 2H), 3.88 (s, 3H), 4.72 (t, J=4 Hz, 1H), 7.10–7.22 (m, 2H), 8.00 (d, J=7.6 Hz, 1H), 8.36 (d, J=3.2 Hz, 1H), 12.38 (s, 1H). MS (electrospray, m/z) 248 (M$^+$+1).

(d) 3-[7-(2-Hydroxyethyl)-1H-Indol-7-yl)-4-(1H-indol-3-yl)-pyrrole-2,5-dione A 1.0 M solution of potassium tert-butoxide in THF (6.2 mL, 6.2 mmol), was added dropwise to solution of 2-(1-methyl-1H-indol-7-yl)-acetamide (1.20 g, 6.35 mmol) in DMF (50 mL) followed after 5 minutes by a solution of [7-(2-hydroxyl-ethyl)-1H-indol-3-yl]-oxo-acetic acid methyl ester (1.57 g, 6.35 mmol) in DMF (25 mL) dropwise over 10 min giving a yellow-brown solution. After another 90 minutes additional potassium tert-butoxide (6.6 mL, 6.6 mmol) was introduced and the reaction was stirred for 24 h. The maroon-purple reaction mixture was quenched with 1N HCl, concentrated to 20–30 mL and the red slurry diluted with EtOAc. The two layers were separated and the organic layer was washed with H$_2$O (2×), saturated aq NaHCO$_3$ (2×) and brine (2×), dried (MgSO$_4$), filtered, and concentrated onto SiO2. Flash chromatography (7:3 EtOAc:hexane) gave a red solid, which was dried under vacuum overnight at 75 C affording the title compound (1.24 g, 50%). $^1$H NMR (400 MHz, DMSO-$_6$) 11.81 (s, 1H), 11.14 (s, 1H), 7.86 (d, J=3 Hz, 1H), 7.60 (d, J=8 Hz, 1H), 7.27 (d, J=3 Hz, 1H), 6.96 (dd, J=7, 7 Hz, 1H), 6.87 (d, J=7 Hz, 1H), 6.81 (d, J=7 Hz, 1H), 6.49 (d, J=3 Hz, 1H), 6.43 (dd, J=8, 8 Hz, 1H), 6.25 (d, J=8 Hz, 1H), 4.67 (t, J=5 Hz, 1H), 3.70 (s, 3H), 3.64 (m, 2H), 2.90 (m, 2H). MS (electrosrpay, m/z) 386 (M$^+$+1), 384 (M$^−$−1). HRMS 386.1495 (M$^+$+1, calcd for C$_{23}$H$_{20}$N$_3$O$_3$ 386.1505). Anal. Calcd for C$_{23}$H$_{19}$N$_3$O$_3$: C, 71.68; H, 4.97; N, 10.90. Found: C, 71.33; H, 5.13; N, 10.83.

Also a product of chromatography was a mixture of the product and the starting acetamide (10:1, 0.365 g). The yield of the product based on recovered starting material was 72%.

(e) 5-Methyl-12-(2-hydroxyethyl)-7H,13H-indolo[6,7-a]-pyrrolo[3,4-c]-carbazole-6,8-dione

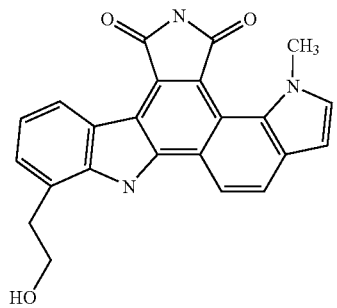

A solution of 3-[7-(2-hydroxyethyl)-1H-indol-7-yl)-4-(1H-indol-3-yl)-pyrrole-2,5-dione (131 mg, 0.34 mmol) and I$_2$ (88 mg, 0.35 mmol) in dioxane (200 mL) was irradiated with a 450 W Hanovia medium pressure lamp through a pyrex filter for 1 h. During the photolysis, the temperature of the reaction mixture rose to ~58° C. The dark red mixture was concentrated to ~20 mL, poured into EtOAc and washed with 10% aq NaHSO$_3$, saturated aq NaHCO$_3$, dried (MgSO$_4$) and concentrated onto SiO$_2$. Flash chromatography (6:4 EtOAc:hexanes) afforded a red-orange solid which was dried under vacuum at 80° C. overnight giving the title compound (122 mg, 91%) as an orange-red solid. $^1$H (400 MHz, DMSO-d$_6$) 12.15 (s, 1H), 11.07 (s, 1H), 8.85 (d, J=8 Hz, 1H), 8.57 (d, J=8 Hz, 1H), 8.05 (d, J=8 Hz, 1H), 7.58 (d, J=3 Hz, 1H), 7.38 (d, J=8 Hz, 1H), 7.29 (dd, J=8 Hz, 1H), 6.84 (d, J=3 Hz, 1H), 4.81 (t, J=5 Hz, 1H), 3.88 (s, 3H), 3.84 (m, 2H), 3.30 (t, J=7 Hz, 2H). MS (electrospray, m/z) 384 (M$^+$+1), 382 (M$^−$−1). HRMS 384.1370 (M$^+$+1, calcd for C$_{23}$H$_{18}$N$_3$O$_3$ 384.1348).

EXAMPLE 4

5-Ethyl-7H,13H-indolo[6,7-a]-pyrrolo[3,4-c]-carbazole-6,8-dione

(a) (1-Ethyl-1H-indol-7-yl)-oxo-acetic acid methyl ester

To a 60% dispersion of sodium hydride in mineral oil (0.80 g, 21 mmol), suspended in DMF (50 mL), was added 7-bromoindole (2.0 g, 10 mmol) in DMF (15 mL) followed by a solution of iodoethane (1.64 mL, 26.3 mmol). After 20 minutes, the mixture was quenched with saturated NaHCO$_3$, and poured into EtOAc. The organic layer which was separated, washed with saturated NaHCO$_3$, dried (MgSO$_4$) and concentrated to afford 1-ethyl-7-bromoindole as a brown oil which was used without further purification.

A solution of 1-ethyl-7-bromoindole (2.1 g, 9.4 mmol) in THF (50 mL) was cooled to −78° C. and a 1.7 M solution of tBuLi in pentane (13.8 mL, 23.5 mmol) was added dropwise over 10 min. After 15 min, the resultant brown solution was transferred over 30 min via a cannula cooled with dry ice to a solution of dimethyl oxalate (3.88 g, 32.9 mmol) in THF (40 mL) maintained at −78° C. After 15 min, the mixture was allowed to warm to room temperature and stirred 4 h. The brown solution was treated with pH 7.0 buffer, poured into EtOAc and the EtOAc washed with pH 7.0 buffer, saturated aq NaHCO$_3$, brine, dried (MgSO$_4$) and concentrated to a brown oil. Flash chromatography (20% EtOAc/hexanes) afforded the title compound (1.8 g, 83%) as a yellow oil, which was used without further purification. $^1$H NMR (400 MHz, DMSO-d$_6$) 7.9 (d, J=8, 1H), 7.55 (m, 2H), 7.2 (dd, J=8, 8 Hz, 1H), 6.66 (d, J=3 Hz, 1H), 4.25 (q, J=7 Hz, 2H), 3.94 (t, J=7 Hz, 3H). MS (electrospray, m/z) 232 (M$^+$+1).

(b) 3-(1H-Indol-3-yl)-4-(1-ethyl-1H-indol-7-yl)-pyrrole-2,5-dione

A 1.0 M solution of KOtBu in THF (6 mL, 6 mmol) was added to a solution of 2-(1H-indol-3-yl)-acetamide (478 mg, 2.75 mmol) and (1-ethyl-1H-indol-7-yl)-oxo-acetic acid methyl ester (635 mg, 2.75 mmol) in DMF (20 mL). The deep red-orange solution was stirred 12 h at 50° C., allowed to cool, and 1N HCl added. The orange mixture was poured into EtOAc, and the EtOAc layer was separated and washed with 1N HCl, water, saturated NaHCO$_3$ and brine, dried (MgSO$_4$), filtered, and concentrated onto SiO$_2$. Flash chromatography (1:1 EtOAc:hexanes) followed by precipitation from hot methanol afforded the title compound (377 mg, 37%) as a orange-red solid. Heating under vacuum at 70° C. afforded material which was used without further purification. $^1$H NMR (400 MHz, DMSO-d$_6$) 11.83 (br s, 1H), 11.13 (s, 1H), 7.94 (d, J=3 Hz, 1H), 7.61 (dd, J=8, 1.5 Hz, 1H), 7.3 (m, 2H), 6.93–7.0 (m, 3H), 6.48 (m, 3H), 6.48 (m, 2H), 6.3 (d, J=7 Hz, 1H), 4.0 (m, 2H), 1.06 (t, J=5 Hz, 3H). MS (electrospray, m/z) 354 (M$^-$−1).

(c) 5-Ethyl-7H,13H-indolo[6,7-a]-pyrrolo[3,4-c]-carbazole-6,8-dione

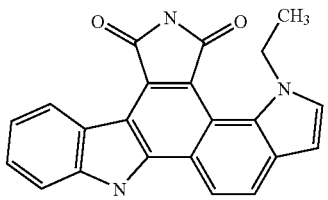

A solution of 3-(1H-indo-3-yl)-4-(1-ethyl-1H-indol-7-yl)-pyrrole-2,5-dione (150 mg, 0.42 mmol) and DDQ (96 mg, 0.42 mmol) in dioxane (200 mL) was irradiated with a 450 W Hanovia medium pressure lamp through a pyrex filter for 1 h. During the photolysis, the temperature of the reaction mixture rose to ~30° C. The dark red mixture was concentrated to ~5 mL, poured onto a column of SiO$_2$. Flash chromatography (1:1 EtOAc:hexanes) afforded the title compound (77 mg, 49%) as a red solid. $^1$H (400 MHz, DMSO-d$_6$) 12.7 (s, 1H), 11.05 (s, 1H), 8.96 (d, J=8 Hz, 1H), 8.24 (d, J=8 Hz, 1H), 8.05 (d, J=8 Hz, 1H), 7.68 (m, 2H), 7.54–7.50 (ddd, J=8, 8, 1 Hz, 1H), 7.37–7.32 (ddd, J=8, 8, 1 Hz, 1H), 6.83 (d, J=3 Hz, 1H), 4.33 (q, J=7 Hz, 2H), 1.08 (t, J=7 Hz, 3H). MS (electrospray, m/z) 352 (M$^-$−1).

EXAMPLE 5

5H,7H,13H-indolo[6,7-a]-pyrrolo[3,4-c]-carbazole-6,8-dione (a). 7-Bromo-1-(2-trimethylsilanyl-ethoxymethyl)-1H-indole Sodium hydride in mineral oil (60% by wt., 0.62 g; 15.5 mmol) was washed with hexanes and suspended in DMF (40 mL). SEM-Cl (2.0 mL, 11.3 mmol) was added followed by a solution of 7-bromoindole in DMF (15 mL) dropwise over 5 min. The resultant white suspension was stirred overnight at room temperature and then the reaction was quenched with saturated aqueous NaHCO$_3$. The mixture was poured into EtOAc and the organic layer was separated and washed with pH 7 buffer, saturated aqueous NaHCO$_3$, brine dried (MgSO$_4$) and concentrated to a light yellow oil. Flash chromatography (2 to 5% EtOAc/hexanes) afforded the title compound as a colorless oil (2.58 g, 79%). $^1$H NMR (400 MHz, DMSO-d$_6$) 7.58–7.61 (m, 2H), 7.36 (d, J=8 Hz, 1H), 6.70 (dd, J=8, 8 Hz, 1H), 6.55 (d, J=3 Hz, 1H), 5.80 (2, 2H), 3.45 (t, J=8 Hz, 2H), 0.80 (t, J=8 Hz, 2H), 0.01 (s, 9H). $^{13}$C NMR (75.7 MHz, DMSO-d$_6$) 132.58, 132.31, 131.92, 126.69, 121.19, 120.26, 103.50, 102.03, 75.69, 64.45, 17.18, −1.46. MS (FD+, m/z) 327, 325 (M$^+$). HRMS 326.0570 (M$^+$+1, calcd for C$_{14}$H$_{21}$NOSiBr 326.0576).

(b) {1-(2-trimethylsilanyl-ethoxymethyl)-1H-indol-7-yl}-oxo-acetic acid methyl ester A solution of 7-bromo-1-(2-trimethylsilanyl-ethoxymethyl)-1H-indole (3.0 g, 9.19 mmol) in THF (100 mL) was cooled to −78° C. and a 1.7 M solution of tBuLi in pentanes (15 mL, 25.5 mmol) added dropwise over 15 min. After 15 min, the resultant bright yellow suspension was transferred over 15 min via a cannula cooled with dry ice to a solution of dimethyl oxalate (3.61 g, 30.6 mmol) in THF (40 mL) maintained at −78° C. After 15 min, the mixture was allowed to warm to room temperature and stirred 3 h. The cloudy yellow mixture was treated with pH 7.0 buffer, poured into-EtOAc and the EtOAc washed with pH 7.0 buffer (brine was added to clarify the layers), brine, dried (MgSO$_4$) and concentrated to a cloudy oil. Flash chromatography (10% EtOAc/hexanes) afforded the title compound (2.59 g, 84%) as a bright yellow oil. $^1$H NMR (400 MHz, DMSO-d$_6$) 7.97 (dd, J=8, 1 Hz, 1H), 7.64 (d, J=3 Hz, 1H), 7.57 (dd, J=8, 1 Hz, 1H), 7.24 (dd, J=8, 8 Hz, 1H), 6.68 (d, J=3 Hz, 1H), 5.59 (s, 2H), 3.91 (s, 3H), 3.04 (t, J=8 Hz, 2H), 0.62 (t, J=8 Hz, 2H), −0.17 (s, 9H). $^{13}$C NMR (75.5 MHz, DMSO-d6) 185.17, 163.31, 132.59, 131.60, 130.87, 127.19, 126.15, 120.09, 118.95, 102.40, 77.05, 63.92, 52.83, 16.74, −1.69. IR (CHCl$_3$, cm$^{-1}$) 1740, 1683. HRMS 334.1481 (M$^+$+1, calcd for C$_{17}$H$_{24}$NO$_4$Si 334.1475).

(c) 3-(1H-Indol-3-yl)-4-[1-(2-trimethylsilanyl-ethoxymethyl)-1H-indol-7-yl]-pyrrole-2,5-dione and 3-(1H-Indol-7-yl)-4-(1H-indol-3-yl)-pyrrole-2,5-dione A 1.0 M solution of KOtBu in THF (8.1 mL, 8.1 mmol) was added to a solution of 2-(1H-indol-3-yl)-acetamide (417 mg, 2.4 mmol) and {1-(2-trimethylsilanyl-ethoxymethyl)-1H-indol-7-yl}-oxo-acetic acid methyl ester (774 mg, 2.32 mmol) in DMF (50 mL). The deep red-orange solution was stirred 16 h at room temperature and then 1 h at 65° C. The heating bath was removed and pH 7.0 buffer added. The mixture was poured into EtOAc, the layers separated and the EtOAc solution washed with 0.1 N HCl, water (3×), saturated aq NaHCO$_3$ and brine (3×), dried (MgSO$_4$), filtered and concentrated onto SiO2. Flash chromatography afforded 3-(1H-Indol-3-yl)-4-[1-(2-trimethylsilanyl-ethoxymethyl)-1H-indol-7-yl]-pyrrole-2,5-dione (141 mg, 13%) as a bright orange solid which was dried under vacuum overnight at 70° C., and 3-(1H-Indol-7-yl)-4-(1H-indol-3-yl)-pyrrole-2,5-dione (165 mg, 22%) as a bright red solid which was dried under vacuum overnight at 70° C.

Spectral data for 3-(1H-Indol-3-yl)-4-[1-(2-trimethylsilanyl-ethoxymethyl)-1H-indol-7-yl]-pyrrole-2,5-dione. $^1$H NMR (400 MHz, DMSO-d$_6$) 11.80 (s, 1H), 11.03 (s, 1H), 7.90 (d, J=3 Hz, 1H), 7.66 (dd, J=8, 1 Hz, 1H), 7.37 (d, J=3 Hz, 1H), 7.31 (d, J=8 Hz, 1H), 71.0 (dd, J=8, 8 Hz, 1H), 7.01 (dd, J=8, 1 Hz, 1H), 6.95 (ddd, J=8, 8, 1 Hz, 1H), 6.51 (d, J=3 Hz, 1H), 6.48 (d, J=8, 8 Hz, 1H), 6.44 (d, J=8 Hz, 1H), 5.22 (s, 2H), 3.09 (t, J=8 Hz, 2H), 0.52 (t, J=8 Hz, 2H), −0.20 (s, 9H). MS (electrospray, m/z) 456.2 (M$^-$−1). HRMS 480.1731 (M+Na$^+$, calcd for C$_{26}$H$_{27}$N$_3$O$_3$SiNa 480.1719). Anal. Calcd for C$_{26}$H$_{27}$N$_3$O$_3$Si: C, 68.24; H, 5.95; N, 9.18. Found: C, 67.95; H, 5.76; N, 9.03.

Spectral data for 3-(1H-Indol-7-yl)-4-(1H-indol-3-yl)-pyrrole-2,5-dione. $^1$H NMR (400 MHz, DMSO-d6) 11.80 (s, 1H), 11.02 (s, 1H), 10.70 (s, 1H), 7.95 (d, J=3 Hz, 1H), 7.58 (m, 1H), 7.31 (d, J=8 Hz, 1H), 7.20 (dd, J=3, 3 Hz, 1H), 6.90–7.0 (m 3H), 6.40–6.48 (m, 2H), 6.18 (d, J=8 Hz, 1H). MS (electrospray, m/z) 328.1 (M$^+$+1), 326 M$^-$−1). HRMS 328.1112 (M$^+$+1, calcd for C$_{20}$H$_{14}$N$_3$O$_2$ 328.1086).

(d) 5H,7H,13H-indolo[6,7-a]-pyrrolo[3,4-c]-carbazole-6,8-dione

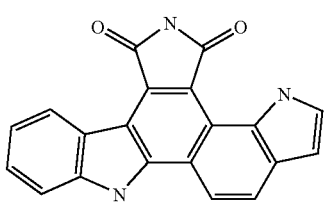

A solution of 3-(1H-indol-7-yl)-4-(1H-indol-3-yl)-pyrrole-2,5-dione (140 mg, 0.428 mmol) and iodine (114 mg, 0.449 mmol) in dioxane (200 mL) was photolyzed with a 450 W Hanovia lamp fitted with pyrex filter for 20 minutes. The mixture was concentrated to ~20 mL, poured into EtOAc and washed with 10% aq NaHSO$_3$, water (3×), saturated aq NaHCO$_3$, and brine, dried (MgSO$_4$), filtered and concentrated onto SiO2. Flash Chromatography (30% EtOAc/hexanes) afforded the title compound as an orange powder which was dried under vacuum at 70° C. for overnight (66 mg, 47%). $^1$H NMR (400 MHz, DMSO-d$_6$) 12.78 (s, 1H), 12.62 (s, 1H), 11.51 (S, 1H), 8.96 (d, J=8 Hz, 1H), 8.31 (d, J=8 Hz, 1H), 8.10 (d, J=8 Hz, 1H), 7.70–7.76 (m, 2H), 7.56 (dd, J=8, 8 Hz, 1H), 7.38 (dd, J=8, 8 Hz, 1H), 6.81 (br s, 1H). MS (electrospray, m/z) 326 (M$^+$+1), 324 (M$^-$−1) 324. HRMS 326.0941 (M$^+$+1, calcd for C$_{20}$H$_{12}$N$_3$O$_2$ 326.0930).

EXAMPLE 6

11-Bromo-5-methyl-5H,13H-indolo[6,7-a]pyrrolo[3,4-c]carbazole-6,8-dione (a) 3-(6-Bromo-1H-indol-3-yl)-4-(1-methy-1H-indol-7-yl)-pyrrole-2,5-dione To solution of 2-(1-methyl-1H-indol-7-yl)-acetamide (0.300 g, 1.59 mmol) in DMF (15 mL) was added a 1.0 M solution of potassium tert-butoxide in THF (1.59 mL, 1.59 mmol), followed after 5 minutes by (6-bromo-1H-indol-3-yl)-oxo-acetic acid methyl ester (0.235 g, 0.83 mmol) in DMF (1.25 mL). After another 5 minutes additional potassium tert-butoxide (1.59 mL) was introduced followed by the additional (6-bromo-1H-indol-3-yl)-oxo-acetic acid methyl ester (0.235 g, 0.83 mmol) in DMF (1.25 mL). The reaction was stirred for 5 minutes and an additional potassium tert-butoxide (1.59 mL) was introduced. After heating at 50° C. over night, then deep red solution and was cooled to room temperature, quenched with 1N HCl and poured in EtOAc. The two layers were separated and the organic layer was washed with H$_2$O, saturated aq NaHCO$_3$, and brine (×3), dried (MgSO$_4$), filtered, and concentrated. Flash chromatography (80% EtOAc/hexane) gave the title compound (0.256 g, 38%) as a red solid. $^1$H NMR (400 MHz, DMSO-d$_6$) 3.64 (s, 3H), 6.26 (d, J=4.4 Hz, 1H), 6.47 (d, J=2.8 Hz, 1H), 6.60 (dd, J=2, 8.8 Hz, 1H), 6.88 (d, J=7.2 Hz, 1H), 6.98 (dd, J=7.2, 7.2 Hz, 1H), 7.24 (d, J=3.6 Hz, 1H), 7.61 (dd, J=1.2, 8 Hz, 1H), 7.87 (d, J=2.8 Hz, 1H), 11.18 (s, 1H), 11.91 (s, 1H). MS (electrospray, m/z) 420/418 (M$^-$−1).

(b) 11-Bromo-5-methyl-5H,13H-indolo[6,7-a]pyrrolo[3,4-c]carbazole-6,8-dione

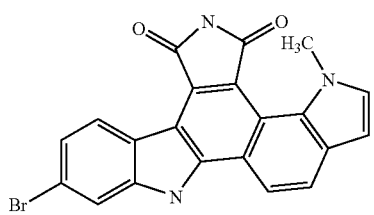

A solution of 3-(6-bromo-1H-indol-3-yl)-4-(1-methy-1H-indol-7-yl)-pyrrole-2,5-dione (0.315 g, 0.74 mmol) and iodine (0.190 g, 0.74 mmol) in dioxane (300 mL) was photolyzed with 450 W Hanovia lamp fitted with pyrex filter for 25 minutes. The mixture was concentrated, the residue was taken up in EtOAc (700 mL) and the solution was washed with 10% NaHSO$_3$, saturated NaHCO$_3$, and brine, dried (MgSO$_4$), filtered, and concentrated. Flash Chromatography (Hot 80% toluene/EtOAc) gave the title compound which was dried at 80° C. under vacuum for 3 h (0.055 g, 19%). $^1$H NMR (400 MHz, DMSO-d$_6$) 3.84 (s, 3H), 6.81 (d, J=2.8 Hz, 1H), 7.49 (dd, J=1.6, 8.2 Hz, 1H), 7.56 (d, J=2.8 Hz, 1H), 7.80 (d, J=1.6 Hz, 1H), 8.03 (d, J=8.8 Hz, 1H), 8.19 (d, J=8.8 Hz, 1H), 8.81 (d, J=8.4 Hz, 1H), 11.11 (s, 1H), 12.81 (s, 1H). MS (electrospray, m/z) 418/416 (M$^-$−1).

EXAMPLE 7

11-Trifluromethyl-5-methyl-5H.13H-indolo[6,7-a]pyrrolo[3,4-c]carbazole-6,8-dione

(a) 3-(6-Trifluoromethyl-1H-indol-3-yl)-4-(1-methyl-1H-indol-7-yl)-pyrrole-2,5-dione To a solution of 2-(1-methyl-1H-indol-7-yl)-acetamide (0.400 g, 2.12 mmol) and (6-trifluoro methyl-1H-indol-3-yl)-oxo-acetic acid methyl ester (0.574 g, 2.12 mmol) in THF (30 mL) at 0° C. was added a 1.0 M solution of potassium tert-butoxide in THF (2.12 mL, 2.12 mmol). The reaction was stirred for 25 minutes at 0° C. followed by addition of additional potassium tert-butoxide (4.24 mL, 4.24 mmol). The reaction was heated at reflux for 2 hours, cooled to room temperature, quenched with concentrated HCl (1 mL), and poured into EtOAc (400 mL). The two layers were separated and the organic solution was washed with saturated NaHCO$_3$ and brine, dried (MgSO$_4$), filtered, and concentrated to a crude orange solid. Flash chromatography (60% hexane/EtOAc to 50% hexane/EtOAc gradient) gave the title compound as an orange solid (607 mg, 70%). $^1$H NMR (DMSO-d$_6$) 12.16 (s, 1H), 11.24 (s, 1H), 8.03 (dd, J=1.2, 3.2 Hz, 1H), 7.69 (br s, 1H), 7.62 (d, J=8 Hz, 1H), 7.26 (dd, J=1.2, 3.4 Hz, 1H), 6.98 (ddd, J=0.8, 8.0, 10.7 Hz, 1H), 6.91 (dd, J=<1, 6.8 Hz, 1H), 6.793 (d, J=8.8 Hz, 1H), 6.59 (d, J=8.0 Hz, 1H), 6.49 (dd, J=1.2, 3.0 Hz, 1H), 3.66 (s, 3H). MS (electrospray,m/z) 410 (M$^+$+1), 408 (M$^-$−1).

(b) 11-Trifluromethyl-5-methyl-5H.13H-indolo[6,7-a]pyrrolo[3,4-c]carbazole-6,8-dione

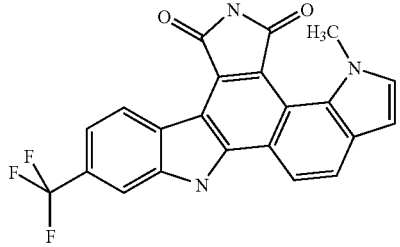

A solution of 3-(6-trifluoromethyl-1-H-indolyl)-4-(1-methyl-1H-indol-7-yl)-pyrrole-2,5-dione (0.456 g, 1.11 mmol) and iodine (0.424 g, 1.67 mmol) in dioxane (~300 mL) was photolyzed with a 450 W Hanovia lamp fitted with pyrex filter for 25 minutes. The reaction solution was concentrated to 5 mL and was taken up in Et$_2$O/Acetone (98:2). The mixture was heated to reflux, filtered hot, and the crude solid was precipitated from the filtrate with hexane. The solid was collected and chromatographed (75% hexane/EtOAc) to give the title compound as a yellow solid (46 mg, 10%). $^1$H NMR (DMSO-d$_6$) 13.07 (s, 1H), 11.19 (s, 1H), 9.10 (d, J=8.0 Hz, 1H), 8.26 (d, J=8.4 Hz, 1H), 8.10 (d, J=8.4 Hz, 1H), 7.96 (s, 1H), 7.68 (d, J=5.2 Hz, 1H), 6.86 (d, J=2.8 Hz, 1H), 3.88 (s, 3H). MS (electrospray, m/z) 408 (M$^+$+1), 406 (M$^-$−1).

EXAMPLE 8

9-Fluoro-5-methyl-7H,13H-indolo[6,7-a]-pyrrolo[3,4-c]-carbazole-6,8-dione

(a) 3-(4-Fluoro-1H-indol-3-yl)-4-(1-methyl-1H-indol-7-yl)-pyrrole-2,5-dione A 1.0 M solution of KOtBu in THF (10.6 mL, 10.6 mmol) was added to a solution of 2-(4-fluoro-1H-indol-3-yl)-acetamide (595 mg, 3.10 mmol) and (1-methyl-1H-indol-7-yl)-oxo-acetic acid methyl ester (646 mg, 2.98 mmol) in DMF (40 mL). The initially light yellow solution turned red-orange over 4 h and was then stirred 4 h at 60–70° C. The heating bath was removed, 1N HCl added and the mixture poured into EtOAc. The EtOAc layer was separated and washed with water (2×), saturated aq NaHCO$_3$ (2×) and brine (3×), dried (MgSO$_4$), filtered and concentrated onto SiO$_2$. Flash chromatography (1:1 EtOAc:hexanes) afforded a red glass that was dried at 70° C. overnight giving the title compound (585 mg, 55%) as a bright red solid. $^1$H NMR (400 MHz, DMSO-$_6$) 11.83 (br s, 1H), 11.21 (s, 1H), 7.53 (dd, J=7, 1 Hz, 1H), 7.40 (d, J=3 Hz, 1H), 7.25 (d, J=3 Hz, 1H), 7.21 (d, J=8 Hz, 1H), 7.0–7.08 (m, 1H), 7.86–7.04 (m, 2H), 6.65 (dd, J=11, 8 Hz, 1H), 6.44 (d, J=3 Hz, 1H), 3.71 (s, 3H). IR (CHCl$_3$, cm$^{-1}$) 1726. MS (electrospray, m/z) 360 (M$^+$+1), 358 (M$^-$−1).

(b) 9-Fluoro-5-methyl-7H,13H-indolo[6,7-a]-pyrrolo[3,4-c]-carbazole-6,8-dione

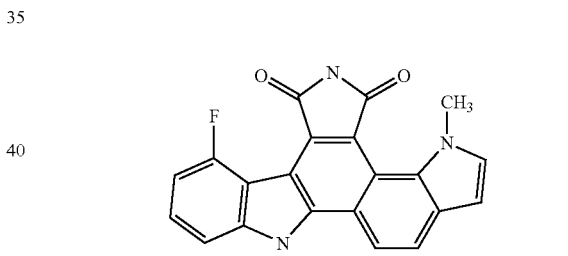

A solution of 3-(4-fluoro-1H-indol-2-yl)-4-(1-methyl-1H-indol-7-yl)-pyrrole-2,5-dione (256 mg, 0.712 mmol) and I$_2$ (181 mg, 0.712 mmol) in dioxane (200 mL) was irradiated with a 450 W Hanovia medium pressure lamp through a pyrex filter for 50 min. The dark red mixture was concentrated to ~50 mL, poured into EtOAc (400 mL) and washed with 10% aq NaHSO$_3$ (2×), saturated aq NaHCO$_3$ (2×), brine, dried (MgSO$_4$) and filtered. The solution was concentrated onto SiO$_2$ and flash chromatography (20% EtOAc: toluene) afforded several fractions containing one compound (TLC) which were combined and concentrated to give the title product (65 mg, 26%) as a red solid. The remaining fractions containing product were combined and concentrated to ~10 mL, and allowed to stand. Additional product (105 mg, 41%) was isolated by filtration as a bright orange solid. $^1$H NMR (400 MHz, DMSO-d$_6$) 12.99 (s, 1H), 10.94 (s, 1H), 8.27 (d, J=8 Hz, 1H), 8.09 (d, J=8 Hz, 1H), 7.60 (d, J=3 Hz, 1H), 7.5–7.56 (m, 2H), 7.06–7.12 (m, 1H), 6.85 (d, J=3 Hz, 1H), 3.88 (s, 3H). MS (electrospray, m/z) 358 (M$^+$+1), 356 (M$^-$−1).

EXAMPLE 9

12-Bromo-5-methyl-5H,13H-indolo[6,7-a]pyrrolo[3,4-c]carbazole-6,8-dione

(a) (7-Bromo-1H-indol-3-yl)-oxo-acetic acid methyl ester

Oxalyl chloride (1.8 mL, 20.7 mmol) was added dropwise to a solution of 7-bromoindole (3.65 g, 18.6 mmol) in $Et_2O$ (100 mL) cooled in an ice bath. After the addition was complete, the ice bath was removed and the mixture was allowed to warm to room temperature and stirred for 8 h. The mixture was then cooled in a dry ice-acetone bath and a 25% by wt solution of sodium methoxide in methanol (9.5 mL, 41.8 mmol) added dropwise over 5 min. The suspension was allowed to warm to room temperature affording a yellow suspension. After stirring 1 h at rt, the suspension was treated with water and the mixture poured into EtOAc. The EtOAc solution was separated and washed with pH 7.0 buffer and brine, dried (MgSO4) and concentrated to ~75 mL. The solution was diluted with Et2O and allowed to stand. Filtration afforded the title compound as pale yellow crystals (0.61 g, 12%). Concentration of the mother liquor to a slurry followed by addition of a small amount of $Et_2O$ (20 mL) and filtration afforded a second crop (2.33 g, 44%). $^1H$ NMR (400 MHz, DMSO-d6) 12.68 (br s, 1H), 8.46 (br s, 1H), 8.17 (d, J=8 Hz, 1H), 7.54 (d, J=8 Hz, 1H), 7.23 (dd, J=8, 8 Hz, 1H), 3.90 (s, 3H). $^{13}C$ NMR (75.5 MHz, DMSO-$d_6$) 178.63, 163.34, 138.72, 135.06, 127.16, 126.45, 124.27, 120.51, 113.22, 105.03, 52.59. IR ($CHCl_3$, $cm^{-1}$) 3450, 1731, 1654. MS (electrospray, m/z) 284/282 ($M^++1$), 282/280 ($M^--1$). HRMS 281.9786 ($M^++1$, calcd for $C_{11}H_9NO_3Br$ 281.9766). Anal. Calcd for $C_{11}H_8BrNO_3$: C, 46.84; H, 2.86; N, 4.97. Found: C, 46.81; H, 2.72; N, 4.91.

(b) 12-Bromo-5-methyl-5H,13H-indolo[6,7-a]pyrrolo[3,4-c]carbazole-6,8-dione

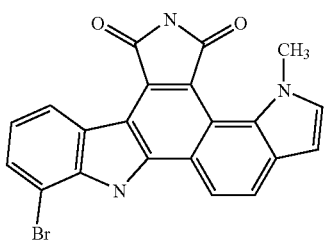

A 1.0 M solution of KOtBu in THF (7.0 mL, 7.0 mmol) was added dropwise to a solution of 2-(1-methyl-1H-indol-7-yl)-acetamide (369 mg, 1.96 mmol) and (7-bromo-1H-indol-7-yl)-oxo-acetic acid methyl ester (569 mg, 2.02 mmol) in DMF (50 mL). The initially light yellow solution turned red-orange and was stirred 18 at 70° C. The mixture was cooled to rt, 1N HCl was added and the mixture poured into EtOAc. The EtOAc layer was separated and washed with water (3×), saturated aq $NaHCO_3$ and brine (2×), dried ($MgSO_4$), filtered and concentrated onto $SiO_2$. Flash chromatography (1:1 EtOAc:hexanes) afforded 3-[7-bromo-1H-indol-3-yl]-4-(1-methyl-1H-indol-7-yl)-pyrrole-2,5-dione (487 mg) as an orange glass that was ~80% pure by $^1H$ NMR and hplc. This material was used without further purification. $^1H$ NMR (400 MHz, DMSO-$d_6$) 12.03 (br s, 1H), 11.23 (s, 1H), 7.83 (d, J=3 Hz, 1H), 7.62 (d, J=8 Hz, 1H), 7.26 (d, J=3 Hz, 1H), 7.20 (d, J=7 Hz, 1H), 6.98 (dd, J=8 Hz, 1H), 6.90 (d, J=7 Hz, 1H), 6.42–6.50 (m, 3H), 3.67 (s, 3H). MS (electrospray, m/z) 422/420 ($M^++1$).

A solution of 3-(7-bromo-1H-indol-3-yl)-4-(1-methyl-1H-indol-7-yl)-pyrrole-2,5-dione (196 mg, 0.47 mmol) and iodine (123 mg, 0.48 mmol) in dioxane (200 mL) was photolyzed with 450 W Hanovia lamp fitted with pyrex filter for 30 minutes. The mixture was concentrated to 20 mL, diluted with EtOAc, and washed with 10% $NaHSO_3$, saturated $NaHCO_3$, and brine, dried ($MgSO_4$), filtered and concentrated to ~20 mL. The solution was filtered and the filtrate concentrated onto $SiO_2$. Flash Chromatography (40% EtOAc/hexanes) gave the title compound which was dried under vacuum at 70° C. overnight (33 mg, 17%) as an orange solid. $^1H$ NMR (400 MHz, DMSO-$d_6$) 12.41 (s, 1H), 11.17 (s, 1H), 9.01 (d, J=8 Hz, 1H), 8.76 (d, J=8 Hz, 1H), 8.06 (d, J=8 Hz, 1H), 7.76 (d, J=8 Hz, 1H), 7.61 (d, J=3 Hz, 1H), 7.32 (dd, J=8, 8 Hz, 1H), 6.86 (d, J=3 Hz, 1H), 3.88 (s, 3H). MS (electrospray, m/z) 418/416 ($M^--1$).

EXAMPLE 10

13-(3-Hydroxy-propyl)-5-methyl-7H-indolo[6,7-a]-pyrrolo[3,4-c]-carbazole-6,8-dione

(a) 3-[1-(3-Hydroxypropyl)-1H-indol-3-yl]-4-(1-methyl-1H-indol-7-yl)-pyrrole-2,5-dione A 1.0 M solution of KOtBu in THF (9.2 mL, 9.2 mmol) was added to a solution of 2-(1-3-hydroxypropyl-1H-indol-3-yl)-acetamide (616 mg, 2.65 mmol) and (1-methyl-1H-indol-7-yl)-oxo-acetic acid methyl ester (566 mg, 2.61 mmol) in DMF (40 mL). The initially light yellow solution turned red-orange and was stirred 14 h at rt. 1N HCl was added and the mixture poured into EtOAc. The EtOAc layer was separated and washed with water (3×), saturated aq $NaHCO_3$ (2×) and brine (3×), dried ($MgSO_4$), filtered and concentrated onto $SiO_2$. Flash chromatography (1:1 EtOAc:$CH_2Cl_2$) afforded a red solid that was dried at 70° C. for 72 h giving the title compound (689 mg, 66%) as a bright red solid. $^1H$ NMR (400 MHz, DMSO-$d_6$) 11.12 (s, 1H), 8.05 (s, 1H), 7.61 (d, J=8 Hz, 1H), 7.43 (d, J=8 Hz, 1H), 7.25 (d, J=3 Hz, 1H), 6.92–7.04 (m, 2H), 6.87 (d, J=8 Hz, 1H), 6.44–6.50 (m, 2H), 6.21 (d, J=8 Hz, 1H), 4.64 (m, 1H), 4.27 (t, J=7 Hz, 2H), 3.68 (s, 3H), 3.30–3.40 (m, 2H), 1.80–1.90 (m, 2H). $^{13}C$ NMR (75.5 MHz, DMSO-$d_6$) 173.43, 172.37, 136.15, 134.62, 134.26, 131.54, 129.58, 129.19, 128.57, 125.20, 124.11, 122.07, 121.53, 121.03, 120.12, 118.56, 115.18, 110.34, 104.28, 100.73, 57.54, 42.94, 34.68, 32.54. IR ($CHCl_3$, $cm^{-1}$) 3436, 1721. MS (electrospray, m/z) 400 ($M^++1$), 398 ($M^--1$). Anal. Calcd for $C_{24}H_{21}N_3O_3$: C, 72.17; H, 5.30; N, 10.52. Found: C, 71.87; H, 5.29; N, 10.45.

(b) 13-(3-Hydroxy-propyl)-5-methyl-7H-indolo[6,7-a]-pyrrolo[3,4-c]-carbazole-6,8-dione

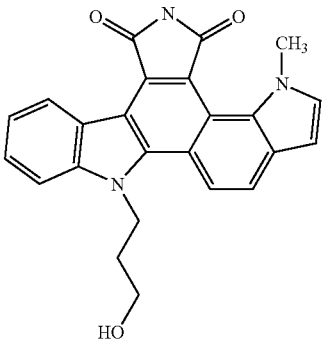

A solution of 3-[1-(3-hydroxypropyl)-1H-indol-2-yl]-4-(1-methyl-1H-indol-7-yl)-pyrrole-2,5-dione (240 mg, 0.602 mmol) and $I_2$ (154 mg, 0.61 mmol) in dioxane (200 mL) was irradiated with a 450 W Hanovia medium pressure lamp through a pyrex filter for 30 min. The dark red mixture was concentrated to ~50 mL, poured into EtOAc (400 mL) and washed with 10% aq $NaHSO_3$ (2×), saturated aq $NaHCO_3$ (2×), brine, dried $MgSO_4$, filtered and concentrated onto $SiO_2$. Flash chromatography (1:1 to 7:3 EtOAc: hexanes) afforded the title product (164 mg, 69%) as a bright orange solid. $^1$H NMR (400 MHz, DMSO-$d_6$) 11.13 (s, 1H), 9.14 (d, J=8 Hz, 1H), 8.41 (d, J=9 Hz, 1H), 8.02 (d, J=9 Hz, 1H), 7.90 (d, J=8 Hz, 1H), 7.59–7.64 (m, 2H), 7.43 (dd, J=8 Hz, 1H), 6.85 (d, J=3 Hz, 1H), 4.95 (br t, J=7 Hz, 2H), 4.86 (t, J=5 Hz, 1H), 3.85 (s, 3H), 3.58 (m, 2H), 2.1–2.20 (m, 2H). MS (electrospray, m/z) 398 ($M^+$+1), 396 ($M^-$−1).

EXAMPLE 11

13-(3-Hydroxy-propyl)-11-methoxy-5-methyl-5H,13H-indolo[6,7-a]pyrrolo[3,4-c]carbazole-6,8-dione

(a) 1-[3-(tert-Butyl-dimethyl-silanyloxy)-propyl]-6-methoxy-1H-indole

To a solution of 6-methoxyindole (10.0 g, 67.9 mmol), and (3-bromo-propoxy)-tert-butyl-dimethylsilane (18.0 g, 71.3 mmol) in DMF (300 mL) was added NaH (0.353 g, 8.82 mmol) as a 60% oil dispersion. The reaction was stirred for 2 h, quenched with saturated aq $NaHCO_3$, diluted with EtOAc (400 mL), washed with saturated aq $NaHCO_3$ and brine, dried ($MgSO_4$), filtered, and concentrated to a transparent oil. The oil was purified by filtration through a plug of silica gel (85% hexane/EtOAc) to give (22.1 g, 100%) of the title compound as a transparent oil. $^1$H NMR (DMSO-$d_6$) 7.38 (d, J=8.4 Hz, 1H), 7.15 (d, J=3.2 Hz, 1H), 6.92 (d, J=2.0 Hz, 1H), 6.65 (dd, J=2.4, 8.4 Hz, 1H), 6.32 (d, J=3.2 Hz, 1H) 4.16 (t, J=6.4 Hz, 2H), 3.77 (s, 3H), 3.53 (t, J=6 Hz, 2H), 1.90 (apparent quintet, J=6.8 Hz, 2H), 0.87 (s, 9H), 0.01 (s, 6H). MS (electrospray, m/z) 320 ($M^+$+1).

(b) {1-[3-(tert-Butyl-dimethyl-silanyloxy)-propyl]-6-methoxy-1H-indol-3-yl}-oxo-axetic acid methyl ester To a solution of 1-[3-(tert-Butyl-dimethyl-silanyloxy)-propyl]-6-methoxy-1H-indole (2.45 g, 7.66 mmol) in $Et_2O$ (40 mL) at 0° C. was added oxalyl chloride (1.07 g, 8.42 mmol). The reaction was stirred for 30 min while warming to room temperature. The reaction was cooled to −78° C. and NaOMe (5.25 mL, 22.98 mmol) as a 25% wt solution in MeOH was introduced. The reaction was stirred overnight while allowing to warm to room temperature. The mixture was poured into EtOAc, washed with $H_2O$, saturated $NaHCO_3$ and brine, dried ($MgSO_4$), filtered and concentrated to an oil. The crude oil was purified by flash chromatography (75% hexane/EtOAc to 65% hexane/EtOAc gradient) to give 2.46 g (79%) of the title compound as an oil. $^1$H NMR (DMSO-$d_6$) 8.30 (s, 1H), 8.02 (d, J=8.4 Hz, 1H), 7.14 (d, J=2 Hz, 1H), 6.93 (dd, J=2.0, 8.4 Hz, 1H), 4.32 (t, J=6.8 Hz, 2H), 3.86 (s, 3H), 3.82 (s, 3H), 3.55 (t, J=6.0 Hz, 2H), 1.98 (apparent quintet, J=8.4 Hz, 2H), 0.86 (s, 9H), 0.01 (s, 6H). MS (electrospray, m/z) 406 ($M^+$+1).

(c) 3-[1-(3-Hydroxy-propyl)-6-methoxy-1H-indol-3-yl]-4-(1-methyl-1H-indol-7-yl)-pyrrole-2,5-dione To a solution of {1-[3-(tert-butyl-dimethyl-silanyloxy)-propyl]-6-methoxy-1H-indol-3-yl}-oxo-axetic acid methyl ester (5.47 g, 13.5 mmol) and 2-(1-methyl-1H-indol-7-yl)-acetamide (2.55 g, 13.5 mmol) in DMF (250 mL) was added potassium tert-butoxide as a 1.0 M solution in THF (40.5 mL, 40.5 mmol). The reaction stirred at room temperature for 24 h and quenched with 1N HCl and stirred for 1 h. The reaction mixture was poured into EtOAc (1.5 L), washed with 1N HCl, saturated aq $NaHCO_3$, and brine (×4), dried ($MgSO_4$), filtered, and concentrated. The crude red solid was triturated and recrystallized with $Et_2O$/hexane to give the title compound as a red solid (3.6 g, 62%). $^1$H NMR (DMSO-$d_6$) 11.10 (s, 1H), 7.94 (s, 1H), 7.60 (d, J=7.8 Hz, 1H), 7.23 (d, J=3 Hz, 1H), 6.98 (m, 2H), 6.85 (d, J=7 Hz, 1H), 6.47 (dd, J=3 Hz, 1H), 6.07 (d, J=9 Hz, 2H), 6.00 (d, J=9 Hz, 1H), 4.62 (t, J=5.2 Hz, 1H), 4.21 (t, J=7.2 Hz, 2H), 3.67 (s, 3H), 3.65 (s, 3H), 3.34 (apparent quartet, J=5.6 Hz, 2H), 1.83 (apparent quintet, J=6.8 Hz, 2H). MS (electrospray, m/z) 430 ($M^+$+1), 428 ($M^-$−1).

(d) 13-(3-Hydroxy-propyl)-1-methoxy-5-methyl-5H,13H-indolo[6,7-a]pyrrolo[3,4-c]carbazole-6,8-dione

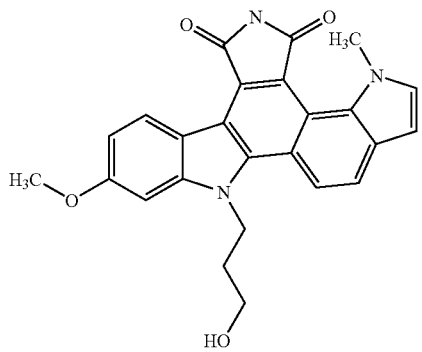

A solution of 3-[1-(3-Hydroxy-propyl)-6-methoxy-1H-indol-3-yl]-4-(1-methyl-1H-indol-7-yl)-pyrrole-2,5-dione (2.0 g, 4.65 mmol) and DDQ (1.06 g, 4.65 mmol) in EtOAc (1 L) was photolyzed with 450 W Hanovia lamp with pyrex filter for 2.25 hours. The mixture was purified by plug filtration through silica gel and eluting with EtOAc and recrystalized from toluene/MeOH/hexane to give 1.1 g (55%) of the title compound as a red solid. ¹H NMR (DMSO-d₆) 11.07 (s, 1H), 8.98 (d, J=8.4 Hz, 1H), 8.36 (d, J=8.8 Hz, 1H), 7.97 (d, J=8.8 Hz, 1H), 7.56 (d, J=3.2 Hz, 1H), 7.40 (d, J=1.6 Hz, 1H), 7.04 (dd, J=2.4, 8.6 Hz, 1H), 6.81 (d, J=3.2 Hz, 1H), 4.90 (t, J=7.2 Hz, 2H), 4.86 (br s, 1H), 3.94 (s, 3H), 3.83 (s, 3H), 3.57 (t, J=5.2 Hz, 2H), 2.14 (apparent quintet, J=6 Hz, 2H). MS (electrospray, m/z) 428 (M⁺+1), 426 (M⁻−1).

EXAMPLE 12

9-Methoxy-5-methyl-5H,13H-indolo[6,7-a]pyrrolo[3,4-c]carbazole-6,8-dione (a) (4-Methoxy-1H-indol-3-yl)-oxo-acetic acid methyl ester A solution of 4-methoxy-indole (1.04 g, 7.07 mmol) in Et₂O (150 mL) cooled to 0–5° C. was treated with oxalyl chloride (0.7 mL, 8.0 mmol). After 1h, the orange solution was allowed to warm to room temperature and stirred 2.5 h. Additional oxalyl chloride (0.25 mL, 2.9 mmol) was then added. After stirring 3 h at room temperature, the mixture was cooled to −78° C. and a 25% solution of sodium methoxide in methanol (5.4 mL, 23.4 mmol) added. The suspension was warmed to room temperature, stirred 3 h and neutralized by the addition of pH 7 buffer. The mixture was poured into EtOAc and the organic layer was separated and washed with saturated aq sodium bicarbonate, brine, dried (MgSO₄) and concentrated to a dark oil. Trituration with Et₂O (75 mL) afforded the title compound as a green solid (0.848 g, 51%) which was used without further purification. ¹H NMR (400 MHz, DMSO-d₆) 12.40 (s, 1H), 8.20 (d, J=4.3 Hz, 1H), 7.19 (dd, J=7.8, 7.8 Hz, 1H), 7.12 (d, J=7.8 Hz, 1H), 6.73 (d, J=7.8 Hz, 1H), 3.84 (s, 3H), 3.82 (s, 3H). MS (electrospray, m/z) 234.0 (M⁺+1), 232.1 (M⁻−1).

(b) 3-(4-Methoxy-1H-indol-3-yl)-4-(1-methyl-1H-indol-7-yl)-pyrrole-2,5-dione

To a solution of 2-(1-methyl-1H-indol-7-yl)-acetamide (0.539 g, 2.87 mmol) and (4-methoxy-1H-indol-3-yl)-oxo-acetic acid methyl ester (0.656 g, 2.81 mmol) in DMF (40 mL) under N₂ was added a 1.0 M solution of potassium-tert-butoxide in THF (10 mL, 10 mmol) dropwise over 5 minutes. The mixture was heated at 60° C. for 15 h, quenched with 1N HCl (excess) and poured into EtOAc. The organic layer was separated, washed with water (3×), saturated aq NaHCO₃, and brine, dried (MgSO₄), filtered and concentrated onto flash SiO₂. Flash chromatography (30–40% hexane/EtOAc) gave the title compound (0.414 g, 40%) as a red solid, which was dried under vacuum overnight. ¹H NMR (400 MHz, DMSO-d₆) 11.49 (br s, 1H), 11.08 (s, 1H), 7.49 (dd, J=7, 3 Hz, 1H), 7.30 (d, J=3 Hz, 1H), 7.25 (d, J=3 Hz, 1H), 6.86–7.05 (m 4H), 6.39 (d, J=7 Hz, 1H), 6.42 (d, J=3 Hz, 1H), 3.76 (s, 3H), 3.34 (s, 3H). MS (electrospray, m/z) 372.1 (M⁺+1), 370 (M⁻−1). HRMS 372.1347 (M⁺+1, calcd for C₂₂H₁₈N₃O₃ 372.1348).

(c) 9-Methoxy-5-methyl-5H,13H-indolo[6,7-a]pyrrolo[3,4-c]carbazole-6,8-dione

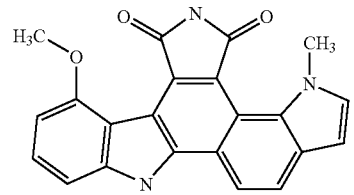

A solution of 3-(4-methoxy-1H-indol-3-yl)-4-(1-methyl-1H-indol-7-yl)-pyrrole-2,5-dione (0.238 g, 0.641 mmol) and DDQ (0.144 g, 0.634 mmol) in EtOAc (200 mL) was photolyzed with 450 W Hanovia lamp fitted with pyrex filter for 3 h. During this time the reaction temperature rose to 58–60° C. The mixture was washed with saturated aq NaHCO₃, 0.1 N NaOH (2×200 mL)), saturated aq NaHCO₃ again, and brine (200 mL), dried (MgSO₄), filtered and concentrated to ~5 mL. The solution was transferred to a flash SiO₂ column and elution with 50% EtOAc/hexanes gave the title compound as orange solid which was dried under vacuum at 90° C. overnight (0.122 g, 37%). ¹H NMR (400 MHz, DMSO-d₆) 12.69 (s, 1H), 10.72 (s, 1H), 8.23 (d, J=8.6 Hz, 1H), 8.04 (d J=8.6 Hz, 1H), 7.57 (d, J=3 Hz, 1H), 7.47 (dd, J=8, 8 Hz, 1 H), 7.28 (d, J=8 Hz, 1H), 6.86 (d, J=8 Hz, 1H), 6.82 (d, J=3 Hz, 1H). MS (electrospray, m/z) 370.1 (M⁺+1), 368.1 (M⁻−1), HRMS 370.1187 (M⁺+1, calcd for C₂₂H₁₆N₃O₃ 370.1192).

EXAMPLE 13

10-Methoxy-5-methyl-5H,13H-indolo[6,7-a]pyrrolo[3,4-c]carbazole-6,8-dione (a)(5-Methoxy-1H-indol-3-yl)-oxo-acetic acid methyl ester A solution of 5-methoxy-indole (5.14 g, 34.9 mmol) in Et₂O (120 mL) cooled to 0–5° C. was treated with oxalyl chloride (3.3 mL, 37.9 mmol). After stirring 30 min, the mixture was cooled to −78° C. and a 25% solution of sodium methoxide in methanol (19 mL, 83.6 mmol) added over 10 min. The suspension was warmed to room temperature, and water and EtOAc added. Filtration afforded the title compound as a yellow solid (6.73 g, 83%) which was used without further purification. ¹H NMR (400 MHz, DMSO-d₆) 12.32 (s, 1H), 8.37 (d, J=3.5 Hz, 1H), 7.66 (d, J=2.3 Hz, 1H), 7.44 (d, J=9 Hz, 1H), 6.92 (dd, J=9, 2.3 Hz, 1H), 3.89 (s, 3H), 3.80 (s, 3H). ¹³C NMR (75.5 MHz, DMSO-d₆) 178.49, 164.01, 156.13, 138.12, 131.38, 126.38, 113.44, 113.35, 112.25, 103.07, 55.27, 52.38. IR (KBr, cm⁻¹) 3168, 1732. MS (electrospray, m/z) 234 (M⁺+1), 232 (M⁻−1). HRMS 234.0760 (M⁺+1, calcd for C₁₂H₁₂NO₄ 234.0766).

(b) 3-(5-Methoxy-1H-indol-3-yl)-4-(1-methyl-1H-indol-7-yl)-pyrrole-2,5-dione

To a solution of 2-(1-methyl-1H-indol-7-yl)-acetamide (0.544 g, 2.89 mmol) and (5-methoxy-1H-indol-3-yl)-oxo-acetic acid methyl ester (0.648 g, 2.81 mmol) in DMF (40 mL) under N₂ was added a 1.0 M solution of potassium-tert-butoxide in THF (9.8 mL, 9.8 mmol) dropwise over 5 minutes. The mixture was stirred 8 h at room temperature and then heated at 65–70° C. for 15 h. The mixture was cooled to room temperature, quenched with 1N HCl (excess) and poured into EtOAc. The organic layer was separated, washed with water (3×), saturated aq NaHCO₃, and brine, dried (MgSO₄), filtered and concentrated to ~30 mL. Upon standing 4 h, a bright red solid precipitated which was isolated by filtration and dried under vacuum at 80–100° C. overnight affording the title compound (0.421 g, 41%). ¹H NMR (400 MHz, DMSO-d₆) 11.81 (br s, 1H), 11.80 (s, 1H), 8.06 (d, J=3.1 Hz, 1H), 7.58, dd, J=7.5, 1 Hz, 1H), 7.31 (d, J=3 Hz, 1H), 7.22 (d, J=9 Hz, 1H), 6.93 (dd, J=7.5 Hz, 1H), 6.81 (d, J=7.5 Hz, 1H), 6.53 (dd, J=9, 2.5 Hz, 1H), 6.50 (d, J=3 Hz, 1H), 5.80 (d, J=2.5 Hz, 1H), 3.80 (s, 3H), 2.70 (s, 3H). MS (electrospray, m/z) 372.1 (M⁺+1), 370 (M⁻−1). HRMS 372.1345 (M⁺+1, calcd for $C_{22}H_{18}N_3O_3$ 372.1348). Anal. Calcd for $C_{22}H_{17}N_3O_3$: C, 71.15; H, 4.61; 11.31. Found: C, 71.05; H, 4.59; N, 11.17.

(c) 10-Methoxy-5-methyl-5H,13H-indolo[6,7-a]pyrrolo[3,4-c]carbazole-6,8-dione

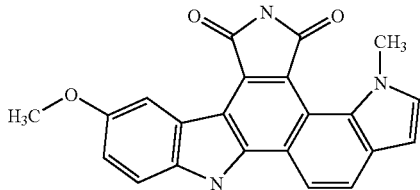

A solution of 3-(5-methoxy-1H-indol-3-yl)-4-(1-methyl-1H-indol-7-yl)-pyrrole-2,5-dione (0.225 g, 0.606 mmol) and DDQ (0.140 g, 0.617 mmol) in EtOAc (200 mL) was photolyzed with 450 W Hanovia lamp fitted with pyrex filter for 1 h. During this time the reaction temperature rose to 53° C. The mixture was washed pH 10 buffer (2×), saturated aq NaHCO₃, and brine (200 mL), dried (MgSO₄), filtered and concentrated onto flash SiO₂. Flash chromatography (50% EtOAc/hexanes) gave the title compound which was dried under vacuum for 48 h affording an orange solid (0.193 g, 86%). ¹H NMR (400 MHz, DMSO-d₆) 12.58 (s, 1H), 11.08 (s, 1H), 8.54 (d, J=3 Hz, 1H), 8.23 (d, J=9 Hz, 1H), 8.03 (d, J=9 Hz, 1H), 7.62 (d, J=9 Hz, 1H), 7.58 (d, J=3 Hz, 1H), 7.20 (dd, J=9, 3 Hz, 1H), 6.83 (d, J=3 Hz, 1H), 3.91 (s, 3H), 3.88 (s, 3H). MS (electrospray, m/z) 370.1 (M⁺+1), 368.1 (M⁻−1). HRMS 370.1193 (M⁺+1, calcd for $C_{22}H_{16}N_3O_3$ 370.1192).

EXAMPLE 14

11-Fluoro-5-methyl-5H,13H-indolo[6,7-a]pyrrolo[3,4-c]carbazole-6,8-dione (a) 3-(6-Fluoro-1H-indol-3-yl)-4-(1-methyl-1H-indol-7-yl)-pyrrole-2,5-dione To a solution of 2-(1-methyl-1H-indol-7-yl)-acetamide (0.466 g, 2.48 mmol) and (6-fluoro-1H-indol-3-yl)-oxoacetic acid methyl ester (0.543 g, 2.45 mmol) in DMF (40 mL) under N₂ was added a 1.0 M solution of potassium-tert-butoxide in THF (8.6 mL, 8.6 mmol) dropwise over 5 minutes. The mixture was heated at 65–70° C. for 15 h. The mixture was cooled to room temperature, quenched with 1N HCl (excess) and poured into EtOAc. The organic layer was separated, washed with water (3×), saturated aq NaHCO₃, and brine, dried (MgSO₄), filtered and concentrated onto flash SiO₂. Flash chromatography (40% EtOAc/hex) gave the title compound as a bright orange solid which was dried under vacuum at 80–100° C. overnight (0.342 g, 39%). ¹H NMR (400 MHz, DMSO-d₆) 11.49 (br s, 1H), 11.08 (s, 1H), 7.49 (dd, J=6, 3 Hz, 1H), 7.30 (d, J=2.3 Hz, 1H), 7.24 (d, J=3 Hz, 1H), 6.86–7.05 (m, 4H), 6.43 (d, J=3 Hz, 1H), 6.40 (d, J=7 Hz, 1H), 3.76 (s, 3H). MS (electrospray, m/z) 360.0 (M⁺+1), 358.0 (M⁻−1). HRMS 360.1161 (M⁺+1, calcd for $C_{21}H_{15}FN_3O_2$ 360.1148). Anal. Calcd for $C_{21}H_{14}FN_3O_2$: C, 70.19; H, 3.93; N, 11.69. Found: C, 69.94; H, 3.92; N, 11.59.

(b) 11-Fluoro-5-methyl-5H,13H-indolo[6,7-a]pyrrolo[3,4-c]carbazole-6,8-dione

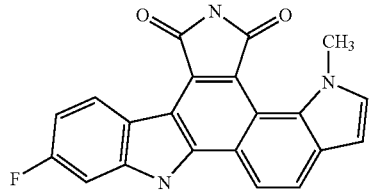

A solution of 3-(6-fluoro-1H-indol-3-yl)-4-(1-methyl-1H-indol-7-yl)-pyrrole-2,5-dione (0.192 g, 0.534 mmol) and DDQ (0.122 g, 0.537 mmol) in EtOAc (200 mL) was photolyzed with 450 W Hanovia lamp fitted with pyrex filter for 30 min. The mixture was washed pH 10 buffer (2×), saturated aq NaHCO₃, and brine (200 mL), dried (MgSO₄), filtered and concentrated onto flash SiO₂. Flash chromatography (50% EtOAc/hexanes) gave an orange solid which was dried under vacuum overnight. This material was then slurried with hot CH₂Cl₂, filtered and dried at 80–100° C. for 4 h affording the title compound (0.145 g, 76%). ¹H NMR (400 MHz, DMSO-d₆) 12.86 (s, 1H), 11.13 (s, 1H), 8.94 (dd, J=9, 2.5 Hz, 1H), 8.23 (d, J=9 Hz, 1H), 8.06 (d, J=9 Hz, 1H), 7.59 (d, J=3 Hz, 1H), 7.46 (dd, J=9, 2.5 Hz, 1H), 7.23 (ddd, J=9, 9, 2.5 Hz, 1H), 6.84 (d, J=3 Hz, 1H), 3.88 (s, 3H). MS (electrospray, m/z) 358.1 (M⁺+1), 356.0 (M⁻−1). MS 358.0994 (M⁺+1, $C_{21}H_{13}FN_3O_2$ 358.0992).

EXAMPLE 15

11-Cyano-5-methyl-5H,13H-indolo[6,7-a]pyrrolo[3,4-c]carbazole-6,8-dione (a) 3-(6-Cyano-1H-indol-3-yl)-4-(1-methyl-1H-indol-7-yl)-pyrrole-2,5-dione To a solution of 2-(1-methyl-1H-indol-7-yl)-acetamide (0.410 g, 2.18 mmol) and (6-cyano-1H-indol-3-yl)-oxoacetic acid methyl ester (0.480 g, 2.10 mmol) in DMF (30 mL) under N₂ was added a 1.0 M solution of potassium-tert-butoxide in THF (7.6 mL, 7.6 mmol) dropwise over 5 minutes. The mixture was heated at 70° C. for 17 h. The mixture was cooled to room temperature, quenched with 1N HCl (excess) and poured into EtOAc. The organic layer was separated, washed with water (3×), saturated aq NaHCO₃, and brine, dried (MgSO₄), filtered and concentrated onto flash SiO₂. Flash chromatography (60–70% EtOAc/hex) gave the title compound as a bright orange-red solid which was dried under vacuum at 75° C. overnight (0.416 g, 54%). ¹H NMR (400 MHz, DMSO-d₆) 12.29 (br s, 1H), 11.26 (s, 1H), 8.03 (d, J=2.3 Hz, 1H), 7.86 (br s, 1H), 7.63 (d, J=8 Hz, 1H), 7.25 (d, J=3 Hz, 1H), 6.99 (dd, J=8, 8 Hz, 1H), 6.91 (d, J=8 Hz, 1H), 6.89 (d, J=8 Hz, 1H), 6.60 (d, J=8 Hz, 1H), 6.49 (d, J=3 Hz, 1H), 3.66 (s, 3H). IR (KBR, cm$^{-1}$) 3282, 2223, 1751, 1698. MS (electrospray, m/z) 367.1 (M$^+$+1), 365.2 (M$^-$−1). HRMS 367.1190 (M$^+$+1, calcd for $C_{22}H_{15}N_4O_2$ 367.1195).

(b) 11-Cyano-5-methyl-5H,13H-indolo[6,7-a]pyrrolo[3,4-c]carbazole-6,8-dione

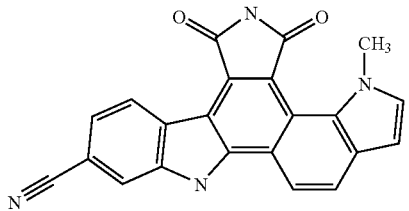

A solution of 3-(6-cyano-1H-indol-3-yl)-4-(1-methyl-1H-indol-7-yl)-pyrrole-2,5-dione (0.192 g, 0.524 mmol) and DDQ (0.117 g, 0.515 mmol) in dioxane (200 mL) was photolyzed with 450 W Hanovia lamp fitted with pyrex filter for 30 min. During this time the reaction temperature rose to 39° C. The mixture was concentrated to ~50 mL and poured into EtOAc. The resulting slurry was concentrated to ~2 mL and MeOH (~2 mL) added. This mixture was then diluted with acetone (50 mL), heated to boiling, cooled and filtered. The yellow-tan solid was washed acetone and dried at 50° C. under vacuum affording the title compound (0.120 g, 63%). $^1$H NMR (400 MHz, DMSO-d$_6$) 13.17 (s, 1H), 11.22 (s, 1H), 9.07 (d, J=8 Hz, 1H), 8.31 (d, J=8 Hz, 1H), 8.15 (s, 1H), 8.11 (d, J=8 Hz, 1H), 7.75 (dd, J=8, 1 Hz, 1H), 7.63 (d, J=3 Hz, 1H), 6.88 (d, J=3 Hz, 1H). MS (electrospray, m/z) 363.1 (M$^-$+1). HRMS 365.1016 (M$^+$+1, calcd for $C_{22}H_{13}N_4O_2$ 365.1039).

EXAMPLE 16

12-Methoxy-5-methyl-5H,13H-indolo[6,7-a]pyrrolo[3,4-c]carbazole-6,8-dione (a) (7-Methoxy-1H-indol-3-yl)-oxo-acetic acid methyl ester A solution of 7-methoxy-indole (1.10 g, 7.47 mmol) in Et$_2$O (150 mL) cooled to 0–5° C. was treated with oxalyl chloride (0.75 mL, 8.6 mmol). After 30 min, the mixture was allowed to warm to room temperature and stirred 1 h. Additional oxalyl chloride (0.25 mL, 2.87 mmol) was added, the mixture stirred an additional 1 h and then cooled to −78° C. A 25% solution of sodium methoxide in methanol (5.4 mL, 23.8 mmol) was added over 10 min. The suspension was warmed to room temperature, stirred 2 h and then poured into EtOAc/pH 7 buffer. The EtOAc layer was separated and washed with water, brine, dried (MgSO$_4$), filtered and concentrated to ~20 mL. The resulting slurry was diluted with Et$_2$O (75 mL), and filtered. The solid obtained was washed with Et$_2$O and dried under vacuum overnight to afford the title compound as an off-white solid (1.23 g, 71%). Upon standing, the mother liquor afforded a second crop (0.26 g, 15%). $^1$H NMR (400 MHz, DMSO-d$_6$) 12.63 (br s, 1H), 8.29 (d, J=3.5 Hz, 1H), 7.73 (d, J=8 Hz, 1H), 7.20 (dd, J=8, 8 Hz, 1H), 6.89 (d, J=8 Hz, 1H). $^{13}$C NMR (75.5 MHz, DMSO-d$_6$) 178.72, 163.88, 146.37, 137.19, 127.02, 125.54, 123.73, 113.52, 112.92, 104.60, 55.34, 52.42. IR (CHCl3, cm$^{-1}$) 3452, 1732, 1648. MS (electrospray, m/z) 234.1 (M$^+$+1), 232.2 (M$^-$−1). Anal. Calcd for $C_{12}H_{11}NO_4$: C, 61.80; H, 4.75; N, 6.01. Found: C, 61.61; H, 4.83; N, 6.01.

(b) 3-(7-Methoxy-1H-indol-3-yl)-4-(1-methyl-1H-indol-7-yl)-pyrrole-2,5-dione

To a solution of 2-(1-methyl-1H-indol-7-yl)-acetamide (0.491 g, 2.61 mmol) and (7-methoxy-1H-indol-3-yl)-oxo-acetic acid methyl ester (0.611 g, 2.62 mmol) in DMF (40 mL) under N$_2$ was added a 1.0 M solution of potassium-tert-butoxide in THF (10 mL, 10 mmol) dropwise over 5 minutes. The mixture was heated at 65–70° C. for 15 h. The mixture was cooled to room temperature, quenched with 1N HCl (excess) and poured into EtOAc. The organic layer was separated, washed with water (3×), saturated aq NaHCO$_3$, and brine, dried (MgSO$_4$), filtered and concentrated to ~40 mL. Upon standing, a bright orange solid precipitated which was isolated by filtration and dried under vacuum at 80–100° C. overnight affording the title compound (0.165 g, 17%). The mother liquor was concentrated onto SiO$_2$ and flash chromatography (30–50% EtOAc/hex) afforded additional product (0.212 g, 22%). $^1$H NMR (400 MHz, DMSO-d$_6$) 11.98 (br s, 1H), 11.13 (s, 1H), 7.76 (d, J=2.7 Hz, 1H), 7.60 (dd, J=8 Hz, 1H), 7.25 (d, J=3.1 Hz, 1H), 6.97 (dd, J=7, 7 Hz, 1H), 6.88 (dd, J=7, 1 Hz, 1H), 6.54 (d, J=7 Hz, 1H), 6.48 (d, J=3.1 Hz, 1H), 6.43 (dd, J=8, 8 Hz, 1H), 5.98 (d, J=8 Hz, 1H), 3.84 (s, 3H), 3.66 (s, 3H). MS (electrospray, m/z) 372.1 (M$^+$+1), 370.1 (M$^-$−1). HRMS 372.1330 (M$^+$+1, calcd for $C_{22}H_{18}N_3O_3$ 372.1348). Anal. Calcd for $C_{22}H_{17}N_3O_3$: C, 71.15; 4.61; N, 11.31. Found: C, 70.80; H, 4.58; N, 11.06.

(c) 12-Methoxy-5-methyl-5H,13H-indolo[6,7-a]pyrrolo[3,4-c]carbazole-6,8-dione

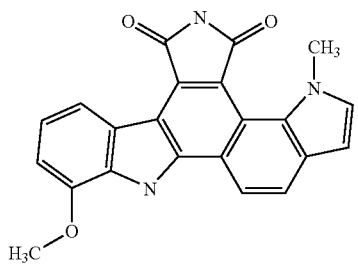

A solution of 3-(7-methoxy-1H-indol-3-yl)-4-(1-methyl-1H-indol-7-yl)-pyrrole-2,5-dione (0.210 g, 0.565 mmol) and DDQ (0.128 g, 0.563 mmol) in EtOAc (200 mL) was photolyzed with 450 W Hanovia lamp fitted with pyrex filter for 25 min. During this time the reaction temperature rose to 48° C. The mixture was washed pH 10 buffer (2×), saturated aq NaHCO$_3$, and brine (200 mL), dried (MgSO$_4$), filtered and concentrated to ~75 mL. Upon standing, a bronze solid formed which was isolated by filtration and dried under vacuum giving the title compound (0.086 g, 41%). The mother liquor was concentrated onto SiO$_2$ and flash chromatography (50–85% EtOAc/hex) gave additional product (0.118 g, 56%). $^1$H NMR (400 MHz, DMSO-d$_6$) 12.66 (s, 1H), 11.07 (s, 1H), 8.62 (d, J=8.6 Hz, 1H), 8.57 (d, J=7.8 Hz, 1H), 7.99 (d, J=8.6 Hz, 1H), 7.57 (d, J=3 Hz, 1H), 7.29 (dd, J=7.8, 7.8 Hz, 1H), 7.15 (d, J=7.8 Hz, 6.82 (d, J=3 Hz, 1H), 4.08 (s, 3H), 3.87 (s, 3H). MS (electrospray, m/z) 370.1 (M$^+$+1), 368.1 (M$^-$−1). HRMS 370.1187 (M$^+$+1, calcd for $C_{22}H_{16}N_3O_3$ 370.1192).

EXAMPLE 17

9-Hydroxymethyl-5-methyl-5H,13H-indolo[6,7-a]pyrrolo[3,4-c]carbazole-6,8-dione

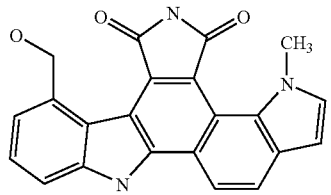

Using procedures similar to those detailed in Example 12, except for using in (a) 4-(t-butyldimethylsilyl)oxymethyl-indole, in (b) (4-hydroxymethyl-1H-indol-3-yl)-oxo-acetic acid methyl ester and in (c) 3-(4-(t-butyldimethylsilyl)oxymethyl-1H-indol-3-yl)-4-(1-methyl-1H-indol-7-yl)-pyrrole-2,5-dione, affords the title compound; MS (electrospray, m/z) 368.1 (M$^-$−1).

EXAMPLE 18

9-Bromo-5-methyl-5H,13H-indolo[6,7-a]pyrrolo[3,4-c]carbazole-6,8-dione

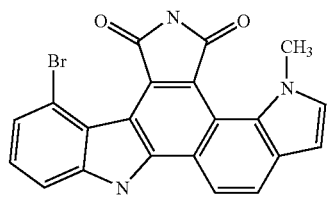

Using procedures similar to those detailed in Example 12, except for using in (a) 4-bromo-indole, in (b) (4-bromo-1H-indol-3-yl)-oxo-acetic acid methyl ester and in (c) 3-(4-brommo-1H-indol-3-yl)-4-(1-methyl-1H-indol-7-yl)-pyrrole-2,5-dione, affords the title compound; MS (electrospray, m/z) 420/418 (M$^+$+1), 418/416 (M$^-$−1).

EXAMPLE 19

9-Hydroxymethyl-13-(3-hydroxypropyl)-5-methyl-5H,13H-indolo[6,7-a]pyrrolo[3,4-c]carbazole-6,8-dione

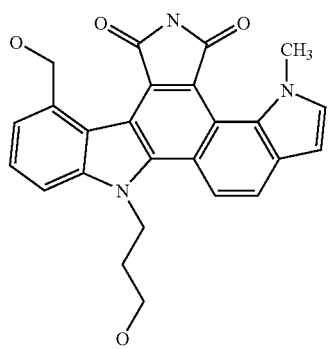

Using procedures similar to those detailed in Example 11, except for using in (a) 4-(t-butyldimethylsilyl)oxymethyl-indole, in (b) 1-[3-(tert-Butyl-dimethyl-silanyloxy)-propyl]-4-(t-butyldimethylsilyl)oxymethyl-1H-indole and in (c) 3-[1-(3-Hydroxy-propyl)-4-hydroxymethyl-1H-indol-3-yl]-4-(1-methyl-1H-indol-7-yl)-pyrrole-2,5-dione, affords the title compound; MS (electrospray, m/z) 410.1 (M$^+$+1).

EXAMPLE 20

9-Bromo-13-(3-hydroxypropyl)-5-methyl-5H,13H-indolo[6,7-a]pyrrolo[3,4-c]carbazole-6,8-dione

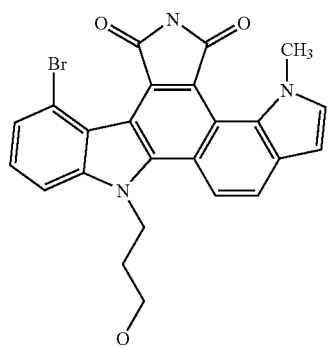

Using procedures similar to those detailed in Example 11, except for using in (a) 4-bromo-indole, in (b) 1-[3-(tert-Butyl-dimethyl-silanyloxy)-propyl]-4-bromo-1H-indole and in (c) 3-[1-(3-Hydroxy-propyl)-4-bromo-1H-indol-3-yl]-4-(1-methyl-1H-indol-7-yl)-pyrrole-2,5-dione, affords the title compound; MS (electrospray, m/z) 478.1/476.1 (M$^+$+1), 476.1/474.1 (M$^-$−1).

EXAMPLE 21

9-Methoxy-13-(3-hydroxypropyl)-5-methyl-5H,13H-indolo[6,7-a]pyrrolo[3,4-c]carbazole-6,8-dione

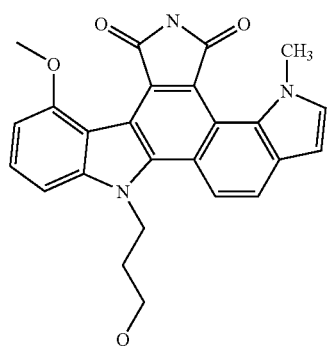

Using procedures similar to those detailed in Example 11, except for using in (a) 4-methoxy-indole, in (b) 1-[3-(tert-Butyl-dimethyl-silanyloxy)-propyl]-4-methoxy-1H-indole and in (c) 3-[1-(3-Hydroxy-propyl)-4-methoxy-1H-indol-3-yl]-4-(1-methyl-1H-indol-7-yl)-pyrrole-2,5-dione, affords the title compound; MS (electrospray, m/z) 428.2 (M$^+$+1), 426.3 (M$^-$−1).

EXAMPLE 22

13-(3-Hydroxypropyl)-5-ethyl-5H,13H-indolo[6,7-a]pyrrolo[3,4-c]carbazole-6,8-dione.

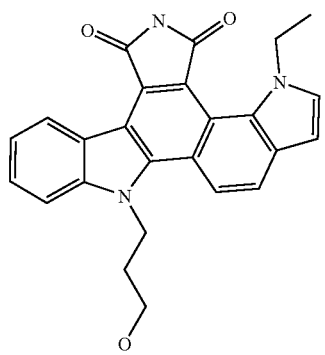

Using procedures similar to those detailed in Example 10, except for using in (a) (1-ethyl-1H-indol-7-yl)-oxo-acetic acid methyl ester, in (b) 3-[1-(3-hydroxypropyl)-1H-indol-2-yl]-4-(1-ethyl-1H-indol-7-yl)-pyrrole-2,5-dione, affords the title compound; MS (electrospray, m/z) 412.2 ($M^+$+1), 410.2 ($M^-$−1).

EXAMPLE 23

13-(3-Hydroxypropyl)-7H-indolo[6,7-a]-pyrrolo[3,4-c]-carbazole-6,8-dione (a) 3-[1-(3-Hydroxypropyl)-1H-indol-3-yl]-4-(1H-indol-7-yl)-pyrrole-2,5-dione A 1.0 M solution of KOtBu in THF (8.1 mL, 8.1 mmol) was added to a solution of 2-(1-3-hydroxypropyl-1H-indol-3-yl)-acetamide (586 mg, 2.52 mmol) and {1-(2-trimethyl-silanyl-ethoxymethyl)-1H-indol-7-yl}-oxo-acetic acid methyl ester (770 mg, 2.31 mmol) in DMF (30 mL). The initially clear orange-red solution turned deep red over 15 min, and was then heated to 65 C. for 18 h. 1N HCl was added, the mixture stirred 8 h and then the volume was reduced to ~20 mL. The residue was poured into EtOAc/0.1 N HCl and the aqueous layer was separated and extracted with EtOAc. The EtOAc solutions were combined and washed with water, saturated aq $NaHCO_3$ and brine (3×), dried ($MgSO_4$), filtered and concentrated onto $SiO_2$. Flash chromatography (8:2 EtOAc:hexanes) afforded a red solid that was dried at 75° C. for overnight giving the title compound (454 mg, 51%) as a bright red solid. $^1H$ NMR (400 MHz, DMSO-$d_6$) 11.04 (s, 1H), 10.71 (s, 1H), 8.03 (s, 1H), 7.56–7.62 (m, 1H), 7.41 (d, J=8 Hz, 1H), 7.20 (dd, J=3, 3 Hz, 1H), 6.94–7.0 (m, 3H), 6.45 (dd, J=8, 8 Hz, 1H), 6.40–6.43 (m, 1H), 6.11 (d, J=8 Hz, 1H), 4.64 (t, J=5 Hz, 1H), 4.29 (t, J=7 Hz, 2H), 3.38 (s, 2H), 1.88 (m, 2H). MS (electrospray, m/z) 386.2 ($M^+$+1), 384.2 ($M^-$−1). HRMS 386.1504 ($M^+$+1, calcd for $C_{23}H_{20}N_3O_3$ 386.1505)

(b) 13-(3-Hydroxypropyl)-7H-indolo[6,7-a]-pyrrolo[3,4-c]-carbazole-6,8-dione

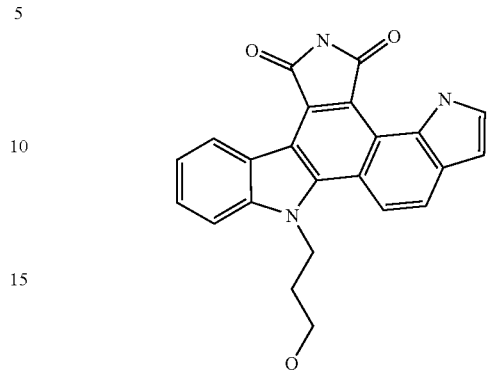

A solution of 3-[1-(3-hydroxypropyl)-1H-indol-2-yl]-4-(1H-indol-7-yl)-pyrrole-2,5-dione (243 mg, 0.631 mmol) and $I_2$ (160 mg, 0.63 mmol) in dioxane (200 mL) was irradiated with a 450 W Hanovia medium pressure lamp through a pyrex filter for 90 min. A 10% aq solution of $NaHSO_3$ was added, the mixture concentrated to ~50 mL, and poured into EtOAc. The EtOAc solution was washed with 10% aq $NaHSO_3$, saturated aq $NaHCO_3$, and brine. The solution was dried (MgSO4 and concentrated. TLC and $^1H$ NMR indicated a 1:1 mixture of starting material and desired product. The residue was taken up in dioxane (200 mL), $I_2$ (74 mg, 0.29 mmol) and the photolysis continued for 2 h. The dark red mixture was worked up as described above and the dried solution was concentrated to ~50 mL, when a precipitate started to form. The mixture was heated to reflux and filtered through a plug of glass wool. The filtrate was allowed to cool, and filtration afforded the title product as a bright red solid which was dried under vacuum at 75–80 C. overnight leaving a maroon solid (99 mg, 41%). $^1H$ NMR (400 MHz, DMSO-$d_6$) 12.96 (s, 1H), 11.59 (s, 1H), 9.19 (d, J=8 Hz, 1H), 8.52 (d, J=9 Hz, 1H), 8.09 (d, J=9 Hz, 1H), 7.90 (d, J=8 Hz, 1H), 7.75 (dd, J=3, 3 Hz, 1H), 7.63 (dd, J=8, 8 Hz, 1H), 7.43 (dd, J=8, 8 Hz, 1H), 6.81 (dd, J=3, 3 Hz, 1H), 5.00 (t, J=7.5 Hz, 2H), 4.90 (t, J=5 Hz, 1H), 3.63 (m, 2H), 2.18 (m, 2H). MS (electrospray, m/z) 384 ($M^+$+1), 382 ($M^-$−1). HRMS 384.1331 ($M^+$+1, calcd for $C_{23}H_{18}N_3O_3$ 384.1348).

EXAMPLE 24

11-hydroxy-5-methyl-5H,13H-indolo[6,7-a]pyrrolo[3,4-c]carbazole-6,8-dione (a) 3-(6-Benzyloxy-1H-indol-3-yl)-4-(1-methyl-1H-indol-7-yl)-pyrrole-2,5-dione To a suspension of (6-benzyloxy-1H-indol-3-yl}-oxo-acetic acid methyl ester (1.0 g, 3.2 mmol) and 2-(1-methyl-1H-indol-7-yl)-acetamide (608 mg, 3.2 mmol) in 15 ml THF was added 3.5 equiv. of tBuOK in THF at 0° C. (11.3 ml of 1.0 M solution in THF) under $N_2$. The mixture was stirred at r.t overnight, quenched with conc. HCl 5.0 ml, and neutralized with 5 N NaOH to PH=8. The mixture was extracted with ethyl acetate, and the extract was washed with saturated NaHCO₃, brine and water, dried over anhydrous MgSO₄, filtered and concentrated. The residue was purified by flash chromatography with Hexane:Ethyl acetate (1:1) to yield the title compound (700 mg) as orange solid, 74% yield. MS(m/z): 448.2 (M⁺+1), 446.1 (M⁻−1); ¹HNMR (DMSO-d₆) 11.62 (s, 1H), 11.07 (s, 1H), 7.77 (d, J=1.80 Hz, 1H), 7.57 (m, 1H ), 7.26 (m, 5H), 7.21 (d, J=2.40 Hz, 1H), 6.94 (tri, J=6.00 Hz, 1H), 6.84 (m, 2H), 6.44(d, J=2.40 Hz, 1H), 6.16 (s, 1H), 4.97 (s, 2H), 3.62 (s, 3H).

(b) 11-benzyloxy-5-methyl-5H,13H-indolo[6,7-a]pyrrolo[3,4-c]carbazole-6,8-dione A solution of 3-(6-Benzyloxy-1H-indol-3-yl)-4-(1-methyl-1H-indol-7-yl)-pyrrole-2,5-dione, 530940 (100 mg, 0.22 mmol) and I₂ (62.5 mg, 0.25 mmol) in 500 ml dioxane was photolyzed for 30 min. The mixture was concentrated to 10 ml and diluted with ethyl acetate. The organic solution was washed with saturated Na₂S₂O₃, NaHCO₃, brine and water, dried over anhydrous MgSO₄, filtered, and concentrated. The residue was purified by flash chromatography with Hexane:Ethyl acetate (1:1) to yield the title compound (68 mg) as orange solid, 67% yield. MS(m/z): 444.1 (M⁺−1); ¹HNMR (DMSO-d₆) 12.57 (s, 1H), 11.01 (s, 1H), 8.77 (d, J=6.60 Hz, 1H), 8.16 (d, J=6.60 Hz, 1H), 7.97 (d, J=6.30 Hz, 1H), 7.55 (m, 3H), 7.40 (m, 2H), 7.28 (d, J=6.30 Hz, 1H ), 7.18 (d, J=1.2 Hz, 1H), 7.06 (m, 1H), 6.78 (d, J=2.10 Hz, 1H), 5.21 (s, 2H), 3.80 (s, 3H).

(c) 11-hydroxy-5-methyl-5H,13H-indolo[6,7-a]pyrrolo[3,4-c]carbazole-6,8-dione

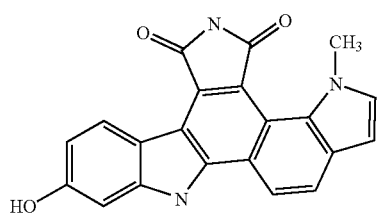

To a solution of 11-benzyloxy-5-methyl-5H,13H-indolo[6,7-a]pyrrolo[3,4-c]carbazole-6,8-dione (30 mg, 0.067 mmol) in 200 ml ethyl acetate was added 20 mg 10% Pd on carbon, and the mixture hydrogenated at rt for 6 hr. The mixture was filtered and concentrated. The residue was washed with small amount of ethyl acetate to yield the title compound (20 mg) as dark redish range solid, 83% yield. MS(m/z): 354.1 (M⁺−1); ¹HNMR (DMSO-d₆) 12.37 (s, 1H), 10.96 (s, 1H), 9.72 (s, 1H, OH), 8.67 (d, J=6.30 Hz, 1H), 8.12 (d, J=6.60 Hz, 1H), 7.95 (d, J=6.00 Hz, 1H), 7.51 (d, J=2.40 Hz, 1H), 7.01 (d, J=1.50 Hz, 1H), 6.81 (m, 2H ), 3.84 (s, 3H).

EXAMPLE 25

1,5-Dimethyl-5H,13H-indolo[6,7-a]pyrrolo[3,4-c]carbazole-6,8-dione

(a) 5-Methyl-7-bromoindole

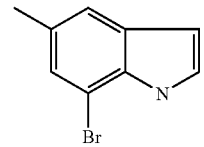

2-Bromo-4-methyl-aniline (10.0 g, 53.7 mmol) was added dropwise to a solution of boron trichloride in methylene chloride (1.0 M, 60 mL, 60 mmol) cooled with ice water. The reaction mixture was warmed to room temperature, stirred for 30 min, and chloroacetonitrile (10 mL, 64.4 mmol) and aluminum chloride (10 g, 59.8 mmol) added, followed by 1,2-dichloroethane (70 mL). The reaction mixture was heated to 70° C. to distill off methylene chloride, and then refluxed for 24 hrs. The mixture was cooled to 0–5° C., treated with 25 M HCl (96 mL) at 0~5° C. carefully, and then heated to 80° C. for 1 h until all solids dissolved. The aqueous layer was separated and extracted with methylene chloride. The combined organic layers were washed with water and brine, dried (sodium sulfate) and concentrated a yellow solid (11.6 g, 82.3%), that was used without-further purification. The crude product was taken into dioxane (76 mL) and water (8.5 mL), and treated with sodium borohydride (1.75 g, 46.3 mmol) in portions. After 30 min at room temperature, all the starting material was consumed, and the reaction mixture was heated to reflux for 14 h. The mixture was then cooled to room temperature, treated with 0.1 N HCl (74 mL), and extracted with ethyl acetate. The extract was washed with water and brine, dried (Na₂SO₄) and concentrated. Column chromatography on silica gel (hexanes/ethyl acetate) gave 5-methyl-7-bromoindole (8.0 g, 90%). 1H NMR (400 MHz, CDCl₃) 2.43 (s, 3H), 6.54 (dd, J1=1.94 Hz, J2=3.13 Hz, 1H), 7.20 (d, J=0.78 Hz, 1H), 7.22 (m, 1H), 7.36 (m, 1H), 8.22 (br, 1H); MS (ES, m/z): C₉H₈BrN: 210 (M+(⁷⁹Br)+1), 212.0 (M+(⁸¹Br)+1).

(b) 1,5-Dimethyl-7-bromoindole

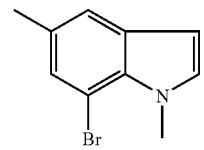

To a suspension of sodium hydride (60%, 0.91 g, 22.9 mmol) in DMF (70 mL) was added a solution of 5-methyl-7-bromoindole (4.0 g, 19.05 mmol) in DMF (10 mL). The mixture was stirred at room temperature for 1 h, and then methyl iodide (1.78 mL, 28.6 mmol) was added with cooling in an ice-water-bath. The reaction mixture was allowed to warm to room temperature and stirred overnight. The reaction was quenched with water and extracted with ethyl acetate. The extract was washed with water and brine, dried (sodium sulfate) and concentrated to give a crude product (4.1 g, 96%), which was used without further purification. 1H NMR (400 MHz, CDCl3) δ 2.38 (s, 3H), 4.12 (s, 3H), 6.36 (d, J=3.12 Hz, 1H), 6.95 (d, J=3.13 Hz, 1H), 7.18 (d, J=1.56 Hz, 1H), 7.31 (dd, J1=0.79 Hz, J2=1.56 Hz, 1H).

(c) (1,5-Dimethyl-1H-indol-7-yl)-oxo-acetic acid methyl ester

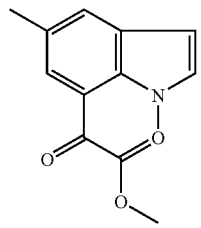

A solution of 1,5-dimethyl-7-bromoindole (4.27 g, 19.05 mmol) in THF (130 mL) was cooled to −78° C. and a solution of tert-butyl lithium in pentanes (1.7 M, 24.6 mL, 41.8 mmol) added dropwise over 30 min. After 30 min at −78° C., the mixture was treated with dimethyl oxalate (5.62 g, 47.6 mmol) in one portion. After 15 min, the mixture was allowed to warm to room temperature and stirred 4 h. The reaction mixture was quenched with water, extracted with ethyl acetate, and the extracts washed with brine, dried ($Na_2SO_4$) and concentrated. Flash chromatography (EtOAc/hexanes) afforded the title compound (4.2 g, 95%) as bright yellow oil. 1H NMR (400 MHz, $CDCl_3$) δ 2.46 (s, 3H), 3.85 (s, 3H), 4.01 (s, 3H), 6.51 (dd, J1=1.17 Hz, J2=3.13 Hz, 1 H), 7.06 (d, J=3.13 Hz, 1H), 7.36 (s, 1H), 7.69 (s, 1H); MS (ES, m/z): $C_{13}H_{13}NO_3$: 232.19 (M++1).

(d) 3-(1,5-Dimethyl-1H-indol-7-yl)-4-(1H-indol-3-yl]-pyrrole-2,5-dione

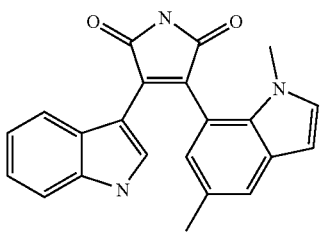

To a mixture of (1,5-dimethyl-1H-indol-7-yl)-oxo-acetic acid methyl ester (0.51 g, 2.21 mmol) and 2-(1H-indol-3-yl-acetamide (0.35 g, 2 mmol) in DMF (20 mL) was added a solution of potassium tert-butoxide in THF (1.0 M, 8.0 mL, 8.0 mmol) at room temperature. The reaction mixture was heated at 50° C. for 18 h, cooled to room temperature, and quenched with hydrochloric acid (1.0 N). After 30 min at room temperature, the mixture was extracted with ethyl acetate and the extract washed with water, saturated aqueous sodium bicarbonate and brine, dried (sodium sulfate), filtered and concentrated. Flash column chromatography on silica gel eluting with chloroform and acetone gave 3-(1,5-dimethyl-1H-indol-7-yl)-4-(1H-indol-3-yl]-pyrrole-2,5-dione (400 mg, 56.3%). 1HNMR (DMSO-$d_6$, 400 MHz) 2.28 (s, 3H), 3.64 (s, 3H), 6.39 (d, J=3.07 Hz, 1H), 6.50 (t, J=7.66 Hz, 1H), 6.53 (t, J=7.00 Hz, 1H), 6.74 (d, J=1.4 Hz, 1H), 7.0 (t, J=7.47 Hz, 1H), 7.20 (d, J=3.09 Hz, 1H), 7.35 (d, J=8.11 Hz, 1H), 7.41 (s, 1H), 7.88 (d, J=3.0 Hz, 1H), 11.13 (s, 1H), 11.84 (s, 1H); MS (ES, m/z): $C_{22}H_{17}N_3O_2$: 356.2 (M++1); 354.2 (M+−1).

e) 1,5-Dimethyl-5H,13H-indolo[6,7-a]pyrrolo[3,4-c]carbazole-6,8-dione

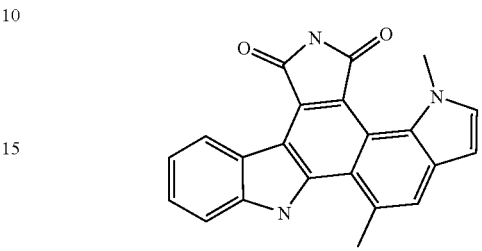

A solution of 3-(1,5-dimethyl-1H-indol-7-yl)-4-(1H-indol-3-yl]-pyrrole-2,5-dione (200 mg, 0.56 mmol) and iodine (150 mg, 0.59 mmol) in ethyl acetate (500 mL) was irradiated with a medium pressure Hanovia lamp (450 w). After 15 min, TLC and HPLC showed that all starting material was consumed, and the reaction mixture was washed with aqueous sodium hydrosulfite and brine, dried (sodium sulfate), filtered and concentrated under vacuum. Flash column chromatography on silica gel eluting with toluene-acetone gave a yellow solid (110 mg, 39.8%). 1HNMR (DMSO-$d_6$, 400 MHz) 3.23 (s, 3H), 3.84 (s, 3H), 6.76 (d, J=3.13 Hz, 1H), 7.42 (t, J=7.43 Hz, 1H), 7.56~7.60 (m, 2), 7.84 (s, 1H), 7.95 (d, J=8.21 Hz, 1H), 9.10 (d, J=7.82 Hz, 1H), 11.12 (s, 1H), 11.62 (s, 1H); MS (ES, m/z): $C_{22}H_{15}N_3O_2$: 354.16 (M++1): 352.24 (M+−1).

EXAMPLE 26

13-(3-Hydroxypropyl)-1,5-Dimethyl-5H,13H-indolo[6,7-a]pyrrolo[3,4-c]carbazole-6,8-dione.

(a) 3-(1,5-Dimethyl-1H-indol-7-yl)-4-[1-(4-hydroxy-propyl)-1H-indol-3-yl]-pyrrole-2,5-dione

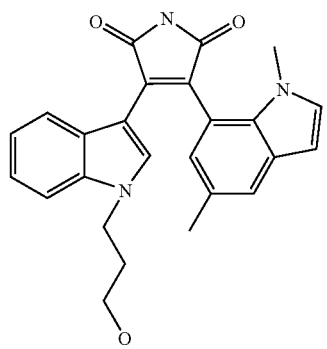

To a mixture of (1,5-dimethyl-1H-indol-7-yl)-oxo-acetic acid methyl ester (0.51 g, 2.20 mmol) and 2-[1-(3-hydroxypropyl)-1H-indol-3-yl]-acetamide (0.46 g, 2 mmol) in DMF (20 mL) was added a solution of potassium tert-butoxide in THF (1.0 M, 8 mL, 8 mmol) at room temperature. The reaction mixture was heated at 55° C. for 6 h, cooled to room temperature, and quenched with hydrochloric acid (1.0 N).

After stirring at room temperature for 30 min, the mixture was extracted with ethyl acetate and the extract washed with water, saturated aqueous sodium bicarbonate and brine, dried (sodium sulfate), filtered and concentrated. Flash column chromatography on silica gel eluting with chloroform and acetone gave 3-(1,5-dimethyl-1H-indol-7-yl)-4-[1-(4-hydroxy-propyl)-1H-indol-3-yl]-pyrrole-2,5-dione (480 mg, 58%). $^1$H NMR (d6-DMSO, 400 MHz) 1.84 (pent, J=7.43 Hz, 2H), 2.26 (s, 3H), 3.33 (m, 2H), 3.62 (s, 3H), 4.26 (t, J=7.04 Hz, 2H), 4.62 (br, 1H), 6.32 (d, J=7.82 Hz, 1H), 6.38 (d, J=3.12 Hz, 1H), 6.52 (t, J=8.21 Hz, 1H), 6.73 (d, J=1.56 Hz, 1H), 7.02 (t, J=7.62 Hz, 1H), 7.18 (d, J=3.13 Hz, 1H), 7.40 (s, 1H), 7.44 (d, J=8.6 Hz, 1H), 8.03 s, 1H), 11.14 (s, 1H); MS (ES, m/z): $C_{25}H_{23}N_3O_3$: 414.2($M^+$+1), 412.3 ($M^+$−1).

(b) 13-(3-Hydroxypropyl)-1,5-Dimethyl-5H,13H-indolo[6,7-a]pyrrolo[3,4-c]carbazole-6,8-dione

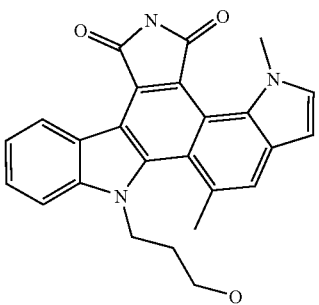

A solution of 3-(1,5-dimethyl-1H-indol-7-yl)-4-[1-(4-hydroxy-propyl)-1H-indol-3-yl]-pyrrole-2,5-dione (250 mg, 0.6 mmol) and iodine (161 mg, 0.63 mmol) in ethyl acetate (500 mL) was irradiated with a medium pressure Hanovia lamp (450 w). After 60 min, TLC and HPLC showed that all starting material was consumed, and the reaction mixture was washed with aqueous sodium hydrosulfite and brine, dried (sodium sulfate), filtered and concentrated under vacuum. Flash column chromatography on silica gel eluting with toluene-acetone afforded a yellow solid (120 mg, 48.7%). $^1$HNMR (d6-DMSO, 400 MHz) 2.79–2.82 (m, 2H), 2.82 (s, 3H), 3.34 (m, 2H), 3.82 (s, 3H), 4.62 (m, 2H), 6.73 (d, J=2.74 Hz, 1H), 7.43 (t, J=7.43 Hz, 1H), 7.54 (d, J=3.13 Hz, 1H), 7.59 (t, J=7.63 Hz, 1H), 7.77 (s, 1H), 7.85 (d, J=8.21 Hz, 1H), 9.06 (d, J=8.21 Hz, 1H), 11.1 (s, 1H); $C_{25}H_{21}N_3O_3$: 412.1 ($M^+$+1), 410.2 ($M^+$−1).

EXAMPLE 27

1-Methoxy-5-methyl-5H,13H-indolo[6,7-a]pyrrolo[3,4-c]-carbazole-6,8-dione (a) 5-Methoxy-7-bromoindole

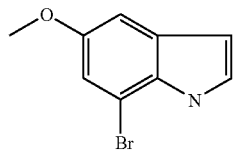

2-Bromo-4-methoxy-aniline (5.0 g, 24.7 mmol) was added dropwise to a solution of boron trichloride in methylene chloride (1.0 M, 27 mL, 27 mmol) cooled with ice water. The reaction mixture was warmed to room temperature, stirred for 30 min, and chloroacetonitrile (4.55 mL, 29.7 mmol) and aluminum chloride (4.54 g, 27.2 mmol) added, followed by 1,2-dichloroethane (32 mL). The reaction mixture was heated to 70° C. to distill off methylene chloride, and then refluxed for 24 h. The mixture was cooled to 0–5° C., treated with 2.5 M HCl (44 mL) at 0–5° C. carefully, and then heated to 80° C. for 1 h until all solids dissolved. The aqueous layer was separated and extracted with methylene chloride. The combined organic layers were washed with water and brine, dried (sodium sulfate) and concentrated a yellow solid, that was used without further purification. The crude product was taken into dioxane (19 mL) and water (2.1 mL), and treated with sodium borohydride (0.46 g, 12.2 mmol) in portions. After 30 min at room temperature, all the starting material had been consumed, and the reaction mixture was heated to reflux overnight. The mixture was then cooled to room temperature, treated with 0.1 N hydrochloric acid (195 mL), diluted with ethyl acetate, treated with concentrated hydrochloric acid and trifluoroacetic acid and stirred until all the hydroxy-intermediate was converted to the final product. The reaction mixture was then extracted with ethyl acetate, and the extract was washed with sodium bicarbonate, water and brine, dried ($Na_2SO_4$) and concentrated. Column chromatography on silica gel (hexanes/ethyl acetate) gave 4-methoxy-7-bromoindole (1.5 g, 59.8%). $^1$H NMR (400 MHz, $CDCl_3$) 3.77 (s, 3H), 6.47~6.49 (m, 1H), 6.99 (s, 2H), 7.17(m, 1H), 8.11 (br, 1H); MS (ES, m/z): $C_9H_8BrNO$: 228 ($M^+$($^{79}$Br)+1), 226.01 ($M^+$($^{81}$Br)+1), 224.03 ($M^+$($^{79}$Br)−1), 226.04 ($M^+$($^{81}$Br)−1).

(b) 1-Methyl-5-methoxy-7-bromoindole

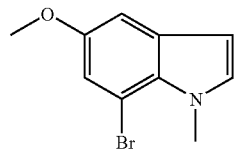

To a suspension of sodium hydride (60%, 0.32 g, 7.96 mmol) in DMF (18 mL) was added a solution of 5-methoxy-7-bromoindole (1.5 g, 6.63 mmol) in DMF (25 mL). The mixture was stirred at room temperature for 1 h, and then methyl iodide (0.62 mL, 9.95 mmol) was added with cooling in an ice-water-bath. The reaction mixture was allowed to warm to room temperature and stirred overnight. The reaction was quenched with water and extracted with ethyl acetate. The extract was washed with water and brine, dried (sodium sulfate) and concentrated to give a crude product (1.6 g, 100%), which was used without further purification. $^1$HNMR (400 MHz, $CDCl_3$) 3.82 (s, 3H), 4.10 (s, 3H), 6.36 (d, J=3.13 Hz, 1H), 6.96 (d, J=2.74 Hz, 1H), 7.0 (d, J=2.35 Hz, 1H), 7.03 (d, J=2.35 Hz, 1H); MS (ES, m/z): $C_{10}H_{10}BrNO$: 240.08 ($M^+$($^{79}$Br)+1), 242.1 ($M^+$($^{81}$Br)+1).

(c) (1-methyl-5-methoxy-1H-indol-7-yl)-oxo-acetic acid methyl ester

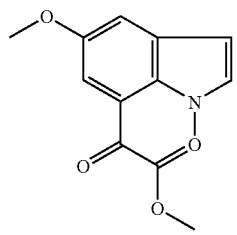

A solution of 1-methyl-5-methoxy-7-bromoindole (1.6 g, 6.66 mmol) in THF (44.5 mL) was cooled to −78° C. and a solution of tert-butyl lithium in pentanes (1.7 M, 8.62 mL, 14.7 mmol) added dropwise over 30 min. After 30 min at −78° C., the mixture was treated with dimethyl oxalate (1.96 g, 16.7 mmol) in one portion. After 15 min, the mixture was allowed to warm to room temperature and stirred 4 h. The reaction mixture was quenched with water, extracted with ethyl acetate, and the extracts washed with brine, dried ($Na_2SO_4$) and concentrated. Flash chromatography (EtOAc/hexanes) afforded the title compound (0.9 g, 54.7%) as bright yellow oil. $^1$HNMR (400 MHz, $CDCl_3$) 3.83 (s, 3H), 3.87 (s, 3H), 4.00 (s, 3H), 6.51 (d, J=3.12 Hz, 1 H), 7.07 (d, J=3.13 Hz, 1H), 7.21 (d, J=2.35 Hz, 1H), 7.7.40 (d, J=2.34 Hz, 1H); MS (ES, m/z): $C_{13}H_{13}NO_4$: 188.06 ($M^+$+1).

(d) 3-(1-Methyl-5-methoxy-1H-indol-7-yl)-4-(1H-indol-3-yl]-pyrrole-2,5-dione

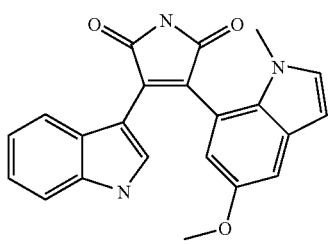

To a mixture of (1-methyl-5-methoxy-1H-indol-7-yl)-oxo-acetic acid methyl ester (0.27 g, 1.1 mmol) and 2-(1H-indol-3-yl-acetamide (0.17 g, 1 mmol) in DMF (5 mL) was added a solution of potassium tert-butoxide in THF (1.0 M, 4 mL, 4 mmol) at room temperature. The reaction mixture was heated at 50° C. for 7 h, cooled to room temperature, quenched with water, and the mixture extracted with ethyl acetate. The extract was washed with water, saturated aqueous sodium bicarbonate and brine, dried (sodium sulfate), filtered and concentrated. Flash column chromatography on silica gel eluting with chloroform and acetone gave 3(1-methyl-5-methoxy-1H-indol-7-yl)-4-(1H-indol-3-yl]-pyrrole-2,5-dione (210 mg, 56.5%). $^1$H NMR ($d_6$-DMSO, 400 MHz) 3.52 (s, 3H), 3.56 (s, 3H), 6.35~6.46 (m, 1H), 6.28 (d, J=2.93 Hz, 1H), 6.41 (t, J=2.44 Hz, 1H), 6.88 (t, J=6.84 Hz, 1H), 7.02 (d, J=2.44 Hz, 1H), 7.10 (d, J=3.42 Hz, 1H), 7.24 (d, J=7.82 Hz, 1H), 7.80 (d, J=2.93 Hz, 1H), 11.03 (s, 1H), 11.76 (m, 1H); MS (ES, m/z): $C_{22}H_{17}N_3O_3$: 372.2 ($M^+$+1); 370.3 ($M^+$−1).

e) 1-Methoxy-5-methyl-5H,13H-indolo[6,7-a]pyrrolo[3,4-c]-carbazole-6,8-dione

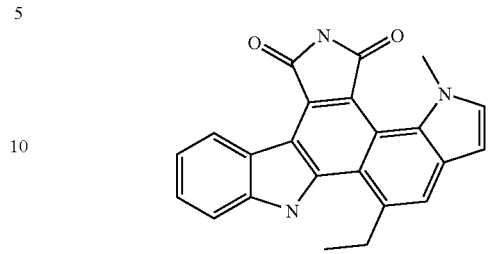

A solution 3-(1-methyl-5-methoxy-1H-indol-7-yl)-4-(1H-indol-3-yl]-pyrrole-2,5-dione (150 mg, 0.40 mmol) and iodine (103 mg, 0.40 mmol) in ethyl acetate (500 mL) was irradiated with a medium pressure Hanovia lamp (450 w). After 10 min, TLC and HPLC showed that all starting material was consumed, and the reaction mixture was washed with aqueous sodium hydrosulfite and brine, dried (sodium sulfate), filtered and concentrated under vacuum. Flash column chromatography on silica gel eluting with toluene-acetone gave a yellow solid (130 mg, 86.7%). $^1$H NMR (d6-DMSO, 400 MHz) 3.73 (s, 3H), 4.15 (s, 3H), 6.67 (d, J=3.13 Hz, 1H), 7.30 (t, J=7.63 Hz, 1H), 7.46~7.50 (m, 3H), 7.84 (d, J=7.82 Hz, 1H), 8.95 (d, J=7.82 Hz, 1H), 11.04 (s, 1H), 11.98 (s, 1H); MS (ES, m/z): $C_{22}H_{15}N_3O_3$: 368.23 ($M^+$−1).

EXAMPLE 28

11-Fluoro-1,5-Dimethyl-5H,13H-indolo[6,7-a]pyrrolo[3,4-c]carbazole-6,8-dione.

(a) 3-(1,5-dimethyl-1H-indol-7-yl)-4-(6-fluoro-1H-indol-3-yl)-pyyrole-2,5-dione

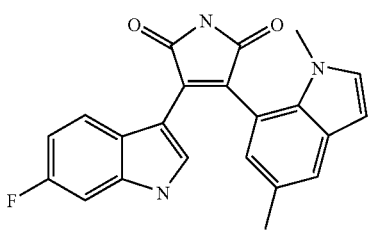

To a mixture of (1,5-dimethyl-1H-indol-7-yl)-oxo-acetic acid methyl ester (0.51 g, 2.21 mmol) and 2-(6-fluoro-1H-indol-3-yl)-acetamide (0.38 g, 2 mmol) in DMF (20 mL) was added a solution of potassium tert-butoxide in THF (1.0 M, 8.0 mL, 8.0 mmol) at room temperature. The reaction mixture was stirred at room temperature for 11 h, treated with concentrated hydrochloric acid (2 mL) and then heated at 50° C. for 2 h. The mixture was cooled to room temperature, extracted with ethyl acetate and the extract was washed with water, saturated aqueous sodium bicarbonate and brine dried (sodium sulfate), filtered and evaporated. Flash column chromatography on silica gel eluting with chloroform and acetone gave 2-(1,5-dimethyl-1H-indol-7-yl)-N-[2-(6-fluoro-1H-indol-3-yl)-acetyl]-2-oxo-acetamide (170 mg, 23%) and 3-(1,5-dimethyl-1H-indol-7-yl)-4-(6-fluoro-1H-indol-3-yl)-pyyrole-2,5-dione (340 mg, 45.5%). $^1$H NMR ($d_6$-DMSO, 400 MHz) δ 2.26 (s, 3H), 3.58 (s, 3H), 6.36 (d, J=3.13 Hz, 1H), 6.40–6.45 (m, 2H), 6.73 (s, 1H), 7.11 (dd, J$_1$=2.34 Hz, J$_2$=9.38 Hz, 1H), 7.16 (d, J=3.13 Hz, 1H), 7.7.39 (s, 1H), 7.80 (d, J=3.13 Hz, 1H), 11.14 (s, 1H), 11.82 (s, 1H); MS (ES, m/z): $C_{22}H_{16}FN_3O_2$: 374.2 (M$^+$+1); 372.2 (M$^+$–1).

b) 11-Fluoro-1,5-Dimethyl-5H,13H-indolo[6,7-a]pyrrolo[3,4-c]carbazole-6,8-dione

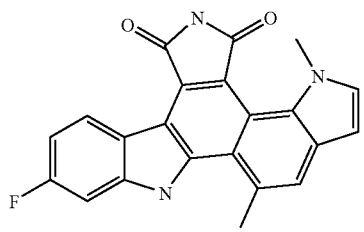

A solution of 3-(1,5-dimethyl-1H-indol-7-yl)-4-(6-fluoro-1H-indol-3-yl)-pyyrole-2,5-dione (200 mg, 0.56 mmol) and iodine (150 mg, 0.59 mmol) in dioxane (200 mL) was irradiated with a medium pressure Hanovia lamp (450 w). After 30 min, TLC and HPLC showed that all starting material was consumed, and the reaction mixture was washed with aqueous sodium hydrosulfite and brine, dried (sodium sulfate), filtered and concentrated under vacuum. Flash column-chromatography on silica gel eluting with toluene-acetone gave a yellow solid (40 mg, 20%). 1HNMR (d$_6$-DMSO, 400 MHz) 3.16 (s, 3H), 3.78 (s, 3H), 6.71 (d, J=2.74 Hz, 1H), 7.22 (m, 1H), 7.53 (d, J=2.73 Hz, 1H), 7.64 (m, 1H), 7.79 (s, 1H), 9.02 (m, 1H), 11.1 (s, 1H), 11.64 (s, 1H); $C_{22}H_{14}FN_3O_2$: 372.09 (M$^+$+1); 370.21 (M$^+$–1).

EXAMPLE 29

11-Methoxy-1,5-Dimethyl-5H,13H-indolo[6,7-a]pyrrolo[3,4-c]carbazole-6,8-dione (a) 3-(1,5-dimethyl-1H-indol-7-yl)-4-(6-methoxy-1H-indol-3-yl)-pyyrole-2,5-dione

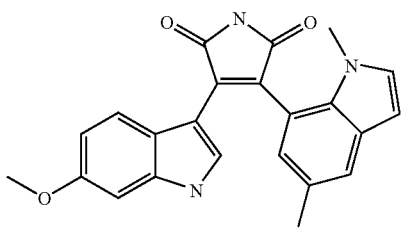

To a mixture of 2-(6-methoxyl-1H-indol-3-yl)-acetamide (0.41 g, 2.0 mmol) and (1,5-dimethyl-1H-indol-7-yl)-oxo-acetic acid methyl ester (0.51 g, 2.21 mmol) in DMF (20 mL) was added a solution of potassium tert-butoxide in THF (1.0 M, 8.0 mL, 8.0 mmol) at room temperature. The reaction mixture was heated at 50° C. for 18 h, cooled to room temperature, and quenched with hydrochloric acid (1.0 N). After stirring at room temperature for 30 min, the mixture was extracted with ethyl acetate and the extract washed with water, saturated aqueous sodium bicarbonate and brine dried (sodium sulfate), filtered and evaporated. Flash column chromatography on silica gel eluting with chloroform and acetone gave 3-(1,5-dimethyl-1H-indol-7-yl)-4-(6-methoxyl-1H-indol-3-yl)-pyyrole-2,5-dione (460 mg, 59.7%). $^1$HNMR (d$_6$-DMSO, 400 MHz) 2.26 (s, 3H), 3.58 (s, 3H), 3.64 (s, 3H), 6.14 (dd, J1=2.4 Hz, J2=9.2 Hz, 1H), 6.28 (d, J=9.2 Hz, 1H), 6.36 (d, J=3.2 Hz, 1H), 6.71 (d, J=1.6 Hz, 1H), 6.80 (d, J=2.4 Hz, 1H), 7.16 (d, J=2.8 Hz, 1H), 7.38 (s, 1H), 7.75 (d, J=2.8 Hz, 1H), 11.07 (s, 1H), 11.60 (s, 1H); MS (ES, m/z): $C_{23}H_{19}N_3O_3$: 386.1 (M$^+$+1); 384.2 (M$^+$–1).

b) 11-Methoxy-1,5-Dimethyl-5H,13H-indolo[6,7-a]pyrrolo[3,4-c]carbazole-6,8-dione

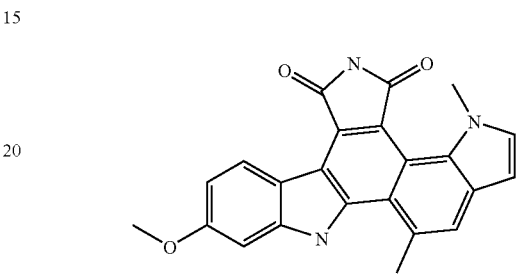

A solution of 3-(1,5-dimethyl-1H-indol-7-yl)-4-(6-methoxyl-1H-indol-3-yl)-pyyrole-2,5-dione (185 mg, 0.48 mmol) and iodine (128 mg, 0.50 mmol) in ethyl acetate (500 mL) was irradiated with a medium pressure Hanovia lamp (450 w). After 10 min, TLC and HPLC showed that all starting material was consumed, and the reaction mixture was washed with aqueous sodium hydrosulfite and brine, dried (sodium sulfate), filtered and concentrated under vacuum. Flash column chromatography on silica gel eluting with toluene-acetone gave a yellow solid (110 mg, 59.8%). $^1$HNMR (d$_6$-DMSO, 400 MHz) 3.15 (s, 3H), 3.78 (s, 3H), 3.90 (s, 3H), 6.69 (d, J=3.2. Hz, 1H), 6.99 (dd, J1=2.4 Hz, J2=8.8 Hz, 1H)), 7.41 (d, J=2.4 Hz, 1H), 7.50 (d, J=3.2 Hz, 1H), 7.76 (s, 1H), 8.88 (d, J=8.8 Hz, 1H), 11.02 (s, 1H), 11.47 (s, 1H); MS (ES, m/z): $C_{23}H_{17}N_3O_3$: 384.16 (M$^+$+1), 382.25 (M$^+$–1).

EXAMPLE 30

11-Trifluoromethyl-1,5-Dimethyl-7H,13H-indolo[6,7-a]pyrrolo[3,4-c]carbazole-6,8-dione (a) 3-(1,5-Dimethyl-1H-indol-7-yl)-4-(6-trifluoromethyl-1H-indol-3-yl)-pyyrole-2,5-dione

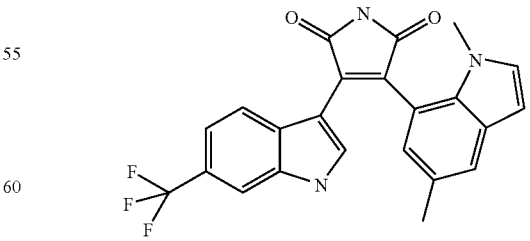

To a mixture of (1,5-dimethyl-1H-indol-7-yl)-oxo-acetic acid methyl ester (0.40 g, 1.73 mmol) and 2-(6-trifluoromethyl-1H-indol-3-yl-acetamide (0.38 g, 1.57 mmol) in DMF (10 mL) was added absolution of potassium tert-butoxide in THF (1.0 M, 6.3 mL, 6.3 mmol) at room temperature. The reaction mixture was heated at 55° C. for 19 h, cooled to room temperature, and quenched with hydrochloric acid (1.0 N). After stirring at room temperature for 30 min, the mixture was extracted with ethyl acetate and the extract washed with water, saturated aqueous sodium bicarbonate and brine dried (sodium sulfate), filtered and evaporated. Flash column chromatography on silica gel eluting with chloroform and acetone gave 3-(1,5-dimethyl-1H-indol-7-yl)-4-(6-trifluoromethyl-1H-indol-3-yl)-pyrrole-2,5-dione (400 mg, 60.2%). $^1$HNMR ($d_6$-DMSO, 400 MHz) 2.26 (s, 3H), 3.58 (s, 3H), 6.36 (d, J=3.2 Hz, 1H), 6.71 (d, J=8.4 Hz, 1H), 6.76 (d, J=1.2 Hz, 1H), 6.83 (d, J=8.0 Hz, 1H), 7.17 (d, J=3.2 Hz, 1H), 7.40 (s, 1H), 7.68 (s, 1H), 7.96 (d, J=2.8 Hz, 1H), 11.21 (s, 1H), 12.13 (s, 1H); MS (ES, m/z): $C_{23}H_{16}F_3N_3O_2$: 424.13 (M$^+$+1): 422.23 (M$^+$−1).

b) 11-Trifluoromethyl-1,5-Dimethyl-5H,13H-indolo[6,7-a]pyrrolo[3,4-c]carbazole-6,8-dione

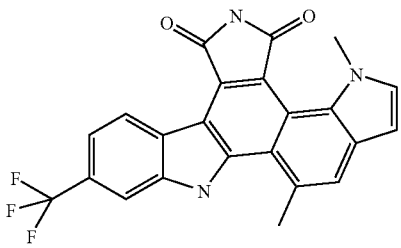

A solution of 3-(1,5-dimethyl-1H-indol-7-yl)-4-(6-trifluoromethyl-1H-indol-3-yl)-pyrrole-2,5-dione (190 mg, 0.449 mmol) and iodine (114 mg, 0.449 mmol) in ethyl acetate (500 mL) was irradiated with a medium pressure Hanovia lamp (450 w). After 10 min, TLC and HPLC showed that all starting material was consumed, and the reaction mixture was washed with aqueous sodium hydrosulfite and brine, dried (sodium sulfate), filtrated and concentrated under vacuum to ca. 5 mL. Upon standing, a yellow solid product precipitated which was collected by filtration (100 mg, 52.6%). $^1$H NMR (d6-DMSO, 400 MHz) 3.12 (s, 3H), 3.75 (s, 3H), 6.67 (d, J=3.2 Hz, 1H), 7.51 (d, J=3.2 Hz, 1H), 7.60 (d, J=8.4 Hz, 1H), 7.77 (s, 1H), 8.22 (s, 1H), 9.11 (d, J=8.0 Hz, 1H), 11.12 (s, 1H), 11.80 (s, 1H); $C_{23}H_{14}F_3N_3O_2$: 422.13 (M$^+$+1), 420.24 (M$^+$−1).

EXAMPLE 31

1-Fluoro-5-methyl-5H,13H-indolo[6,7-a]pyrrolo[3,4-c]carbazole-6,8-dione (a) 5-Fluoro-7-bromoindole

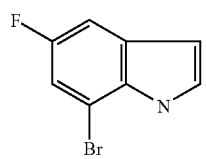

2-Bromo-4-fluoro-aniline (13.8 g, 72.6 mmol) was added dropwise to a solution of boron trichloride in methylene chloride (1.0 M, 81.1 mL, 81.1 mmol) cooled with ice water. The reaction mixture was warmed to room temperature, stirred for 30 min, and chloroacetonitrile (13.5 mL, 87.1 mmol) and aluminum chloride (13.5 g, 98.4 mmol) added, followed by 1,2-dichloroethane (95 mL). The reaction mixture was heated to 70° C. to distill off methylene chloride, and then refluxed for 24 h. After cooling to 0–5° C., the mixture was treated with 2.5 M HCl (130 mL) carefully, and then heated to 80° C. for 1 h until all solids dissolved. The aqueous layer was separated and extracted with methylene chloride. The combined organic solutions were washed with water and brine, dried (sodium sulfate) and concentrated to a yellow solid (11, 56.9%), which was used without further purification. The crude product was taken into dioxane (68 mL) and water (7.6 mL), and treated with sodium borohydride (1.64 g) in portions. After 30 min at room temperature, all the starting material was consumed, and the reaction mixture was heated to reflux for 18 h. The mixture was cooled to room temperature, treated with 0.1 N HCl (70 mL), 2N HCl (20 mL) and concentrated HCl (15 mL), and extracted with ethyl acetate. The organic layer was separated and washed with water and brine, dried (sodium sulfate), and concentrated. Column chromatography on silica gel (hexanes/ethyl acetate) gave 5-fluoro-7-bromoindole (4.4 g, 52.2%). $^1$H NMR (400 MHz, CDCl$_3$) 6.49, (dd, J1=2.35 Hz, J2=3.13 Hz, 1H), 7.06 (d, J1=2.35 Hz, J2=8.60 Hz, 1H), 7.14~7.17 (m, 2H), 8.18 (br, 1H); MS (ES, m/z): $C_8H_5BrFN$: 211.9 (M$^+$($^{79}$Br)−1), 214.0 (M$^+$($^{81}$Br)−1).

(b) 1-Methyl-5-fluoro-7-bromoindole

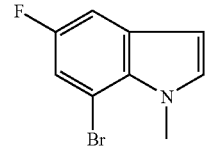

To a suspension of sodium hydride (60%, 1.75 g, 43.8 mmol) in DMF (134 mL) was added a solution of 5-fluoro-7-bromoindole (7.8 g, 36.4 mmol) in DMF (10 mL). After 1 h at room temperature, the mixture was treated with methyl iodide (3.4 mL, 54.6 mmol) with cooling in an ice-water bath. The reaction mixture was allowed to warm up room temperature and stirred overnight. The reaction was quenched with water, extracted with ethyl acetate, and the organic layer was washed with water and brine, dried (sodium sulfate) and concentrated to give a crude product, which was used without further purification. $^1$H NMR (400 MHz, CDCl$_3$) 4.06 (s, 3H), 6.34 (d, J=3.13 Hz, 1H), 6.96 (d, J=3.13 Hz, 1H), 7.07 (dd, J1=2.34 Hz, J2=8.60 Hz, 1H), 7.12 (dd, J1=2.34 Hz, J2=9.0 Hz, 1H).

(c) (1-Methyl-5-fluoro-1H-indol-7-yl)-oxo-acetic acid methyl ester

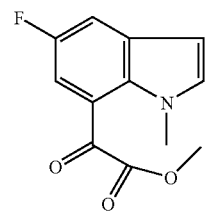

A solution of 1-methyl-5-fluoro-7-bromoindole (8.3 g, 36.4 mmol) in THF (250 mL) was cooled to −78° C. and a solution of tert-butyl lithium in pentanes (1.7 M, 47 mL, 80.1 mmol) added dropwise over 30 min. After 30 min at −78° C., the mixture was treated with dimethyl oxalate (10.75 g, 91 mmol) in one portion. After 15 min, the mixture was allowed to warm to room temperature and stirred 4 h. The reaction mixture was quenched with water, extracted with ethyl acetate and the extract washed with brine, dried ($Na_2SO_4$) and concentrated. Flash chromatography (EtOAc/hexanes) afforded the title compound (4.2 g, 49%). $^1$H NMR (400 MHz, $CDCl_3$) 3.83(s, 3H), 4.01 (s, 3H), 6.56 (d, J=3.13 Hz, 1H), 7.15 (d, J=3.13 Hz, 1H), 7.35 (dd, J1=2.0 Hz, J2=9.4 Hz, 1H), 7.57 (dd, J1=2.34 Hz, J2=8.21 Hz, 1H); MS (ES, m/z): $C_{12}H_{10}FNO_3$: 235.22 ($M^+$+1).

(d) 3-(1-Methyl-5-fluoro-1H-indol-7-yl)-4-(1H-indol-3-yl]-pyrrole-2,5-dione

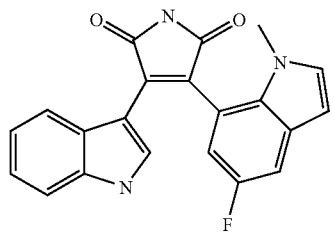

To a mixture of (1-methyl-5-fluoro-1H-indol-7-yl)-oxoacetic acid methyl ester (0.94 g, 4.0 mmol) and 2-(1H-indol-3-yl-acetamide (0.63 g, 3.64 mmol) in DMF (36 mL) was added a solution of potassium tert-butoxide in THF (1.0 M, 14.6 mL, 14.6 mmol) at room temperature. The reaction mixture was heated at 55° C. for 18 h, cooled to room temperature, and quenched with hydrochloric acid (conc.). After stirring at room temperature for 30 min, the mixture was extracted with ethyl acetate and the extract washed with water, saturated aqueous sodium bicarbonate and brine, dried (sodium sulfate), filtered and concentrated. Flash column chromatography on silica gel eluting with chloroform and acetone gave 3-(1-methyl-5-fluoro-1H-indol-7-yl)-4-(1H-indol-3-yl]-pyrrole-2,5-dione (0.72 mg, 55%). $^1$H NMR ($d_6$-DMSO, 400 MHz) 3.67 (s, 3H), 6.34 (d, J=7.82 Hz, 1H), 6.48 (d, J=3.12 Hz, 1H), 6.54 (t, J=7.62 Hz, 1H), 6.77 (dd, J1=2.34 Hz, J2=9.77 Hz, 1H), 6.99 (t, J=7.42 Hz, 1H), 7.33~7.42 (m, 3H), 7.97 (d, J=3.13 Hz, 1H), 11.20 (s, 1H), 11.93 (s, 1H); MS (ES, m/z): $C_{21}H_{14}FN_3O_2$: 360.15 ($M^+$+1), 358.23 ($M^+$−1).

e) 1-Fluoro-5-methyl-5H,13H-indolo[6,7-a]pyrrolo[3,4-c]carbazole-6,8-dione

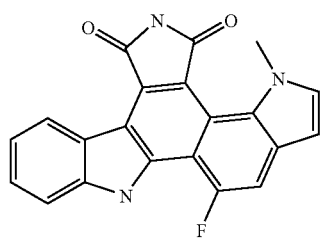

A solution of 3-(1-methyl-5-fluoro-1H-indol-7-yl)-4-(1H-indol-3-yl]-pyrrole-2,5-dione (250 mg, 0.70 mmol) and iodine (185 mg, 0.73 mmol) in ethyl acetate (500 mL) was irradiated with a medium pressure Hanovia lamp (450 w). After 26 min, TLC and HPLC showed that all starting material was consumed, and the reaction mixture was washed with aqueous sodium hydrosulfite and brine, dried (sodium sulfate), filtered and concentrated under vacuum. Flash column chromatography on silica gel eluting with toluene-acetone afforded a yellow solid (140 mg, 56%). $^1$H NMR ($d_6$-DMSO, 400 MHz) 3.90 (s, 3H), 6.88 (d, J=2.73 Hz, 1H), 7.44 (t, J=7.62 Hz, 1H), 7.61 (m, 1H), 7.91~7.96 (m, 2H), 9.06 (m, J=7.82 Hz, 1H), 12.30 (s, 1H), 12.31 (s, 1H); MS (ES, m/z): $C_{21}H_{12}FN_3O_2$: 358.13 ($M^+$+1): 356.2 ($M^+$−1).

EXAMPLE 32

1-Fluoro-13-(3-hydroxypropyl)-5-methyl-5H,13H-indolo[6,7-a]pyrrolo[3,4-c]carbazole-6,8-dione (a) 3-(1-Methyl-5-fluoro-1H-indol-7-yl)-4-[1-(4-hydroxy-propyl)-1H-indol-3-yl]-pyrrole-2,5-dione

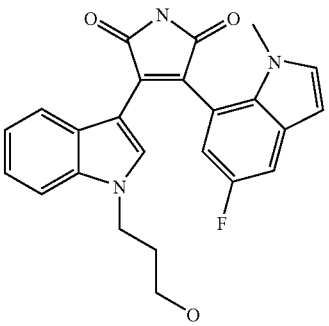

To a mixture of (1-methyl-5-fluoro-1H-indol-7-yl)-oxoacetic acid methyl ester (0.43 g, 1.82 mmol) and 2-[1-(4-hydroxy-propyl)-1H-indol-3-yl]-acetamide (0.39 g, 1.68 mmol) in DMF (12 mL) was added a solution of potassium tert-butoxide in THF (1.0 M, 7.3 mL, 7.3 mmol) at room temperature. The reaction mixture was heated at 50° C. for 5 h, and TLC and MS showed that the reaction was complete. The mixture was cooled to room temperature, quenched by hydrochloric acid (1.0 N) and stirred at room temperature for 30 min. The mixture was extracted with EtOAc and the extract washed with water, saturated aqueous sodium bicarbonate and brine, dried (sodium sulfate), filtered and evaporated. Flash column chromatography on silica gel eluting with chloroform and acetone gave 3-(1-methyl-5-fluoro-1H-indol-7-yl)-4-(1H-indol-3-yl]-pyrrole-2,5-dione (80 mg, 13.3%) and desired product 3-(1-methyl-5-fluoro-1H-indol-7-yl)-4-[1-(4-hydroxy-propyl)-1H-indol-3-yl]-pyrrole-2,5-dione as red solid (340 mg, 48.5%). $^1$H NMR ($d_6$-DMSO, 400 MHz) 1.90 (pent, J=6.26 Hz, 2H), 3.37 (m, 2H), 4.33 (t, J=6.84 Hz, 2H), 4.65 (m, 1H), 6.27 (d, J=8.21 Hz, 1H), 6.52 (d, J=3.12 Hz, 1H), 6.58 (t, J=7.82 Hz, 1H), 6.80 (dd, J1=2.35 Hz, J2=9.77 Hz, 1H), 7.08 (t, J=7.63 Hz, 1H), 7.38 (d, J=3.13 Hz, 1H), 7.45 (dd, J1=2.35 Hz, J2=9.38 Hz, 1H), 7.51 (d, J=8.21 Hz, 1H), 8.14 (s, 1H), 11.26 (s, 1H); MS (ES, m/z): $C_{24}H_{20}FN_3O_3$: 418.1($H^+$+1): 416.2 ($M^+$−1).

b) 1-Fluoro-13-(3-hydroxypropyl)-5-methyl-5H, 13H-indolo[6,7-a]pyrrolo[3,4-c]carbazole-6,8-dione

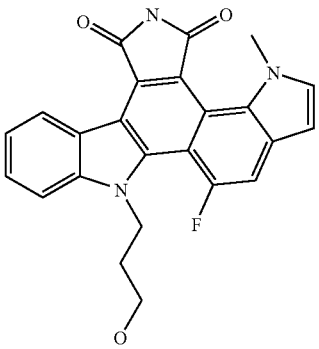

A solution of 3-(1-methyl-5-fluoro-1H-indol-7-yl)-4-[1-(4-hydroxy-propyl)-1H-indol-3-yl]-pyrrole-2,5-dione (200 mg, 0.48 mmol) and iodine (121 mg, 0.48 mmol) in ethyl acetate (500 mL) was irradiated with a medium pressure Hanovia lamp (450 w). After 10 min, TLC and HPLC showed that all starting material was consumed, and the reaction mixture was washed with aqueous sodium hydrosulfite and brine, dried (sodium sulfate), filtrated and concentrated under vacuum. Flash column chromatography on silica gel eluting with toluene-acetone gave a yellow solid (90 mg, 45%). 1H NMR (d$_6$-DMSO, 400 MHz) 1.78 (m, 2H), 3.18 (m, 2H), 3.77 (s, 3H), 4.45 (t, J=4.8 Hz, 1H), 4.61 (t, J=7 Hz, 2H), 6.76 (dd, J1=1.2 Hz, J2=3.2 Hz, 1H), 7.40 (t, J=11 Hz, 1H), 7.56~7.60 (m, 2H), 7.76 (d, J=12.8 Hz, 1H), 7.83 (d, J=8.4 Hz, 1H), 8.25 (d, J=1.2 Hz, 1H), 9.1 (d, J=8 Hz, 1H), 11.19 (s, 1H); MS (ES, m/z): C$_{24}$H$_{18}$FN$_3$O$_3$: 416.18 (M$^+$+1): 414.21 (M$^+$–1).

EXAMPLE 33

2-Methoxy-5-methyl-5H,13H-indolo[6,7-a]pyrrolo[3,4-c]carbazole-6,8-dione (a) 4-Methoxy-7-bromoindole

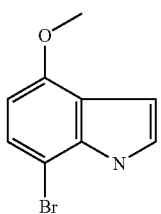

2-Bromo-5-methoxy-aniline (4.4 g, 21.8 mmol) was added dropwise to a solution of boron trichloride in methylene chloride (1.0 M, 24 mL, 24 mmol) cooled with ice water. The reaction mixture was warmed to room temperature, stirred for 30 min, and chloroacetonitrile (4.01 mL, 26.2 mmol) and aluminum chloride (4.01 g, 24.0 mmol) were added, followed by 1,2-dichloroethane (28.5 mL). The reaction mixture was heated to 70° C. to distill off methylene chloride, and then heated to reflux for 24 hrs. After cooling to 0–5° C., the mixture was treated with 2.5 M HCl (38.4 mL) carefully, and then heated to 80° C. for 1 h until all solids dissolved. The aqueous layer was separated, extracted with methylene chloride and the combined extracts washed with water and brine, dried (sodium sulfate) and evaporated to a yellow solid, which was used without further purification. The crude product was taken into dioxane (37 mL) and water (4.2 mL), and treated with sodium borohydride (0.91 g, 24.0 mmol) in portions. After stirring at room temperature for 30 min, all the starting material was consumed and the reaction mixture was then heated to reflux for 14 hrs. After cooling to room temperature, the mixture was treated with concentrated HCl, and extracted with ethyl acetate. The organic extract was washed with water and brine; dried (sodium sulfate), and concentrated. Column chromatography on silica gel (hexanes/ethyl acetate) gave 4-methoxyl-7-bromoindole (1.2 g, 24%). $^1$H NMR (400 MHz, CDCl$_3$) 3.94 (s, 3H), 6.44 (d, J=8.21 Hz, 1H), 6.73 (m, 1H), 7.17 (t, J=2.74 Hz, 1H), 7.22~7.26 (m, 1H), 8.32 (br, 1H); MS (ES, m/z): C$_9$H$_8$BrNO: 227.99 (M$^+$($^{79}$Br)+1), 230.0(M$^+$($^{81}$Br)+1).

(b) 1-Methyl-4-methoxyl-7-bromoindole

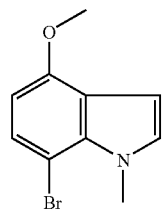

To a suspension of sodium hydride (60%, 0.23 g, 5.75 mmol) in DMF (18 mL) was added a solution of 4-methoxyl-7-bromoindole (1.1 g, 4.87 mmol) in DMF (2 mL). After 1 h at room temperature, the mixture was treated with methyl iodide (0.45 mL, 7.23 mmol) with cooling in an ice-water bath. The reaction mixture was allowed to warm up room temperature and stirred overnight. The reaction was quenched with water, extracted with ethyl acetate and the extract washed with water and brine, and dried (sodium sulfate). Evaporation of solvent gave a crude product, which was used without further purification. $^1$H NMR (400 MHz, CDCl$_3$) 3.92(σ,3H), 4.13 (s, 3H), 6.35 (d, J=8.21 Hz, 1H), 6.55 (d, J=3.13 Hz, 1H), 6.89 (d, J=3.52 Hz, 1H), 7.22 (d, J=8.21 Hz, 1H).

(c) (1-Methyl-4-methoxyl-1H-indol-7-yl)-oxo-acetic acid methyl ester

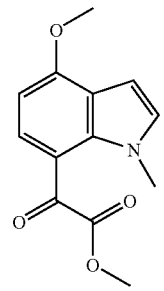

A solution of 1-methyl-4-methoxyl-7-bromoindole (1.17 g, 4.87 mmol) in THF (33 mL) was cooled to −78° C. and a solution of tert-butyl lithium in pentanes (1.7 M, 6.3 mL, 10.7 mmol) added dropwise over 30 min. After 30 min at −78° C., the mixture was treated with dimethyl oxalate (1.44 g, 12.2 mmol) in one portion. After 15 min, the mixture was allowed to warm to room temperature and stirred 4 h. The reaction mixture was quenched with water and extracted with ethyl acetate. The extract was washed with brine and dried (Na2SO4), and concentrated. Flash chromatography (EtOAc/hexanes) afforded the title compound (0.7 g, 58.1%). $^1$H NMR (400 MHz, CDCl$_3$) 3.95 (s, 3H), 4.0 (s, 3 H), 4.02 (s, 3H), 6.56 (d, J=8.61 Hz, 1H), 6.67 (d, J=3.13 Hz, 1H), 6.99 (d, J=3.13 Hz, 1H), 7.61 (d, j=8.6 Hz, 1H); MS (ES, m/z): $C_{13}H_{13}NO_4$: 248.16 (M$^+$+1).

(d) 3-(1H-indol-3-yl)-4-(4-methoxy-1-methyl-1H-indol-7-yl)-pyrrole-2,5-dione

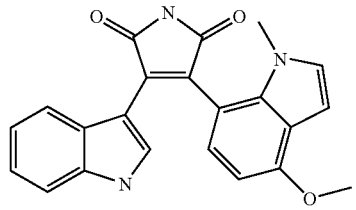

To a mixture of (1-methyl-4-methoxyl-1H-indol-7-yl)-oxo-acetic acid methyl ester (0.27 g, 1.10 mmol) and 2-(1H-indol-3-yl-acetamide (0.17 g, 1 mmol) in DMF (5 mL) was added a solution of potassium tert-butoxide in THF (1.0 M, 4.0 mL, 4.0 mmol) at room temperature. The reaction mixture was heated at 60° C. for 4 hrs, cooled to room temperature, and quenched with hydrochloric acid (1.0 N). After stirring at room temperature for 30 min, the mixture was extracted with ethyl acetate and the extract was washed with water, saturated aqueous sodium bicarbonate and brine, dried (sodium sulfate), filtered and evaporated. Flash column chromatography on silica gel eluting with chloroform and acetone gave 3-(1H-indol-3-yl)-4-(4-methoxy-1-methyl-1H-indol-7-yl)-pyrrole-2,5-dione (270 mg, 72.7%). $^1$H NMR (d$_6$-DMSO, 400 MHz) 3.65 (s, 3H), 3.84 (s, 3H), 6.46~6.55 (m, 4H), 6.78 (d, J=7.6 Hz, 1H), 6.95 (t, J=7.2 Hz, 1H), 7.13 (d, J=3.2 Hz, 1H), 7.32 (d, J=8.0 Hz, 1H), 7.86 (d, J=3.2 Hz, 1H), 11.05 (s, 1H), 11.79 (s, 1H); MS (ES, m/z): $C_{22}H_{17}FN_3O_3$: 372.19(M$^+$+1), 370.29 (M$^+$−1).

e) 2-Methoxy-5-methyl-5H,13H-indolo[6,7-a]pyr-rolo[3,4-c]carbazole-6,8-dione

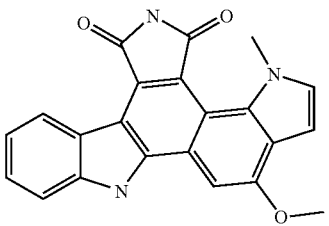

A solution of 3-(1H-indol-3-yl)-4-(4-methoxy-1-methyl-1H-indol-7-yl)-pyrrole-2,5-dione (170 mg, 0.458 mmol) and iodine (116 mg, 0.458 mmol) in ethyl acetate, (500 mL) was irradiated with a medium pressure Hanovia lamp (450 w). After 41 min, TLC and HPLC showed that all starting material was consumed, and the reaction mixture was washed with aqueous sodium hydrosulfite and brine, dried (sodium sulfate), filtrated and concentrated under vacuum. Flash column chromatography on silica gel eluting with toluene-acetone gave a yellow solid (80 mg, 47%). $^1$H NMR (d$_6$-DMSO, 400 MHz) 3.80 (s, 3H), 4.09 (s, 3H), 6.75 (d, J=3.2 Hz, 1H), 7.29 (t, J=7.2 Hz, 1H), 7.45~7.64 (m, 2H), 7.64 (s, 1H), 7.65 (d, J=8.0 Hz, 1H), 8.88 (d, J=8.0 Hz, 1H), 10.93 (s, 1H), 12.51 (s, 1H); MS (ES, m/z): $C_{22}H_{15}FN_3O_3$: 368.3 (M$^+$−1); HR MS calcd for $C_{22}H_{16}FN_3O_3$ (M$^+$+1) 370.1192. found 370.1199.

EXAMPLE 34

1,5,13-Trimethyl-5H,13H-indolo[6,7-a]pyrrolo[3,4-c]carbazole-6,8-dione

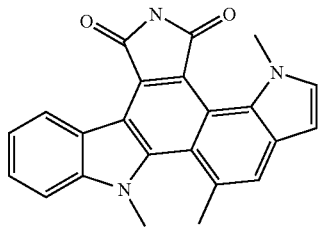

A solution of 3-(1,5-dimethyl-1H-indol-7-yl)-4-(1-methyl-1H-indol-3-yl)-pyrrole-2,5-dione (300 mg, 0.81 mmol) and iodine (216 mg, 0.85 mmol) in ethyl acetate (500 mL) was irradiated with a medium pressure Hanovia lamp (450 w). After 12 min, TLC and HPLC showed that all starting material was consumed, and the reaction mixture was washed with aqueous sodium hydrosulfite and brine, dried (sodium sulfate), filtered and concentrated under vacuum. Flash column chromatography on silica gel eluting with toluene-acetone afforded a yellow solid (150 mg, 50%). $^1$H NMR (d$_6$-DMSO, 400 MHz) 2.82 (s, 3H), 3.79 (s, 3H), 3.87 (s, 3H), 6.72 (m, 1H), 7.44 (t, J=7.82 Hz, 1H), 7.53 (m, 1H), 7.61 (t, J=7.63 Hz, 1H), 7.63~7.76 (m, 2H), 9.02 (d, J=7.82 Hz, 1H), 11.09 (s, 1H); MS (ES, m/z): $C_{21}H_{19}N_3O_2$: 368.19 (M$^+$+1), 366.2 (M$^+$31 1).

EXAMPLE 35

13-(3-isonipecotamide)-5-methyl-7H-indolo[6,7-a]pyrrolo[3,4-c]-carbazole-6,8-dione (a) 1-[3-(tert-Butyldimethylsilyloxy)propyl]-1H-indole. To a solution of indole (21 g, 179 mmol) and (3-bromopropoxy)-tert-butyldimethyl-silane (43.6 mL, 188 mmol) in DMF (400 mL) was added sodium hydride (60% in mineral oil, 10.68 g, 267 mmol). After 1.5 h, the reaction was quenched with saturated NaHCO$_3$ (200 mL) and diluted with EtOAc (500 mL). The organic layer was washed with water (3×500 mL), saturated aq NaHCO$_3$ (500 mL), and brine (2×500 mL), dried (MgSO$_4$), filtered, and concentrated to give the title compound (52.9 g, 100%) as a light brown oil. $^1$H NMR (300 MHz, CDCl$_3$) 7.55 (m, 1H), 7.31 (m, 1H), 7.12 (m, 1H), 7.03 (m, 2H), 6.40 (m, 1H), 4.21 (m, 2H), 3.53 (m, 2H), 1.94 (m, 2H), 0.88 (m, 9H), 0.03 (m, 6H). MS (atmospheric pressure chemical ionization, m/z) 290 (M$^+$+1).

(b) Methyl [1-(3-hydroxypropyl)-1H-indol-3-yl]oxoacetate

To a solution of 1-[3-(tert-butyldimethylsilyloxy) propyl]-1H-indole (4.99 g, 17.2 mmol) in diethyl ether (20 mL) at 4° C. was added a 2.0 M solution of oxalyl chloride in methylene chloride (9.5 mL, 19.0 mmol). The resulting solution was allowed to warm to room temperature. After 2 h, the solution was cooled to −78° C. To this solution was added a 25% (w/w) solution of sodium methoxide in methanol (8.7 mL, 38.0 mmol). The resulting mixture was allowed to warm to room temperature and stirred for 3 h. The reaction was quenched with water (10 mL) and poured into EtOAc (100 mL). The aqueous layer was extracted with EtOAc (20 mL). The combined organic layers were washed with saturated aq $NH_4Cl$ (100 mL) and brine (100 mL), dried ($MgSO_4$), filtered, and concentrated. Flash chromatography ($SiO_2$, 20% to 80% EtOAc/hexanes) gave the title compound (3.24 g, 71%) as a white solid. $^1H$ NMR (300 MHz, $CDCl_3$) 8.42 (m, 2H), 7.47 (m, 1H), 7.36 (m, 2H), 4.38 (m, 2H), 3.94 (s, 3H), 3.67 (m, 2H), 2.25 (m, 2H), 1.50 (m, 1H). MS (atmospheric pressure chemical ionization, m/z) 262 ($M^++1$).

(c) 3-[1-(3-Hydroxypropyl)-1H-indol-3-yl]-4-(1-methyl-1H-indol-7-yl)-pyrrole-2,5-dione A 1.0 M solution of KOtBu in THF (9.2 mL, 9.2 mmol) was added to a solution of 2-[1-(3-hydroxypropyl)-1H-indol-3-yl]-acetamide (616 mg, 2.65 mmol) and (1-methyl-1H-indol-7-yl) -oxo-acetic acid methyl ester (566 mg, 2.61 mmol) in DMF (40 mL). The initially light yellow solution turned red-orange and was stirred 14 h at rt. 1N HCl was added and the mixture poured into EtOAc. The EtOAc layer was separated and washed with water (3×), saturated aq $NaHCO_3$ (2×) and brine (3×), dried ($MgSO_4$), filtered and concentrated onto $SiO_2$. Flash chromatography (1:1 EtOAc:$CH_2Cl_2$) afforded a red solid that was dried at 70° C. for 72 h giving the title compound (689 mg, 66%) as a bright red solid. $^1H$ NMR (400 MHz, DMSO-$d_6$) 11.12 (s, 1H), 8.05 (s, 1H), 7.61 (d, J=8 Hz, 1H), 7.43 (d, J=8 Hz, 1H), 7.25 (d, J=3 Hz, 1H), 6.92–7.04 (m, 2H), 6.87 (d, J=8 Hz, 1H), 6.44–6.50 (m, 2H), 6.21 (d, J=8 Hz, 1H), 4.64 (m, 1H), 4.27 (t, J=7 Hz, 2H), 3.68 (s, 3H), 3.30–3.40 (m, 2H), 1.80–1.90 (m, 2H). $^{13}C$ NMR (75.5 MHz, DMSO-$d_6$) 173.43, 172.37, 136.15, 134.62, 134.26, 131.54, 129.58, 129.19, 128.57, 125.20, 124.11, 122.07, 121.53, 121.03, 120.12, 118.56, 115.18, 110.34, 104.28, 100.73, 57.54, 42.94, 34.68, 32.54. IR ($CHCl_3$, $cm^{-1}$) 3436, 1721. MS (electrospray, m/z) 400 ($M^++1$), 398 ($M^--1$). Anal. Calcd. for $C_{24}H_{21}N_3O_3$: C, 72.17; H, 5.30; N, 10.52. Found: C, 71.87; H, 5.29; N, 10.45.

This compound is also prepared via condensation of methyl[1-(3-hydroxypropyl)-1H-indol-3-yl]oxoacetate with 2-(1-methyl-1H-indol-7-yl)acetamide.

(d) 13-(3-Hydroxypropyl)-5-methyl-7H-indolo[6,7-a]-pyrrolo[3,4-c]-carbazole-6,8-dione A solution of 3-[1-(3-hydroxypropyl)-1H-indol-2-yl]-4-(1-methyl-1H-indol-7-yl)-pyrrole-2,5-dione (240 mg, 0.602 mmol) and $I_2$ (154 mg, 0.61 mmol) in dioxane (200 mL) was irradiated with a 450 W Hanovia medium pressure lamp through a pyrex filter for 30 min. The dark red mixture was concentrated to about 50 mL, poured into EtOAc (400 mL) and washed with 10% aq $NaHSO_3$ (2×), saturated aq $NaHCO_3$ (2×), brine, dried ($MgSO_4$), filtered and concentrated onto $SiO_2$. Flash chromatography (1:1 to 7:3 EtOAc: hexanes) afforded the title product (164 mg, 69%) as a bright orange solid, mp 260–263 C. $^1H$ NMR (400 MHz, DMSO-$d_6$), 11.13 (s, 1H), 9.14 (d, J=8 Hz, 1H), 8.41 (d, J=9 Hz, 1H), 8.02 (d, J=9 Hz, 1H), 7.90 (d, J=8 Hz, 1H), 7.59–7.64 (m, 2H), 7.43 (dd, J=8, 8 Hz, 1H), 6.85 (d, J=3 Hz, 1H), 4.95 (br t, J=7 Hz, 2H), 4.86 (t, J=5 Hz, 1H), 3.85 (s, 3H), 3.58 (m, 2H), 2.1–2.20 (m, 2H). MS (electrospray, m/z) 398 ($M^++1$), 396 ($M^--1$).

DDQ is also used to produce this compound.

(e) 13-(3-Bromopropyl)-5-methyl-7H-indolo[6,7-a]pyrrolo[3,4-c]-carbazole-6,8-dione To a solution of 13-(3-hydroxypropyl)-5-methyl-7H-indolo[6,7-a]pyrrolo[3,4-c]-carbazole-6,8-dione (1.18 g, 2.97 mmol) in DMF (45 mL) was added triphenylphosphine (1.17 g, 4.45 mmol) followed by carbon tetrabromide (1.48 g, 4.45 mmol). The resulting solution was allowed to stir at room temperature for 30 min. The solution was diluted with EtOAc (200 mL) and washed with water (2×200 mL) and brine (200 mL). The combined aqueous layers were washed with EtOAc (100 mL). The combined organic layers were dried ($MgSO_4$), filtered, and concentrated to a red-orange solid. Flash chromatography ($SiO_2$, 20% EtOAc/hexanes) gave the title compound (1.05 g, 77%) as an orange solid, mp 238 C. $^1H$ NMR (DMSO-$d_6$)11.15 (s, 1H), 9.16 (d, J=7.5 Hz, 1H), 8.36 (d, J=9 Hz, 1H), 8.04 (d, J=9 Hz, 1H), 7.93 (d, J=7.5 Hz, 1H), 7.60–7.67 (m, 2H), 7.44 (dd, J=7.5, 7.5 Hz, 1H), 6.85 (d, J=3 Hz, 2H), 5.03 (t, J=7 Hz, 2H), 3.85 (s, 3H), 3.72 (t, J=7 Hz, 2H), 2.50 (m, 2H, partially buried under DMSO signal). MS (atmospheric pressure chemical ionization, m/z) 460, 462 $[C_{24}H_{18}BrN_3O_2+H]^+$.

f) 13-(1-propyl-piperidine-4-carboxylic acid amide)-5-methyl-7H-indolo[6,7-a]pyrrolo[3,4-c]-carbazole-6,8-dione

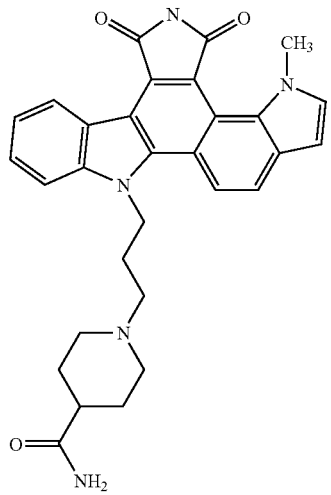

A mixture of 13-(3-Bromopropyl)-5-methyl-7H-indolo[6,7-a]pyrrolo[3,4-c]-carbazole-6,8-dione (152 mg, 0.33 mmol), isonipecotamide (429 mg, 3.35 mmol), and DMF (10 mL) was heated at 65° C. overnight. The mixture was poured into EtOAc and was washed with H₂O, 10% aqueous LiCl, and brine, dried (MgSO₄) filtered and concentrated to about 5 mL. Upon standing overnight at rt, orange crystals precipitated and were isolated by filtration, washed with EtOAc and dried to give the title compound (116 mg, 69%). 1H NMR (400 MHz, DMSO-d₆) 11.14 (s, 1H), 9.15 (d, J=8 Hz, 1H), 8.39 (d, J=9 Hz, 1H), 8.04 (d, J=9 Hz, 1H), 7.92 (d, J=8 Hz, 1H), 7.58–7.64 (m, 2H), 7.24 (br s, 1H), 6.85 (d, J=3 Hz, 1H), 6.75 (br s, 1H), 4.95 (t, J=7, 2H), 3.85 (s, 3H), 2.82 (m, 2H), 2.33 (m, 2H), 2.07 (m, 4H), 1.85 (m, 2H), 1.61–1.72 (m, 4H). MS (electrospray, m/z) 508.2 (M⁺+1), 506.2 (M⁻−1). HRMS 508.2340 (M⁺+1, calcd for $C_{30}H_{30}N_5O_3$ 508.2349).

EXAMPLES 36–43

(a) 1-[2-(tert-Butyldimethylsilyloxy)ethyl]-6-methoxy-1H-indole

To a solution of 6-methoxy-1H-indole (7.0 g, 47.6 mmol) and (2-bromoethoxy)-tert-butyldimethylsilane (10.7 mL, 50.0 mmol) in DMF (100 mL) under nitrogen was added, portionwise, sodium hydride (65% dispersion in oil) (2.8 g, 71.4 mmol) at room temperature. The reaction mixture was stirred for 1 h, quenched with saturated aq NaHCO₃ (100 mL) and diluted with EtOAc (150 mL). The organic phase was washed with water (3×150 mL), saturated aq NaHCO₃ (100 mL), brine (2×100 mL), dried (MgSO₄), filtered and concentrated. Flash chromatography (SiO₂, 10% EtOAc/hexanes) gave the title compound (14.8 g, 98%) as a colorless oil. ¹H NMR (300 MHz, CDCl₃) 7.62 (d, J=7.2 Hz, 1H), 7.38 (s, 1H), 7.12 (d, J=3.1 Hz, 1H), 6.87 (d, J=7.2 Hz, 1H), 6.52 (d, J=3.1 Hz, 1H), 4.28 (m, 2H), 4.02 (m, 2H), 3.96 (s, 3H), 0.98 (s, 9H), 0.02 (s, 6H).

(b) Methyl {1-[2-(tert-butyldimethylsilyloxy)ethyl]-6-methoxy-1H-indol-3-yl}-oxoacetate A solution of 1-[2-(tert-butyldimethylsilyloxy)ethyl]-6-methoxy-1H-indole (14.6 g, 46.5 mmol) in Et₂O (300 mL) was cooled to 4° C. (ice bath) and 2.0 M solution of oxalyl chloride in THF (25.6 mL, 51.2 mmol) was added dropwise. The ice bath was removed and the reaction was allowed to warm to room temperature (1.5 h). The reaction was then cooled to −78° C. and a solution of 25% (w/w) NaOMe in MeOH (23.2 mL, 107.0 mmol) was introduced over 5 min. The reaction was allowed to warm to room temperature. The reaction was quenched with H₂O (300 mL) and poured into EtOAc (300 mL). The water layer was separated and extracted with EtOAc (2×200 mL). The combined organic solution was washed with saturated aqueous NH₄Cl (300 mL) and brine (400 mL), dried (MgSO₄), filtered and concentrated. Flash chromatography (SiO₂, 50% hexanes/EtOAc) gave the title compound (16.2 g, 89%) as a yellow solid. ¹H NMR (300 MHz, CDCl₃) 8.44 (m, 2H), 7.12 (d, J=7.2 Hz, 1H), 6.98 (s, 1H), 4.38 (m, 2H), 4.10–4.00 (m, 5H), 3.96 (s, 3H), 0.94 (s, 9H), 0.02 (s, 6H).

(c) 3-[1-(2-Hydroxyethyl)-6-methoxy-1H-indol-3-yl]-4-(1-methyl-1H-indol-7-yl)-pyrrole-2,5-dione To a solution of methyl {1-[2-(tert-butyldimethylsilyloxy)ethyl]-6-methoxy-1H-indol-3-yl}oxoacetate (10.4 g, 26.5 mmol) and 2-(1-methyl-1H-indol-7-yl)acetamide (5.0 g, 26.5 mmol) in DMF (250 mL) was added a 1.0 M solution of potassium tert-butoxide (79.5 mL, 79.5 mmol) at room temperature and under nitrogen. The reaction was stirred overnight. A solution of concentrated HCl (10 mL) was added and the mixture was stirred at room temperature for 1 h, then quenched with water (200 mL) and diluted with EtOAc (300 mL). The two layers were separated and the aqueous phase was extracted with EtOAc (3×200 mL). The organic phases were combined and washed with water (3×300 mL), brine (500 mL), dried (MgSO₄), filtered and concentrated. Flash chromatography (SiO₂, 30% hexanes/EtOAc) gave the title compound (9.5 g, 86%) as a red solid. ¹H NMR (300 MHz, DMSO-d₆) 11.10 (s, 1H), 8.08 (s, 1H), 7.65 (d, J=6.1 Hz, 1H), 7.22 (d, J=2.8 Hz, 1H), 7.00–6.83 (m, 3H), 6.49 (d, J=2.8 Hz, 1H), 6.03 (d, J=5.8 Hz, 1H), 5.94 (d, J=6.3 Hz, 1H), 4.88 (t, J=5.3 Hz, 1H), 4.22 (t, J=5.5 Hz, 2H), 3.70–3.55 (m, 8H).

(d) 3-[1-(2-Bromoethyl)-6-methoxy-1H-indol-3-yl]-4-(1-methyl-1H-indol-7-yl)pyrrole-2,5-dione To a solution of 3-[1-(2-hydroxyethyl)-6-methoxy-1H-indol-3-yl]-4-(1-methyl-1H-indol-7-yl)pyrrole-2,5-dione (7.3 g, 17.7 mmol) in a mixture of CH₂Cl₂ (360 mL) and THF (240 mL) was added PPh₃ (4.6 g, 17.7 mmol) and CBr₄ (5.8 g, 17.7 mmol). The reaction mixture was stirred at room temperature and under nitrogen for 1 h. Another equivalent of PPh₃ (4.6 g, 17.7 mmol) was added followed by an equivalent of CBr₄ (5.8 g, 17.7 mmol). This operation was repeated one more time after 1 h. The reaction was monitored by TLC and was completed after 1 h. The reaction mixture was diluted with EtOAc (300 mL) and washed with saturated aqueous NaHCO₃ (500 mL), and brine (500 mL). The organic solution was dried (MgSO₄), filtered and concentrated. Flash chromatography (SiO₂, 50% EtOAc/hexanes) gave the title compound (6.5 g, 77%) as a red solid. ¹H NMR (300 MHz, DMSO-d₆) 11.08 (s, 1H), 7.95 (s, 1H), 7.61 (d, J=7.8 Hz, 1H), 7.23 (d, J=3.1 Hz, 1H), 7.03–6.96 (m, 3H), 6.88 (d, J=6.2 Hz, 1H), 6.47 (d, J=3.1 Hz, 1H), 6.13 (s, 1H), 4.60 (t, J=6.0 Hz, 2H), 3.81 (t, J=6.0 Hz, 2H), 3.69 (s, 3H), 3.65 (s, 3H).

(e) 11-Methoxy-5-methyl-13-(2-bromoethyl)-7H-indolo[6,7-a]pyrrolo[3,4-c]carbazole-6,8-dione A solution 3-[1-(2-bromoethyl)-6-methoxy-1H-indol-3-yl]-4-(1-methyl-1H-indol-7-yl)pyrrole-2,5-dione (0.8 g, 1.6 mmol) and DDQ (0.4 g, 1.6 mmol) in dioxane (1 L) was irradiated with a 450 W Hanovia medium pressure lamp through a Pyrex filter. After 1 h, the reaction mixture was washed with a 0.1 N solution of NaOH (500 mL). The aqueous phase was extracted with EtOAc (3×200 mL). The combined organic phases were washed with brine (500 mL), dried (MgSO₄), filtered and concentrated. Flash chromatography (SiO₂, EtOAc) gave the title compound (0.6 g, 87%) as a red solid, mp 274 C (dec). ¹H NMR (DMSO-d₆) 11.11 (s, 1H), 9.00 (d, J=8.7 Hz, 1H), 8.19 (d, J=8.9 Hz, 1H), 8.01 (d, J=8.8 Hz, 1H), 7.59 (d, J=2.9 Hz, 1H), 7.47 (d, J=1.9 Hz, 1H), 7.05 (d, J=8.8 Hz, 1H), 6.83 (d, J=2.9 Hz, 1H), 5.33–5.29 (m, 2H), 4.01–3.90 (m, 2H), 3.84 (s, 3H). MS (electrospray, m/z) 476, 478 $[C_{24}H_{18}BrN_3O_3+H]^+$.

EXAMPLE 36

11-Methoxy-5-methyl-13-(1-ethyl-piperidine-4-carboxylic acid amide)-7H-indolo[6,7-a]pyrrolo[3,4-c]carbazole-6,8-dione

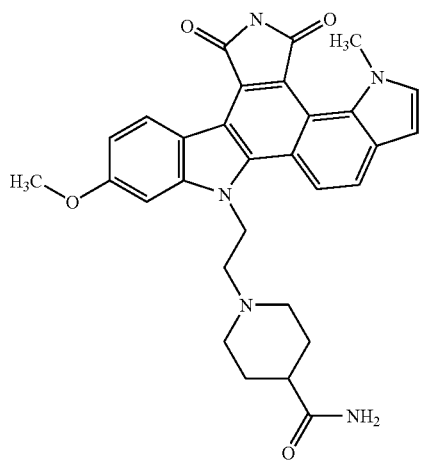

A mixture of 11-Methoxy-5-methyl-13-(2-bromoethyl)-7H-indolo[6,7-a]pyrrolo[3,4-c]carbazole-6,8-dione (250 mg, 0.52 mmol), isonipecotamide (336 mg, 2.6 mmol), and DMF (10 mL) was heated at 60° C. overnight and then allowed to cool to room temperature. The mixture was diluted with EtOAc (200 mL) and washed with H$_2$O (×2). The organic solution was passed through an SCX column (prewashed with MeOH and 5% AcOH/MeOH). An orange/red band formed at the top of the column. The column was rinsed with EtOAc and MeOH. The compound was removed from the column using 2M NH$_3$ in MeOH and the filtrate concentrated. The compound was then further purified by reverse phase preparatory HPLC (SymmetryPrep C18 7 μm 19×300 mm, 95% H$_2$O (0.1% HCl):5% CH$_3$CN to 5% H$_2$O (0.1% HCl):95% CH$_3$CN. The fractions containing the pure compound were collected and filtered through an SCX column (prewashed with MeOH and 5% AcOH/MeOH). The compound was removed from the column using 2M NH$_3$ in MeOH and the filtrate concentrated to give the title compound (107 mg, 39%) as an orange solid. $^1$H NMR (400 MHz, DMSO-d$_6$) 11.08 (s, 1H), 8.96 (d, J=8 Hz, 1H), 8.35 (d, J=9 Hz, 1H), 7.97 (d, J=9 Hz, 1H), 7.56 (d, J=3 Hz, 1H), 7.35 (d, J=2 Hz, 1H), 7.18 (br s, 1H), 7.02 (dd, J=8, 2 Hz, 1H), 6.81 (d, J=3 Hz, 1H), 6.70 (br s, 1H), 4.91 (t, J=7 Hz, 2H), 3.94 (s, 3H), 3.82 (s, 3H), 2.97 (br d, J=11 Hz, 2H), 2.82 (br t, J=6 Hz, 2H), 2.02 (m, 3H), 1.62, 2H), 1.44–1.53 (m, 2H). MS (electrospray, m/z) 524.1 (M$^+$+1), 522.1 (M$^-$–1).

EXAMPLE 37

11-Methoxy-5-methyl-13-(2-ethyl-piperazinyl)-7H-indolo[6,7-a]pyrrolo[3,4-c]carbazole-6,8-dione

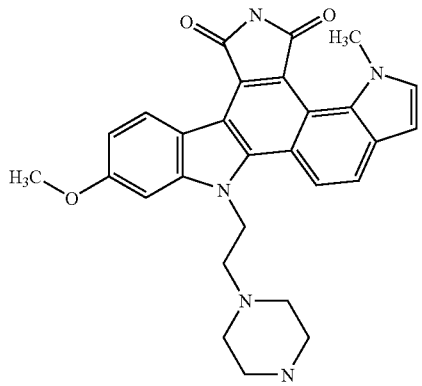

Prepared from 11-Methoxy-5-methyl-13-(2-bromoethyl)-7H-indolo[6,7-a]pyrrolo[3,4-c]carbazole-6,8-dione (250 mg, 0.52 mmol) and piperazine (452 mg, 5.2 mmol) in a manner analogous to that described for the preparation of Example 36. The title compound (77 mg, 30%) was obtained as an orange solid. $^1$H NMR (400 MHz, DMSO-d$_6$) 8.96 (d, J=8 Hz, 1H), 8.35 (d, J=9 Hz, 1H), 7.97 (d, J=9 Hz, 1H), 7.56 (d, J=3 Hz, 1H), 7.33 (d, J=2 Hz, 1H), 7.02 (dd, J=8, 2 Hz, 1H), 6.89 (d, J=3 Hz, 1H), 4.90 (t, J=7 Hz, 2H), 3.94 (s, 3H), 3.82 (s, 3H), 2.81 (t, J=7 Hz, 2H), 2.64 (t, J=4 Hz, 2H), 2.43 (m, 4H). MS (electrospray, m/z) 482 (M$^+$+1), 480 (M$^-$–1).

EXAMPLE 38

11-Methoxy-5-methyl-13-(1-ethyl-piperidin-4-ol)-7H-indolo[6,7-a]pyrrolo[3,4-c]carbazole-6,8-dione

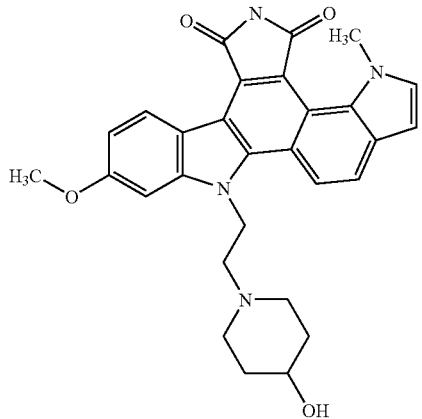

Prepared from 11-Methoxy-5-methyl-13-(2-bromoethyl)-7H-indolo[6,7-a]pyrrolo[3,4-c]carbazole-6,8-dione (250 mg, 0.52 mmol) and 4-hydroxypiperidine (265 mg, 2.6 mmol) in a manner analogous to that described for the preparation of Example 36. The title compound (80 mg, 30%) was obtained as an orange solid. $^1$H NMR (400 MHz, DMSO-d$_6$) 11.08 (s, 1H), 8.97 (d, J=8 Hz, 1H), 8.36 (d, J=8

Hz, 1H), 7.98 (d, J=8 Hz, 1H), 7.56 (s, 1H), 7.34 (s, 1H), 7.03 (d, J=8 Hz, 1H), 6.81 (s, 1H), 4.91 (m, 2H), 4.53 (s, 1H), 3.94 (s, 3H), 3.82 (s, 3H), 3.41 (m, 1H), 2.81 (m, 4H), 2.16 (m, 2H), 1.67 (m, 2H), 1.33 (m, 2H). MS (electrospray, m/z) 497 (M$^+$+1), 495 (M$^-$−1).

EXAMPLE 39

(S)-(+)-11-Methoxy-5-methyl-13-[(1-ethyl-pyrrolidin-2-yl)-methanol]-7H-indolo[6,7-a]pyrrolo[3,4-c]carbazole-6,8-dione

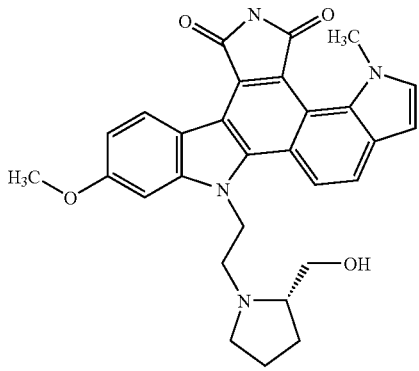

Prepared from 11-Methoxy-5-methyl-13-(2-bromoethyl)-7H-indolo[6,7-a]pyrrolo[3,4-c]carbazole-6,8-dione (250 mg, 0.52 mmol) and (S)-(+)-2-pyrrolidinemethanol (0.25 mL, 2.6 mmol) in a manner analogous to that described for the preparation of Example 36. The title compound (106 mg, 41%) was obtained as an orange solid. $^1$H NMR (400 MHz, DMSO-d$_6$) 11.08 (s, 1H), 8.96 (d, J=9 Hz, 1H), 8.36 (d, J=9 Hz, 1H), 7.97 (d, J=9 Hz, 1H), 7.56 (d, J=3 Hz, 1H), 7.34 (d, J=2 Hz, 1H), 7.03 (dd, J=9, 2 Hz, 1H), 6.81 (d, J=3 Hz, 1H), 4.92 (m, 2H), 4.85 (m, 1H), 4.47 (t, J=5 Hz, 1H), 3.93 (s, 3H), 3.83 (s, 3H), 3.41 (m, 1H), 3.24 (m, 3H), 2.92 (m, 1H), 2.55 (m, 1H), 2.40 (m, 1H), 1.55–1.8 (m, 4H), 1.46 (m, 1H). MS (electrospray, m/z) 597.2 (M$^+$+1), 495.2 (M$^-$−1).

EXAMPLE 40

11-Methoxy-5-methyl-13-(1-ethyl-4-methyl-piperazine)-7H-indolo[6,7-a]pyrrolo[3,4-c]carbazole-6,8-dione

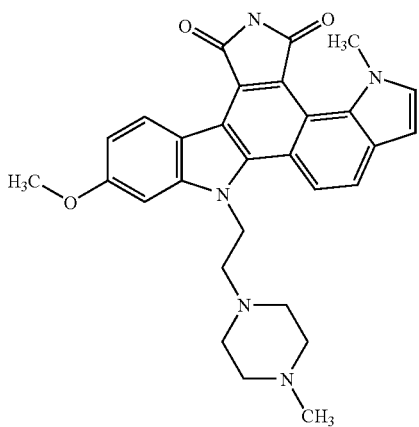

Prepared from 11-Methoxy-5-methyl-13-(2-bromoethyl)-7H-indolo[6,7-a]pyrrolo[3,4-c]carbazole-6,8-dione (250 mg, 0.52 mmol) and N-methylpiperazine (0.25 mL, 2.6 mmol) in a manner analogous to that described for the preparation of Example 36. The title compound (87 mg (33%) was obtained as an orange solid. $^1$H NMR (400 MHz, DMSO-d$_6$) 11.08 (s, 1H), 8.97 (d, J=9 Hz, 1H), 8.35 (d, J=9 Hz, 1H), 7.97 (d, J=9 Hz, 1H), 7.56 (d, J=3 Hz, 1H), 7.35 (d, J=2 Hz, 1H), 7.03 (dd, J=9, 2 Hz, 1H), 6.81 (d, J=3 Hz, 1H), 4.91 (t, J=7 Hz, 2H), 3.93 (s, 3H), 3.82 (s, 3H), 2.83 (t, J=7, 1H), 2.50 (m, 4H), 2.25 (m, 4H), 2.10 (s, 3H). MS (electrospray, m/z) 496.2 (M$^+$+1), 494.1 (M$^-$−1).

EXAMPLE 41

11-Methoxy-5-methyl-13-(2-ethylamino-ethanol)-7H-indolo[6,7-a]pyrrolo[3,4-c]carbazole-6,8-dione

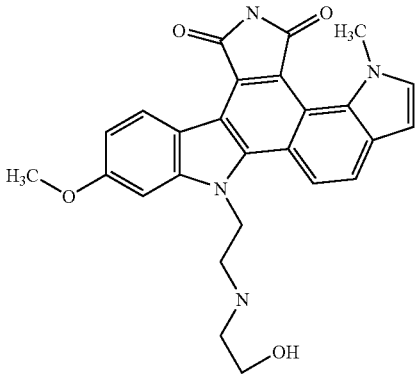

Prepared from 11-Methoxy-5-methyl-13-(2-bromoethyl)-7H-indolo[6,7-a]pyrrolo[3,4-c]carbazole-6,8-dione (250 mg, 0.52 mmol) and 2-aminoethanol (0.18 mL, 2.6 mmol) in a manner analogous to that described for the preparation of Example 36. The title compound (120 mg, 50%) was obtained as an orange solid. $^1$H NMR (400 MHz, DMSO-d$_6$) 11.0 (s, 1H), 8.97 (d, J=9 Hz, 1H), 8.32 (d, J=9 Hz, 1H), 7.98 (d, J=9 Hz, 1H), 7.56 (d, J=3 Hz, 1H), 7.41 (d, J=2 Hz, 1H), 7.03 (dd, J=9, 2 Hz, 1H), 6.81 (d, J=3 Hz, 1H), 4.88 (t, J=6 Hz, 2H), 4.51 (br s, 1H), 3.93 (s, 3H), 3.82 (s, 3H), 3.43 (m, 2H), 3.13 (t, J=7 Hz, 2H), 2.67 (t, J=6 Hz, 2H). MS (electrospray, m/z) 457.2 (M$^+$+1), 455.2 (M$^-$−1).

EXAMPLE 42

11-Methoxy-5-methyl-13-(N'-ethyl-N,N-dimethyl-ethane-1,2-diamine)-7H-indolo[6,7-a]pyrrolo[3,4-c]carbazole-6,8-dione

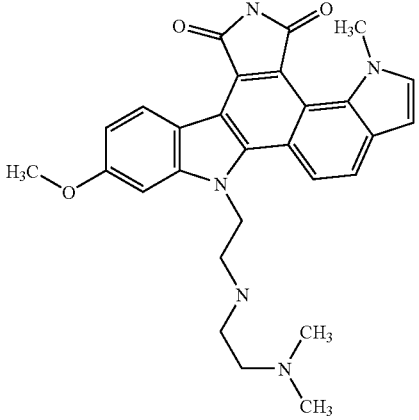

Prepared from 11-Methoxy-5-methyl-13-(2-bromoethyl)-7H-indolo[6,7-a]pyrrolo[3,4-c]carbazole-6,8-dione (250 mg, 0.52 mmol) and N,N-dimethylethylenediamine (0.28 mL, 2.6 mmol) in a manner analogous to that described for the preparation of Example 36. The title compound (82 mg, 32%) was obtained as an orange solid. $^1$H NMR (400 MHz, DMSO-$d_6$) 11.01 (br s, 1H), 8.97 (d, J=9 Hz, 1H), 8.32 (d, J=9 Hz, 1H), 7.97 (d, J=9 Hz, 1H), 7.56 (d, J=3 Hz, 1H), 7.41 (d, J=2 Hz, 1H), 7.03 (dd, J=9, 2 Hz, 1H), 6.81 (d, J=3 Hz, 1H), 4.88 (t, J=7 Hz, 2H), 3.94 (s, 3H), 3.82 (s, 3H), 3.11 (t, J=7 Hz, 2H), 2.63 (t, J=6 Hz, 2H), 2.25 (t, J=6 Hz, 2H), 2.07 (s, 6H). MS (electrospray, m/z) 484.2 (M$^+$+1), 482.2 (M$^-$−1).

EXAMPLE 43

11-Methoxy-5-methyl-13-(trans-4-ethylamino-cyclohexanol)-7H-indolo[6,7-a]pyrrolo[3,4-c]carbazole-6,8-dione

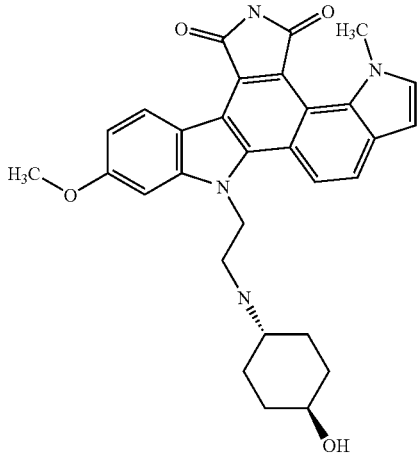

Prepared from 11-Methoxy-5-methyl-13-(2-bromoethyl)-7H-indolo[6,7-a]pyrrolo[3,4-c]carbazole-6,8-dione (250 mg, 0.52 mmol) and trans-4-amino-cyclohexanol (302 mg, 2.6 mmol), and DMF (10 mL) in a manner analogous to that described for the preparation of Example 36. The title compound (111 mg, 41%) was obtained as an orange solid. $^1$H NMR (400 MHz, DMSO-$d_6$) 11.05 (br s, 1H), 8.96 (d, J=9 Hz, 1H), 8.30 (d, J=9 Hz, 1H), 7.96 (d, J=9 Hz, 1H), 7.56 (d, J=3 Hz, 1H), 7.38 (d, J=2 Hz, 1H), 7.03 (dd, J=9, 2 Hz, 1H), 6.81 (d, J=3 Hz, 1H), 4.83 (t, J=6 Hz, 2H), 4.44 (d, J=4 Hz, 1H), 3.94 (s, 3H), 3.82 (s, 3H), 3.08 (m, 2H), 2.42 (m, 1H), 1.76 (m, 4H), 1.01–1.12 (m, 4H), one CH signal buried under residual H$_2$O. MS (electrospray, m/z) 511.2 (M$^+$+1), 509.2 (M$^-$−1).

EXAMPLES 44–60

(a) 1-[3-(tert-Butyl-dimethyl-silanyloxy)-propyl]-6-methoxy-1H-indole

To a solution of 6-methoxyindole (10.0 g, 67.9 mmol), and (3-bromo-propoxy)-tert-butyl-dimethylsilane (18.0 g, 71.3 mmol) in DMF (300 mL) was added NaH (0.353 g, 8.82 mmol) as a 60% oil dispersion. The reaction was stirred for 2 h, quenched with saturated aq NaHCO$_3$, diluted with EtOAc (400 mL), washed with saturated aq NaHCO$_3$ and brine, dried (MgSO$_4$), filtered, and concentrated to a transparent oil. The oil was purified by filtration through a plug of silica gel (85% hexane/EtOAc) to give (22.1 g, 100%) of the title compound as a transparent oil. $^1$H NMR (DMSO-$d_6$) 7.38 (d, J=8.4 Hz, 1H), 7.15 (d, J=3.2 Hz, 1H), 6.92 (d, J=2.0 Hz, 1H), 6.65 (dd, J=2.4, 8.4 Hz, 1H), 6.32 (d, J=3.2 Hz, 1H) 4.16 (t, J=6.4 Hz, 2H), 3.77 (s, 3H), 3.53 (t, J=6 Hz, 2H), 1.90 (apparent quintet, J=6.8 Hz, 2H), 0.87 (s, 9H), 0.01 (s, 6H). MS (electrospray, m/z) 320 (M$^+$+1).

(b) {1-[3-(tert-Butyl-dimethyl-silanyloxy)-propyl]-6-methoxy-1H-indol-3-yl}-oxo-axetic acid methyl ester To a solution of 1-[3-(tert-Butyl-dimethyl-silanyloxy)-propyl]-6-methoxy-1H-indole (2.45 g, 7.66 mmol) in Et$_2$O (40 was at 0° C. was added oxalyl chloride (1.07 g, 8.42 mmol). The reaction was stirred for 30 min while warming to room temperature. The reaction was cooled to −78° C. and NaOMe (5.25 mL, 22.98 mmol) as a 25% wt solution in MeOH was introduced. The reaction was stirred overnight while allowing to warm to room temperature. The mixture was poured into EtOAc, washed with H$_2$O, saturated NaHCO$_3$ and brine, dried (MgSO$_4$), filtered and concentrated to an oil. The crude oil was purified by flash chromatography (75% hexane/EtOAc to 65% hexane/EtOAc gradient) to give 2.46 g (79%) of the title compound as an oil. $^1$H NMR (DMSO-$d_6$) 8.30 (s, 1H), 8.02 (d, J=8.4 Hz, 1H), 7.14 (d, J=2 Hz, 1H), 6.93 (dd, J=2.0, 8.4 Hz, 1H), 4.32 (t, J=6.8 Hz, 2H), 3.86 (s, 3H), 3.82 (s, 3H), 3.55 (t, J=6.0 Hz, 2H), 1.98 (apparent quintet, J=8.4 Hz, 2H), 0.86 (s, 9H), 0.01 (s, 6H). MS (electrospray, m/z) 406.3 (M$^+$+1).

(c) 3-[1-(3-Hydroxypropyl)-6-methoxy-1H-indol-3-yl]-4-(1-methyl-1H-indol-7-yl)-pyrrole-2,5-dione To a solution of {1-[3-(tert-butyl-dimethyl-silanyloxy)-propyl]-6-methoxy-1H-indol-3-yl}-oxo-axetic acid methyl ester (5.47 g, 13.5 mmol) and 2-(1-methyl-1H-indol-7-yl)-acetamide (2.55 g, 13.5 mmol) in DMF (250 mL) was added potassium tert-butoxide as a 1.0 M solution in THF (40.5 mL, 40.5 mmol). The reaction was stirred at room temperature for 24 h and quenched with 1N HCl and stirred for an additional 1 h. The reaction mixture was poured into EtOAc (1.5 L), washed with 1N HCl, saturated aq NaHCO$_3$, and brine (×4), dried (MgSO$_4$), filtered, and concentrated. The crude red solid was triturated and recrystallized with Et$_2$O/hexane to give the title compound as a red solid (3.6 g, 62%). $^1$H NMR (DMSO-$d_6$) 11.10 (s, 1H), 7.94 (s, 1H), 7.60 (d, J=7.8 Hz, 1H), 7.23 (d, J=3 Hz, 1H), 6.98 (m, 2H), 6.85 (d, J=7 Hz, 1H), 6.47 (d, J=3 Hz, 1H), 6.07 (d, J=9 Hz, 2H), 6.00 (d, J=9 Hz, 1H), 4.62 (t, J=5.2 Hz, 1H), 4.21 (t, J=7.2 Hz, 2H), 3.67 (s, 3H), 3.65 (s, 3H), 3.34 (apparent quartet, J=5.6 Hz, 2H), 1.83 (apparent quintet, J=6.8 Hz, 2H). MS (electrospray, m/z) 430 (M$^+$+1), 428 (M$^-$−1).

(d) 3-[1-(3-Bromopropyl)-6-methoxy-1H-indol-3-yl]-4-(1-methyl-1H-indol-7-yl)-pyrrole-2,5-dione To a solution of 3-[1-(3-hydroxypropyl)-6-methoxy-1H-indol-3-yl]-4-(1-methyl-1H-indol-7-yl)-pyrrole-2,5-dione (3.0 g, 7.0 mmol) in solution of DMF (300 mL) was added PPh$_3$ (2.6 g, 10.5 mmol) and CBr$_4$ (3.3 g, 10.5 mmol). The reaction mixture was stirred at room temperature and under nitrogen for 1 h. The reaction was monitored by TLC and was completed after 2 h. The reaction mixture was diluted with EtOAc (300 mL) and water (800 mL). The aqueous phase was extracted with EtOAc (3×300 ml). The combined organic phases were washed with saturated aq NaHCO$_3$ (300 mL), brine (500 mL) dried (MgSO$_4$), filtered and concentrated. Flash chromatography (SiO$_2$, 30% EtOAc/hexanes) gave the title compound (2.4 g, 71%) as a red solid. $^1$H NMR (300 MHz, DMSO-d$_6$) 11.04 (s, 1H), 7.88 (s, 1H), 7.62 (d, J=6.1 Hz, 1H), 7.19 (d, J=2.6 Hz, 1H), 7.00–6.91 (m, 2H), 6.84 (d, J=6.0 Hz, 1H), 6.48 (d, J=2.5 Hz, 1H), 6.10 (m, 2H), 4.27 (t, J=5.8 Hz, 2H), 3.71 (s, 3H), 3.62 (s, 3H), 3.32 (t, J=5.8 Hz, 2H), 2.11 (m, 2H). MS (electrospray, m/z) 492.1/494.1 (M$^+$+1), 490.2/492.2 (M$^-$–1).

(e) 11-Methoxy-5-methyl-13-(3-bromopropyl)-7H-indolo[6,7-a]pyrrolo[3,4-c]-carbazole-6,8-dione. A solution of 3-[1-(3-bromopropyl)-6-methoxy-1H-indol-3-yl]-4-(1-methyl-1H-indol-7-yl)pyrrole-2,5-dione (0.7 g, 1.4 mmol) and DDQ (0.3 g, 1.4 mmol) in EtOAc/dioxane (600/400 mL) was irradiated with a 450 W Hanovia medium pressure lamp through a Pyrex filter. After 1 h, the reaction mixture was washed with 0.1 N NaOH (500 mL), brine (500 mL), dried (MgSO$_4$), filtered and concentrated. Flash chromatography (SiO$_2$, EtOAc) gave the title compound (0.6 g, 87%) as a red solid. $^1$H NMR (DMSO-d$_6$) 11.09 (s, 1H), 8.99 (d, J=8.7 Hz, 1H), 8.30 (d, J=8.9 Hz, 1H), 7.99 (d, J=8.9 Hz, 1H), 7.58 (d, J=3.0 Hz, 1H), 7.41 (d, J=1.8 Hz, 1H), 7.06 (dd, J=8.7 Hz, J=2.1 Hz, 1H), 6.83 (d, J=3.0 Hz, 1H), 4.96 (t, J=7.2 Hz, 2H), 3.96 (s, 3H), 3.84 (s, 3H), 3.70 (t, J=6.1 Hz, 2H), 2.51 (m, 2H).

EXAMPLE 44

11-Methoxy-5-methyl-13-(1-propyl-piperidine-4-carboxylic acid methyl ester)-7H-indolo[6,7-a]pyrrolo[3,4-c]carbazole-6,8-dione

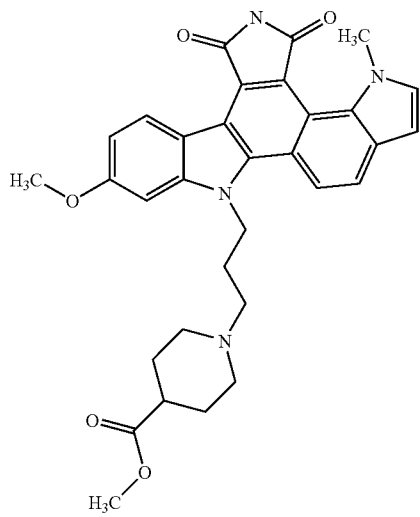

A mixture of 11-Methoxy-5-methyl-13-(3-bromopropyl)-7H-indolo[6,7-a]pyrrolo[3,4-c]carbazole-6,8-dione (100 mg, 0.20 mmol), methyl isonipecotate (0.67 mL, 5.0 mmol), and DMF (10 mL) was heated at 65° C. overnight. The reaction was allowed to cool and was concentrated to a red oil. The oil was taken up in EtOAc and was washed with H$_2$O, saturated NaHCO$_3$, and brine, dried (MgSO$_4$) filtered and concentrated. Flash chromatography (EtOAc/Hexane) gave 46 mg (41%) of the title compound as a tan/yellow solid. $^1$H NMR (400 MHz, DMSO-d$_6$) 11.07 (s, 1H), 8.99 (d, J=8 Hz, 1H), 8.32 (d, J=9 Hz, 1H), 7.97 (d, J=9 Hz, 1H), 7.57 (d, J=3 Hz, 1H), 7.37 (s, 1H), 7.04 (d, J=7 Hz, 1H), 6.81 (d, J=3 Hz, 1H), 4.90 (m, 2H), 3.94 (s, 3H), 3.83 (s, 3H), 3.60 (s, 3H), 3.30 (m, 1H), 2.65 (m, 2H), 2.28 (m, 4H), 2.02 (m, 2H), 1.88 (m, 2H), 1.75 (m, 2H), 1.52 (m, 2H). MS (electrospray, m/z) 553.3 (M$^+$+1).

EXAMPLE 45

11-Methoxy-5-methyl-13-(1-propyl-piperidine-4-carboxylic acid amide)-7H-indolo[6,7-a]pyrrolo[3,4-c]carbazole-6,8-dione

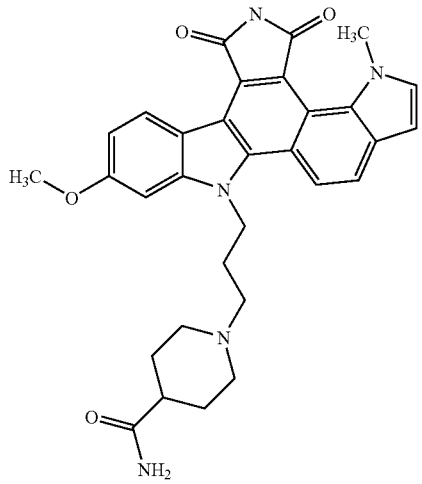

A mixture of 11-Methoxy-5-methyl-13-(3-bromopropyl)-7H-indolo[6,7-a]pyrrolo[3,4-c]carbazole-6,8-dione (100 mg, 0.20 mmol), isonipecotamide (640 mg, 5 mmol), and DMF (10 mL) in a manner analogous to that described for the preparation of Example 44. Upon standing, the title compound precipitated from the solution and was collected by filtration to give an orange solid (64 mg, 59%). $^1$H NMR (400 MHz, DMSO-d$_6$) 11.07 (s, 1H), 8.99 (d, J=8 Hz, 1H), 8.33 (d, J=9 Hz, 1H), 7.98 (d, J=9 Hz, 1H), 7.57 (d, J=3 Hz, 1H), 7.35 (d, J=2 Hz, 1H), 7.21 (br s, 1H), 7.04 (dd, J=8, 2 Hz, 1H), 6.81 (d, J=3 Hz, 1H), 6.72 (br s, 1H), 4.89 (t, J=8 Hz, 2H), 3.95 (s, 3H), 3.83 (s, 3H), 2.83 (br d, J=11 Hz, 2H), 2.34 (m, 2H), 2.04 (m, 3H), 1.84 (m, 2H), 1.55–1.70 (m, 4H). MS (electrospray, m/z) 538.3 (M$^+$+1), 536.3 (M$^-$–1).

EXAMPLE 46

11-Methoxy-5-methyl-13-(1-propyl-piperidine-4-carboxylic acid amide)-7H-indolo[6,7-a]pyrrolo[3,4-c]carbazole-6,8-dione hydrochloride

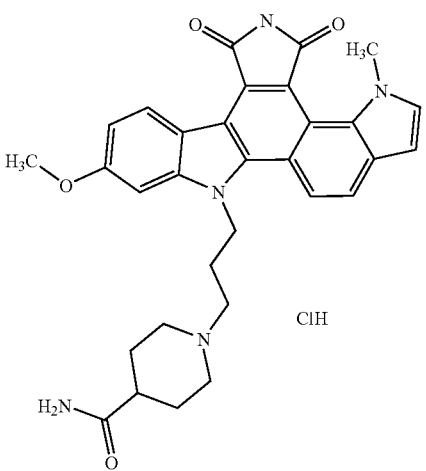

A mixture of 11-Methoxy-5-methyl-13-(3-bromopropyl)-7H-indolo[6,7-a]pyrrolo[3,4-c]carbazole-6,8-dione (100 mg, 0.18 mmol), 15 mL CH$_3$CN, and 0.19 mL of 1N HCl was sonicated to give a homogeneous solution. The solution was freeze dried to give the title compound (105 mg, 99%) as an orange solid. $^1$H NMR (400 MHz, DMSO-d$_6$) 11.12 (s, 1H), 10.02 (br s, 1H), 9.01 (d, J=9 Hz, 1H), 8.27 (d, J=9 Hz, 1H), 8.02 (d, J=9 Hz, 1H), 7.58 (d, J=3 Hz, 1H), 7.47 (br s, 1H), 7.36 (br s, 1H), 7.07 (dd, J=9, 2 Hz, 1H), 6.90 (br s 1H), 6.84 (d, J=3 Hz, 1H), 4.96 (t, J=7 Hz, 2H), 3.98 (s, 3H), 3.83 (s, 3H), 3.45 (br d, J=11 Hz, 2H), 3.24 (m, 2H), 2.85 (m, 3H), 2.35 (m, 2H), 1.7–1.9 (m, 4H). MS (electrospray, m/z) 538.2 (M$^+$+1), 536.2 (M$^-$–1), 572/574 (M$^-$+Cl).

EXAMPLE 47

11-Methoxy-5-methyl-13-(1-propyl-piperidine-4-carboxylic acid amide)-7H-indolo[6,7-a]pyrrolo[3,4-c]carbazole-6,8-dione methanesulfonic acid

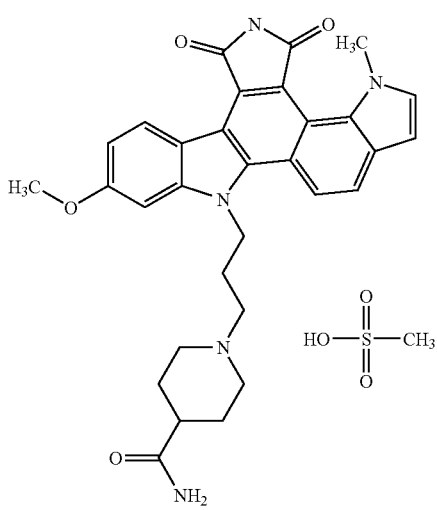

A mixture of 11-Methoxy-5-methyl-13-(3-bromopropyl)-7H-indolo[6,7-a]pyrrolo[3,4-c]carbazole-6,8-dione (150 mg, 0.30 mmol), isonipecotamide (521 mg, 3.8 mmol), and DMF (10 mL) in a manner analogous to that described for the preparation of Example 44. The crude solid was dissolved in 50% aqueous CH$_3$CN (2 mL) and 0.56 mL of a 0.154 mM solution of methansulfonic acid in CH$_3$CN added. Additional H$_2$O (1 mL) and CH$_3$CN (1 mL) were added and the mixture was swirled to give a homogeneous solution which was extracted with EtOAc. The aqueous layer was freeze dried to give the title compound (77 mg, 39%). $^1$H NMR (400 MHz, DMSO-d$_6$) 11.47 (s, 1H), 8,96 (d, J=9 Hz, 1H), 8.86 (br s, 1H), 8.21 (d, J=9 Hz, 1H), 7.96 (d, J=9 Hz, 1H), 7.53 (d, J=3 Hz, 1H), 7.37 (br s, 1H), 7.03 (dd, J=9, 2 Hz, 1H), 6.78 (d, J=3 Hz, 1H), 4.89 (m, 2H), 3.90 (s, 3H), 3.77 (s, 3H), 3.0–3.5 (m, 9H), 2.84 (m, 1H), 2.23 (m, 1H), 2.23 (s, 3H), 1.83 (m, 1H), 1.69 (m, 2H), 1.35–1.44 (m, 1H).

EXAMPLE 48

11-Methoxy-5-methyl-13-(1-propyl-piperazine)-7H-indolo[6,7-a]pyrrolo[3,4-c]carbazole-6,8-dione

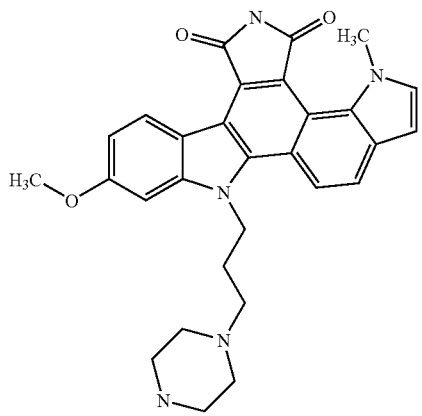

A mixture of 11-Methoxy-5-methyl-13-(3-bromopropyl)-7H-indolo[6,7-a]pyrrolo[3,4-c]carbazole-6,8-dione (200 mg, 0.40 mmol), piperazine (861 g, 10 mmol), and DMF (20 mL) in a manner analogous to that described for the preparation of Example 44. The mixture was purified by SCX chromatography followed by preparative reverse phase HPLC [95% H$_2$O (0.1% TFA)/CH$_3$CN to 70% CH$_3$CN/H$_2$O (0.1% TFA)] to give the title compound (101 mg, 41%). This salt (64 mg, 0.10 mmmol) was stirred in H$_2$O (3 mL) containing 0.1N NaOH (2.1 mL). The resulting precipitate was collected by filtration and freeze dried to give the title compound (30 mg, 60%) as an orange solid. $^1$H NMR (400 MHz, DMSO-d$_6$) 8.98 (d, J=9 Hz, 1H), 8.33 (d, J=9 Hz, 1H), 7.97 (d, J=9 Hz, 1H), 7.57 (d, J=3 Hz, 1H), 7.36 (d, J=2 Hz, 1H), 7.04 (dd, J=9, 2 Hz, 1H), 6.82 (d, J=3 Hz, 1H), 4.89 (t, J=8 Hz, 2H), 3.94 (s, 3H), 3.83 (s, 3H), 2.68 (m, 4H), 2.30 (t, J=6 Hz, 2H), 2.22 (m, 4H), 2.03 (m, 2H). MS (electrospray, m/z) 496.2 (M$^+$+1), 494.2 (M$^-$–1).

EXAMPLE 49

11-Methoxy-5-methyl-13-(1-propyl-piperidin-4-ol)-7H-indolo[6,7-a]pyrrolo[3,4-c]carbazole-6,8-dione

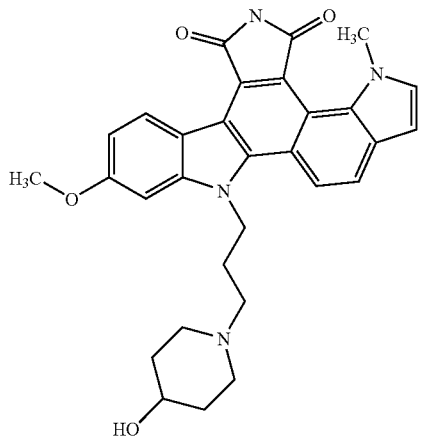

Prepared from 11-Methoxy-5-methyl-13-(3-bromopropyl)-7H-indolo[6,7-a]pyrrolo[3,4-c]carbazole-6,8-dione (380 mg, 0.77 mmol) and 4-hydroxypiperidine (384 mg, 3.8 mmol) in a manner analogous to that described for the preparation of Example 44. The title compound (225 mg, 57%) was obtained as an orange solid. $^1$H NMR (400 MHz, DMSO-d$_6$) 11.08 (s, 1H), 8.98 (d, J=9 Hz, 1H), 8.32 (d, J=9 Hz, 1H), 7.97 (d, J=9 Hz, 1H), 7.57 (d, J=3 Hz, 1H), 7.35 (d, J=1.6 Hz, 1H), 7.03 (dd, J=9, 1.6 Hz, 1H), 6.82 (d, J=3 Hz, 1H), 4.88 (t J=7 Hz, 2H), 4.56 (s, 1H), 3.94 (s, 3H), 3.83 (s, 3H), 3.43 (m, 1H), 2.64 (m, 2H), 2.32 (m, 2H), 1.9–2.1 (m, 4H), 1.71 (m, 2H), 1.41 (m, 2H). MS (electrospray, m/z) 511.2 (M$^+$+1), 509.2 (M$^-$–1).

EXAMPLE 50

11-Methoxy-5-methyl-13-(1-propyl-piperidin-4-ol)-7H-indolo[6,7-a]pyrrolo[3,4-c]carbazole-6,8-dione methanesulfonic acid

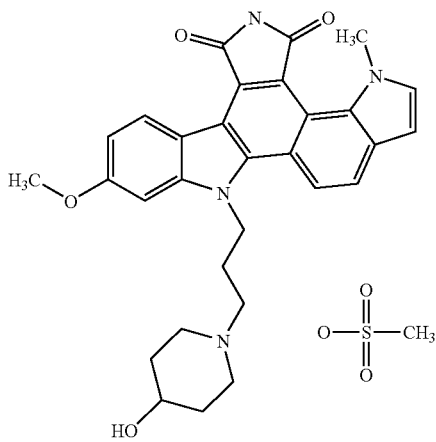

A mixture of 11-Methoxy-5-methyl-13-(3-bromopropyl)-7H-indolo[6,7-a]pyrrolo[3,4-c]carbazole-6,8-dione (150 mg, 0.30 mmol), 4-hydroxypiperidine (411 mg, 3.81 mmol), and DMF (10 mL) in a manner analogous to that described for the preparation of Example 44. The solid was dissolved 50% aqueous CH$_3$CN (4 mL), and 0.9 mL of 0.154 mM solution of methanesulfonic acid in CH$_3$CN added. The mixture was filtered and the filtrate was freeze dried to give the title compound (45 mg, 24%) as an orange solid. $^1$H NMR (400 MHz, DMSO-d$_6$) 11.06 (s, 1H), 10.13 (br s, 1H), 8.94 (d, J=9 Hz, 1H), 8.22 (d, J=9 Hz, 1H), 7.96 (d, J=9 Hz, 1H), 7.53 (d, J=3 Hz, 1H), 7.42 (d, J=2 Hz, 1H), 7.01 (dd, J=9, 2 Hz, 1H), 6.78 (d, J=3 Hz, 1H), 4.91 (t, J=7 Hz, 2H), 3.92 (s, 3H), 3.77 (s, 3H), 3.1–3.4 (m, 14H), 2.24 (s, 3H). MS (electrospray, m/z) 511.2 (M$^+$+1), 509.2 (M$^-$–1).

EXAMPLE 51

(S)-(+)-11-Methoxy-5-methyl-13-[(1-propyl-pyrrolidin-2-yl)-methanol]-7H-indolo[6,7-a]pyrrolo[3,4-c]carbazole-6,8-dione methanesulfonic acid

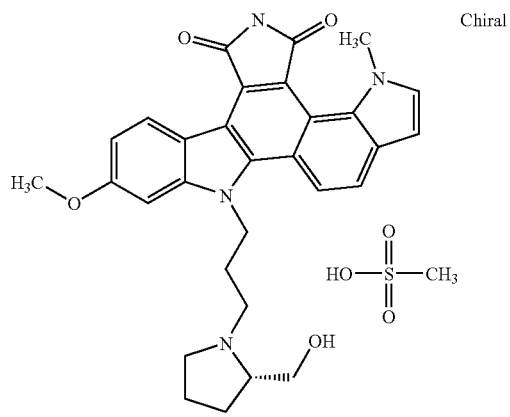

A mixture of 11-Methoxy-5-methyl-13-(3-bromopropyl)-7H-indolo[6,7-a]pyrrolo[3,4-c]carbazole-6,8-dione (150 mg, 0.30 mmol), L-prolinol (411 mg, 3.81 mmol), and DMF (10 mL) in a manner analogous to that described for the preparation of Example 44. The solid was dissolved 50% aqueous CH$_3$CN (2 mL), and 1.42 mL of a 0.154 mM solution of methansulfonic acid in CH$_3$CN added. The mixture was filtered and the filtrate was washed with CH$_2$Cl$_2$ and the aqueous layer freeze dried to give the title compound (98 mg, 52%). $^1$H NMR (400 MHz, DMSO-d$_6$) 11.14 (s, 1H), 9.18 (br s, 1H), 9.03 (d, J=9 Hz, 1H), 8.29 (d, J=9 Hz, 1H), 8.04 (d, J=9 Hz, 1H), 7.61 (d, J=3 Hz, 1H), 7.47 (d, J=2 Hz, 1H), 7.10 (dd, J=9, 2 Hz, 1H), 6.86 (d, J=3 Hz, 1H), 5.41 (m, 2H), 3.99 (s, 3H), 3.86 (s, 3H), 3.4–3.8 (m, 11H), 3.30 (m, 1H), 3.10 (m, 1H), 2.32 (s, 3H), 1.17–2.15 (m, 3H). MS (electrospray, m/z) 511.3 (M$^+$+1), 509.3 (M$^-$–1).

EXAMPLE 52

11-Methoxy-5-methyl-13-(1-methyl-4-propyl-piperazine)-7H-indolo[6,7-a]pyrrolo[3,4-c]carbazole-6,8-dione

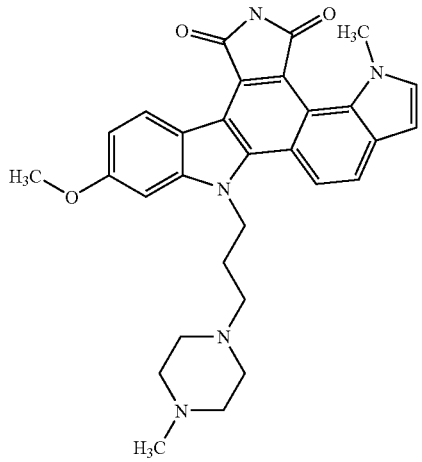

A mixture of 11-Methoxy-5-methyl-13-(3-bromopropyl)-7H-indolo[6,7-a]pyrrolo[3,4-c]carbazole-6,8-dione (150 mg, 0.30 mmol), N-methylpiperazine (0.45 mL, 3.81 mmol), and DMF (10 mL) was heated at 65° C. overnight and then allowed to cool to room temperature. The mixture was poured into EtOAc and was washed with H$_2$O (3×10 mL). The combined H$_2$O layers were back extracted with EtOAc (1×25 mL). The combined organic layers were further washed with H$_2$O (10 mL), saturated NaHCO$_3$ (10 mL), and brine (10 mL), dried (MgSO$_4$), filtered, and concentrated to about 0.5 mL. Et$_2$O was introduced followed by slow addition of hexane to precipitate the product which was collected by filtration. The product was dissolved 50% aqueous CH$_3$CN (4 mL), and 2.37 mL of 0.154 mM solution of methansulfonic acid in CH$_3$CN added. The mixture was filtered and the filtrate was freeze dried to give 11.MsOH (125 mg). The salt was dissolved in H$_2$O (5 mL) and 1N NaOH (0.43 mL) was introduced. The resulting precipitate was collected by filtration and rinsed with H$_2$O. The solid was dissolved in EtOAc/MeOH (100 mL with heating) and the solution dried (MgSO$_4$), filtered and concentrated to give the title compound (102 mg, 65%) as an orange solid. $^1$H NMR (400 MHz, DMSO-d$_6$) 11.07 (s, 1H), 8.98 (d, J=8 Hz, 1H), 8.31 (d, J=9 Hz, 1H), 7.97 (d, J=9 Hz, 1H), 7.57 (d, J=3 Hz, 1H), 7.36 (d, J=2 Hz, 1H), 7.03 (dd, J=8, 2 Hz, 1H), 6.82 (d, J=3 Hz, 1H), 4.89 (t, J=8 Hz, 2H), 3.95 (s, 3H), 3.83 (s, 3H), 2.2–2.35 (m, 12H), 2.12 (s, 3H), 2.03 (m, 2H). MS (electrospray, m/z) 510.1 (M$^+$+1), 508.2 (M$^-$−1).

EXAMPLE 53

11-Methoxy-5-methyl-13-(2-propylamino-ethanol)-7H-indolo[6,7-a]pyrrolo[3,4-c]carbazole-6,8-dione

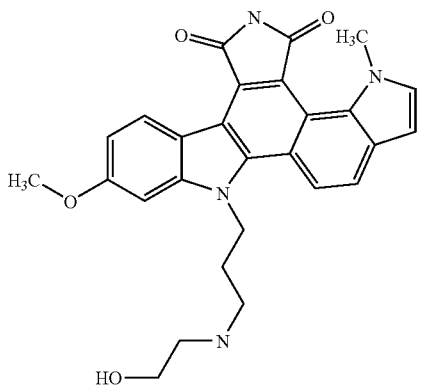

A mixture of 11-Methoxy-5-methyl-13-(3-bromopropyl)-7H-indolo[6,7-a]pyrrolo[3,4-c]carbazole-6,8-dione (150 mg, 0.30 mmol), 2-aminoethanol (0.25 mL, 3.81 mmol), and DMF (10 mL) in a manner analogous to that described for the preparation of Example 44. A 0.154 mM solution of methansulfonic acid in CH$_3$CN (1.95 mL) was introduced to the crude product, and the organic layer was extracted with H$_2$O (10 and 5 mL). The combined aqueous solutions were freeze dried. The salt obtained disolved in H$_2$O (2 mL) and 0.1N NaOH (3 mL) added. The product precipitated and was collected by filtration, rinsed with H$_2$O and freeze dried to give the title compound (73 mg, 42%), mp 168–172 C. $^1$H NMR (400 MHz, DMSO-d$_6$) 8.98 (d, J=8 Hz, 1H), 8.37 (d, J=9 Hz, 1H), 7.98 (d, J=9 Hz, 1H), 7.57 (d, J=3 Hz, 1H), 7.42 (d, J=2 Hz, 1H), 7.03 (dd, J=8, 2 Hz, 1H), 6.81 (d, J=3 Hz, 1H), 4.91 (t, J=7 Hz, 2H), 4.48 (br s, 1H), 3.95 (s, 3H), 3.83 (s, 3H), 3.48 (t, J=6 Hz, 2H), 2.64 (t, J=6 Hz, 2H), 2.58 (t, J=6 Hz, 2H), 2.07 (m, 2H). MS (electrospray, m/z) 471.2 (M$^+$+1).

EXAMPLE 54

11-Methoxy-5-methyl-13-(2-propylamino-ethanol)-7H-indolo[6,7-a]pyrrolo[3,4-c]carbazole-6,8-dione hydrochloride

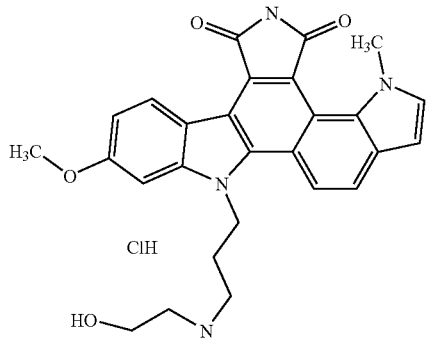

A mixture of 11-Methoxy-5-methyl-13-(3-bromopropyl)-7H-indolo[6,7-a]pyrrolo[3,4-c]carbazole-6,8-dione (555 mg, 1.13 mmol), 2-aminoethanol (0.68 mL, 11.3 mmol), and DMF (30 mL) in a manner analogous to that described for the preparation of Example 44. The crude reaction mixture was purified in a manner analogous to that described for Example 22, except fractions from the preparative HPLC containing the desired product were combined and freeze dried to give the title compound (352 mg, 61%) as an orange solid. $^1$H NMR (400 MHz, DMSO-d$_6$) 11.11 (s, 1H), 8.99 (d, J=9 Hz, 1H), 8.95 (br s, 2H), 8.28 (d, J=9 Hz, 1H), 8.01 (d, J=9 Hz, 1H), 7.58 (d, J=3 Hz, 1H), 7.49 (d, J=2 Hz, 1H), 7.05 (dd, J=9, 2 Hz, 1H), 6.83 (d, J=3 Hz, 1H), 5.00 (t, J=7 Hz, 2H), 4.19 (br s, 1H), 3.97 (s, 3H), 3.83 (s, 3H), 3.62 (t, J=5 Hz, 2H), 3.08 (m, 2H), 2.93 (m, 2H), 2.30 (m, 2H). MS (electrospray, m/z) 471.2 (M$^+$+1), 505.2 (M$^-$+Cl).

EXAMPLE 55

11-Methoxy-5-methyl-13-(N,N-dimethyl-N'-propyl-ethane-1,2-diamine)-7H-indolo[6,7-a]pyrrolo[3,4-c]carbazole-6,8-dione

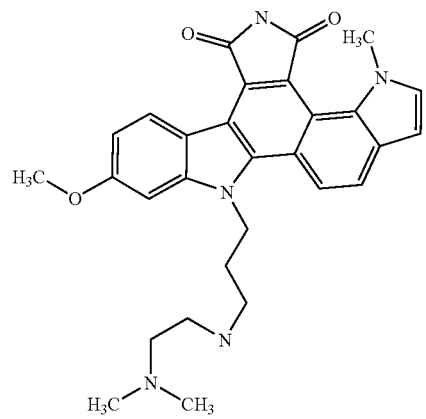

A mixture of 11-Methoxy-5-methyl-13-(3-bromopropyl)-7H-indolo[6,7-a]pyrrolo[3,4-c]carbazole-6,8-dione (150 mg, 0.30 mmol), N,N-dimethylethylenediamine (0.45 mL, 3.81 mmol), and DMF (10 mL) in a manner analogous to that described for the preparation of Example 44. The mixture was heated at 65° C. overnight and then allowed to cool to room temperature. The mixture was poured into EtOAc and was washed with $H_2O$ (3×10 mL). The combined $H_2O$ layers were back extracted with EtOAc (1×25 mL). The combined organic layers were further washed with $H_2O$ (10 mL), saturated $NaHCO_3$ (10 mL), and brine (10 mL). A 0.154 mM solution of methansulfonic acid in $CH_3CN$ (1.95 mL) solution was introduced and the organic layer was extracted with $H_2O$ (10 and 5 mL). The combined $H_2O$ layers were washed with EtOAc (2×) and freeze dried. The salt was dissolved in water and 0.1N NaOH (5.67 mL) added. The title compound precipitated and was collected by filtration, rinsed with $H_2O$ and freeze dried to give an orange solid (86 mg, 57%). $^1$H NMR (400 MHz, DMSO-$d_6$) 8.93 (d, J=8 Hz, 1H), 8.31 (d, J=9 Hz, 1H), 7.92 (d, J=9 Hz, 1H), 7.51 (d, J=3 Hz, 1H), 7.36 (d, J=2 Hz, 1H), 6.98 (dd, J=8, 2 Hz, 1H), 6.76 (d, J=3 Hz, 1H), 4.84 (t, J=8 Hz, 2H), 3.89 (s, 3H), 3.77 (s, 3H), 2.54 (t, J=6 Hz, 2H), 2.50 (t, J=8 Hz, 2H), 2.24 (t, J=6 Hz, 2H), 2.05 (s, 6H), 2.00 (m, 2H), NH's washed out. MS (electrospray, m/z) 498.2 ($M^+$+1).

EXAMPLE 56

11-Methoxy-5-methyl-13-(N,N-dimethyl-N'-propyl-ethane-1,2-diamine)-7H-indolo[6,7-a]pyrrolo[3,4-c]carbazole-6,8-dione dihydrochloride

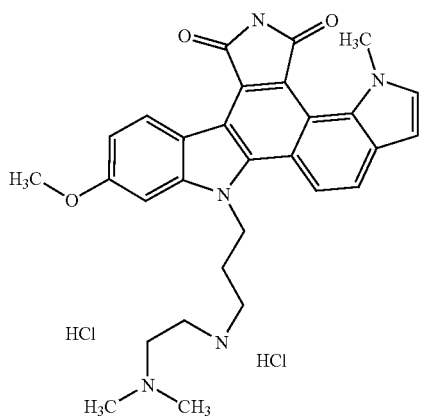

11-Methoxy-5-methyl-13-(N,N-dimethyl-N'-propyl-ethane-1,2-diamine)-7H-indolo[6,7a] pyrrolo[3,4-c]carbazole-6,8-dione (50 mg, 0.1 mmol) was dissolved in $CH_3CN$ (15 mL) and 0.1 N HCl (1 mL) added. The mixture was purified by reverse phase HPLC as described above. The title compound (15 mg, 26%) was obtained as an orange solid.

EXAMPLE 57

11-Methoxy-5-methyl-13-(trans-4-propylamino-cyclohexanol)-7H-indolo[6,7-a]pyrrolo[3,4-c]carbazole-6,8-dione

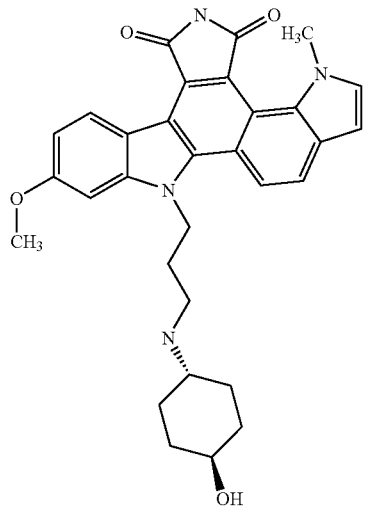

Prepared from 11-Methoxy-5-methyl-13-(3-bromopropyl)-7H-indolo[6,7-a]pyrrolo[3,4-c]carbazole-6,8-dione (240 mg, 0.48 mmol) and trans-4-amino-cyclohexanol (563 mg, 4.8 mmol) in a manner analogous to that described for the preparation of Example 44. The title compound (218 mg, 86%) as an orange solid. $^1$H NMR (400 MHz, DMSO-$d_6$) 8.98 (d, J=9 Hz, 1H), 8.38 (d, J=9 Hz, 1H), 7.96 (d, J=9 Hz, 1H), 7.56 (d, J=3 Hz, 1H), 7.41 (d, J=2 Hz, 1H), 7.04 (dd, J=9, 2 Hz, 1H), 6.82 (d, J=3 Hz, 1H), 4.90 (t, J=7 Hz, 2H), 4.45 (d, J=4 Hz, 1H), 3.95 (s, 3H), 3.83 (s, 3H), 2.58 (m, 2H), 2.24 (m, 1H), 2.03 (m, 2H), 1.76 (m, 4H), 0.9–1.22 (m, 4H), NH's washed out and one CH signal buried under residual $H_2O$. MS (electrospray, m/z) 525.2 ($M^+$+1), 523.2 ($M^-$−1).

EXAMPLE 58 d,l-(+/−)-11-Methoxy-5-methyl-13-(2-propylamino-succinic acid dimethyl ester)-7H-indolo[6,7-a]pyrrolo[3,4-c]carbazole-6,8-dione

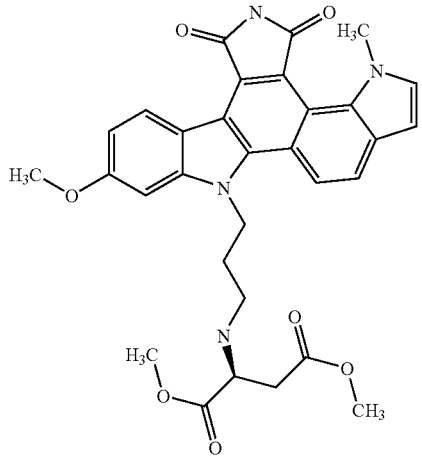

A mixture of 11-Methoxy-5-methyl-13-(3-bromopropyl)-7H-indolo[6,7-a]pyrrolo[3,4-c]carbazole-6,8-dione (450 mg, 0.91 mmol), d,l-(+/−) aspartic acid dimethylester and DMF (40 mL) in a manner analogous to that described for the preparation of Example 44. Flash chromatography (50% hexane/EtOAc to 100% EtOAc) gave 2-(3-{6-Methoxy-3-[4-(1-methyl-1H-indol-7-yl)-2,5-dioxo-2,5-dihydro-1H-pyrrol-3-yl]-indol-1-yl}-propylamino)-succinic acid dimethyl ester (403 mg, 76%) as an orange solid. This material (220 mg, 0.384 mmol) was combined with $Et_3N$ (0.16 mL, 1.15 mmol) and iodine (97 mg, 0.384 mmol) in Dioxane (250 mL) and the solution photolyzed (450 W Hanovia medium pressure Hg Lamp fitted with a pyrex filter) for 1.75 hours. The reaction mixture was concentrated to 10 mL and loaded onto a flash $SiO_2$ column, The column was eluted with EtOAc/hexanes. Fractions containing product were combined and concentrated and the resulting solid was recrystalized from refluxing $Et_2O$/Acetone to give the title compound (103 mg, 47%) as an orange solid. $^1H$ NMR (400 MHz, DMSO-$d_6$) 11.07 (s, 1H), 8.98 (d, J=9 Hz, 1H), 8.33 (d, J=9 Hz, 1H), 7.97 (d, J=9 Hz, 1H), 7.57 (d, J=3 Hz, 1H), 7.39 (s, 1H), 7.03 (d, J=9 Hz, 1H), 6.82 (d, J=3 Hz, 1H), 4.87 (t, J=7 Hz, 2H), 3.95 (s, 3H), 3.83 (s, 3H), 3.59 (s, 3H), 3.55 (s, 3H), 2.65–2.80 (m, 2H), 2.55–2.65 (m, 2H), 2.50–2.55 (m, 1H), 2.02 (m, 2H). MS (electrospray, m/z) 571.3 ($M^+$+1), 569.3 ($M^-$−1).

EXAMPLE 59

(S)-(+)-11-Methoxy-5-methyl-13-(2-propylamino-propionic acid methyl ester)-7H-indolo[6,7-a]pyrrolo[3,4-c]carbazole-6,8-dione

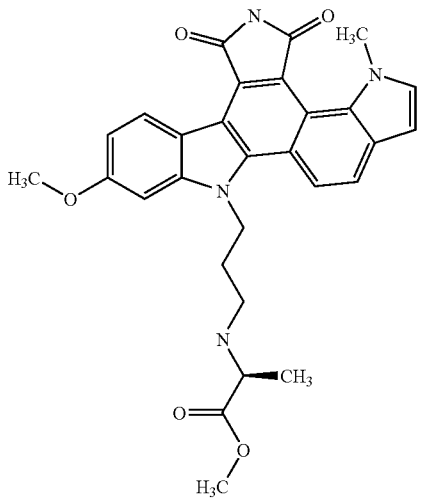

A mixture of 11-Methoxy-5-methyl-13-(3-bromopropyl)-7H-indolo[6,7-a]pyrrolo[3,4-c]carbazole-6,8-dione (100 mg, 0.20 mmol), L-Ala-OMe (3.7 mmol), and DMF (10 mL) in a manner analogous to that described for the preparation of Example 44. $^1H$ NMR (400 MHz, DMSO-$d_6$) 11.07 (s, 1H), 8.98 (d, J=9 Hz, 1H), 8.35 (d, J=9 Hz, 1H), 7.97 (d, J=9 Hz, 1H), 7.57 (d, J=3 Hz, 1H), 7.41 (d, J=1.6 Hz, 1H), 7.04 (dd, J=9, 1.6 Hz, 1H), 6.82 (d, J=3 Hz, 1H), 4.90 (m, 2H), 3.95 (s, 3H), 3.83 (s, 3H), 3.59 (s, 3H), 3.24 (m, 1H), 2.66 (m, 1H), 2.45 (m, 1H), 2.04 (m, 2H), 1.19 (d, J=7 Hz, 2H). MS (electrospray, m/z) 513.2 ($M^+$+1), 511.2 ($M^-$−1).

EXAMPLE 60

(S)-(+)-11-Methoxy-5-methyl-13-(3-hydroxy-2-propylamino-propionic acid methyl ester)-7H-indolo[6,7-a]pyrrolo[3,4-c]carbazole-6,8-dione trifluoro-acetic acid

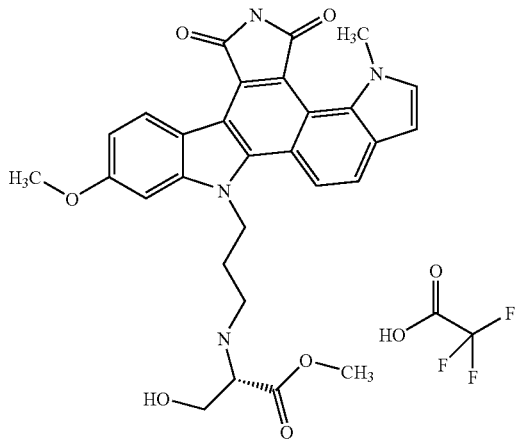

A mixture of intermediate 4 (100 mg, 0.20 mmol), L-Ser-OMe (Free base) (3.7 mmol), and DMF (10 mL) in a manner analogous to that described for the preparation of Example 44. The crude mixture was separated by reverse phase preparatory HPLC (95% $H_2O$ (0.1% TFA)/$CH_3CN$ 25 mL/min gradient to 70% $CH_3CN$/$H_2O$ (0.1% TFA). Fraction containing the desired product were combined, concentrated and freeze-dried to afford the title compound (168 mg, 65%) as an orange solid. $^1H$ NMR (400 MHz, DMSO-$d_6$) 11.13 (s, 1H), 9.11 (br s, 1H), 9.01 (d, J=9 Hz, 1H), 8.28 (d, J=9 Hz, 1H), 8.01 (d, J=9 Hz, 1H), 7.59 (d, J=3 Hz, 1H), 7.45 (d, J=2 Hz, 1H), 7.07 (dd, J=9, 2 Hz, 1H), 6.84 (d, J=3 Hz, 1H), 4.98 (t, J=7 Hz, 2H), 4.20 (br s, 1H), 3.95 (s, 3H), 3.83 (s, 3H), 3.81 (m, 2H), 3.72 (s, 3H), 3.10 (m, 2H), 2.30 (m, 2H). MS (electrospray, m/z) 529.2 ($M^+$+1), 527.2 ($M^-$−1).

EXAMPLES 61–74

(a) tert-Butyl-dimethyl-[2-(2-nitro-phenyl)-ethoxy]-silane

A solution of 2-(2-nitro-phenyl)ethanol (100 g, 590 mmol) in $CH_2Cl_2$ (800 mL), was treated with imidazole (117 g, 777 mmol) followed by tert-butyl-dimethylsilylchloride (562 g, 826 mmol). A white precipitate formed upon the addition and the reaction was stirred 2.5 hours. The mixture was filtered and diluted with $CH_2Cl_2$ (300 mL) and was washed with 0.1 N HCl (300 mL), $H_2O$ (400 mL), saturated aq $NaHCO_3$ (400 mL), and brine (400 mL). The organic layer was dried over $MgSO_4$, filtered and concentrated to give the title compound (160 g, 96%) as a transparent oil. $^1H$ NMR (400 MHz, DMSO-$d_6$) −0.11 (s, 6H), 0.77 (s, 9H), 3.03 (t, J=6 Hz, 2H), 3.79 (t, J=6 Hz), 7.42–7.54 (m, 2H), 7.62 (ddd, J=<1, 6, 7 Hz, 1H), 7.88 (dd, J=<1, 7 Hz, 1H). MS (electrospray, m/z) 282 ($H^+$+1).

(b) 7-[2-(tert-Butyl-dimethyl-silanyloxy)-ethyl]-1H-indole

A solution of tert-butyl-dimethyl-[2-(2-nitro-phenyl)-ethoxy]-silane (85.6 g, 304 mmol) in THF (1 L) was cooled to −65° C. and a 1.0 M solution of vinyl magnesium bromide in THF (913 mL, 913 mmol) was introduced while maintaining a temperature below −60° C. The reaction was stirred for 15 minutes at −45° C., additional vinyl magnesiumbromide (152 mL, 152 mmol) was added and the reaction was stirred at −45° C. for 30 minutes. The cold reaction was poured into saturated aq ammonium chloride (800 mL) and diluted with EtOAc (500 mL). The two layers were separated and the aqueous layer was extracted with EtOAc(2× 200 mL). The organic layers were combined, washed with brine (400 mL), dried (MgSO$_4$), filtered and concentrated. Flash chromatography (95% hexane/EtOAc) gave the title compound (47.1 g, 56%) as a transparent brown oil. $^1$H NMR (400 MHz, DMSO-d$_6$) −0.11 (s, 6H), 0.80 (s, 9H), 3.03 (t, J=6.8 Hz, 2H), 3.85 (t, J=6.8 Hz, 2H), 6.39 (dd, J=1.2, 3.2 Hz, 1H), 6.86–6.92 (m, 2H), 7.28 (dd, J=3, 3 Hz, 1H), 7.36 (dd, J=4.8, 4.8 Hz, 1H), 11.02 (br s, 1H). MS (electrospray, m/z) 276 (M$^+$+1).

(c) [7-(2-Hydroxyl-ethyl)-1H-indol-3-yl]-oxo-acetic acid methyl ester

A solution of 7-[2-(tert-butyl-dimethyl-silanyloxy)-ethyl]-1H-indole (47.0 g, 170 mmol) in Et$_2$O (600 mL) was cooled to 4° C. (ice bath) and a 2M solution of oxalyl chloride in THF (92.0 mL, 184 mmol) added dropwise. The ice bath was removed and the reaction was allowed to warm to room temperature (1.5 h). The reaction was then cooled to −78° C. and solution of NaOMe in MeOH (85.1 mL, 25% wt, 357 mmol) was introduced over 5 minutes. The cold bath was removed and the reaction was allowed to warm to room temperature (1 h). The reaction was quenched with H$_2$O (500 mL) and poured into EtOAc (400 mL). The water layer was separated and extracted with EtOAc (2×200 mL) and the organic layers were combined, washed with saturated aq NH$_4$Cl (400 mL) and brine (500 mL), dried over MgSO$_4$, filtered and concentrated. Flash chromatography (30% EtOAc/hexanes) gave the title compound (23.9 g, 57%) as a yellow solid. $^1$H NMR (400 MHz, DMSO-d$_6$) 3.04 (t, J=6.8 Hz, 1H), 3.70 (m, 2H), 3.88 (s, 3H), 4.72 (t, J=4 Hz, 1H), 7.10–7.22 (m, 2H), 8.00 (d, J=7.6 Hz, 1H), 8.36 (d, J=3.2 Hz, 1H), 12.38 (s, 1H). MS (electrospray, m/z) 248 (M$^+$+1).

(d) 3-[7-(2-Hydroxyethyl)-1H-Indol-7-yl)-4-(1H-indol-3-yl)-pyrrole-2,5-dione A 1.0 M solution of potassium tert-butoxide in THF (6.2 mL, 6.2 mmol), was added dropwise to solution of 2-(1-methyl-1H-indol-7-yl)-acetamide (1.20 g, 6.35 mmol) in DMF (50 mL) followed after 5 minutes by a solution of [7-(2-hydroxyl-ethyl)-1H-indol-3-yl]-oxo-acetic acid methyl ester (1.57 g, 6.35 mmol) in DMF (25 mL) dropwise over 10 min giving a yellow-brown solution. After another 90 minutes additional potassium tert-butoxide (6.6 mL, 6.6 mmol) was introduced and the reaction was stirred for 24 h. The maroon-purple reaction mixture was quenched with 1N HCl, concentrated to 20–30 mL and the red slurry diluted with EtOAc. The two layers were separated and the organic layer was washed with H$_2$O (2×), saturated aq NaHCO$_3$ (2×) and brine (2×), dried (MgSO$_4$), filtered, and concentrated onto SiO2. Flash chromatography (7:3 EtOAc:hexane) gave a red solid, which was dried under vacuum overnight at 75 C. affording the title compound (1.24 g, 50%). $^1$H NMR (400 MHz, DMSO-d$_6$) 11.81 (s, 1H), 11.14 (s, 1H), 7.86 (d, J=3 Hz, 1H), 7.60 (d, J=8 Hz, 1H), 7.27 (d, J=3 Hz, 1H), 6.96 (dd, J=7, 7 Hz, 1H), 6.87 (d, J=7 Hz, 1H), 6.81 (d, J=7 Hz, 1H), 6.49 (d, J=3 Hz, 1H), 6.43 (dd, J=8, 8 Hz, 1H), 6.25 (d, J=8 Hz, 1H), 4.67 (t, J=5 Hz, 1H), 3.70 (s, 3H), 3.64 (m, 2H), 2.90 (m, 2H). MS (electrosrpay, m/z) 386 (M$^+$+1), 384 (M$^-$−1). HRMS 386.1495 (M$^+$+1, calcd for C$_{23}$H$_{20}$N$_3$O$_3$ 386.1505). Anal. Calcd for C$_{23}$H$_{19}$N$_3$O$_3$: C, 71.68; H, 4.97; N, 10.90. Found: C, 71.33; H, 5.13; N, 10.83.

(e) 3-[7-(2-Bromoethyl)-1H-indol-3-yl]-4-(1-methyl-1H-indol-7-yl)pyrrole-2,5-dione Method A: Carbon tetrabromide (3.05 g, 9.20 mmol) was added in one portion to a solution of 3-[7-(2-hydroxyethyl)-1H-indol-3-yl]-4-(1-methyl-1H-indol-7-yl)-pyrrole-2,5-dione (2.88 g, 7.47 mmol) and triphenylphosphine (2.32 g, 8.84 mmol) in DMF (50 mL) and the mixture stirred at room temperature 4 h. The solution was concentrated to about10 mL, poured into EtOAc, and the solution washed with water, saturated aq. sodium bicarbonate and brine, dried (MgSO$_4$) and concentrated onto SiO$_2$. Flash chromatography (30 to 50% EtOAc/hexanes) afforded the title compound as a orange solid which was dried at 75 C under vacuum (2.31 g, 69%). $^1$H NMR (400 MHz, acetone-d$_6$) 11.13 (s, 1H), 9.90 (s, 1H), 8.30 (d, J=3 Hz, 1H), 7.62 (m, 1H), 7.17 (d, J=3 Hz, 1H), 6.92–6.98 (m, 3H), 6.44–6.55 (m, 3H), 3.82 (s, 3H), 3.68 (t, J=8 Hz, 2H), 3.39 (t, J=8 Hz, 2H). $^{13}$C NMR (250 MHz, DMSO-d$_6$) 173.46, 172.36, 135.16, 134.19, 131.56, 131.04, 129.55, 129.23, 124.99, 124.02, 122.56, 122.45, 121.53, 120.10, 119.51, 118.62, 115.11, 105.51, 100.75, 34.75, 33.88, 33.13 (one aromatic signal is buried). IR (KBr, cm$^{-1}$) 3430, 1756, 1699. MS (electrospray, m/z) 448/450 (M$^+$+1), 446/448 M$^-$−1). HRMS 448.0665 (M$^+$+1, calcd for C$_{23}$H$_{19}$BrN$_3$O$_2$ -448.0661). Anal. Calcd for C$_{23}$H$_{18}$BrN$_3$O$_2$: C, 61.62; H, 4.05; N, 9.37. Found: C, 61.60; H, 4.20; N, 9.08.

Method B: To a solution of 3-[7-(2-hydroxyethyl)-1H-indol-3-yl]-4-(1-methyl-1H-indol-7-yl)-pyrrole-2,5-dione (0.5 g, 1.3 mmol) in solution of CH$_2$Cl$_2$/THF (40/30 ml) was added PPh$_3$ (0.3 g, 1.3 mmol) and CBr$_4$ (0.4 g, 1.3 mmol). The reaction mixture was stirred at room temperature and under nitrogen for 1 h. Another equivalent of PPh$_3$ (0.3 g, 1.3 mmol) was added followed by an equivalent of CBr$_4$ (0.4 g, 1.3 mmol). This operation was repeated one more time after 1 h. The reaction was monitored by TLC and was completed after 1 h. The reaction mixture was diluted with EtOAc (100 ml) and washed with saturated aq NaHCO$_3$ (100 mL), brine (100 ml). The organic solution was dried (MgSO$_4$), filtered and concentrated. Flash chromatography (SiO$_2$, 50% EtOAc/hexanes) gave the title compound (0.5 g, 87%) as a red solid.

(e) 5-Methyl-12-(2-bromoethyl)-7H,13H-indolo[6,7-a]pyrrolo[3,4-c]carbazole-6,8-dione A solution of 3-[7-(2-bromo-ethyl)-1H-indol-3-yl]-4-(1-methyl-1H-indol-7-yl)pyrrole-2,5-dione (2.23 g, 4.98 mmol) and DDQ (1.13 g, 4.98 mmol) in dioxane (800 mL) was irradiated with a 450 W Hanovia mercury arc lamp fitted with a pyrex filter for 2.5 h. The dark solution was concentrated to about 40 mL and poured into EtOAc. The EtOAc solution was washed with 0.1 N NaOH, saturated aq sodium bicarbonate (3×) and brine, dried (MgSO4) and concentrated to about 50 mL. Hexanes (2–3 mL) were added and the solution allowed to stand 4 h. Filtration afforded the title compound as a red solid which was dried under vacuum at 75 C (1.41 g, 64%). The mother liquor was concentrated onto SiO2, and flash chromatography (30% EtOAc/hexanes) afforded additional product as an orange-red solid (0.62 g, 28%), mp 262–264 C. $^1$H NMR (DMSO-$d_6$) 12.24 (s, 1H), 11.10 (s, 1H), 8.91 (d, J=8 Hz, 1H), 8.55 (d, J=8 Hz, 1H), 8.07 (d, J=8 Hz, 1H), 7.60 (d, J=3 Hz, 1H), 7.47 (d, J=8 Hz, 1H), 7.33 (dd, J=8, 8 Hz, 1H), 6.85 (d, J=3 Hz, 1H), 3.92 (t, J=7.5 Hz, 2H), 3.88 (s, 3H), 3.70 (t, J=7.5 Hz, 2H). MS (electrospray, m/z) 446, 448 $[C_{23}H_{16}BrN_3O_2+H]^+$. Anal. Calc for $C_{23}H_{16}BrN_3O_2$: C, 61.90; H, 3.61; N, 9.42. Found: C, 61.61; H, 3.55; N, 9.48.

EXAMPLE 61

5-Methyl-12-(1-ethyl-piperidine-4-carboxylic acid methyl ester)-7H,13H-indolo[6,7-a]pyrrolo[3,4-c]carbazole-6,8-dione

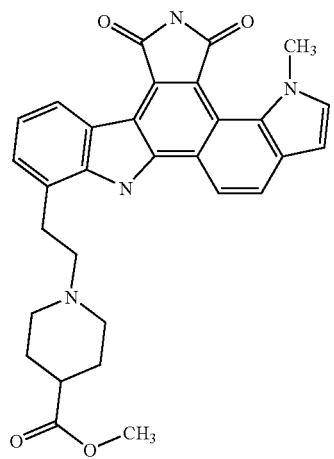

A mixture of 5-Methyl-12-(2-bromoethyl)-7H,13H-indolo[6,7-a]pyrrolo[3,4-c]carbazole-6,8-dione (99 mg, 0.22 mmol), methyl isonipecotate (0.30 mL, 2.22 mmol), and DMF (10 mL) was heated at 65° C. for 3.5 h. The mixture was poured ino EtOAc and washed with H$_2$O (3×), 10% aqueous LiCl (2×), brine and dried (MgSO$_4$). Concentration of the solution afforded a yellow oil which was absorbed onto flash SiO$_2$. Chromatography (5% MeOH/CH$_2$Cl$_2$) afforded the title compound (73 mg, 65%) as an orange solid. $^1$H NMR (400 MHz, DMSO-$d_6$) 12.28 (s, 1H), 11.08 (s, 1H), 8.84 (d, J=8 Hz, 1H), 8.54 (d, J=8.6 Hz, 1H), 8.05 (d, J=8.6 Hz, 1H), 7.58 (d, J=3 Hz, 1H), 7.37 (d, J=7.5 Hz, 1H), 7.29 (dd, J=7.5, 7.5 Hz, 1H), 6.85 (d, J=3 Hz, 1H), 3.88 (s, 3H), 3.62 (s, 3H), 3.30 (t, J=8 Hz, 2H), 3.05 (d, J=10 Hz, 2H), 2.71 (m, 2H), 2.38 (m, 1H), 2.11 (t, J=10 Hz, 2H), 1.88 (br d, J=11 Hz, 2H), 1.66 (m, 2H). MS (electrospray, m/z) 509.1 (M$^+$+1), 507.1 (M$^-$−1). HRMS 509.2215 (M$^+$+1, calcd for $C_{30}H_{29}N_4O_4$ 509.2189).

EXAMPLE 62

5-Methyl-12-(1-ethyl-piperidine-4-carboxylic acid amide)-7H,13H-indolo[6,7-a]pyrrolo[3,4-c]carbazole-6,8-dione

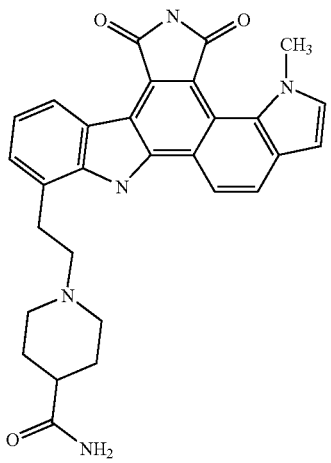

A mixture of 5-Methyl-12-(2-bromoethyl)-7H,13H-indolo[6,7-a]pyrrolo[3,4-c]carbazole-6,8-dione (173 mg, 0.388 mmol), isonipecotamide (497 mg, 3.88 mmol), and DMF (10 mL) in a manner analogous to that described for the preparation of Example 61. The title compound precipitated from the solution upon standing and was collected by filtration and dried to afford an orange solid (65 mg, 34%). $^1$H NMR (400 MHz, DMSO-$d_6$) 12.37 (s, 1H), 11.08 (s, 1H), 8.85 (d, J=8 Hz, 1H), 8.54 (d, J=8.6 Hz, 1H), 8.06 (d, J=8.6 Hz, 1H), 7.59 (d, J=3 Hz, 1H), 7.38 (d, J=7 Hz, 1H), 7.27–7.32 (m, 2H), 6.84 (d, J=3 Hz, 1H), 6.79 (br s, 1H), 3.88 (s, 3H), 3.33 (m, 2H), 3.16 (m, 2H), 2.72 (m, 2H), 2.15 (m, 1H), 2.02 (m, 2H), 1.68–1.80 (m, 4H). MS (electrospray, m/z) 494.2 (M$^+$+1), 492.2 (M$^-$−1). HRMS 494.2217 (M$^+$+1, calcd for $C_{29}H_{28}N_5O_3$ 494.2192).

EXAMPLE 63

5-Methyl-12-(1-ethyl-piperazine)-7H,13H-indolo[6,7-a]pyrrolo[3,4-c]carbazole-6,8-dione

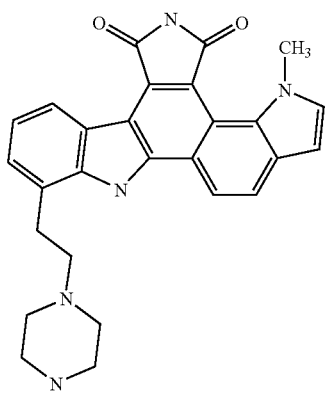

A mixture of 5-Methyl-12-(2-bromoethyl)-7H,13H-indolo[6,7-a]pyrrolo[3,4-c]carbazole-6,8-dione (173 mg, 0.388 mmol), piperazine (456 mg, 5.3 mmol), and DMF (10 mL) in a manner analogous to that described for the preparation of Example 61. Trituration with MeOH followed by washing with EtOAc and drying afforded the title compound (38 mg, 21%) as a yellow solid. $^1$H NMR (400 MHz, DMSO-$d_6$) 12.24 (s, 1H), 11.07 (s, 1H), 8.84 (d, J=8 Hz, 1H), 8.56 (d, J=8 Hz, 1H), 8.05 (d, J=8 Hz, 1H), 7.58 (d, J=3 Hz, 1H), 7.38 (d, J=7.5 Hz, 1H), 7.29 (dd, J=7.5, 7.5 Hz, 1H), 6.84 (d, J=3 Hz, 1H), 3.87 (s, 3H), 3.26–3.4 (br m, 6H), 2.81 (m, 4H), 2.70 (t, J=7 Hz, 2H). MS (electrospray, m/z) 452.2 (M$^+$+1), 450.2 (M$^-$−1). HRMS 452.2109 (M$^+$+1, calcd for $C_{27}H_{26}N_5O_2$ 452.2086).

EXAMPLE 64

5-Methyl-12-(1-ethyl-piperidin-4-ol)-7H,13H-indolo[6,7-a]pyrrolo[3,4-c]carbazole-6,8-dione

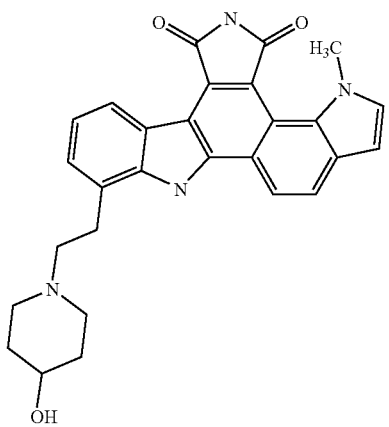

A mixture of 5-Methyl-12-(2-bromoethyl)-7H,13H-indolo[6,7-a]pyrrolo[3,4-c]carbazole-6,8-dione (200 mg, 0.448 mmol), 4-hydroxypiperidine (453 mg, 2.76 mmol) and DMF (10 mL) was prepared in a manner analogous to that described for the preparation of Example 61. The resulting precipitate was collected by filtration and dried to give the title compound (147 mg, 70%) as an orange solid. $^1$H NMR (400 MHz, DMSO-$d_6$) 12.28 (s, 1H), 11.07 (s, 1H), 8.83 (d, J=8 Hz, 1H), 8.54 (d, J=9 Hz, 1H), 8.04 (d, J=9 Hz, 1H), 7.57 (d, J=3 Hz, 1H), 7.35 (d, J=8 Hz, 1H), 7.28 (dd, J=8, 8 Hz, 1H), 6.83 (d, J=3 Hz, 1H), 4.61 (d, J=4 Hz, 1H), 3.87 (s, 3H), 3.50 (m, 1H), 3.28 (t, J=8 Hz, 2H), 2.92 (m, 2H), 2.69 (t, J=8 Hz, 2H), 2.17 (m, 2H), 1.78 (m, 2H), 1.46 (m, 2H). MS (electrospray, m/z) 467.2 (M$^+$+1), 465.2 (M$^-$−1).

EXAMPLE 65

5-Methyl-12-(1-ethyl-piperidin-4-ol)-7H,13H-indolo[6,7-a]pyrrolo[3,4-c]carbazole-6,8-dione hydrochloride

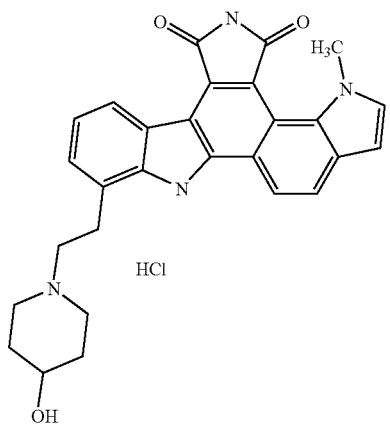

A mixture of 5-Methyl-12-(2-bromoethyl)-7H,13H-indolo[6,7-a]pyrrolo[3,4-c]carbazole-6,8-dione (150 mg, 0.33 mmol), 4-hydroxypiperidine (33 mg, 3.3 mmol), and DMF (10 mL) in a manner analogous to that described for the preparation of Example 61. The mixture was concentrated and the crude product was purified by reverse phase preparatory HPLC to give title compound (94 mg, 56%) as an orange solid. MS (electrospray, m/z) 466.2 (M$^+$+1).

EXAMPLE 66

(S)-(+)-5-Methyl-12-[(1-ethyl-pyrrolidin-2-yl)-methanol]-7H,13H-indolo[6,7-a]pyrrolo[3,4-c]carbazole-6,8-dione

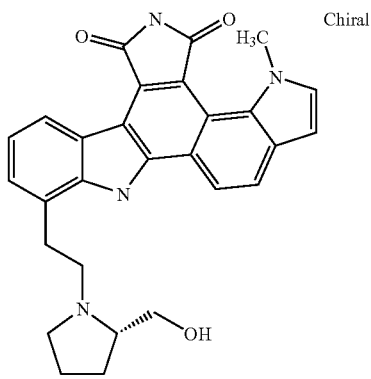

A mixture of 5-Methyl-12-(2-bromoethyl)-7H,13H-indolo[6,7-a]pyrrolo[3,4-c]carbazole-6,8-dione (184 mg, 0.412 mmol), S-(+)-2-pyrrolidinemethanol (0.5 mL, 5.1 mmol), and DMF (10 mL) in a manner analogous to that described for the preparation of Example 61. Preparative reverse phase HPLC (95% H2O (0.1% TFA)/CH3CN 25 mL/min gradient to 70% CH3CN/H2O(0.1% TFA) afforded compound 28.TFA (92 mg, 39%) as an orange solid. This material (63 mg, 0.108 mmol) was mixed with $H_2O$ (5 mL) and 0.1N NaOH (1.6 mL). The resulting suspension was extracted with EtOAc and the extracts diluted with hexane (2 volumes). The resultant percipitate was collected by filtration, rinsed with $H_2O$, and dried to give the title compound (25 mg, 50%) as an orange solid. $^1$H NMR (400 MHz, DMSO-$d_6$) 12.55 (s, 1H), 11.07 (s, 1H), 8.83 (d, J=8 Hz, 1H), 8.45 (d, J=8 Hz, 1H), 8.04 (d, J=8 Hz, 1H), 7.57 (d, J=3 Hz, 1H), 7.37 (d, J=8 Hz, 1H), 7.28 (dd, J=8, 8 Hz, 1H), 6.83 (d, J=3 Hz, 1H), 4.48 (br s, 1H), 3.87 (s, 3H), 3.43 (m, 1H), 3.28 (m, 5H), 2.74 (m, 1H), 2.59 (m, 1H), 2.38 (m, 1H), 1.86 (m, 1H), 1.6–1.8 (m, 3H). MS (electrospray, m/z) 467.2 ($M^+$+1), 465.2 ($M^-$–1).

EXAMPLE 67

(S)-(+)-5-Methyl-12-[(1-ethyl-pyrrolidin-2-yl)-methanol]-7H,13H-indolo[6,7-a]pyrrolo[3,4-c]carbazole-6,8-dione hydrochloride

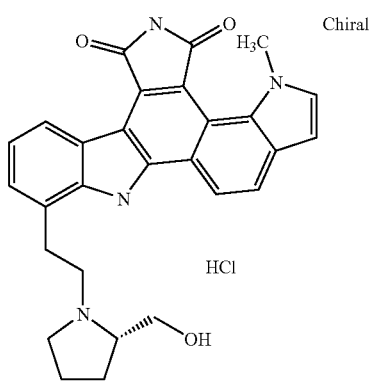

A mixture of 5-Methyl-12-(2-bromoethyl)-7H,13H-indolo[6,7-a]pyrrolo[3,4-c]carbazole-6,8-dione (150 mg, 0.33 mmol), L-prolinol (0.32 mL, 3.3 mmol), and DMF (10 mL) in a manner analogous to that described for the preparation of Example 61. The mixture was concentrated and the crude product was purified by reverse phase preparatory HPLC to give the title compound (87 mg, 52%) as an orange solid. $^1$H NMR (400 MHz, DMSO-$d_6$) 12.37 (s, 1H), 11.05 (s, 1H), 9.85 (br s, 1H), 8.85 (d, J=9 Hz, 1H), 8.65 (d, J=9 Hz, 1H), 8.80 (d, J=9 Hz, 1H), 7.55 (d, J=3 Hz, 1H), 7.36 (d, J=9 Hz, 1H), 7.28 (dd, J=9, 9 Hz, 1H), 6.78 (d, J=3 Hz, 1H), 5.42 (m, 1H), 3.85 (s, 3H), 3.5–3.8 (m, 8H), 3.42 (m, 1H), 1.95–2.15 (m, 2H), 1.85–1.95 (m, 1H), 1.7–1.8 (m, 1H). MS (electrospray, m/z) 467.2 ($M^+$+1).

EXAMPLE 68

5-Methyl-12-(1-ethyl-4-methyl-piperazine)-7H,13H-indolo[6,7-a]pyrrolo[3,4-c]carbazole-6,8-dione

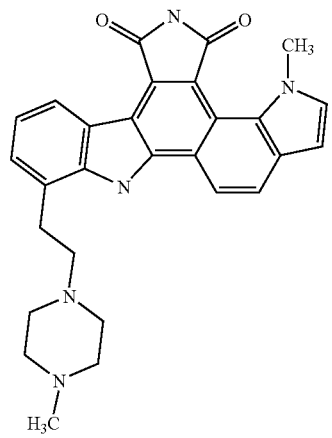

A mixture of 5-Methyl-12-(2-bromoethyl)-7H,13H-indolo[6,7-a]pyrrolo[3,4-c]carbazole-6,8-dione (174 mg, 0.390 mmol), N-methylpiperazine (0.5 mL, 4.1 mmol), and DMF (10 mL) in a manner analogous to that described for the preparation of Example 61. Upon standing, a precipitate formed which was isolated by filtration and dried to afford the title compound (78 mg, 43%) as a yellow solid. $^1$H NMR (400 MHz, DMSO-$d_6$) 12.25 (s, 1H), 11.08 (s, 1H), 8.84 (d, J=8 Hz, 1H), 8.56 (d, J=8.6 Hz, 1H), 8.06 (d, J=8.6 Hz, 1H), 7.58 (d, J=3 Hz, 1H), 7.38 (d, J=7 Hz, 1H), 7.29 (dd, J=7, 7 Hz, 1H), 6.84 (d, J=3 Hz, 1H), 3.88 (s, 3H), 3.30 (t, J=7 Hz, 2H), 2.72 (t, J=7 Hz, 2H), 2.77 (br m, 4H), 2.41 (br m, 4H), 2.20 (s, 3H). MS (electrospray, m/z) 466:2 ($M^+$+1). HRMS 466.2231 ($M^+$+1, calcd for $C_{28}H_{28}N_5O_2$ 466.2243).

EXAMPLE 69

5-Methyl-12-(1-ethyl-4-methyl-piperazine)-7H,13H-indolo[6,7-a]pyrrolo[3,4-c]carbazole-6,8-dione dihydrochloride

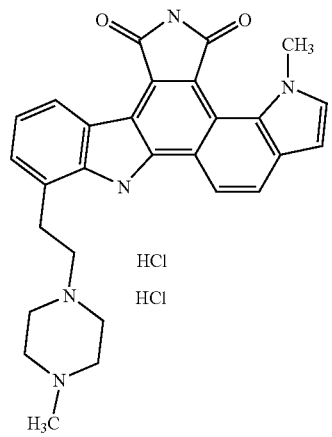

A mixture of 5-Methyl-12-(2-bromoethyl)-7H,13H-indolo[6,7-a]pyrrolo[3,4-c]carbazole-6,8-dione (100 mg, 0.33 mmol), N-methylpiperazine (220 mg, 2.2 mmol), and DMF (4 mL) in a manner analogous to that described for the preparation of Example 61 The mixture was concentrated and the crude product was purified by reverse phase the method described for Example 36. Fractions containing the product were combined and freeze-dried to give the title compound (68 mg, 57%) as an orange solid. $^1$H NMR (400 MHz, DMSO-$d_6$) 12.42 (br s, 1H), 11.11 (s, 1H), 8.91 (d, J=8 Hz, 1H), 8.79 (br s, 1H), 8.03 (d, J=8 Hz, 1H), 7.58 (d, J=3 Hz, 1H), 7.44 (d, J=8 Hz, 1H), 7.34 (dd, J=8, 8 Hz, 1H), 6.84 (d, J=3 Hz, 1H), 3.87 (s, 3H), 3.67 (br m, 8H), 2.8.6 (m, 4H), 2.49 (s, 3H). MS (electrospray, m/z) 466.2 (M$^+$+1), 464.2 (M$^-$−1).

EXAMPLE 70

5-Methyl-12-(2-ethylamino-ethanol)-7H,13H-indolo[6,7-a]pyrrolo[3,4-c]carbazole-6,8-dione

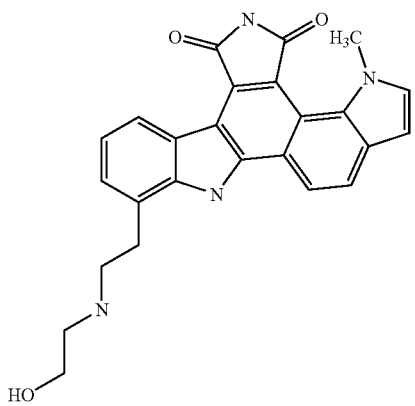

A mixture of 5-Methyl-12-(2-bromoethyl)-7H,13H-indolo[6,7-a]pyrrolo[3,4-c]carbazole-6,8-dione (150 mg, 0.33 mmol) 2-aminoethanol (0.20 mL, 3.3 mmol), and DMF (10 mL) in a manner analogous to that described for the preparation of Example 61. The residue was purified by preparative reverse phase HPLC (95% H$_2$O (0.1% TFA)/CH$_3$CN 25 mL/min to 70% CH$_3$CN/H$_2$O (0.1% TFA). Fractions containing the desired product were combined, concentrated and freeze-dried to afford the title compound as a trifluoromethanesulfonic acid salt (70 mg). The salt was treated with 0.1N NaOH (1.4 mL) and H$_2$O (1 mL). Filtration afforded the title compound (48 mg, 34%) as an orange solid. $^1$H NMR (400 MHz, DMSO-$d_6$) 8.83 (dd, J=8, 1 Hz, 1H), 8.47 (d, J=9 Hz, 1H), 8.01 (d, J=9 Hz, 1H), 7.56 (d, J=3 Hz, 1H), 7.36 (d, J=8 Hz, 1H), 7.28 (dd, J=8, 8 Hz, 1H), 6.83 (d, J=3 Hz, 1H), 4.70 (br s, 1H), 3.87 (s, 3H), 3.56 (t, J=6 Hz, 2H), 3.29 (t, J=6 Hz, 2H), 3.04 (t, J=6 Hz, 2H), 2.77 (t, J=6 Hz, 2H), NH's washed out. MS (electrospray, m/z) 427.2 (M$^+$+1), 425.2 (M$^-$−1).

EXAMPLE 71

5-Methyl-12-(N'-ethyl-N,N-dimethyl-ethane-1,2-diamine)-7H,13H-indolo[6,7-a]pyrrolo[3,4-c]carbazole-6,8-dione

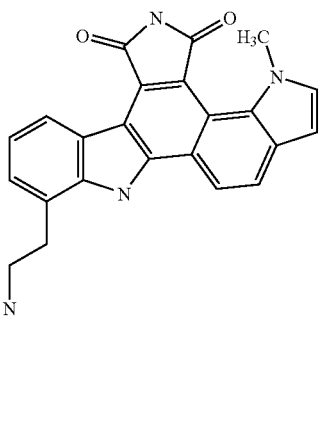

Prepared from 5-Methyl-12-(2-bromoethyl)-7H,13H-indolo[6,7-a]pyrrolo[3,4-c]carbazole-6,8-dione (250 mg, 0.56 mmol) and N,N-dimethylethylenediamine (0.59 mg, 5.6 mmol) in a manner analogous to that described for the preparation of Example 61. Fractions from-the preparatory reverse phase purification containing the product were combing and split into two equal fractions. One was freeze-dried resulting in decomposition of the product. The other was filtered through an SCX column (prewashed with MeOH and 5% AcOH/MeOH). The product was removed from the column using 2M NH$_3$ in MeOH and the eluent concentrated to give the title compound (55 mg, 43%) as an orange solid. $^1$H NMR (400 MHz, DMSO-$d_6$) 8.83 (d, J=8 Hz, 1H), 8.49 (d, J=8 Hz, 1H), 8.02 (d, J=8 Hz, 1H), 7.57 (d, J=3 Hz, 1H), 7.35 (dd, J=8 Hz, 1H), 7.27 (dd, J=8, 8 Hz, 1H), 6.82 (d, J=3 Hz, 1H), 3.86 (s, 3H), 3.30 (t, J=7 Hz, 2H), 3.04 (t, J=7 Hz, 2H), 2.78 (t, J=6 Hz, 2H), 2.43 (t, J=6 Hz, 2H), 2.16 (s, 6H), NH's washed out. MS (electrospray, m/z) 454.2 (M$^+$+1), 452.2 M$^-$−1).

EXAMPLE 72

5-Methyl-12-(trans-4-ethylamino-cyclohexanol)-7H,13H-indolo[6,7-a]pyrrolo[3,4-c]carbazole-6,8-dione

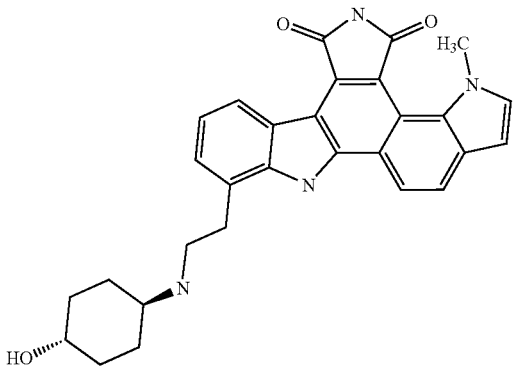

Prepared from 5-Methyl-12-(2-bromoethyl)-7H,13H-indolo[6,7-a]pyrrolo[3,4-c]carbazole-6,8-dione (147 mg, 0.33 mmol) and trans-4-aminocyclohexanol (378 mg, 3.29 mmol) in a manner analogous to that described for Example 63. The title compound (108 mg, 68%) was obtained as an orange solid. $^1$H NMR (400 MHz, DMSO-d$_6$) 8.81 (d, J=8 Hz, 1H), 8.41 (d, J=8 Hz, 1H), 8.03 (d, J=8 Hz, 1H), 7.57 (d, J=3 Hz, 1H), 7.33 (d, J=8 Hz, 1H), 7.25 (dd, J=8, 8 Hz, 1H), 6.82 (d, J=3 Hz, 1H), 4.47 (br s, 1H), 3.86 (s, 3H), 3.13 (t, J=7 Hz, 2H), 2.97 (t, J=7 Hz, 2H), 2.45 (m, 1H), 1.88 (m, 2H), 1.80 (m, 2H), 1.13 (m, 4H), NH's washed out. MS (electrospray, m/z) 481.2 (M$^+$+1), 479.2 (M$^-$−1).

EXAMPLE 73

5-Methyl-12-(trans-4-ethylamino-cyclohexanol)-7H,13H-indolo[6,7-a]pyrrolo[3,4-c]carbazole-6,8-dione hydrochloride

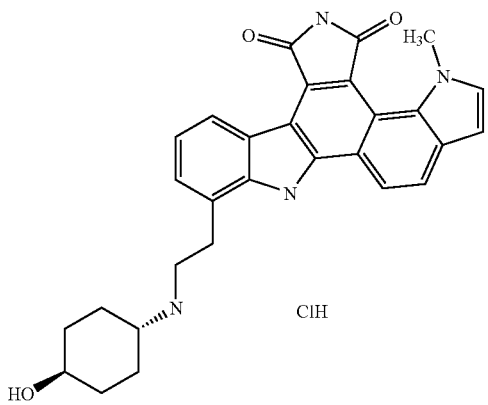

A mixture of 5-Methyl-12-(2-bromoethyl)-7H,13H-indolo[6,7-a]pyrrolo[3,4-c]carbazole-6,8-dione (130 mg, 0.29 mmol), trans-4-aminocyclohexanol (335 mg, 2.91 mmol) and DMF (10 mL) in a manner analogous to that described for the preparation of Example 61. The reaction mixture was allowed to cool and the crude reaction mixture was purified by preparatory reverse phase HPLC. Fractions containing the product were combined and freeze dried to give the title compound (66 mg, 44%) as an orange solid. $^1$H NMR (400 MHz, DMSO-d$_6$) 12.51 (s, 1H), 11.10 (s, 1H), 9.02 (br s, 2H), 8.91 (d, J=7 Hz, 1H), 8.85 (d, J=8 Hz, 1H), 8.01 (d, J=8 Hz, 1H), 7.58 (d, J=3 Hz, 1H), 7.43 (d, J=8 Hz, 1H), 7.33 (dd, J=7, 7 Hz, 1H), 6.83 (d, J=3 Hz, 1H), 3.87 (s, 3H), 3.56 (t, J=8 Hz, 2H), 3.08 (m, 2H), 2.08 (br d, J=10 Hz, 2H), 1.87 (br d, J=10 Hz, 2H), 1.41 (m, 2H), 1.17 (m, 2H). MS (electrospray, m/z) 481.2 (M$^+$+1), 479.2 (M$^-$−1).

EXAMPLE 74

5-Methyl-12-(trans-N-Ethyl-cyclohexane-1,4-diamine)-7H,13H-indolo[6,7-a]pyrrolo[3,4-c]carbazole-6,8-dione dihydrochloride

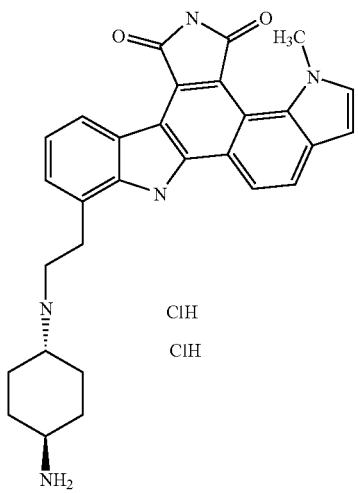

A mixture of 5-Methyl-12-(2-bromoethyl)-7H,13H-indolo[6,7-a]pyrrolo[3,4-c]carbazole-6,8-dione (150 mg, 0.33 mmol), trans-1,4-diaminocyclohexane (376 mg, 3.3 mmol), and DMF (10 mL) in a manner analogous to that described for the preparation of Example 61. The mixture was concentrated and the crude product was purified by reverse phase preparatory HPLC to give compound the title compound (158 mg, 86%) as an orange solid. $^1$H NMR (400 MHz, DMSO-d$_6$) 12.61 (s, 1H), 11.09 (s, 1H), 9.3 (br s, 2H), 8.94 (d, J=8 Hz, 1H), 8.91 (d, J=8 Hz, 1H), 7.98 (m, 4H), 7.57 (d, J=3 Hz, 1H), 7.43 (d, J=7 Hz, 1H), 7.32 (dd, J=7, 7 Hz, 1H), 6.83 (d, J=3 Hz, 1H), 3.86 (s, 3H), 3.60 (t, J=7 Hz, 2H), 3.13 (m, 1H), 2.98 (m, 1H), 2.19 (br d, J=9 Hz, 2H), 2.01 (br d, J=9, 2H), 1.48 (m, 2H), 1.37 (m, 2H), 2H buried under residual H$_2$O. MS (electrospray, m/z) 480.3 (M$^+$+1), 478.3 (M$^-$−1).

EXAMPLES 75–82

(a) Ethyl 3-(indol-7-yl)acrylate

A 1.0 M solution of potassium tert-butoxide in THF (12.0 mL, 12.0 mmol) was added to THF (50 mL) at −78° C. under N$_2$ followed by triethyl phosphonoacetate (2.6 mL, 13.1 mmol). A solution of 7-formylindole (1.01 g, 7.0 mmol) in THF (10 mL) was then added dropwise over 5 min. The resulting red solution was stirred for 2 h, quenched with saturated NaHCO$_3$ (50 mL) and extracted with EtOAc (100 mL). The organic layer was washed with H$_2$O (60 mL), brine (60 mL), dried (MgSO$_4$) and concentrated to a brown oil. Flash chromatography (SiO$_2$, 8%EtOAc/hexanes containing 2% TEA) gave the title compound (1.0 g, 80%) as a white solid. $^1$H NMR (300 MHz, CDCl$_3$) 8.53 (bs, 1H), 7.98 (m, 1H), 7.71 (m, 1H), 7.42 (m, 1H), 7.27 (m, 1H), 7.14 (m, 1H), 6.60 (m, 1H), 6.51 (m, 1H), 4.31 (m, 2H), 1.40 (m, 3H).

(b) Ethyl 3-(indol-7-yl)-propionate

A solution of ethyl 3-(indol-7-yl)acrylate (13.0 g, 60.5 mmol) in 1:1 THF/MeOH (120 mL), was added to a Parr bottle containing 10% Pd/C (0.87 g, 0.83 mmol). The mixture was hydrogenated in a Parr shaker over 3 h. The mixture was filtered over Celite and concentrated to afford the title compound (12.8 g, 97%) as a white solid. $^1$H NMR (400 MHz, DMSO-$d_6$) 11.09 (s, 1H), 7.36 (dd, J=6, 2.4 Hz, 1H), 7.29 (t, J=2.4 Hz, 1H), 6.86–6.90 (m, 2H), 6.40 (dd, J=2.8, 2.0 Hz, 1H), 4.04 (q, J=6.8 Hz, 2H), 3.09 (t, J=7.2 Hz, 2H), 2.68 (t, J=7.2 Hz, 2H), 1.13 (t, J=6.8 Hz, 3H). MS (electrospray, m/z) 218.1 (M$^+$+1).

(c) 7-Hydroxypropyl-1H-indole. To a 1.0 M solution of lithium aluminum hydride in THF (140.0 mL, 140.0 mmol) in additional THF (360 mL), heated to 60° C. under $N_2$, was added dropwise a solution of ethyl 3-(indol-7-yl)propionate (5.52 g, 25.4 mmol) in THF (60 mL). The mixture was stirred for 4 h, quenched with $H_2O$ (5.4 mL), followed by 3.0 M NaOH (5.4 mL), and followed by $H_2O$ (16.2 mL). The reaction mixture was filtered and concentrated to afford the title compound (4.5 g, 99%) as a yellow oil. $^1$H NMR (400 MHz, CDCl$_3$) 8.92 (bs, 1H), 7.45 (dd, J=8, 1.5 Hz, 1H), 7.14 (d, J=3 Hz, 1H), 6.99 (dd, J=8, 8 Hz, 1H), 6.93 (d, J=8 Hz, 1H) 6.48 (d, J=3 Hz, 1H), 3.62 (t+OH, J=6 Hz, 3H), 2.94 (t, J=7 Hz, 2H), 1.92 (m, 2H).

(d)
7-[3-(tert-Butyldimethylsilyloxy)propyl]-1H-indole

To a solution of 7-hydroxypropyl-1H-indole (4.45 g, 25.4 mmol) in methylene chloride (50 mL), was added imidazole (2.31 g, 34.0 mmol), followed by tert-butyldimethylsilyl chloride (5.44 g, 36.1 mmol). The reaction mixture was stirred at room temperature for 12 h, filtered and concentrated to a brown oil. Flash chromatography (SiO$_2$, 10% EtOAc/hexanes) gave the title compound (4.9 g, 66%) as a colorless oil. $^1$H NMR (300 MHz, CDCl$_3$) 9.38 (bs, 1H), 7.54 (m, 1H), 7.22 (m, 1H), 7.18–6.06 (m, 2H), 6.60 (m, 1H), 3.71 (m, 2H), 3.07 (m, 2H), 1.98 (m, 2H), 1.03 (s, 9H), 0.20 (s, 6H).

(e) Methyl 2-[7-(3-hydroxypropyl)-1H-indol-3-yl]oxoacetate

A 2.0 M solution of oxalyl chloride in methylene chloride (9.30 mL, 18.6 mmol) was added to a solution of 7-[3-(tert-butyldimethylsilyloxy)propyl]-1H-indole (4.9 g, 16.9 mmol) in ether (40 mL) dropwise over 15 min at 4° C. under $N_2$. The ice bath was removed and the resulting mixture was stirred for 1.5 h. A 25% sodium methoxide in methanol solution (8.1 mL, 32.4 mmol) was added at −78° C. over 5 min. The mixture was allowed to warm up to room temperature and stirred for 2 h. The reaction was quenched with water (30 mL) and extracted with EtOAc (2×100 mL). The organic layers were combined, washed with saturated NH$_4$Cl (60 mL), saturated NaCl (60 mL), dried (MgSO$_4$) and concentrated to a red solid. Flash chromatography (SiO$_2$, 50% EtOAc/CH$_2$Cl$_2$) gave the title compound (4.3 g, 97%) as a white solid. $^1$H NMR (400 MHz, DMSO-$d_6$) 12.44 (s, 1H), 8.43 (d, J=3 Hz, 1H), 8.04 (d, J=8 Hz, 1H), 7.24 (dd, J=8, 8 Hz, 1H), 7.15 (d, J=8 Hz, 1H), 3.94 (s, 3H), 3.50 (t, J=6 Hz, 2H), 2.95 (t, J=7.6 Hz, 2H), 1.78 (m, 2H). MS (electrospray, m/z) 260.1 (M$^-$−1).

(f) 3-[7-(3-Hydroxypropyl)-1H-indol-3-yl]-4-(1-methyl-1H-indol-7-yl)pyrrole-2,5-dione To a solution of 2-(1-methyl-1H-indol-7-yl)acetamide (105 mg, 0.55 mmol) and methyl 2-(7-hydroxypropyl-1H-indol-3-yl)oxoacetate (146 mg, 0.56 mmol) in DMF (2.0 mL) at 4° C. under $N_2$, was added a 1.0 M solution of potassium tert-butoxide in THF (1.7 mL, 1.7 mmol) dropwise over 25 min. The reaction was heated to 60° C. and stirred for 12 h. The reaction mixture was then cooled to room temperature and quenched with 1.0 N hydrochloric acid (5.0 mL). The mixture was extracted with EtOAc (2×15 mL), washed with saturated NaHCO$_3$ (30 mL), saturated NaCl (30 mL), dried (MgSO$_4$), filtered and concentrated. Flash chromatography (SiO$_2$, 3:47:50 MeOH/EtOAc/CH$_2$Cl$_2$) gave the title compound (196 mg, 87%) as a red solid, mp 183–185° C. $^1$H NMR (300 MHz, DMSO-$d_6$) 11.81 (s, 1H), 11.12 (s, 1H), 7.87 (m, 1H), 7.61 (m, 1H), 7.28 (m, 1H), 6.98 (m, 3H), 6.50 (m, 2H), 6.29 (m, 1H), 3.68 (s, 3H), 3.41 (m, 2H), 2.78 (m, 2H), 1.76 (m, 2H). MS (electrospray, m/z) 398 [C$_{24}$H$_{21}$N$_3$O$_3$–H]$^-$ (g) 3-[7-(3-Bromopropyl)-1H-indol-3-yl]-4-(1-methyl-1H-indol-7-yl)pyrrole-2,5-dione To a solution of 3-[7-(3-hydroxypropyl)-1H-indol-3-yl]-4-(1-methyl-1H-indol-7-yl)pyrrole-2,5-dione (505 mg, 1.27 mmol) in 1:1 tetrahydrofuran/methylene chloride (60 mL) was added triphenylphosphine (330 mg, 1.25 mmol) followed by carbon tetrabromide (418 mg, 1.26 mmol). After one hour, additional triphenylphosphine (332 mg, 1.27 mmol) and carbon tetrabromide (414 mg, 1.25 mmol) was added. After 1 h, triphenylphosphine (330 mg, 1.26 mmol) and carbon tetrabromide (430 mg, 1.30 mmol) was added and stirred for 1 h. The reaction mixture was diluted with methylene chloride (100 mL), washed with saturated aq NaHCO$_3$ (100 mL), brine (100 mL), dried (MgSO$_4$) and concentrated. Flash chromatography (SiO$_2$, 30% EtOAc/hexanes) gave the title compound (462 mg, 91%) as a red solid. $^1$H NMR (CDCl$_3$) 8.93 (m, 1H), 8.66 (m, 1H), 8.07–7.87 (m, 4H), 6.64 (m, 1H), 6.49 (m, 2H), 3.72 (s, 3H), 3.41 (m, 2H), 2.96 (m, 2H), 2.21 (m, 2H). MS (electrospray, m/z) 464/462 (C$_{24}$H$_{20}$BrN$_3$O$_2$+H)$^+$.

(h) 12-(3-Bromopropyl)-5-methyl-7H,13H-indolo[6,7-a]pyrrolo[3,4-c]carbazole-6,8-dione A solution of 3-[7-(3-bromopropyl)-1H-indol-3-yl]-4-(1-methyl-1H-indol-7-yl)pyrrole-2,5-dione (508 mg, 1.1 mmol) and DDQ (255 mg, 1.1 mmol) in EtOAc (1.0 L) was irradiated with 450 Watt Hanovia lamp fitted with a Pyrex filter for 40 min. The resulting light brown solution was washed with 0.1 and concentrated. Flash chromatography (SiO$_2$, 50% EtOAc/hexanes) gave the title compound (414 mg, 81%) as a red solid, which was used as is without further purification; HPLC: 85.0%. $^1$H NMR (300 MHz, DMSO-$d_6$) 12.13 (s, 1H), 11.11 (s, 1H), 8.91 (d, J=8 Hz, 1H), 8.59 (d, J=8 Hz, 1H), 8.09 (d, J=8 Hz, 1H); 7.62 (d, J=3 Hz, 1H), 7.42–7.32 (m, 2H), 6.89 (d, J=3 Hz, 1H), 3.88 (s, 3H), 3.67 (m, 2H), 3.28 (m, 2H), 2.34 (m, 2H). MS (atmospheric pressure chemical ionization, m/z) 462/460 [C$_{24}$H$_8$BrN$_3$O$_2$+H]+.

EXAMPLE 75

12-(1-Propyl-piperidine-4-carboxylic acid amide)-5-methyl-7H,13H-indolo[6,7-a]pyrrolo[3,4-c]carbazole-6,8-dione

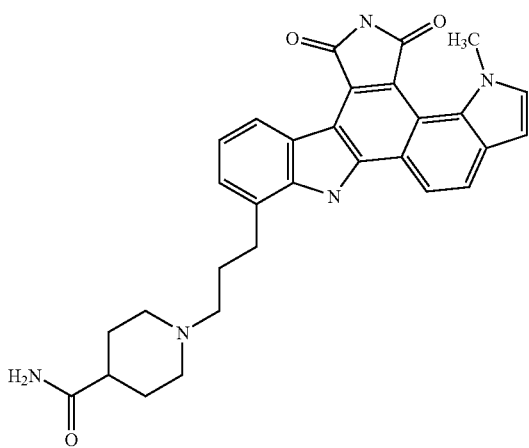

A mixture of 12-(3-Bromopropyl)-5-methyl-7H,13H-indolo[6,7-a]pyrrolo[3,4-c]carbazole-6,8-dione (300 mg, 0.65 mmol), isonipecotamide (355 mg, 2.76 mmmol) and DMF (10 mL) was heated at 60° C. over night, cooled and poured into EtOAc. The EtOAc solution was washed with $H_2O$ (3×) and then passed through an SCX column (prewashed with MeOH and 5% AcOH/MeOH). The compound was removed from the column using 2M $NH_3$ in MeOH. Concentration of the eluent gave the title compound (179 mg, 54%) as an orange solid. $^1$H NMR (400 MHz, DMSO-$d_6$) 12.06 (s, 1H), 11.07 (s, 1H), 8.83 (d, J=9 Hz, 1H), 8.57 (d, J=9 Hz, 1H), 8.04 (d, J=9 Hz, 1H), 7.57 (d, J=3 Hz, 1H), 7.35 (d, J=9 Hz, 1H), 7.28 (dd, J=9, 9 Hz, 1H), 7.19 (br s, 1H), 6.83 (d, J=3 Hz, 1H), 6.70 (br s, 1H), 3.86 (s, 3H), 3.11 (t, J=7 Hz, 2H), 2.89 (m, 2H), 2.40 (m, 2H), 1.8–2.1 (m, 5H), 1.50–1.85 (m, 4H). MS (electrospray, m/z) 508 (M$^+$+1), 506 (M$^-$−1).

EXAMPLE 76

12-(1-Propyl-piperazine)-5-methyl-7H,13H-indolo[6,7-a]pyrrolo[3,4-c]carbazole-6,8-dione

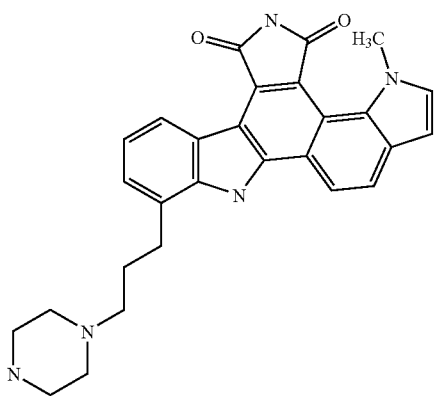

Prepared from 12-(3-Bromopropyl)-5-methyl-7H,13H-indolo[6,7-a]pyrrolo[3,4-c]carbazole-6,8-dione (300 mg, 0.65 mmol) and piperazine (238 mg, 2.76 mmol) in a manner analogous to that described for the preparation of Example 75. Additional purification using reverse phase preparatory HPLC gave the title compound (126 mg, 41%) as an orange solid. $^1$H NMR (400 MHz, DMSO-$d_6$) 12.05 (s, 1H), 8.82 (d, J=9 Hz, 1H), 8.57 (d, J=9 Hz, 1H), 8.04 (d, J=9 Hz, 1H), 7.57 (d, J=3 Hz, 1H), 7.35 (d, J=9 Hz, 1H), 7.28 (dd, J=9, 9 Hz, 1H), 6.83 (d, J=3 Hz, 1H), 3.86 (s, 3H), 3.11 (t, J=7 Hz, 2H), 2.67 (m, 4H), 2.36 (t, J=7 Hz, 2H), 2.28 (m, 4H), 1.91 (m, 2H). MS (electrospray, m/z) 466.2 (M$^+$+1), 4644.2 (M$^-$−1).

EXAMPLE 77

12-(1-Propyl-piperidin-4-ol)-5-methyl-7H,13H-indolo[6,7-a]pyrrolo[3,4-c]carbazole-6,8-dione

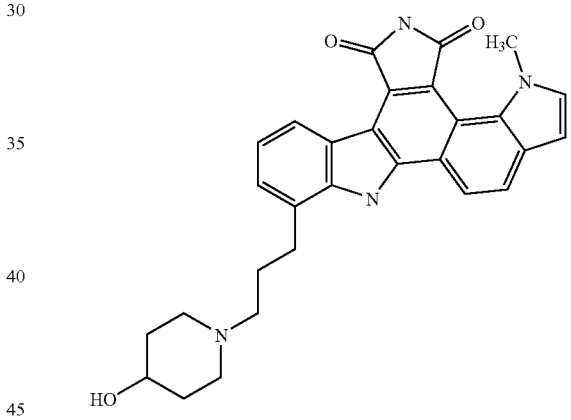

Prepared from 12-(3-Bromopropyl)-5-methyl-7H,13H-indolo[6,7-a]pyrrolo[3,4-c]carbazole-6,8-dione (300 mg, 0.65 mmol) and 4-hydroxypiperidine (280 mg, 2.76 mmol) in a manner analogous to that described for the preparation of Example 75. The title compound (274 mg, 87%) was obtained as an orange solid. $^1$H NMR (400 MHz, DMSO-$d_6$) 12.05 (s, 1H), 11.06 (s, 1H), 8.83 (d, J=9 Hz, 1H), 8.57 (d, J=9 Hz, 1H), 8.04 (d, J=9 Hz, 1H), 7.57 (d, J=3 Hz, 1H), 7.35 (d, J=9 Hz, 1H), 7.28 (dd, J=9, 9 Hz, 1H), 6.83 (d, J=3 Hz, 1H), 4.51 (d, J=4 Hz, 1H), 3.86 (s, 3H), 3.40 (m, 1H), 3.10 (t, J=8 Hz, 2H), 2.70 (m, 2H), 2.38 (m, 2H), 1.98 (m, 2H), 1.88 (m, 2H), 1.68 (m, 2H), 1.37 (m, 2H). MS (electrospray, m/z) 481.2 (M$^+$+1), 479.2 (M$^-$−1).

EXAMPLE 78

(S)-(+)-12-[(1-Propyl-pyrrolidin-2-yl)-methanol]-5-methyl-7H,13H-indolo[6,7-a]pyrrolo[3,4-c]carbazole-6,8-dione

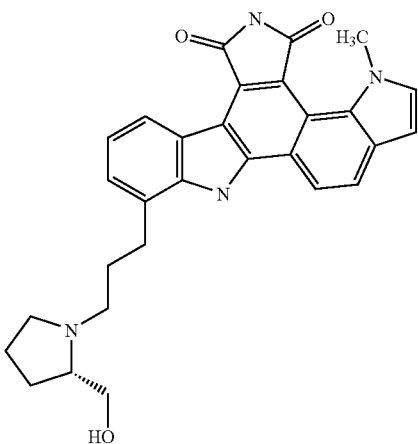

Prepared from 12-(3-Bromopropyl)-5-methyl-7H,13H-indolo[6,7-a]pyrrolo[3,4-c]carbazole-6,8-dione (300 mg, 0.65 mmol) and (S)-(+)-2-pyrrolidinemethanol (0.27 mL, 2.76 mmol) in a manner analogous to that described for the preparation of Example 75. The title compound (278 mg, 88%) was obtained as an orange solid. $^1$H NMR (400 MHz, DMSO-$d_6$) 12.07 (s, 1H), 11.07 (s, 1H), 8.84 (d, J=8 Hz, 1H), 8.57 (d, J=9 Hz, 1H), 8.06 (d, J=9 Hz, 1H), 7.58 (d, J=3 Hz, 1H), 7.36 (d, J=8 Hz, 1H), 7.29 (dd, J=8, 8 Hz, 1H), 6.84 (d, J=3 Hz, 1H), 4.38 (br s, 1H), 3.88 (s, 3H), 3.40 (m, 1H), 3.21 (m, 1H), 3.15 (m, 2H), 3.06 (m, 1H), 2.90 (m, 1H), 2.39 (m, 1H), 2.37 (m, 1H), 2.17 (t, J=8 Hz, 2H), 1.8–2.0 (m, 3H), 1.65–1.75 (m, 2H). MS (electrospray, m/z) 481.1 (M$^+$+1), 479.1 (M$^-$–1).

EXAMPLE 79

12-(1-Methyl-4-propyl-piperazine)-5-methyl-7H,13H-indolo[6,7-a]pyrrolo[3,4-c]carbazole-6,8-dione

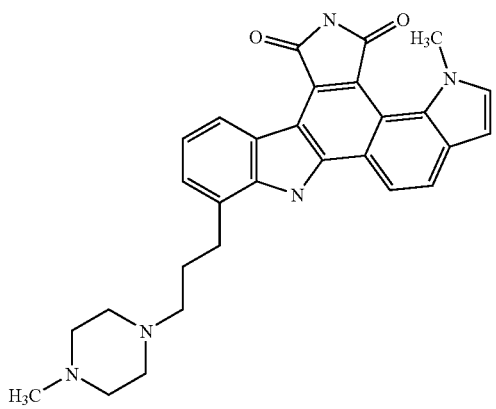

Prepared from 12-(3-Bromopropyl)-5-methyl-7H,13H-indolo[6,7-a]pyrrolo[3,4-c]carbazole-6,8-dione (300 mg, 0.65 mmol) and N-methylpiperazine (279 mg, 2.76 mmol) in a manner analogous to that described for the preparation of Example 75. The title compound (279 mg, 89%) was obtained as an orange solid. $^1$H NMR (400 MHz, DMSO-$d_6$) 12.04 (s, 1H), 11.06 (s, 1H), 8.83 (dd, J=8, 1 Hz, 1H), 8.57 (d, J=9 Hz, 1H), 8.04 (d, J=9 Hz, 1H), 7.57 (d, J=3 Hz, 1H), 7.35 (d, J=8 Hz, 1H), 7.28 (dd, J=8, 8 Hz, 1H), 6.83 (d, J=3 Hz, 1H), 3.86 (s, 3H), 3.11 (t, J=8 Hz, 2H), 2.39 (t, J=7 Hz, 2H), 2.32 (m, 8H), 2.12 (s, 3H), 1.91 (m, 2H). MS (electrospray, m/z) 480.2 (M$^+$+1), 478 M$^-$–1).

EXAMPLE 80

12-(2-Propylamino-ethanol)-5-methyl-7H,13H-indolo[6,7-a]pyrrolo[3,4-c]carbazole-6,8-dione

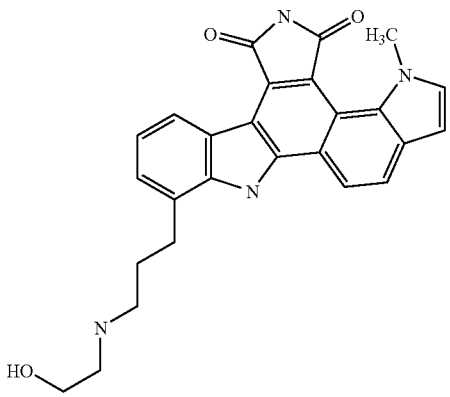

Prepared from 12-(3-Bromopropyl)-5-methyl-7H,13H-indolo[6,7-a]pyrrolo[3,4-c]carbazole-6,8-dione (300 mg, 0.65 mmol) and 2-aminoethanol(0.20 mL, 2.76 mmol) in a manner analogous to that described for the preparation of Example 75. The title compound (219 mg, 76%) was obtained as an orange solid. $^1$H NMR (400 MHz, DMSO-$d_6$) 8.82 (dd, J=8, 1 Hz, 1H), 8.52 (d, J=9 Hz, 1H), 8.04 (d, J=9 Hz, 1H), 7.57 (d, J=3 Hz, 1H), 7.34 (dd, J=8, 1 Hz, 1H), 7.28 (dd, J=8, 8 Hz, 1H), 6.83 (d, J=3 Hz, 1H), 3.86 (s, 3H), 3.49 (t, J=6 Hz, 2H), 3.15 (t, J=6 Hz, 2H), 2.6–2.7 (m, 4H), 1.90 (m, 2H), NH's washed out. MS (electrospray, m/z) 441.1 (M$^+$+1), 439.1 M$^-$–1).

EXAMPLE 81

12-(N'-ethyl-N,N-dimethyl-propane-1,2-diamine)-5-methyl-7H,13H-indolo[6,7-a]pyrrolo[3,4-c]carbazole-6,8-dione

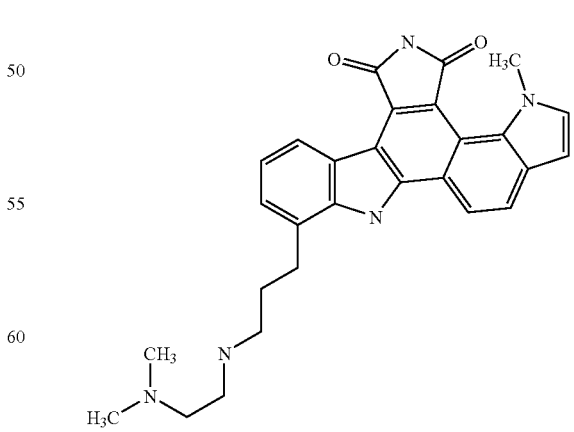

Prepared from 12-(3-Bromopropyl)-5-methyl-7H,13H-indolo[6,7-a]pyrrolo[3,4-c]carbazole-6,8-dione (300 mg, 0.65 mmol) and N,N-dimethylethylenediamine (0.30 mL, 2.76 mmol) in a manner analogous to that described for the preparation of Example 75. Additional preparatory reverse phase HPLC and SCX chromatography gave the title compound (134 mg, 44%) as an orange solid. $^1$H NMR (400 MHz, DMSO-d6) 8.82 (dd, J=8, 1 Hz, 1H), 8.51 (d, J=8 Hz, 1H), 8.03 (d, J=8 Hz, 1H), 7.57 (d, J=3 Hz, 1H), 7.34 (dd, J=8 Hz, 1H), 7.28 (dd, J=8, 8 Hz, 1H), 6.83 (d, J=3 Hz, 1H), 3.86 (s, 3H), 3.13 (t, J=7 Hz, 2H), 2.58–2.64 (m, 4H), 2.32 (t, J=6 Hz, 2H), 2.11 (s, 6H), 1.91 (m, 2H), NH's washed out. MS (electrospray, m/z) 468.2 (M$^+$+1), 466.2 (M$^-$–1).

EXAMPLE 82

12-(trans-4-Propylamino-cyclohexanol)-5-methyl-7H,13H-indolo[6,7-a]pyrrolo[3,4-c]carbazole-6,8-dione

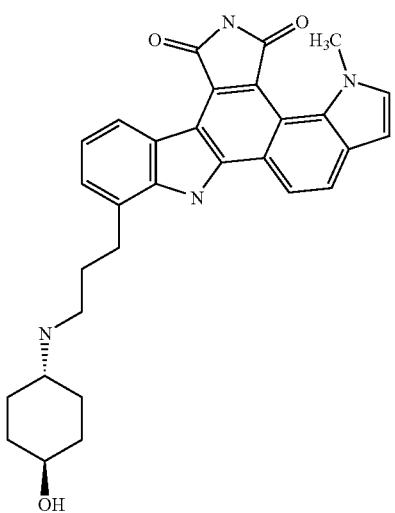

Prepared from 12-(3-Bromopropyl)-5-methyl-7H,13H-indolo[6,7-a]pyrrolo[3,4-c]carbazole-6,8-dione (300 mg, 0.65 mmol) and trans-4-aminocyclohexanol (319 mg, 2.76 mmol) in a manner analogous to that described for the preparation of Example 75. The title compound (155 mg, 48%) was obtained as an orange solid. $^1$H NMR (400 MHz, DMSO-d$_6$) 8.82 (dd, J=8, 1 Hz, 1H), 8.52 (d, J=9 Hz, 1H), 8.03 (d, J=9 Hz, 1H), 7.57 (d, J=3 Hz, 1H), 7.33 (d, J=8 Hz, 1H), 7.28 (dd, J=8, 8 Hz, 1H), 6.82 (d, J=3 Hz, 1H), 4.42 (br s, 1H), 3.86 (s, 3H), 3.31 (m, 1H), 3.13 (t, J=7 Hz, 2H), 2.61 (t, J=7 Hz, 2H), 2.31 (m, 1H), 1.89 (t, J=7 Hz, 2H), 1.72–1.82 (m, 4H), 1.07 (m, 4H), NH's washed out. MS (electrospray, m/z) 495.2 (M$^+$+1), 493.2 (M$^-$–1).

EXAMPLE 83

5-Methyl-12-(2-ethylpiperidine)-7H,13H-indolo[6,7-a]pyrrolo[3,4-c]carbazole-6,8-dione

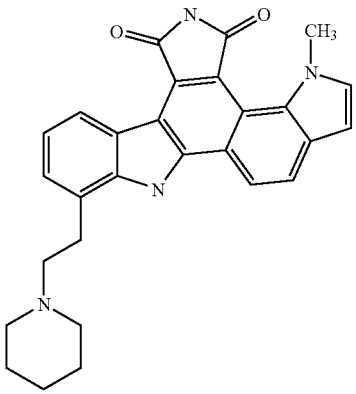

A solution of 5-Methyl-12-(2-bromo-ethyl)-7H,13H-indolo[6,7-a]pyrrolo[3,4-c]carbazole-6,8-dione (100 mg, 0.22 mmol) and piperidine (0.21 mL, 2.2 mmol) in DMF (5 mL) was heated at 60 C. overnight. The mixture was cooled and the product separated by directly injecting the mixture in two 2.5 mL portions onto a 7 um C18 reverse phase hplc column (19×300 mm) with gradient elution with 95:5 H$_2$O (0.1% HCl):CH$_3$CN to 5:95 H$_2$O (0.1% HCl):CH$_3$CN. Fractions containing product where passed through an SCX column, washing first with MeOH and EtOAc, and then a 1:1 mixture of 2M NH$_3$ in MeOH and EtOAc. Concentration of the later afforded the title compound (95 mg, 95%) as an orange solid. $^1$H NMR (400 MHz, DMSO-d$_6$) 12.32 (br s, 1H), 11.07 (s, 1H), 8.83 (d, J=7 Hz, 1H), 8.55 (d, J=8 Hz, 1H), 8.03 (d, J=8 Hz, 1H), 7.57 (d, J=3 Hz, 1H), 7.35 (d, J=7 Hz, 1H), 7.28 (dd, J=7, 7 Hz, 1H), 6.83 (d, J=3 Hz, 1H), 3.87 (s, 3H), 3.32 (br t, J=7.6 Hz, 4H), 2.74 (m, 2H), 2.59 (m, 2H), 1.60 (m, 4H), 1.45 (m, 2H). MS (electrospray, m/z) 451.2 (M$^+$+1), 449.2 (M$^-$–1). TFA salt $^1$H NMR (400 MHz, DMSO-d$_6$) 12.15 (s, 1H), 11.14 (s, 1H), 9.46 (br s, 1H), 8.93 (d, J=7 Hz, 1H), 8.50 (d, J=8 Hz, 1H), 8.09 (d, J=8 Hz, 1H), 7.61 (d, J=3 Hz, 1H), 7.46 (d, J=7 Hz, 1H), 7.38 (dd, J=7, 7 Hz, 1H), 6.87 (d, J=3 Hz, 1H), 3.89 (s, 3H), 3.68 (m, 2H), 3.56 (m, 4H), 3.06 (m, 2H), 1.92 (m, 2H), 1.75 (m, 3H), 1.46 (m, 1H). HRMS 451.2127 (M$^+$+1, calcd for C$_{28}$H$_{27}$N$_4$O$_2$- 451.2134).

EXAMPLE 84

5-Methyl-12-(2-ethylmorpholine)-7H,13H-indolo[6,7-a]pyrrolo[3,4-c]carbazole-6,8-dione

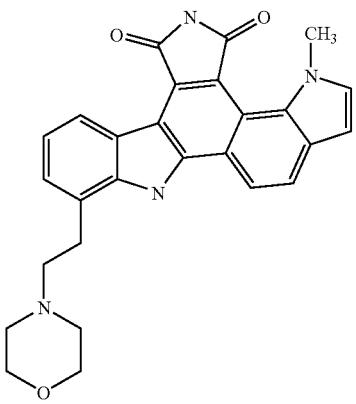

A solution of 5-Methyl-12-(2-bromo-ethyl)-7H,13H-indolo[6,7-a]pyrrolo[3,4-c]carbazole-6,8-dione (231 mg, 0.51 mmol) and morpholine (0.45 mL, 5.1 mmol) in DMF (10 mL) was heated at 60 C. overnight. The mixture was cooled and the product separated by directly injecting the mixture in five 2.5 mL portions onto a 7 um C18 reverse phase hplc column (19×300 mm) with gradient elution with 95:5 H$_2$O (0.1% HCl):CH$_3$CN to 5:95 H$_2$O (0.1% HCl):CH$_3$CN. Upon standing, fractions containing product yielded a precipitate with was isolated by filtration and dried affording the hydrochloride salt of the title compound (87 mg) as an orange solid. The filtrate was passed through an SCX column, washing first with MeOH and EtOAc, and then a 1:1 mixture of 2M NH$_3$ in MeOH and EtOAc. Concentration of the later afforded the title compound (114 mg) as an orange solid. The combined yield was 83%. Spectral characterization: $^1$H NMR (400 MHz, DMSO-d$_6$) 12.18 (s, 1H), 11.07 (s, 1H), 8.84 (d, J=7 Hz, 1H), 8.56 (d, J=9 Hz, 1H), 8.05 (d, J=9 Hz, 1H), 7.58 (d, J=3 Hz, 1H), 7.38 (d, J=7 Hz, 1H), 7.29 (dd, J=7, 7 Hz, 1H), 6.84 (d, J=3 Hz, 1H), 3.87 (s, 3H), 3.63 (m, 4H), 3.31 (t, J=8 Hz, 2H), 2.72 (t, J=8 Hz, 2H), 2.54 (br m, 4H). MS (electrospray, m/z) no M$^+$ observed, 451.1 (M$^-$–1). Spectral characterization of the HCl salt: $^1$H NMR (400 MHz, DMSO-d$_6$) 12.41 (s, 1H), 11.11 (s, 1H), 11.08 (br s, 1H), 8.92 (d, J=8 Hz, 1H), 8.78 (d, J=8 Hz, 1H), 8.04 (d, J=7 Hz, 1H), 7.59 (d, J=3 Hz, 1H), 7.43 (d, J=7 Hz, 1H), 7.35 (dd, J=7, 7 Hz, 1H), 6.84 (d, J=3 Hz, 1H), 4.07 br d, J=11 Hz, 2H), 3.87 (s, 3H), 3.82 (br t, J=11 Hz, 2H), 3.65 (m, 4H), 3.53 (m, 2H), 3.22 (m, 2H). MS (electrospray, m/z) 453.1 (M$^+$+1), 451.1 (M$^-$–1), 487.1 (M+Cl$^-$).

EXAMPLE 85

5-Methyl-12-(2-thiomorpholino-4-yl-ethyl)-7H-indolo[6,7-a]pyrrolo[3,4-c]carbazole-6,8-dione.

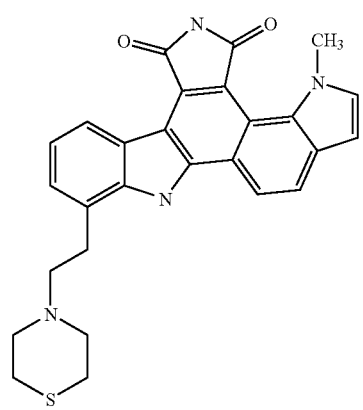

Using procedures similar to those detailed in Example 84, except for using thiomorpholine, affords the title compound; MS (electrospray, m/z) 469.2 (M$^+$+1), 467.2 (M$^-$–1).

EXAMPLE 86

2-(5-Methyl-7H-indolo[6,7-a]pyrrolo[3,4-c]carbazole-6,8-dione-12-yl)-ethyl-diethylamine hydrochloride.

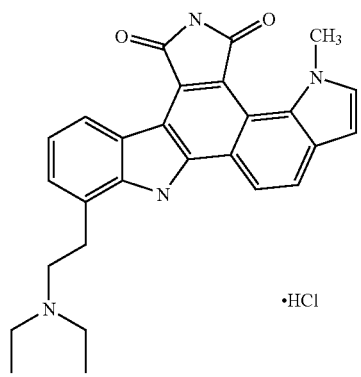

Using procedures similar to those detailed in Example 84, except for using diethylamine, affords the title compound; MS (electrospray, m/z) 439.2 (M$^+$+1), 437.2 (M$^-$–1).

EXAMPLE 87

5-Methyl-12-(3-thiomorpholino-4-yl-propyl)-7H-indolo[6,7-a]pyrrolo[3,4-c]carbazole-6,8-dione.

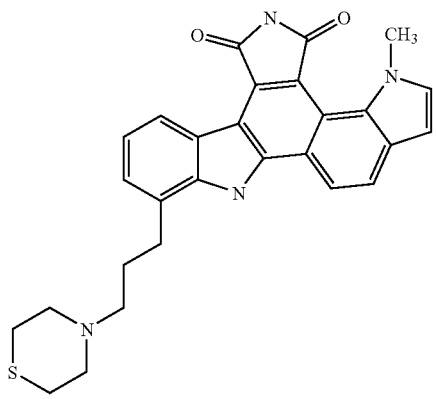

Using procedures similar to those detailed in Example 84, except for using thiomorpholine, affords the title compound; MS (electrospray, m/z) 483.1 (M$^+$+1), 481.1 (M$^-$–1).

EXAMPLE 88

5-Methyl-12-(3-morpholino-4-yl-propyl)-7H-indolo[6,7-a]pyrrolo[3,4-c]carbazole-6,8-dione.

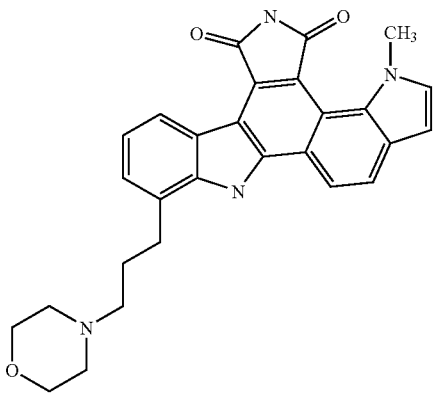

Using procedures similar to those detailed in Example 75, except for using morpholine, affords the title compound; MS (electrospray, m/z) 467.1 (M$^+$+1), 465.2 (M$^-$−1).

EXAMPLE 89

3-(5-Methyl-7H-indolo[6,7-a]pyrrolo[3,4-c]carbazole-6,8-dione-12-yl)-propyl-diethylamine.

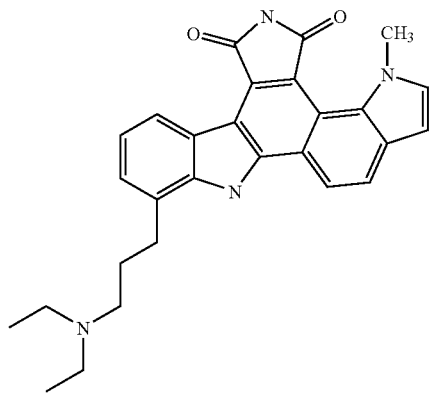

Using procedures similar to those detailed in Example 81, except for using diethylamine, affords the title compound; MS (electrospray, m/z) 453.2 (M$^+$+1), 451.2 (M$^-$−1).

EXAMPLE 90

5-Methyl-12-(2-piperidin-1-yl-ethyl)-7H-indolo[6,7-a]pyrrolo[3,4-c]carbazole-6,8-dione

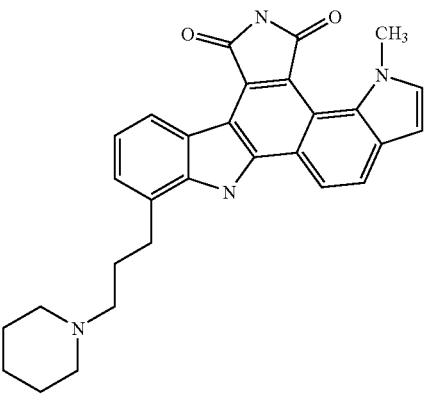

Using procedures similar to those detailed in Example 75, except for using piperidine, affords the title compound; MS (electrospray, m/z) 465.2 (M$^+$+1), 463.2 (M$^-$−1).

EXAMPLE 91

10-Methyl-5-methyl-7H,13H-indolo[6,7-a]pyrrolo[3,4-c]carbazole-6,8-dione

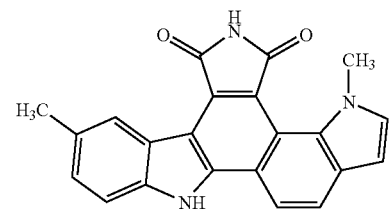

(a) Methyl 2-(5-methyl-1H-indol-3-yl)oxoacetate

To a solution of 5-methyl-1H-indole (1.00 g, 7.6 mmol) in diethyl ether (10 mL) at 4° C. was added a 2.0 M solution of oxalyl chloride in methylene chloride (4.0 mL, 8.0 mmol). The resulting solution was allowed to warm to room temperature and stirred for 1.5 h. The solution was cooled to −78° C. To this solution was added 25% (w/w) solution of sodium methoxide in methanol (3.65 mL, 16.0 mmol). The resulting solution was allowed to warm to room temperature. After one hour, the solution was filtered to give the title compound (1.16 g, 70%) as a light brown solid. $^1$H NMR (DMSO-d$_6$) δ 8.31 (m, 1H), 7.95 (s, 1H), 7.42 (m, 1H), 7.11 (m, 1H), 3.88 (s, 3H), 2.41 (s, 3H).

(b) 3-(5-Methyl-1H-indol-3-yl)-4-(1-methyl-1H-indol-7-yl)pyrrole-2,5-dione

To a solution of 2-(1-methyl-1H-indol-7-yl)acetamide (260 mg, 1.4 mmol) and methyl 2-(5-methyl-1H-indol-3-yl)oxoacetate (300 mg, 1.4 mmol) in DMF (5.4 mL) was added a 1.0 M solution of potassium tert-butoxide in THF (1.4 mL, 1.4 mmol) at 4° C. under N$_2$. The reaction was stirred for 20 min, and additional potassium tert-butoxide (1.0 M, 2.8 mL, 2.8 mmol) was added. The resulting dark purple solution was heated to 50° C. and stirred over night. The mixture was cooled to 4° C. and quenched with 1.0 N hydrochloric acid (9 mL), and extracted with EtOAc (300 mL). The organic layer was separated, washed with saturated aqueous NaHCO$_3$ (150 mL), brine (150 mL), and dried (MgSO$_4$). The mixture was filtered, and concentrated to a red solid. Flash chromatography (SiO$_2$, 40% EtOAc/hexanes) gave the title compound (320 mg, 65%) as a red solid, mp 174–176° C. $^1$H NMR (DMSO-d$_6$) δ 8.02 (s, 1H), 7.61 (m, 1H), 7.24 (s, 1H), 7.16 (m, 1H), 6.95 (m, 1H), 6.85 (m, 1H), 6.75 (m, 1H), 6.46 (s, 1H), 5.71 (s, 1H) 3.62 (s, 3H), 1.71 (s, 3H). MS (ESI): m/z=356 [C$_{22}$H$_{17}$N$_3$O$_2$+H]$^+$ (c) 10-Methyl-5-methyl-7H,13H-indolo[6, 7-a]pyrrolo[3,4-c]carbazole-6, 8-dione A solution of 3-(5-methyl-1H-indol-3-yl)-4-(1-methyl-1H-indol-7-yl)pyrrole-2,5-dione (273 mg, 0.77 mmol) and DDQ (175 mg, 0.77 mmol) in EtOAc (800 mL) was irradiated with 450 Watt Hanovia lamp fitted with a Pyrex filter for 10 min. The resulting light brown solution was passed through a silica gel plug (200 mL), which was washed with a solution of 50% EtOAc in hexanes (500 mL). The combined filtrate was concentrated to a residue. Flash chromatography (SiO$_2$, 30% EtOAc/hexanes) gave the title compound (188 mg, 69%) as an orange solid, mp 290–300° C. dec. $^1$H NMR (DMSO-d$_6$) δ 12.60 (m, 1H), 11.08 (s, 1H), 8.78 (s, 1H), 8.–24 (m, 1H), 8.02 (m, 1H), 7.58 (m, 2H), 7.38 (m, 1H), 6.82 (m, 1H), 3.90 (s, 3H), 2.56 (s, 3H). MS (ESI, Negative Mode): m/z=352 [C$_{22}$H$_{15}$N$_3$O$_2$–H]$^-$

EXAMPLE 92

11-Methyl-5-methyl-7H,13H-indolo[6,7-a]pyrrolo[3,4-c]6,8-dione

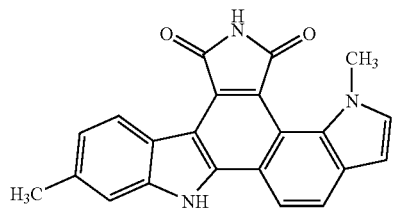

(a) Methyl 2-(6-methyl-1H-indol-3-yl)oxoacetate

To a solution of 6-methylindole (1.00 g, 7.62 mmol) in diethyl ether (10 mL) at 4° C. was added a 2.0 M solution of oxalyl chloride in methylene chloride (4.0 mL, 8.0 mmol). The resulting solution was allowed to warm to room temperature. After 90 min, the solution was cooled to –78° C. To this solution was added 25% (w/w) solution of sodium methoxide in methanol (3.65 mL, 16.0 mmol). The resulting solution was allowed to warm to room temperature. After 1 h, the solution was filtered to give the title compound (894 mg, 54%) as a beige solid.

$^1$H NMR (DMSO-d$_6$) δ 8.37 (m, 1H), 8.01 (m, 1H), 7.32 (s, 1H), 7.10 (m, 1H), 3.88 (s, 3H), 2.39 (s, 3H).

(b) 3-(6-Methyl-1H-indol-3-yl)-4-(1-methyl-1H-indol-7-yl)pyrrole-2,5-dione

To a solution of 2-(1-methyl-1H-indol-7-yl)acetamide (260 mg, 1.38 mmol) and methyl 2-(6-Methyl-1H-indol-3-yl)oxoacetate (300 mg, 1.38 mmol) in DMF (5.4 mL) was added a 1.0 M solution of potassium tert-butoxide in THF (1.38 mL, 1.38 mmol) at 4° C. under N$_2$. The reaction was stirred for 20 min at this temperature, and additional KOtBu (2.76 mL, 2.76 mmol) was added. The resulting dark red solution was heated to 50° C. and stirred overnight. The mixture was cooled to room temperature and quenched with 1.0 N HCl (9 mL) and poured into EtOAc (300 mL). The organic layer was separated, washed with saturated aqueous NaHCO$_3$ (150 mL), and brine (3×150 mL). The solution was dried (MgSO$_4$), filtered, and concentrated to a red solid. Flash chromatography (SiO$_2$, 30% EtOAc/hexanes) gave the title compound (227 mg, 46%) as a red solid, mp 200–220° C. dec. $^1$H NMR (DMSO-d$_6$) δ 11.72 (s, 1H), 11.09 (s, 1H), 7.90 (s, 1H), 7.59 (m, 1H), 7.24 (s, 1H), 7.10 (s, 1H), 6.96 (m, 1H), 6.83 (m, 1H), 6.45 (s, 1H), 6.27 (m, 1H), 6.11 (m, 1H), 3.64 (s, 3H), 2.18 (s, 3H). MS (APCI): m/z=356 [C$_{22}$H$_{17}$N$_3$O$_2$+H]$^+$ (c) 11-Methyl-5-methyl-7H,13H-indolo[6,7-a]pyrrolo[3,4-c]6,8-dione A solution 3-(6-methyl-1H-indol-3-yl)-4-(1-methyl-1H-indol-7-yl)pyrrole-2,5-dione (206 mg, 0.58 mmol) and DDQ (132 mg, 0.58 mmol) in EtOAc (1 L) was irradiated with a 450 Watt Hanovia lamp fitted with a Pyrex filter for 20 min. The resulting light brown solution was dried over MgSO$_4$, filtered, and concentrated to a red solid. Flash chromatography (SiO$_2$, 30% EtOAc/hexanes) gave the title compound (114 mg, 56%) as a red solid, mp 170° C. dec. $^1$H NMR (DMSO-d$_6$) δ 12.60 (s, 1H), 11.06 (s, 1H), 8.81 (m, 1H), 8.24 (m, 1H), 8.03 (m, 1H), 7.58 (s, 1H), 7.49 (s, 1H), 7.20 (m, 1H), 6.81 (s, 1H), 3.85 (s, 3H), 2.55 (s, 3H). MS (APCI): m/z=354 [C$_{22}$H$_{15}$N$_3$O$_2$+H]$^+$

EXAMPLE 93

10-Cyano-5-methyl-7H,13H-indolo[6,7-a]pyrrolo[3,4-c]carbazole-6,8-dione

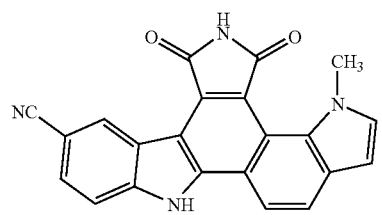

(a) Methyl 2-(5-cyano-1H-indol-3-yl)oxoacetate

To a solution of 1H-indole-5-carbonitrile (1.14 g, 8.04 mmol) in diethyl ether (12 mL) at 4° C. was added a 2.0 M solution of oxalyl chloride in methylene chloride (4.2 mL, 8.4 mmol). The resulting solution was allowed to warm to room temperature. After 90 min, the solution was cooled to −78° C. To this solution was added 25% (w/w) solution of sodium methoxide in methanol (3.83 mL, 16.8 mmol). The resulting solution was allowed to warm to room temperature. After one hour, the solution was filtered to give the title compound (768 mg, 42%) as a light brown solid. $^1$H NMR (DMSO-$d_6$) δ 9.39 (s, 1H), 8.67 (m, 1H), 8.50 (s, 1H), 7.29 (m, 1H), 3.87 (s, 3H).

(b) 3-(5-Cyano-1H-indol-3-yl)-4-(1-methyl-1H-indol-7-yl)pyrrole-2,5-dione

To a solution of 2-(1-methyl-1H-indol-7-yl)acetamide (296 mg, 1.57 mmol) and methyl 2-(5-cyano-1H-indol-3-yl)oxoacetate (356 mg, 1.56 mmol) in DMF (6.5 mL) was added a 1.0 M solution of potassium tert-butoxide in THF (4.8 mL, 4.8 mmol) dropwise over 20 min at 4° C. under $N_2$. The resulting dark red solution was heated up to 50° C. for 6 h. The mixture was cooled to 4° C. and quenched with 1.0 N hydrochloric acid (10 mL) and poured into EtOAc (100 mL). The organic layer was separated, washed with saturated NaHCO$_3$ (60 mL), saturated NaCl (60 mL), dried (MgSO$_4$), and concentrated to a red solid. Filtration from a slurry in CH$_2$Cl$_2$ (15 mL) afforded the first batch of the title compound (58 mg, 7.4%) as a red crystalline solid, mp 220° C. dec. Tritration of the concentrated filtrate with Et$_2$O (8.0 mL) afforded a second batch of the title compound (288 mg, 36.9%). $^1$H NMR (DMSO-$d_6$) δ 8.09 (s, 1H), 7.68 (m, 1H), 7.51 (m, 1H), 7.28–7.19 (m, 2H), 7.09–6.92 (m, 2H), 6.47 (m, 2H), 3.60 (s, 3H). MS (ESI): m/z=367 [$C_{22}H14N_4O_2$+H]$^+$ (c) 10-Cyano-5-methyl-7H,13H-indolo[6,7-a]pyrrolo[3,4-c]carbazole-6,8-dione A solution of 3-(5-cyano-1H-indol-3-yl)-4-(1-methyl-1H-indol-7-yl)pyrrole-2,5-dione (274 mg, 0.75 mmol) and DDQ (170 mg, 0.75 mmol) in EtOAc (700 mL) was irradiated with 450 Watt Hanovia lamp fitted with a Pyrex filter for 25 min. The resulting light brown solution was concentrated to 500 mL, washed with H$_2$O (200 mL), saturated NaCl (150 mL), dried (MgSO$_4$), and concentrated. Flash chromatography (SiO$_2$, 60% EtOAc/hexanes) gave the title compound (208 mg, 76.2%) as a red solid, mp 240° C. dec. $^1$H NMR (DMSO-$d_6$) δ 13.22 (s, 1H), 11.24 (s, 1H), 9.20 (s, 1H), 8.21 (m, 1H), 8.05 (m, 1H), 7.82 (m, 2H), 7.59 (s, 1H), 6.84 (s, 1H), 3.89 (s, 3H). MS (ESI, Negative Mode) m/z=363 [$C_{22}H_{12}N_4O_2$−H]$^-$

EXAMPLE 94

10-Trifluoromethyl-5-methyl-7H,13H-indolo[6,7-a]pyrrolo[3,4-c]6,8-dione

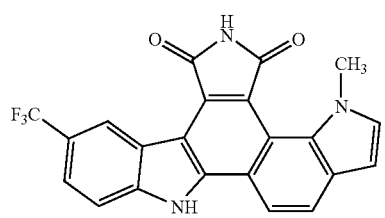

(a) Methyl 2-(5-trifluoromethyl-1H-indol-3-yl)oxoacetate

To a solution of 5-trifluoromethylindole (2.0 g, 10.8 mmol) in diethyl ether (30 mL) at 4° C. was added a 2.0 M solution of oxalyl chloride in methylene chloride (5.5 mL, 11.0 mmol). The resulting solution was allowed to warm to room temperature. After 90 min, the solution was cooled to −78° C. To this solution was added 25% (w/w) solution of sodium methoxide in methanol (5.0 mL, 21.9 mmol). The resulting solution was allowed to warm to room temperature. After one hour, the solution was filtered to give the title compound (1.24 g, 43%) as a yellow solid. $^1$H NMR (DMSO-$d_6$) δ 8.66 (m, 1H), 8.45 (s, 1H), 7.78 (m, 1H), 7.60 (m, 1H), 3.89 (s, 3H).

(b) 3-(5-Trifluoromethyl-1H-indol-3-yl)-4-(1-methyl-1H-indol-7-yl)pyrrole-2,5-dione To a solution of 2-(1-methyl-1H-indol-7-yl)acetamide (208 mg, 1.1 mmol) and methyl 2-(5-trifluoromethyl-1H-indol-3-yl)oxoacetate (300 mg, 1.1 mmol) in DMF (5.4 mL) was added a 1.0 M solution of potassium tert-butoxide in THF (1.1 mL, 1.1 mmol) at 4° C. under $N_2$. The reaction was stirred for 20 min at this temperature, and additional KOtBu (2.2 mL, 2.2 mmol) was added. The resulting dark red solution was heated up to 50° C. over night. The mixture was cooled to room temperature and quenched with 1 N HCl (9 mL) and poured into EtOAc (300 mL). The organic layer was separated, washed with saturated aqueous NaHCO$_3$ (150 mL), and brine (3×150 mL). The solution was dried (MgSO$_4$), filtered, and concentrated to a red solid. Flash chromatography (SiO$_2$, 30% EtOAc/hexanes) gave the title compound (157 mg, 35%) as a red solid, mp 270–280° C. dec. $^1$H NMR (DMSO-$d_6$) δ 12.24 (s, 1H), 11.26 (s, 1H), 8.11 (s, 1H), 7.63 (m, 1H), 7.55 (m, 1H), 7.27 (m, 2H), 6.92 (m, 2H), 6.65 (s, 1H), 6.49 (s, 1H), 3.73 (s, 3H). MS (ESI): m/z=411 [$C_{22}H_{14}F_3N_3O_2$+H]$^+$ (c) 10-Trifluoromethyl-5-methyl-7H,13H-indolo[6,7-a]pyrrolo[3,4-c]6,8-dione A solution of 3-(5-trifluoromethyl-1H-indol-3-yl)-4-(1-methyl-1H-indol-7-yl)pyrrole-2,5-dione (412 mg, 1.01 mmol) and DDQ (228 mg, 1.01 mmol) in EtOAc (1 L) was irradiated with a 450 Watt Hanovia lamp fitted with a Pyrex filter for 20 min. The resulting light brown solution was dried over MgSO$_4$, filtered, and concentrated to an orange solid. Flash chromatography (SiO$_2$, 20% EtOAc/hexanes) gave the title compound (161 mg, 39%) as an orange solid, mp 100–110° C. dec. $^1$H NMR (DMSO-$d_6$) δ 13.12 (s, 1H), 11.24 (s, 1H), 9.32 (s, 1H), 8.31 (m, 1H), 8.15 (m, 1H), 7.87 (m, 2H), 7.63 (s, 1H), 6.88 (s, 1H), 3.90 (s, 3H). MS (ESI): m/z=407 [$C_{22}H_{12}O_2N_3F_3$+H]$^+$

EXAMPLE 95

10-Fluoro-5-methyl-7H,13H-indolo[6,7-a]pyrrolo[3,4-c]carbazole-6,8-dione

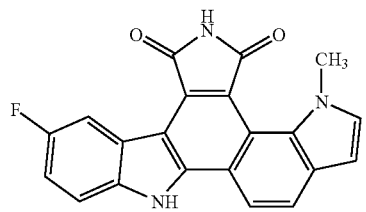

(a) Methyl 2-(5-Fluoro-1H-indol-3-yl)oxoacetate

A 2.0 M solution of oxalyl chloride in methylene chloride (4.50 mL, 9.0 mmol) was added to a solution of 5-fluoroindole (1.14 g, 8.4 mmol) in ether (19 mL) dropwise over 10 min at 4° C. under $N_2$. The ice bath was removed and the resulting mixture was stirred for 2 h. A 25% sodium methoxide in methanol solution (4.3 mL, 18.8 mmol) was added at −78° C. over 5 min. The mixture was allowed to warm up to room temperature and stirred for 1 h. The reaction was quenched with water (50 mL), filtered and rinsed with cold ether to afford the title compound (1.34, 72%) as a yellow solid. $^1$H NMR (DMSO-$d_6$) δ 12.51 (bs, 1H), 8.56 (s, 1H), 7.86 (m, 1H), 7.60 (m, 1H), 7.15 (m, 1H), 3.90 (s, 3H).

(b) 3-(5-Fluoro-1H-indol-3-yl)-4-(1-methyl-1H-indol-7-yl)pyrrole-2,5-dione

To a solution of 2-(1-methyl-1H-indol-7-yl)acetamide (350 mg, 1.86 mmol) and methyl 2-(5-fluoro-1H-indol-3-yl)oxoacetate (427 mg, 1.93 mmol) in DMF (25 mL) was added a 1.0 M solution of potassium tert-butoxide in THF (6.5 mL, 6.5 mmol) at room temperature under $N_2$. The reaction was heated to 65° C. and stirred for 20 h at this temperature. The reaction mixture was then cooled to room temperature and quenched with 1.0 N hydrochloric acid, extracted with EtOAc (50 mL), washed with $H_2O$ (2×30 mL), saturated NaCl (2×30 mL), dried (MgSO$_4$), filtered and concentrated. Flash chromatography (SiO$_2$, 30% EtOAc/hexanes) gave the title compound (282 mg, 42%) as a maroon solid, mp 230° C. dec. $^1$H NMR (DMSO-$d_6$) δ 11.95 (bs, 1H), 11.18 (bs, 1H), 7.98 (s, 1H), 7.64 (m, 1H), 7.34 (m, 1H), 7.28 (m, 1H), 6.99 (m, 1H), 6.92 (m, 1H), 6.83 (m, 1H), 6.48 (m, 1H), 5.91 (m, 1H), 3.67 (s, 3H). MS (APCI): m/z=360 [C$_{21}$H$_{14}$FN$_3$O$_2$+H]$^+$

(c) 10-Fluoro-5-methyl-7H,13H-indolo[6,7-a]pyrrolo[3,4-c]carbazole-6,8-dione A solution of 3-(5-fluoro-1H-indol-3-yl)-4-(1-methyl-1H-indol-7-yl)pyrrole-2,5-dione (221 mg, 0.62 mmol) and DDQ (140 mg, 0.62 mmol) in EtOAc (1.0 L) was irradiated with 450 Watt Hanovia lamp fitted with a Pyrex filter for 15 min. The resulting light brown solution was concentrated to 250 mL, washed with 0.1 N sodium hydroxide (2×50 mL), saturated NaCl (2×50 mL), dried (MgSO$_4$) and concentrated to a brown solid. Trituration in methylene chloride (10 mL) afforded the title compound (50.3 mg, 22.9%) as a red solid, mp 250° C. dec. $^1$H NMR (DMSO-$d_6$) δ 12.81 (s, 1H), 11.13 (s, 1H), 8.66 (m, 1H), 8.27 (m, 1H), 8.04 (m, 1H), 7.78 (m, 1H), 7.58 (s, 1H), 7.41 (m, 1H), 6.89 (m, 1H), 3.93 (s, 3H). MS (ESI): m/z=358 [C$_{21}$H$_{12}$FN$_3$O$_2$+H]$^+$

EXAMPLE 96

11-Ethyl-5-methyl-7H,13H-indolo[6,7-a]pyrrolo[3,4-c]carbazole-6,8-dione

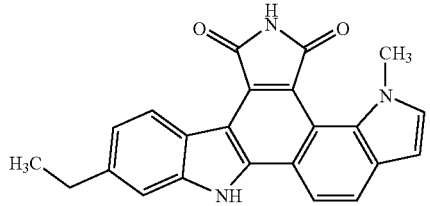

(a) (2,2-Diethoxyethyl)-(3-ethylphenyl)amine

To a 250-mL round bottom flask was added 3-ethylaniline (10.1 g, 83.2 mmol), bromoacetaldehyde diethyl acetal (10.8 g, 54.8 mmol) and sodium bicarbonate (7.04 g, 83.8 mmol) in absolute ethanol (40 mL). The resulting mixture was stirred at reflux for 5 d. The mixture was concentrated, diluted with ether (30 mL) and washed with water (2×60 mL). The organic solution was dried (MgSO$_4$) and concentrated at reduced pressure. The residue was purified by flash chromatography (SiO$_2$, 5% then 15% EtOAc/hexanes) to give the title compound (4.5 g, 75%) as a white solid. $^1$H NMR (DMSO-$d_6$) δ 6.98 (m, 1H), 6.42 (m, 2H), 5.34 (m, 1H), 4.53 (m, 1H), 3.59–3.35 (m, 4H), 3.19 (m, 2H), 2.41 (m, 2H), 1.17 (m, 9H).

(b) 6-Ethyl-1H-indole

To a solution of trifluoroacetic anhydride (45 mL) in trifluoroacetic acid (45 mL) at 4° C. under $N_2$ was added (2,2-diethoxyethyl)-(3-ethylphenyl)amine (11.47 g, 48.36 mmol). After stirring for 30 min, the cold mixture was diluted with trifluoroacetic acid (60 mL). The mixture was stirred at reflux for 2.5 d, concentrated and extracted with methylene chloride (3×100 mL). The combined organic layers were washed with saturated NaHCO$_3$ (3×60 mL), saturated NaCl (60 mL), dried (MgSO$_4$) and concentrated. Flash chromatography (SiO$_2$, 25% EtOAc/hexanes) gave the title compound (1.6 g, 23%) as a brown crystalline solid. $^1$H NMR (CDCl$_3$) δ 8.03 (bs, 1H), 7.57 (m, 1H), 7.18 (s, 1H), 7.12 (m, 1H), 6.68 (m, 1H), 6.46 (m, 1H), 2.73 (m, 2H), 1.26 (m, 3H)

(c) Methyl 2-(6-ethyl-1H-indol-3-yl)oxoacetate

A 2.0 M solution of oxalyl chloride in methylene chloride (4.75 mL, 9.6 mmol) was added to a solution of 6-ethylindole (1.39 g, 9.6 mmol) in ether (20 mL) dropwise over 10 min at 4° C. under $N_2$. The ice bath was removed and the resulting mixture was stirred for 2 h. A 25% sodium methoxide in methanol solution (4.3 mL, 18.8 mmol) was added at −78° C. over 5 min. The mixture was allowed to warm up to room temperature and stirred for 1 h. The reaction was quenched with water (10 mL), filtered and rinsed with cold ether to afford the title compound (1.34, 72%) as a yellow solid. $^1$H NMR (CDCl$_3$) δ 9.07 (bs, 1H), 8.43 (m, 1H), 8.32 (m, 1H), 7.29–7.21 (m, 2H), 3.95 (m, 3H), 2.78 (m, 2H), 1.29 (m, 3H).

(d) 3-(6-Ethyl-1H-indol-3-yl)-4-(1-methyl-1H-indol-7-yl)pyrrole-2,5-dione

To a solution of 2-(1-methyl-1H-indol-7-yl)acetamide (370 mg, 1.97 mmol) and methyl 2-(6-ethyl-1H-indol-3-yl)oxoacetate (446 mg, 1.93 mmol) in DMF (8.0 mL) at 4° C. under N$_2$, was added a 1.0 M solution of potassium tert-butoxide in THF (6.0 mL, 6.0 mmol) dropwise over 20 min. The reaction was heated to 50° C. and stirred for 7 h at this temperature. The reaction mixture was then cooled to room temp and quenched with 1.0 N hydrochloric acid (5.0 mL), extracted with EtOAc (2×15 mL), washed with saturated NaHCO$_3$ (30 mL), saturated NaCl (30 mL), dried (MgSO$_4$), filtered and concentrated. Flash chromatography (SiO$_2$, 50% EtOAc/hexanes containing 1% TEA) gave the title compound (214 mg, 30%) as a red solid, mp 98–100° C. $^1$H NMR (DMSO-d$_6$) δ 11.69 (s, 1H), 11.06 (s, 1H), 7.78 (m, 1H), 7.60 (m, 1H), 7.28 (m, 1H), 7.16 (s, 1H), 6.95 (m, 1H), 6.86 (m, 1H), 6.50 (m, 1H), 6.32 (m, 1H), 6.20 (m, 1H), 3.69 (s, 3H), 3.32 (m, 2H), 1.11 (m, 3H). MS (ESI, negative mode): m/z=368 [C$_{23}$H$_{19}$N$_3$O$_2$–H]$^-$ (e) 11-Ethyl-5-methyl-7H,13H-indolo[6,7-a]pyrrolo[3,4-c]carbazole-6,8-dione A solution of 3-(6-ethyl-1H-indol-3-yl)-4-(1-methyl-1H-indol-7-yl)pyrrole-2,5-dione (430 mg, 1.2 mmol) and DDQ (270 mg, 1.2 mmol) in EtOAc (1.0 L) was irradiated with 450 Watt Hanovia lamp fitted with a Pyrex filter for 20 min. The resulting light brown solution was concentrated to a brown solid. Flash chromatography (SiO$_2$, 30% EtOAc/hexanes) gave the title compound (254 mg, 59%) as a red solid, mp 290° C. dec. $^1$H NMR (DMSO-d$_6$) δ 12.60 (s, 1H), 11.05 (s, 1H), 8.30 (m, 1H), 8.24 (m, 1H), 8.07 (m, 1H), 7.57 (m, 2H), 7.24 (m, 1H), 6.83 (m, 1H), 3.93 (s, 3H), 3.43 (m, 2H), 1.32 (m, 3H). MS (APCI): m/z=368 [C$_{23}$H$_{17}$N$_3$O$_2$+H]$^+$

EXAMPLE 97

10-Bromo-5-methyl-7H,13H-indolo[6,7-a]pyrrolo[3,4-c]carbazole-6,8-dione

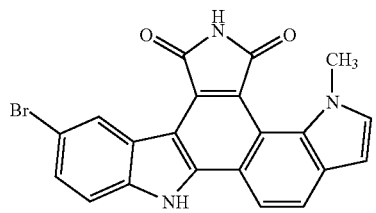

(a) Methyl 2-(5-bromo-1H-indol-3-yl)oxoacetate

To a solution of 5-bromoindole (2.05 g, 10.5 mmol) in diethyl ether (20 mL) at 4° C. was added a 2.0 M solution of oxalyl chloride in methylene chloride (5.5 mL, 11.0 mmol). The resulting solution was allowed to warm to room temperature. After 90 min, the solution was cooled to –78° C. To this solution was added 25% (w/w) solution of sodium methoxide in methanol (5.0 mL, 21.9 mmol). The resulting solution was allowed to warm to room temperature. After 1 h, the solution was filtered to give the title compound (2.235 g, 76%) as a brown solid. $^1$H NMR (DMSO-d$_6$) δ 8.53 (s, 1H), 8.28 (s, 1H), 7.54 (m, 1H), 7.43 (m, 1H), 3.90 (s, 3H).

(b) 3-(5-Bromo-1H-indol-3-yl)-4-(1-methyl-1H-indol-7-yl)pyrrole-2,5-dion

To a solution of 2-(1-methyl-1H-indol-7-yl)acetamide (200 mg, 1.06 mmol) and methyl 2-(5-bromo-1H-indol-3-yl)oxoacetate (300 mg, 1.06 mmol) in DMF (5.4 mL) was added a 1.0 M solution of potassium tert-butoxide in THF (1.06 mL, 1.06 mmol) at 4° C. under N$_2$. The reaction was stirred for 20 min at this temperature, and additional KOtBu (2.12 mL, 2.12 mmol) was added. The resulting dark red solution was heated up to 50° C. overnight. The mixture was cooled to room temperature, quenched with 1N HCl (9 mL) and poured into EtOAc (300 mL). The organic layer was separated, washed with saturated aqueous NaHCO$_3$ (150 mL), and brine (3×150 mL). The solution was dried (MgSO$_4$), filtered, and concentrated to an orange solid. Flash chromatography (SiO$_2$, 30% EtOAc/hexanes) gave the title compound (201 mg, 45%) as an orange solid, mp 270–290° C. dec.
$^1$H NMR (DMSO-d$_6$) δ 12.00 (s, 1H), 11.22 (s, 1H), 7.97 (s, 1H), 7.66 (m, 1H), 7.25 (m, 2H), 7.08 (m, 1H), 7.01 (m, 1H), 6.93 (m, 1H), 6.47 (s, 1H), 6.32 (s, 1H), 3.65 (s, 1H). MS (APCI): m/z=420, 422 [C$_{21}$H$_{14}$O$_2$N$_3$Br+H]$^+$ (c) 10-Bromo-5-methyl-7H,13H-indolo[6,7-a]pyrrolo[3,4-c]carbazole-6,8-dione A solution 3-(5-bromo-1H-indol-3-yl)-4-(1-methyl-1H-indol-7-yl)-pyrrole-2,5-dione (529.6 mg, 1.27 mmol) and DDQ (286.1 mg, 1.27 mmol) in EtOAc (1 L) was irradiated with a 450 Watt Hanovia lamp fitted with a Pyrex filter for 20 min. The resulting solution was concentrated to a volume of 100 mL and washed with saturated aqueous NaHCO$_3$ (50 mL) and brine (50 mL). The solution was dried (MgSO$_4$), filtered, and concentrated to a reddish brown solid. Flash chromatography (SiO$_2$, 30% EtOAc/hexanes) gave the title compound (370 mg, 70%) as a red-orange solid, mp >300° C. $^1$H NMR (DMSO-d$_6$) δ 12.92 (s, 1H), 11.21 (s, 1H), 9.09 (s, 1H), 8.26 (m, 1H), 8.08 (m, 1H), 7.69 (m, 2H), 7.62 (m, 1H), 6.87 (m, 1H), 3.88 (s, 3H). MS (APCI): m/z=418, 420 [C$_{21}$H$_{12}$O$_2$N$_3$Br+H]$^+$

EXAMPLE 98

11-Ethoxy-5-methyl-7H,13H-indolo[6,7-a]pyrrolo[3,4-c]carbazole-6,8-dione

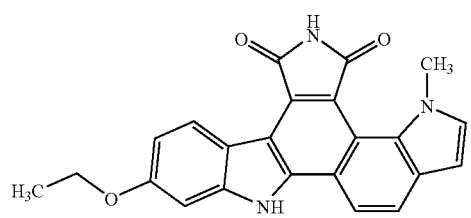

(a) 6-Ethoxy-1H-indole

Sodium hydride (60% in mineral oil, 1.65 g, 41 mmol) was added to a solution of 6-hydroxyindole (5.0 g, 38 mmol) in anhydrous DMF (25 mL) at −20° C. under $N_2$. The resulting dark green solution was allowed to warm up to room temperature and stirred for 10 min. Ethyl iodide (3.3 mL, 6.4 g, 41 mmol) was added, and the resulting solution was stirred at room temperature for 1 h. The mixture was poured into ice-water (150 mL), and extracted with EtOAc (3×200 mL). The organic solution was dried ($MgSO_4$) and concentrated at reduced pressure. The residue was purified by flash chromatography ($SiO_2$, 5% then 15% EtOAc/hexanes) to give the title compound (4.5 g, 75%) as a white solid. $^1$H NMR ($CDCl_3$) δ 7.98 (br. s, 1H), 7.50 (m, 1H), 7.10 (m, 1H), 6.90 (m, 1H), 6.80 (m, 1H), 6.45 (m, 1H), 4.10 (q, J=6.5 Hz, 2H), 1.45 (t, J=6.5 Hz, 3H).

(b) Methyl 2-(6-Ethoxy-1H-indol-3-yl)oxoacetate

A 2.0 M solution of oxalyl chloride in methylene chloride (6.65 mL, 13.3 mmol) was added to a solution of 6-ethoxyindole (2.0 g, 12.4 mmol) in ether (25 mL) dropwise over 10 min at 4° C. under $N_2$. The resulting mixture was stirred for 1 h at 4° C. A 25% (w/w) sodium methoxide in methanol solution (6.2 mL, 28.5 mmol) was added at −78° C. The mixture was allowed to warm up to room temperature and stirred for 4 h. The reaction was quenched with water (50 mL) and extracted with methylene chloride. The organic solution was dried ($MgSO_4$) and concentrated at reduced pressure. The residue was stirred in a solution of EtOAc (50 mL) and ether (50 mL) for 10 min. Solid was collected by filtration to give the title compound (2.2 g, 73%) after drying. $^1$H NR ($CDCl_3$) δ 8.20 (s, 1H), 7.90 (d, J=9 Hz, 1H), 6.92 (s, 1H), 6.82 (d, J=9 Hz, 1H), 4.00 (q, J=6.5 Hz, 2H), 3.78 (s, 3H), 1.30 (t, J=6.5 Hz, 3H)

(c) 3-(6-Ethoxy-1H-indol-3-yl)-4-(1-methyl-1H-indol-7-yl)pyrrole-2,5-dione

To a solution of 2-(1-methyl-1H-indol-7-yl)acetamide (381 mg, 2.02 mmol) and methyl 2-(6-ethoxy-1H-indol-3-yl)oxoacetate (500 mg, 2.02 mmol) in DMF (17 mL) was added a 1.0 M solution of potassium tert-butoxide in THF (2.0 mL, 2.0 mmol) at 4° C. under $N_2$. The reaction was stirred for 20 min at this temperature, and additional potassium tert-butoxide (1.0 M, 4.1 mL, 4.1 mmol) was added. The resulting dark purple solution was heated up to 70° C. over night. The mixture was cooled to 4° C. and quenched with 1.0 N hydrochloric acid (12 mL) and poured into EtOAc (500 mL). The organic layer was separated, dried ($MgSO_4$), and concentrated to a red solid. Flash chromatography ($SiO_2$, 30% EtOAc/hexanes) gave the title compound (200 mg, 26%) as a red solid, mp 212–215° C. $^1$H NMR ($CDCl_3$) δ 8.44 (s, 1H), 7.88 (s, 1H), 7.68 (m, 1H), 7.60 (s, 1H), 7.00 (m, 2H), 6.92 (s, 1H), 6.72 (s, 1H), 6.52 (s, 1H), 6.32 (s, 2H), 3.92 (q, J=6.5 Hz, 2H), 3.72 (s, 3H), 1.38 (t, J=6.5 Hz, 3H). MS (ESI, Negative Mode): m/z=384 $[C_{23}H_{19}N_3O_3–H]^-$

(d) 11-Ethoxy-5-methyl-7H,13H-indolo[6,7-a]pyrrolo[3,4-c]carbazole-6,8-dione A solution of 3-(6-ethoxy-1H-indol-3-yl)-4-(1-methyl-1H-indol-7-yl)pyrrole-2,5-dione (170 mg, 0.44 mmol) and DDQ (100 mg, 0.44 mmol) in EtOAc (800 mL) was irradiated with 450 Watt Hanovia lamp fitted with a Pyrex filter for 8 min. The resulting light brown solution was passed through a silica gel plug (200 mL), which was washed with EtOAc (200 mL). The combined filtrate was concentrated to an orange solid. Flash chromatography ($SiO_2$, 30% then 40% EtOAc/hexanes) gave the title compound (101 mg, 60%) as a dark red solid, mp 270–275° C. dec. $^1$H NMR ($CDCl_3$) δ 9.03 (br s, 1H), 9.00 (m, 1H), 8.00 (m, 1H), 7.80 (m, 1H), 7.44 (s, 1H), 7.34 (s, 1H), 7.00–7.12 (m, 2H), 6.84 (m, 1H), 4.22 (q, J=6.5 Hz, 2H), 3.95 (s, 3H), 1.55 (t, J=6.5 Hz, 3H). MS (ESI, Negative Mode): m/z=382 $[C_{23}H_{17}N_3O_3–H]^-$

EXAMPLE 99

2-(11-methoxy-5-methyl-7H-indolo[6,7-a]pyrrolo[3,4-c]carbazole-6,8-dione)acetamide

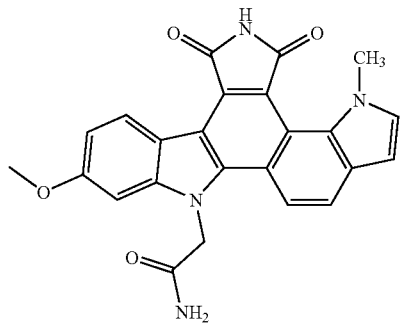

(a) tert-Butyl-(3-chloro-1-phenyl-propoxy)-dimethyl-silane

3-Chloro-1-phenyl-propan-1-ol (3.87 g, 22.6 mmol), tert-butyldimethylsilyl chloride (3.75 g, 24.9 mmol), imidazole (2.00 g, 29.3 mmmol), and methylene chloride (50 mL) are combined and stirred for 1 hour. The mixture is quenched with saturated aqueous sodium bicarbonate and diluted with methylene chloride (100 mL). The mixture is washed with saturated aqueous ammonium chloride, water, and brine, then is dried over magnesium sulfate, filtered, and concentrated to a crude oil. Purification by flash chromatography, eluting with ethyl acetate:hexane gave 4.82 g (75% yield) of the title compound as a transparent oil. $^1$HNMR (DMSO-$d_6$) 7.76–7.84 (m, 4H), 7.68–7.74 (m, 1H), 5.39 (dd, J=4, 4 Hz, 1H), 4.19–4.22 (m, 1H), 4.00–4.08(m, 1H), 2.55–2.65 (m, 1H), 2.38–2.48 (m, 1H), 1.34 (s, 9H), 0.53 (s, 3H), 0.28 (s, 3H).

(b) 2-{11-Methoxy-5-methyl-7-[3-(t-butyldimethyl-silyloxy)-3-phenylpropyl]indolo[6,7-a]pyrrolo[3,4-c]carbazole-6,8-dione}-acetamide 11-Methoxy-5-methyl-7H,13H-indolo[6,7-b]pyrrolo[3,4-c]6,8-dione (1.00 g, 2.70 mmmol), tert-butyl-(3-chloro-1-phenyl-propoxy)-dimethyl-silane (0.771 g, 2.70 mmol), cesium carbonate (0.957 g, 2.94 mmol), and anhydrous dimethylformamide (20 mL) are combined and heated at 60° C. for 18 hours. Additional tert-Butyl-(3-chloro-1-phenyl-propoxy)-dimethyl-silane (0.192 g, 0.67 mmol) and cesium carbonate (0.435 g, 1.35 mmol) are added to the mixture and heated at 60° C. for an additional 22 hours. Iodoacetamide (1.49 g, 8.1 mmol) and anhydrous dimethylformamide (10 mL) are further added, and the mixture is heated at 60° C. for 5 more hours. After being diluted with ethyl acetate (300 mL), the mixture is washed with water, saturated sodium bicarbonate, and brine, then dried with magnesium sulfate, and concentrated. Purification by flash chromatography and eluting with ethyl acetate:hexane gave 1.09 g (62% yield) of the title compound: MS (electrospray, m/e): 673.2 (M$^-$−1).

(c) 2-{11-Methoxy-5-methyl-7-(3-hydroxy-3-phenylpropyl)indolo[6,7-a]pyrrolo[3,4-c]carbazole-6,8-dione}-acetamide 2-{11-Methoxy-5-methyl-7-[3-(t-butyldimethylsilanoxy)-3-phenylpropyl]indolo[6,7-a]pyrrolo[3,4-c]carbazole-6,8-dione}-acetamide (1.08 g, 1.60 mmol), anhydrous tetrahydrofuran (25 mL), and 3 N HCl (8.3 mL) are combined and stirred for 8 hours. Dilution with ethyl acetate (200 mL) and water (30 mL) separated the two layers and the organic layer was washed with saturated sodium bicarbonate and brine. The resulting extract was dried with magnesium sulfate, filtered, and concentrated to 50 mL. Crystallization by addition of hexane, filtration, and drying gave 0.688 g (72% yield) of the title compound. MS (electrospray, m/e): 559.2 (M$^-$−1).

(d) 2-(11-methoxy-5-methyl-7H-indolo[6,7-a]pyrrolo[3,4-c]carbazole-6,8-dione)acetamide 2-{11-Methoxy-5-methyl-7-(3-hydroxy-3-phenylpropyl) indolo[6,7-a]pyrrolo[3,4-c]carbazole-6,8-dione}-acetamide (0.543 g, 0.968 mmol), pyridinium chlorochromate (0.313 g, 1.45 mmol), silica gel (60 Å, 0.800 g), and methylene chloride (100 mL)are combined and stirred for 18 hours. Additional pyridinium chlorochormate (0.052 g, 0.242 mmol) is added and the mixture is stirred for 24 more hours. Purification by flash chromatography and eluting with ethyl acetate:hexane and ethyl acetate:methyl alcohol gave 0.305 g of the ketone product. This ketone (0.305 g, 0.546 mmol) was combined with cesium carbonate (0.534 g, 1.63 mmol) and anhydrous dimethylformamide (20 ml) and heated at 80° C. for 3 hours. Purification by flash chromatography and eluting with ethyl acetate:hexane plus reverse phase preparatory high pressure chromatography and eluting with acetonitrile and water gave 0.041 g (10% yield) of the title compound. NS (electrospray, m/e)425.1 (M$^-$−1).

EXAMPLE 100

1,1-Dimethyl-3-{12-(5-methyl-7H, 13H-indolo[6,7-a]pyrrolo[3,4-c]carbazole-6,8-dione-yl)-methyl}-urea

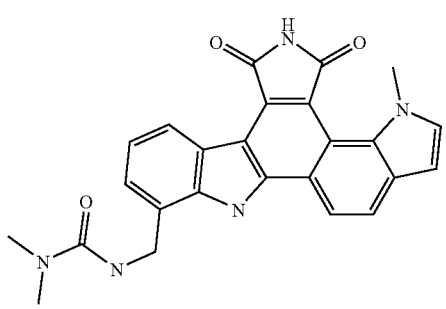

(a) C-(1H-Indol-7-yl)-methylamine

To a solution of 1H-indole-7-carboxaldehyde (3.0 g, 20.68 mmol) in ethanol:H$_2$O (3:1) (120 ml) was added hydroxylamine hydrochloride (2.87 g, 41.37 mmol) and ammonium acetate (4.78 g, 62.06 mmol). The reaction was stirred at room temperature for 2 h. To the reaction was added NH$_4$OH (25 ml, 0.72 mmol) and zinc metal (11.0 g, 8.1 mmol) portion-wise. Upon completion, the reaction mixture was filtered, poured into ethyl acetate and washed with water. The organic layer was extracted with 1N HCl. The aqueous layer was then mad basic by the addition of 1N NaOH and extracted with ethyl acetate. The organic layer was washed with water, brine, dried (MgSO$_4$), and concentrated to give a white solid that was dried under high vacuum overnight to give the title compound (2.69 g, 89%) which was used as is. $^1$H NMR (400 MHz, DMSO-d$_6$) 11.0 (s, 1H), 7.38 (d, 1H, J=7.0 Hz), 7.29 (d, 1H, J=3.0 Hz), 7.0 (d, 1H, J=7.0 Hz), 6.92 (dd, 1H, J=7.0, <1 Hz), 6.4 (d, 1H, J=3.0 Hz), 3.97 (s, 2H). MS (electrospray, m/z) 147 (M$^+$+1), 145 (M$^-$−1).

(b) [7-(tert-Butoxycarbonylamino-methyl)-1H-indol-3-yl]-oxo-acetic acid methyl ester To a solution of C-(1H-Indol-7-yl)-methylamine (2.69 g, 18.42 mmol) was added di-tert-butyl dicarbonate (4.22 g, 19.34 mmol) and dimethyl-pyridin-4-yl-amine (0.02 g, 0.18 mmol). The reaction was stirred for 1 h and concentrated. Exactly 2.0 g of the resulting white solid was re-dissolved in diethyl ether, cooled to 0° C., and to the solution was added oxalyl chloride dropwise (1.05 ml, 12.2 mmol). The reaction was stirred for 2 h, cooled to −78° C., and to it was added a solution of NaOMe (4.7 ml, 20.32 mmol of a 25% w/v solution in MeOH). The reaction was gently warmed to room temperature, quenched with satd. NaHCO$_3$, and poured into ethyl acetate. The organic layer was washed with saturated NaHCO$_3$, brine, dried (MgSO$_4$), and concentrated. Re-crystallization (ether/hexanes) gave the title compound (2.22 g, 82%) as a light yellow solid. $^1$H NMR (400 MHz, DMSO-d$_6$) 12.26 (s, 1H), 8.44 (d, 1H, J=3.1 Hz), 8.04 (d, 1H, J=8.0 Hz), 7.46 (t, 1H, J=6.0 Hz), 7.23 (dd, 1H, J=8.0, <1 Hz), 7.14 (d, 1H, J=8.0 Hz), 4.41 (d, 2H, J=6.0 Hz), 3.89 (s, 3H). MS (electrospray, m/z) 333 (M$^+$+1), 331.1 (M$^-$−1).

(c) 1,1-Dimethyl-3-{3-[4-(1-methyl-1H-indol-7-yl)-2,5-dioxo-2,5-dihydro-1H-pyrrol-3-yl]-1H-indol-7-ylmethyl}-urea A 1.0 M solution of KOtBu in THF (4.77 ml, 4.77 mmol) was added to a solution of 2-(1-methyl-1H-indol-7-yl-acetamide (0.3 g, 1.59 mmol) and [7-(tert-Butoxycarbonylamino-methyl)-1H-indol-3-yl]-oxo-acetic acid methyl ester (0.53 g, 1.59 mmol) in DMF (15 ml) at room temperature. The reaction was heated at 140° C. for 4 h, allowed to cool to room temperature quenched with pH 7 buffer. The mixture was poured into EtOAc, extracted, washed with saturated aq NaHCO$_3$, brine, dried (MgSO$_4$), filtered, and concentrated onto SiO$_2$. Flash chromatography (50:50 ethyl acetate: hexanes) afforded the title compound (0.1 g, 14%) as an orange solid. MS (electrospray, m/z) 442.2 (M$^+$+1), 440.3 (M$^-$−1).

(d) 1,1-Dimethyl-3-{12-(5-methyl-7H, 13H-indolo[6,7-a]pyrrolo[3,4-c]carbazole-6,8-dione-yl)-methyl}-urea A solution of 1,1-Dimethyl-3-{3-[4-(1-methyl-1H-indol-7-yl)-2,5-dioxo-2,5-dihydro-1H-pyrrol-3-yl]-1H-indol-7-ylmethyl}-urea (50 mg, 0.11 Mmol), I₂ (28 mg, 0.11 mmol) and dioxane (200 ml) was photolyzed with a 450 W Hanovia lamp fitted with a pyrex filter for 2 h. During the irradiation, the temperature of the reaction rose to 90° C. The solution was concentrated to ~5 ml and poured into ethyl acetate (300 ml) and washed with 10% NaHSO₃ (3×50 ml), saturated aqueous NaCl, dried (MgSO4), and concentrated to yield the title compound (30 mg, 0.06 mmol) as a dark yellow solid. MS (electrospray, m/z) 440.3 (M++1).

EXAMPLE 101

N-(2-Hydroxyethl)-N-{12-(5-methyl-7H, 13H-indolo[6,7-a]pyrrolo[3,4-c]carbazole-6,8-dione-yl)methyl}acetamide

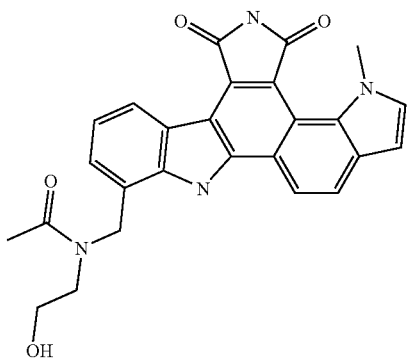

(a) 2-[(1H-Indol-7-ylmethyl)amino]ethanol

To a solution of indole-7-carboxaldehyde (10.0 g, 68.9 mmol) in 1,2-dichloroethane (300 mL) stirred under N₂ at 20–24° C. was added ethanolamine (8.5 mL, 140.8 mmol), acetic acid (4.0 mL, 70.0 mmol) and NaBH(OAc)₃ (16.8 g, 75.3 mmol). The resulting mixture was stirred at 20–24° C. overnight. The mixture was diluted with CH₂Cl₂ (200 mL), washed carefully with NaHCO₃ (200 mL). The layers were separated and the aqueous layer was extracted with CH₂Cl₂ (3×200 mL). The combined organic layer was washed with brine (100 mL) and dried over Na₂SO₄, filtered and concentrated in vacuo to give 12.4 g (95%) of the crude amine as a light yellow solid which was used without further purification. ¹H NMR (400 MHz, CDCl₃) δ 10.93 (s, 1 H), 7.41–7.39 (d, 1 H, J=7.81 Hz), 7.29 (s, 1 H), 7.0–6.99 (d, 1 H, J=6.84 Hz), 6.93–6.89 (t, 1 H, J=8.06 Hz), 6.41–6.4 (d, 1 H, J=2.44 Hz), 4.55–4.45 (bs, 1 H), 3.98 (s, 2 H), 3.49–3.47 (bt, 2 H, J=5.13 Hz), 2.61–2.58 (t, 2 H, J=5.86 Hz).

(b) Acetic acid 2-[acetyl-(1H-indol-7-ylmethyl)-amino]-ethyl ester

To a solution of 2-[(1H-Indol-7-ylmethyl)-amino]-ethanol (3.93 g, 20.68 mmol) in CH₂Cl₂ was added triethyl amine (6.26 g, 62.04 ml). The solution was cooled to 0° C. and acetyl chloride (3.22 gg, 41.36 mmol) added. The reaction was stirred at 0° C. for 1 hour. Aqueous workup gave the title compound (4.76 g, 84%). ¹H NMR (400 MHz, DMSO-d₆) rotamers (2:1) δ 11.15 (bs, 1 H, minor rotamer), 10.7 (bs, 1H, major rotamer), 7.45 (m, 1H, both rotamers), 7.38 (m, 1H, both rotamers), 6.8–7.0 (2H, both rotamers), 6.42–6.5 (m, 1H, both rotamers), 4.82 (s, 1H, minor rotamer), 4.75 (m, 1H, both rotamers), 4.2 (t, 2H, major rotamer), 4.1 (t, 2H, minor rotamer), 3.42 (m, 2H), 2.15 (s, 3H), 2.0 (s, 3H).

(c) (7-{[Acetyl-(2-hydroxy-ethyl)-amino]-methyl}-1H-indol-3-yl)-oxo-acetic acid methyl ester A solution of acetic acid 2-[acetyl-(1H-indol-7-ylmethyl)-amino]-ethyl ester (4.76 g, 17.36 mmol) in CH₂Cl₂ (100 ml) was cooled to 0° C. Oxalyl chloride (3.27 g, 26.04 mmol) was added and the reaction was warmed to room temperature. Upon completion, the reaction was cooled to −78° C. and sodium methoxide (4.14 mmol, 18.1 mmol, 25% w/v in methanol) was added. The solution was warmed to 20–24° C., and the mixture was diluted with ethyl acetate (400 mL), washed with saturated aqueous NaHCO₃, brine, dried (MgSO₄), filtered, and concentrated. SiO₂ chromatography afforded the title compound (1.12 g, 20%) and (7-{[(2-Acetoxy-ethyl)-acetyl-amino]-methyl}-1H-indol-3-yl)-oxo-acetic acid methyl ester (3.0 g, 48%). MS (electrospray, m/z) 319.2 (M⁺+1), 317.2 (M⁻−1).

(d) N-2-Hydroxy-ethyl)-N-{3-[4-(1-methyl-1H-indol-7-yl)-2,5-dioxo-2,5-dihydro-1H-pyrrol-3-yl]-1H-indol-7-ylmethyl}-acetamide KOtBu in THF (1.32 ml, 1.32 mmol, 1M solution in THF) was added to a solution of 2-(1-methyl-1H-indol-7-yl-acetamide (0.25 g, 1.32 mmol) and (7-{[acetyl-(2-hydroxy-ethyl)-amino]-methyl}-1H-indol-3-yl)-oxo-acetic acid methyl ester (0.42 g, 1.32 mmol) in DMF (10 ml) at room temperature. Additional KOtBu in THF (2.64 ml, 2.64 mmol, 1M solution in THF) was added and the reaction was heated at 50° C. overnight. The reaction was quenched with 1N HCl, poured into EtOAc, extracted, washed with saturated aqueous NaHCO₃, brine, dried (MgSO₄), filtered, and concentrated onto SiO₂. Flash chromatography and successive washings repeatedly gave impure material (0.15 g, 25%) that was taken onto the next step without further purification. MS (electrospray, m/z) 457.0 (M⁺+1), 455.1 (M⁻−1).

(e) N-(2-Hydroxyethl)-N-{12-(5-methyl-7H, 13H-indolo[6,7-a]pyrrolo[3,4-c]carbazole-6,8-dione-yl)methyl}acetamide A solution of N-2-Hydroxy-ethyl)-N-{3-[4-(1-methyl-1H-indol-7-yl)-2,5-dioxo-2,5-dihydro-1H-pyrrol-3-yl]-1H-indol-7-ylmethyl}-acetamide (100 mg, 0.22 Mmol), I₂ (56 mg, 0.22 mmol) and (200 ml) was photolyzed with a 450 W Hanovia lamp fitted with a pyrex filter for 1 h. During the irradiation, the temperature of the reaction rose to 47° C. The solution was concentrated to ~5 ml and loaded onto a bed of SiO₂. Chromatography, elution with 40% Acetone/CH₂Cl₂ gave 90% pure material. The solid was re-dissolved in CH₂Cl2 and to it was added tert-Butyl-chloro-dimethyl-silane (50 mg, 0.33 mmol) and imidazole (23 mg, 0.33 mmol). Aqueous work-up followed by SiO₂ chromatography gave the pure compound (60 mg, 59%). The compound was then dissolved in THF (10 ml) and 1N HCl was added. The reaction was poured into ethyl acetate, washed with saturated aqueous NaHCO$_3$, brine, dried (MgSO$_4$), filtered, and concentrated. SiO$_2$ flash chromatography gave the title compound (37 mg, 91%) as an orange solid. MS (electrospray, m/z) 371.2 (M$^+$+1), 370.2 (M$^-$−1).

EXAMPLE 102

11-Methoxy-5H, 7H-indolo[6,7-a]pyrrolo[3,4-c]carbazole-6,8-dione (a) (1H-Indol-7-yl)-acetonitrile To a mixture of 7-indolecarboxaldehyde (1.0 g, 6.90 mmol) and LiCN 1.5THF (72.5 mg, 0.69 mmol) in 50 ml THF, was added (EtO)$_2$P(O)CN (1.36 ml) at 0° C. The reaction was stirred at rt overnight, and then t-butanol (0.79 ml) was added. The mixture was cannulated into a flask containing an 0.1 M solution of SmI2 in THF (159 ml). Additional SMI$_2$ (10 mol %) was added until no color change was observed. The mixture was stirred for 30 min, and then concentrated and the residue poured into ethyl acetate. The organic layer was washed with 1.0 N HCl, saturated aqueous NaHCO$_3$ and brine, dried over anhydrous MgSO$_4$, filtered and concentrated. The residue was purified by flash chromatography with Hexane:Ethyl acetate=2:1, to give (1H-Indol-7-yl)-acetonitrile as white solid, (300 mg, 30%). MS (m/z) 157.0 (M$^+$+1), 155.0 (M$^+$−1). $^1$HNMR (DMSO) 11.26 (s, 1H), 7.50 (d, J=6.0 Hz, 1H), 7.39 (m, 1H), 7.06 (d, J=5.4 Hz, 1H), 6.97 (dd, J=5.4 Hz, 1H), 6.46 (m, 1H), 4.18 (s, 2H).

(b) 2-(1H-Indol-7-yl)-acetamide

To a solution of (1H-Indol-7-yl)-aceonitrile (300 mg, 1.92 mmol) in t-butabol, was added KOH (1.4 g) at reflux. The mixture was stirred at reflux for 30 min, cooled and diluted with ethyl acetate. The organic layer was washed with 1.0 N HCl, saturated aqueous NaHCO$_3$, and brine, dried over anhydrous MgSO$_4$, filtered and concentrated. The residue was purified by flash chromatography with Hexane:Ethyl acetate=1:1 to give 2-(1H-Indol-7-yl)-acetamide as white solid (100 mg, 32%). MS (m/z) 175.0 (M$^+$+1), 173.0 (M$^+$−1). $^1$HNMR (DMSO) 10.88 (s, 1H), 7.38 (m, 1H), 7.30 (m, 1H), 6.92 (m, 2H), 6.38 (m, 1H), 3.62 (s, 2H).

(c) 3-(1H-Indol-7-yl)-4-(6-methoxy-1H-indol-3-yl)-pyrrole-2,5-dione

To a suspension of the 6-methoxy-1H-indol-3-yl)oxoacetic acid methyl ester (133 mg, 0.57 mmol) and 2-(1H-Indol-7-yl)-acetamide (100 mg, 0.57 mmol) in 1.0 ml DMF was added a solution of t-BuOK in THF at 0° C. (2.0 ml of 1.0 M solution in THF) under N$_2$. The mixture was stirred at rt overnight, quenched with conc hydrochloric acid (1.0 ml). The mixture was extracted with ethyl acetate and the extracts washed with saturated aq NaHCO$_3$, brine and water, dried over anhydrous MgSO4, filtered and concentrated. The residue was purified by flash chromatography with Hexane: Ethyl acetate=1:2 to give 3-(1H-indol-7-yl)-4-(6-methoxy-1H-indol-3-yl)-pyrrole-2,5-dione (26 mg, 18%) as orange solid. MS (m/z) 358.1 (M$^+$+1), 356.1 (M$^+$−1). $^1$HNMR (DMSO) 11.56 (s, 1H), 10.95 (s, 1H), 10.67 (s, 1H), 7.81 (d, J=2.40 Hz, 1H), 7.55 (m, 1H ), 7.17 (m, 1H), 6.92 (m, 2H), 6.76 (d, J=1.80 Hz, 1H), 6.38 (m, 1H), 6.02 (m, 1H), 5.95 (m, 1H), 3.61 (s, 3H).

(d) 11-Methoxy-5H, 7H-indolo[6,7-a]pyrrolo[3,4-c]carbazole-6,8-dione

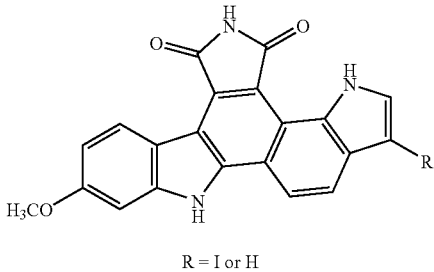

R = I or H

A solution of 3-(1H-indol-7-yl)-4-(6-methoxy-1H-indol-3-yl)-pyrrole-2,5-dione (80mg, 0.22 mmol) and I$_2$ (62.5 mg, 0.25 mmol) in 500 ml dioxane was photolyzed for 30 min. The mixture was concentrated to 10 ml and diluted with ethyl acetate. The organic layer was washed with saturated aq Na$_2$S$_2$O$_3$, saturated aq NaHCO$_3$, brine and water, dried over anhydrous MgSO4, filtered and concentrated. The residue was purified by column chromatography with Hexane:Ethyl acetate=1:1 yielded 3-iodo-11-methoxy-5H, 7H-indolo[6,7-a]pyrrolo[3,4-c]carbazole-6,8-dione (5.0 mg) as orange solid, and a mixture of 3-iodo-11-methoxy-5H, 7H-indolo[6,7-a]pyrrolo[3,4-c]carbazole-6,8-dione and 11-methoxy-5H, 7H-indolo[6,7-a]pyrrolo[3,4-c]carbazole-6,8-dione (50mg). The mixture was then dissolved in ethyl acetate and hydrogenation with 10% Pd/C, afforded pure 11-methoxy-5H, 7H-indolo[6,7-a]pyrrolo[3,4-c]carbazole-6,8-dione (15 mg). MS (m/z) 356.1 (M$^+$+1), 354.1 (M$^+$−1). $^1$HNMR (DMSO) 12.66 (s, 1H), 12.57 (s, 1H), 11.45 (s, 1H), 8.78 (d, J=6.60 Hz, 1H), 8.22 (d, J=6.30 Hz, 1H), 8.05 (d, J=6.60 Hz, 1H), 7.68 (m, 1H), 7.15 (m, 1H), 6.98 (m, 1H), 6.77 (m, 1H), 3.90 (s, 3H).

The compounds of Formula I were tested using in vitro. An important in vitro test is the ability of the compound to inhibit the activity of the CDK4 enzyme. This test is done using Rb$^{ING}$ and/or Rb$^{21}$ substrates as described in the literature (KONSTANTINIDIS, A. K., et al, *J. Biol. Chem.* 273, 26506–26515 (1998)). The test yields the micromolar concentration of the test compound, which produces a 50% inhibition of the CDK4 enzyme activity. The lower the value in this test, the more active the test compound is. Representative examples are shown in Table 1.

TABLE 1

| Example | RbING IC50 (µM) | Rb21 IC50 (µM) |
| --- | --- | --- |
| 1 | 0.043053203 | 0.001650581 |
| 2 | 0.046975806 | 0.0215102 |
| 5 | 0.03573784 | 0.02199236 |
| 11 | 0.054035088 | 0.011595745 |
| 32 | 0.345912 | 0.447552 |
| 36 | 0.082404 | 0.035697 |
| 55 | 0.042029 | 0.024558 |
| 56 | 0.099211 | 0.017712 |
| 59 | 0.120275 | 0.045149 |
| 68 | 0.022621 | 0.010922 |
| 79 | 0.076349 | 0.034694 |
| 83 | 0.078170522 | 0.010934066 |

A major in vitro test is the cell growth inhibition test. In this test, the concentration of the test compound that causes a 50% inhibition of cell growth for a selected cell line. A low value is desirable in this test. This test is done according to a standard protocol (SCHULTZ, R. M., et al, *Oncology Res*. 5, 223–228 (1993)). Another major in vitro test is the G1 arrest test. This test measures the proportion of the cells that are arrested in the G1 phase relative to control. A result above 1.5 is desirable in this test. This test is done again according to standard protocols (ROBINSON, J. P. and DARZYNKIEWICZ, Z., *Current Protocols in Cytometry* (1997). Another major in vitro test is the inhibition of Rb phosphorylation. It is desirable that the test compound be able to inhibit the phosphorylation of the Rb protein. Cyclin D-CDK4 is known to specifically phosphorylate Ser-780 of human pRb with a 25- to 60-fold higher efficiency than either cyclin E-CDK2 or cyclin A-CDK2 (KITAGAWA, M. et al., *EMBO J*. 15, 7060–7069 (1996) and BRUGAROLAS, J. et al., *Proc. Natl. Acad. Sci. USA* 96, 1002–1007 (1999)). A commercially available alpha-Phospho-Ser-780 pRb antibody (New England Biolab, Beverly, Mass.) was used in a pRb phosphorylation assay as a means of detecting CDK4 activity in vivo using a HCT116 cell line. The results are expressed as a percentage inhibition of ser-780 pRb phosphorylation in drug treated cells versus control cells treated with DMSO alone. A greater than 50% inhibition of Rb phosphorylation is desirable in this assay. A representative example is shown in Table 2.

TABLE 2

| Example | CDK4 Inhibition (IC50/μM) $Rb^{ING}/Rb^{21}$ | Cell Growth Inhibition[a] (IC50/μM) HCT116/H460 | G1 Arrest; _x vs control[b] | % Inhibtion of Rb Phosphorylation in vitro[b] @IC50/@3XIC50 |
|---|---|---|---|---|
| 1 | 0.04/0.001 | 1.80/1.09 | 2.6[c] | 90/97 |

[a]HCT116/H460 cells.
[b]HCT116 cells after 24 h incubation period.
[c]At IC50 conc.

Assay 1

Assay of Cyclin D1-cdk4 Kinase Activity with the ING Peptide as Substrate.

The cyclin D1-cdk4 kinase activity of a compound was assayed by preparing a 100 ul reaction at the following concentrations: 35 mM Hepes pH 7.0, 10 mM $MgCl_2$, 300 uM ATP, 200 uM ING peptide, 1.0 uCi of $\gamma$-$^{33}$P-ATP, 4.34 ug of cyclin D-cdk4 enzyme, 4% DMSO, and various concentrations of inhibitor. The reaction was incubated at room temperature (about 74° F.) for 60 minutes, and then terminated by the addition of 100 ul of 10% phosphoric acid. Next, the reaction was filtered through a Millipore Multiscreen-PH Plate—Catalog number MAPH NOB 10, and the plate was washed 2 times with 320 ul each of 0.5% phosphoric acid, followed by the addition of 100 ul of scintillation fluid and quantitation on a Packard Instruments, Top Count, scintillation counter.

Assay 2

Assay of Cyclin D1-cdk4 Kinase Activity with the Rb21 Protein as Substrate.

The cyclin D1-cdk4 kinase activity of a compound was assayed by preparing a 100 ul reaction at the following concentrations: 20 mM Hepes pH 7.0, 10 mM $MgCl_2$, 30 uM ATP, 5 ug of Rb21 protein (Santa Cruz Biotech, Catalog # sc-4112), 1.0 uCi of $\gamma$-$^{33}$P-ATP, 1.09 ug of cyclin D-cdk4 enzyme, 4% DMSO, and various concentrations of inhibitor. The reaction was incubated at room temperature (about 74° F.) for 60 minutes, and then terminated by the addition of 100 ul of 25% trichloroacetic acid. Next, the reaction was filtered through a Millipore Multiscreen-FC Plate—Catalog number MAFC NOB 10, and the plate was washed 2 times with 320 ul each of 10% trichloroacetic acid, followed by the addition of 100 ul of scintillation fluid and quantitation on a Packard Instruments, Top Count, scintillation counter.

Assay 3

Cell Growth Inhibition Assay.

The MTT assay was used to measure growth inhibitory activity (Schultz, R. M., et. al. Oncology Res. 5, 223–228, 1993). The IC50 was determined as the concentration of drug required to inhibit cell growth by 50% over 72 h of drug exposure. Basically, 1000 HCT-116 or NCI H460 cells were added per well to 96-well flat-bottom plates in 100-ul RPMI 1640 medium containing 10% dialyzed fetal bovine serum. The plates were incubated for 24 h prior to addition of test compounds. A stock solution (10 mM) was prepared in DMSO and serially diluted in medium. Compound dilutions were added to triplicate wells, and the plates were incubated for 72 hours.

Assay 4

Cell Cycle Analysis Using Flow Cytometry.

The HCT-116 and NCI H460 cell lines were seeded in 75 $cm^2$ flasks at $5\times10^5$ cells/25 ml RPMI 1640 medium containing 10% dialyzed fetal bovine serum. They were incubated for 24 hours. Compound is then added at 1× IC50 and 3× IC50 (determined from above section "growth inhibition studies") and incubated for an additional 24 hours. The cells are subsequently harvested and the protocol (Robinson, J. P. and Darzynkiewicz, Z. Current Protocols in Cytometry. 1997) for staining was followed. DNA histogram analysis was performed using ModFit LT(Verity House).

Assay 5

Inhibition of Rb Phosphorylation Assay.

Human HCT116 colon carcinoma cell line was purchased from American Tissue Culture Collection (Rockville, Md.) and maintained as monolayer in RPMI-1640 with L-Glutamine and 25 mM HEPES supplemented with 10% fetal bovine serum in a 37° C. incubator with a 10% $CO_2$ atmosphere. The detection of mycoplasm in cultured cells was performed using Mycoplasma Rapid Detection System (TaKaRa Shuzo Co. Ltd., Shiga, Japan) every 2–3 months and the cells were found consistently negative throughout these experiments. The Rb phosphorylation assay was done be plating $4\times10^5$ cells/well in 6-well plates. After 24 h, exponentially growing HCT116 cells were treated with compounds at 1×, 2× and 3× $IC_{50}$ (as determined by MMT assay) or DMSO in complete medium for 24 h. At the end of the incubation period the medium was removed and the cells were washed twice with cold PBS containing 1 mM sodium orthovanadate ($Na_3VO_4$). Cellular protein lysates were prepared by adding freshly prepared 50 uL/well lysis buffer (50 mM HEPES pH 7.5, 1% Triton X-100, 5 mM EDTA, 50 mM NaCl, 10 mM sodium pyrophospate, 50 mM sodium fluoride, 1 mM Na3VO4, 1 mM phenylmethylsulfonyl fluoride, 10 ug/mL Aprotinin, 10 ug/mL Leupeptin, and 10 ug/mL Pepstatin). The cell lysates were collected and incubated on ice for 30 min with frequent brief vortexing. Cellular debris was removed by centrifugation at 14000×g for 10 min at 4° C. Protein concentration was determined by the Bio-Rad DC protein assay (Bio-Rad, Hercules, Calif.). To analyze extracts, equal amounts of protein (30 ug) were dissolved in 1× Laemmli sample buffer, bioled for 5 min and resolved by electrophoresis on 10% polyacrylamide gels containing SDS. The proteins were transferred to Immobilon-P membrane (Millipore, Bedford, Mass.). Membranes were incubated with 5% non-fat dried milk in TBS-T (10 mM Tris-Cl, pH 7.4, 150 mM NaCl, and 0.1% Tween-20) for 1 h at room temperature to block non-specific sites. Immunoblotting was done by incubating membranes with alpha-Phospho-Ser-780 pRb (1 ug/mL, New England Biolab, Beverly, Mass.) and alpha-actin (0.2 ug/mL) antibodies in TBS-T containing 5% non-fat dried milk for overnight at 4° C. Membranes were washed three times (15 min each) in TBS-T, and subsequently incubated for 2 h at room temperature with horseradish peroxidase-conjugated anti-rabbit (1:2000) and anti-mouse (1:1000) antibody (Amersham) in TBS-T. Membranes were eashed three times (15 min each) with TBS-T, and incubated for 5 min in SuperSignal West Pico Chemiluminescent reagents (Pierce, Rockford Ill.). Proteins were detected by capturing image of the membrane using Quantity One Software on a Fluor-S multi-Imager (Bio-Rad, Hercules, Calif.) in a linear range. Specific bands were quantified using Quantity One Software. After correcting for variable loading using actin as a control, Ser-780 phosphorylated pRb protein levels in the drug treated samples were compared with that of cells treated with vehicle (DMSO). The results (Table II) were expressed as a percentage inhibition of Ser-780 pRb phosphorylation in drug treated cells versus control DMSO treated cells.

Compounds of Formula I may be administered by the oral, transdermal, percutaneous, intravenous, intramuscular, intranasal or intrarectal route, in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of Formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the Formula I, or its pharmaceutical salt, from about 0.1 to about 10% w/v (weight per unit volume).

We claim:

1. A compound of Formula I

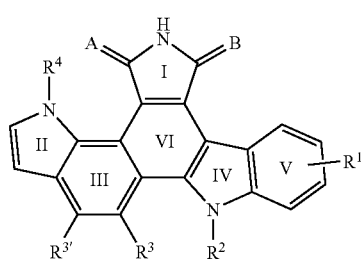

Formula I wherein

A and B are independently O or S;

$R^1$ is hydrogen, $C_1$–$C_4$ alkyl, $C_1$–$C_4$ alkoxy, hydroxy, hydroxy($C_1$–$C_4$)alkyl, halogen, cyano, halo($C_1$–$C_4$) alkyl, ($C_1$–$C_4$ alkyl)-$NR^5R^6$, or ($C_1$–$C_4$ alkyl)-($C_1$–$C_4$ alkyl ester of an amino acid residue);

$R^2$ is hydrogen, $C_1$–$C_4$ alkyl, hydroxy($C_1$–$C_4$)alkyl, ($C_1$–$C_4$ alkyl)-$NR^5R^6$, ($C_1$–$C_4$ alkyl)-$C(O)NR^5R^6$, or ($C_1$–$C_4$ alkyl)-($C_1$–$C_4$ alkyl ester of an amino acid residue);

$R^3$ and $R^{3'}$ are independently hydrogen, $C_1$–$C_4$ alkyl, $C_1$–$C_4$ alkoxy, or halogen;

$R^4$ is hydrogen or $C_1$–$C_4$ alkyl;

$R^5$ is independently at each occurrence hydrogen, $C_1$–$C_4$ alkyl, hydroxy($C_1$–$C_4$)alkyl, ($C_1$–$C_4$ alkyl)-$NR^7R^8$, $C(O)NR^7R^8$, $C(O)$—($C_1$–$C_4$ alkyl), or optionally substituted $C_3$–$C_8$ cycloalkyl; and $R^6$ is independently at each occurrence hydrogen or $C_1$–$C_4$ alkyl;

$R^7$ and $R^8$ are independently at each occurrence hydrogen or $C_1$–$C_4$ alkyl;

or a pharmaceutically acceptable salt thereof.

2. A method for the treatment of antiproliferative diseases in a mammal selected from the group consisting of breast cancer, colorectal cancer, head and neck carcinomas, esophageal cancer, soft tissue carcinoma, osteosarcoma, hepatoblastomas, non-small cell lung cancer, prostate cancer, and ovarian cancer comprising administering to a mammal in need of such treatment an effective amount of a compound of Formula I Formula I wherein A and B are independently O or S;

$R^1$ is hydrogen, $C_1$–$C_4$ alkyl, $C_1$–$C_4$ alkoxy, hydroxy, hydroxy($C_1$–$C_4$)alkyl, halogen, cyano, halo($C_1$–$C_4$) alkyl, ($C_1$–$C_4$ alkyl)-$NR^5R^6$, or ($C_1$–$C_4$ alkyl)-($C_{1-4}$ alkyl ester of an amino acid residue);

$R^2$ is hydrogen, $C_1$–$C_4$ alkyl, hydroxy($C_1$–$C_4$)alkyl, ($C_1$–$C_4$ alkyl)-$NR^5R^6$, ($C_1$–$C_4$ alkyl)-$C(O)NR^5R^6$, or ($C_1$–$C_4$ alkyl)-($C_1$–$C_4$ alkyl ester of an amino acid residue);

$R^3$ and $R^{3'}$ are independently hydrogen, $C_1$–$C_4$ alkyl, $C_1$–$C_4$ alkoxy, or halogen;

$R^4$ is hydrogen or $C_1$–$C_4$ alkyl;

$R^5$ is independently at each occurrence hydrogen, $C_1$–$C_4$ alkyl, hydroxy($C_1$–$C_4$)alkyl, ($C_1$–$C_4$ alkyl)-$NR^7R^8$, $C(O)NR^7R^8$, $C(O)$—($C_1$–$C_4$ alkyl), or optionally substituted $C_3$–$C_8$ cycloalkyl; and $R^6$ is independently at each occurrence hydrogen or $C_1$–$C_4$ alkyl;

$R^7$ and $R^8$ are independently at each occurrence hydrogen or $C_1$–$C_4$ alkyl;

or a pharmaceutically acceptable salt thereof.

3. A pharmaceutical composition comprising a compound of Formula I

Formula I wherein

A and B are independently O or S;

$R^1$ is hydrogen, $C_1$–$C_4$ alkyl, $C_1$–$C_4$ alkoxy, hydroxy, hydroxy($C_1$–$C_4$) alkyl, halogen cyano, halo($C_1$–$C_4$) alkyl, ($C_1$–$C_4$ alkyl)-$NR^5R^6$, or ($C_1$–$C_4$ alkyl)-($C_1$–$C_4$ alkyl ester of an amino acid residue);

$R^2$ is hydrogen, $C_1$–$C_4$ alkyl, hydroxy($C_1$–$C_4$)alkyl, ($C_1$–$C_4$ alkyl)-$NR^5R^6$, ($C_1$–$C_4$ alkyl)-$C(O)NR^5R^6$, or ($C_1$–$C_4$ alkyl)-($C_1$–$C_4$ alkyl ester of an amino acid residue);

$R^3$ and $R^{3'}$ are independently hydrogen, $C_1$–$C_4$ alkyl, $C_1$–$C_4$ alkoxy, or halogen;

$R^4$ is hydrogen or $C_1$–$C_4$ alkyl;

$R^5$ is independently at each occurrence hydrogen, $C_1$–$C_4$ alkyl, hydroxy($C_1$–$C_4$)alkyl, ($C_1$–$C_4$ alkyl)-$NR^7R^8$, $C(O)NR^7R^8$, $C(O)$—($C_1$–$C_4$ alkyl), or optionally substituted $C_3$–$C_8$ cycloalkyl; and $R^6$ is independently at each occurrence hydrogen or $C_1$–$C_4$ alkyl;

$R^7$ and $R^8$ are independently at each occurrence hydrogen or $C_1$–$C_4$ alkyl;

or a pharmaceutically acceptable salt thereof, in association with a pharmaceutically acceptable carrier, diluent or excipient.

4. A compound according to claim 1 wherein A and B are both O.

5. A compound according to claim 1 wherein $R^3$ and $R^{3'}$ are both hydrogen.

6. A compound according to claim 1 wherein $R^4$ is methyl.

7. A compound according to any one of claims 4–6 wherein $R^1$ is ($C_1$–$C_4$)-$NR^5R^6$.

8. A compound according to any one of claims 4–6 wherein $R^1$ is methoxy.

* * * * *